US012350329B2

(12) United States Patent
Reed et al.

(10) Patent No.: US 12,350,329 B2
(45) Date of Patent: Jul. 8, 2025

(54) RNA VACCINES AGAINST INFECTIOUS DISEASES

(71) Applicant: HDT Bio Corp., Seattle, WA (US)

(72) Inventors: Steven Gregory Reed, Bellevue, WA (US); Darrick Albert Carter, Seattle, WA (US); Amit Praful Khandhar, Issaquah, WA (US); Jacob Freeman Archer, Seattle, WA (US); Lars Peter Aksel Berglund, Seattle, WA (US); Jesse Erasmus, Port Orchard, WA (US); Bryan Berube, Issaquah, WA (US); Malcolm S. Duthie, Sammamish, WA (US)

(73) Assignee: HDT Bio Corp., Seattle, WA (US)

( * ) Notice: Subject to any disclaimer, the term of this patent is extended or adjusted under 35 U.S.C. 154(b) by 0 days.

(21) Appl. No.: 18/610,681

(22) Filed: Mar. 20, 2024

(65) Prior Publication Data

US 2024/0307521 A1 Sep. 19, 2024

Related U.S. Application Data

(63) Continuation of application No. PCT/US2022/013516, filed on Jan. 24, 2022.

(60) Provisional application No. 63/297,498, filed on Jan. 7, 2022, provisional application No. 63/247,175, filed on Sep. 22, 2021.

(51) Int. Cl.

| | |
|---|---|
| ***A61K 39/145*** | (2006.01) |
| ***A61K 9/127*** | (2006.01) |
| ***A61K 9/51*** | (2006.01) |
| ***A61K 47/02*** | (2006.01) |
| ***A61K 47/10*** | (2017.01) |
| *A61K 39/00* | (2006.01) |

(52) U.S. Cl.

CPC ............ *A61K 39/145* (2013.01); *A61K 9/127* (2013.01); *A61K 9/5123* (2013.01); *A61K 47/02* (2013.01); *A61K 47/10* (2013.01); *A61K 2039/53* (2013.01); *A61K 2039/55505* (2013.01); *A61K 2039/55555* (2013.01); *A61K 2039/55566* (2013.01); *C12N 2760/16134* (2013.01); *C12N 2760/16234* (2013.01)

(58) Field of Classification Search

None

See application file for complete search history.

(56) References Cited

U.S. PATENT DOCUMENTS

| | | | |
|---|---|---|---|
| 7,045,335 | B2 | 5/2006 | Smith |
| 7,425,337 | B2 | 9/2008 | Smith |
| 8,709,441 | B2 | 4/2014 | Rayner |
| 8,734,832 | B2 | 5/2014 | O'Hagan et al. |
| 8,853,179 | B2 | 10/2014 | Mauro |
| 9,295,646 | B2 | 3/2016 | Kline |
| 9,555,136 | B2 | 1/2017 | Khandhar et al. |
| 9,655,845 | B2 | 5/2017 | Brito |
| 10,238,733 | B2 | 3/2019 | Brito |
| 10,307,374 | B2 | 6/2019 | Brito |
| 11,026,890 | B2 | 6/2021 | Brito |
| 11,083,786 | B2 | 8/2021 | Kamrud |
| 11,135,287 | B2 | 10/2021 | Brito |
| 11,141,377 | B2 | 10/2021 | Fox |
| 11,318,213 | B2 | 5/2022 | Khandhar |
| 11,364,310 | B2 | 6/2022 | Kamrud |
| 11,376,335 | B2 | 7/2022 | Khandhar |
| 11,406,699 | B2 | 8/2022 | Kehn-Hall |
| 11,433,142 | B2 | 9/2022 | Khandhar |
| 11,458,209 | B2 | 10/2022 | Khandhar |
| 11,534,497 | B2 | 12/2022 | Khandhar |
| 2006/0128011 | A1 | 6/2006 | Zhu |
| 2009/0155301 | A1 | 6/2009 | Mason |
| 2009/0252721 | A1 | 10/2009 | Buschmann |
| 2012/0156251 | A1 | 6/2012 | Brito |
| 2013/0177639 | A1 | 7/2013 | Geall |
| 2013/0195751 | A1 | 8/2013 | Hahn |
| 2013/0202707 | A1 | 8/2013 | Ali |
| 2016/0000886 | A1 | 1/2016 | Parker |
| 2016/0201067 | A1 | 7/2016 | Ataullakhanov |
| 2017/0189368 | A1 | 7/2017 | Troiano |
| 2018/0008694 | A1 | 1/2018 | Ciaramella |
| 2018/0104325 | A1 | 4/2018 | Gale, Jr. |
| 2018/0147298 | A1 | 5/2018 | Besin |
| 2018/0153848 | A1 | 6/2018 | Chen |
| 2018/0207295 | A1 | 7/2018 | Fotin-Mleczek |
| 2018/0311336 | A1 | 11/2018 | Ciaramella |
| 2018/0318409 | A1 | 11/2018 | Valiante |

(Continued)

FOREIGN PATENT DOCUMENTS

| | | | |
|---|---|---|---|
| WO | 2001021810 | A1 | 3/2001 |
| WO | 2002080982 | A2 | 10/2002 |

(Continued)

OTHER PUBLICATIONS

Erasmus et al., Molecular Therapy vol. 26 No. 10, pp. 2507-5022). (Year: 2018).*

(Continued)

*Primary Examiner* — Shanon A. Foley

*Assistant Examiner* — Myron G Hill

(74) *Attorney, Agent, or Firm* — Greenberg Traurig, LLP

(57) ABSTRACT

The disclosure provides compositions, methods of treatment, and methods of making and using compositions to deliver a nucleic acid to a subject. Methods of using these compositions as a vaccine for treatment of an infectious disease are also provided.

18 Claims, 12 Drawing Sheets

Specification includes a Sequence Listing.

(56) References Cited

U.S. PATENT DOCUMENTS

| | | | |
|---|---|---|---|
| 2019/0015501 A1 | 1/2019 | Ciaramella | |
| 2019/0274968 A1 | 9/2019 | Weissman | |
| 2019/0382450 A1 | 12/2019 | Belov | |
| 2020/0006973 A1 | 1/2020 | Petersen | |
| 2020/0069599 A1 | 3/2020 | Smith | |
| 2020/0123573 A1 | 4/2020 | Kamrud | |
| 2020/0157571 A1 | 5/2020 | Nakanishi | |
| 2020/0224174 A1 | 7/2020 | Irvine | |
| 2020/0230056 A1 | 7/2020 | Fox | |
| 2020/0297834 A1 | 9/2020 | Kehn-Hall | |
| 2020/0368344 A1 | 11/2020 | Ciaramella | |
| 2020/0370052 A1 | 11/2020 | Wilson | |
| 2021/0128583 A1 | 5/2021 | Zhang | |
| 2021/0283242 A1 | 9/2021 | Hutchins | |
| 2021/0290752 A1 | 9/2021 | Sullivan | |
| 2021/0290756 A1 | 9/2021 | Sullivan | |
| 2021/0330781 A1 | 10/2021 | Kamrud | |
| 2023/0310569 A1* | 10/2023 | Voigt | A61K 39/12 424/41 |

FOREIGN PATENT DOCUMENTS

| | | |
|---|---|---|
| WO | 2005107760 A1 | 11/2005 |
| WO | 2007024826 A2 | 3/2007 |
| WO | 2008124647 A2 | 10/2008 |
| WO | 2008153541 A1 | 12/2008 |
| WO | WO2009049083 | 4/2009 |
| WO | 2010141861 A1 | 12/2010 |
| WO | WO 2011/156761 | 12/2011 |
| WO | 2014042780 A1 | 3/2014 |
| WO | 2015103167 A2 | 7/2015 |
| WO | 2017200852 A1 | 11/2017 |
| WO | 2017200957 A1 | 11/2017 |
| WO | 2017205225 A2 | 11/2017 |
| WO | 2017210364 A1 | 12/2017 |
| WO | 2017218704 A1 | 12/2017 |
| WO | WO2018022957 | 2/2018 |
| WO | 2018/044028 | 3/2018 |
| WO | 2018053294 A1 | 3/2018 |
| WO | WO 2018/147710 | 8/2018 |
| WO | 2018232257 | 12/2018 |
| WO | WO20182322257 | 12/2018 |
| WO | WO 2019/152884 | 8/2019 |
| WO | 2020132279 A1 | 6/2020 |
| WO | 2020/243115 | 12/2020 |
| WO | 2020254804 A1 | 12/2020 |
| WO | 2021021605 A1 | 2/2021 |
| WO | 2021076630 A1 | 4/2021 |
| WO | WO 2021/067480 | 4/2021 |
| WO | WO 2021/072112 | 4/2021 |
| WO | WO 2021/163536 | 8/2021 |
| WO | 2021178886 A1 | 9/2021 |
| WO | 2021183564 A1 | 9/2021 |
| WO | 2021194672 A1 | 9/2021 |
| WO | WO 2021/194672 | 9/2021 |
| WO | 2021210686 A1 | 10/2021 |
| WO | WO 2022/051022 | 3/2022 |
| WO | 2022136952 A1 | 6/2022 |
| WO | WO-2022217079 A1 * | 10/2022 ............ A61K 39/12 |
| WO | 2023286076 A1 | 1/2023 |
| WO | 2023026301 A1 | 3/2023 |
| WO | 2023049636 A1 | 3/2023 |
| WO | 2023049636 A2 | 3/2023 |
| WO | 2023056202 A2 | 4/2023 |

OTHER PUBLICATIONS

Kulkarni et al. Nanoscale, 9, 13600-13609 (Year: 2017).*

International Search Report issued Jun. 29, 2023 in PCT/US2022/076787.

International Search Report issued Jun. 7, 2023 in PCT/US2022/076304.

Agnihothram, S., et al., "Development of a Broadly Accessible Venezuelan Equine Encephalitis Virus Replicon Particle Vaccine Platform" J Virol. May 14, 2018;92(11):e00027-18. doi: 10.1128/JVI.00027-18.

Anderluzzi, G., et al., "Investigating the Impact of Delivery System Design on the Efficacy of Self-Amplifying RNA Vaccines" Vaccines (Basel). May 8, 2020;8(2):212. doi: 10.3390/vaccines8020212.

Bazhan, S., et al., "Immunogenicity and Protective Efficacy of Influenza A DNA Vaccines Encoding Artificial Antigens Based on Conservative Hemagglutinin Stem Region and M2 Protein in Mice." Vaccines vol. 8,3 448. Aug. 9, 2020, doi:10.3390/vaccines8030448.

Boettler, T., et al., "SARS-CoV-2 vaccination can elicit a CD8 T-cell dominant hepatitis" J Hepatol. Sep. 2022;77(3):653-659. doi: 10.1016/j.jhep.2022.03.040.

Brito, L.A., et al., "A Cationic Nanoemulsion for the Delivery of Next-Generation RNA Vaccines" Mol Ther. 2014;22(12):2118-2129. doi:10.1038/mt.2014.133.

Chiu, C.Y.H., et al., "Association of antibodies to Plasmodium falciparum reticulocyte binding protein homolog 5 with protection from clinical malaria" Front Microbiol. Jun. 30, 2014;5:314. doi: 10.3389/fmicb.2014.00314.

Deo, S., et al. "Evaluation of self-amplifying mRNA platform for protein expression and genetic stability: Implication for mRNA therapies." Biochemical and Biophysical Research Communications 680 (2023): 108-118.

Dewey, E.C., et al., "Programming of RIG-I Signaling Through Co-Factor Interactions," The Journal of Immunology 96 (1 Suppl):203, May 2016, 4 pages.

Du, L., et al., "The Spike Protein of SARS-CoV—A Target for Vaccine and Therapeutic Development", Nat Rev Microbiol 7, 226-236 (2009). https://doi.org/10.1038/nrmicro2090.

Duerrwald, R., et al., "Influenza A virus (A/swine/Bueren/5439/2006(H3N2)) segment 4 hemagglutinin (HA) gene, complete cds". Genbank entry (online). National Center for Biotechnology Information. URL: Https://www.ncbi.nlm.nih.gov/nucleotide/MK362039.1J. Jan. 31, 2020; pp. 1-2.

Erasmus, J.A., et al., "A Nanostructured Lipid Carrier for Delivery of a Replicating Viral RNA Provides Single, Low-Dose Protection against Zika", Mol Ther. Oct. 3, 2018;26(10):2507-2522. doi: 10.1016/j.ymthe.2018.07.010. Epub Aug. 2, 2018. PMID: 30078765; PMCID: PMC6171036.

Felgner, Philip L., et al. "Lipofection: a highly efficient, lipid-mediated DNA-transfection procedure." Proceedings of the National Academy of Sciences 84.21 (1987): 7413-7417.

Fleeton, M. N., et al., "Self-Replicative RNA Vaccines Elicit Protection Against Influenza A Virus, Respiratory Syncytial Virus, and a Tickborne Encephalitis Virus", The Journal of Infectious Diseases, vol. 183, Issue 9, May 1, 2001, pp. 1395-1398, https://doi.org/10.1086/319857.

Fox, C.B., "Squalene emulsions for parenteral vaccine and drug delivery" Molecules. Sep. 1, 2009;14(9):3286-312. doi:10.3390/molecules14093286.

Gao, Y., et al, "Structure of the RNA-dependent RNA polymerase from COVID-19 virus" Science. May 15, 2020;368(6492):779-782. doi: 10.1126/science.abb7498.

Gehardt, Alana, et al., "A flexible, thermostable nanostructured lipid carrier platform for RNA vaccine delivery" Mol Ther Methods Clin Dev. Jun. 9, 2022;25:205-214. doi: 10.1016/j.omtm.2022.03.009.

Hartmann, G. "Chapter 4: Nucleic Acid Immunity," in F. Alt (ed.), "Advances in Immunology," 133:121-169, 2017.

Hatmal, M.M., et al., "Comprehensive Structural and Molecular Comparison of Spike Proteins of SARS-CoV-2, SARS-CoV and MERS-CoV, and Their Interactions with ACE2" Cells Dec. 8, 2020;9(12):2638. doi: 10.3390/cells9122638.

Hawman, D. W. et al., "SARS-CoV2 variant-specific replicating RNA vaccines protect from disease and pathology and reduce viral shedding following challenge with heterologous SARS-CoV2 variants of concern" bioRxiv [Preprint]. Dec. 13, 2021:2021.12.10.472134. doi: 10.1101/2021.12.10.472134 bioRxiv 2021.12.10.472134; doi: https://doi.org/10.1101/2021.12.10.472134.

Heinz, F.X., and Stiasny, K., "Distinguishing features of current COVID-19 vaccines: knowns and unknowns of antigen presentation and modes of action" NPJ Vaccines. Aug. 16, 2021;6(1):104. doi: 10.1038/s41541-021-00369-6.

(56) References Cited

OTHER PUBLICATIONS

Huang, H.C., et al., "Formulation of novel lipid-coated magnetic nanoparticles as the probe for in vivo imaging" J Biomed Sci. Sep. 21, 2009;16(1):86. doi: 10.1186/1423-0127-16-86.
Huang, Y., et al., "Structural and functional properties of SARS-CoV-2 spike protein: potential antivirus drug development for COVID-19" Acta Pharmacol Sin 41, 1141-1149 (2020). https://doi.org/10.1038/s41401-020-0485-4.
International Search Report issued Jun. 6, 2022 in PCT/US2022/13513.
International Search Report issued Jun. 8, 2022 in PCT/US2022/013516.
International Search Report issued Jun. 14, 2022 in PCT/US2022/13508.
International Search Report issued in PCT/US2023/060225 dated Jul. 28, 2023.
International Search Report issued Jun. 6, 2022 in PCT/US2022/013513.
International Search Report issued Jun. 8, 2023 in PCT/US2022/076821.
Kautz, T. F., et al., "Low-fidelity Venezuelan equine encephalitis virus polymerase mutants to improve live-attenuated vaccine safety and efficacy" Virus Evol.:4(1); pp. 1-14, Mar. 6, 2018;. doi: 10.1093/ve/vey004.
Kimuira, T, et al., "A localizing nanocarrier formulation enables multi-target immune responses to multivalent replicating RNA with limited systemic inflammation", Molecular Therapy (2023), doi: https://doi.org/10.1016/j.ymthe.2023.06.017.
Kwon, S.M., et al., "In vivo time-dependent gene expression of cationic lipid-based emulsion as a stable and biocompatible non-viral gene carrier" J Control Release. May 22, 2008;128(1):89-97. doi: 10.1016/j.jconrel.2008.02.004. Epub Feb. 19, 2008. Erratum in: J Control Release. Nov. 16, 2009;140(1):74.
Li, X-Y., et al., "Tumor Suppressor Activity of RIG-I," Molecular and Cellular Oncology 1(4):e968016, Dec. 2014.
Marcus, M., et al., "Iron oxide nanoparticles for neuronal cell applications: uptake study and magnetic manipulations", J Nanobiotechnology, vol. 14, Issue 37, May 2016, https://doi.org/10.1186/s12951-016-0190-0.
Maruggi, G., et al., "A self-amplifying mRNA SARS-CoV-2 vaccine candidate induces safe and robust protective immunity in preclinical models" Mol Ther. Jan. 3, 2022:S1525-0016(22)00001-6. doi: 10.1016/j.ymthe.2022.01.001.
Min, J. W., et al., "Hemagglutinin (Influenza A virus (A/Aichi/2/1968(H3N2))]". Genbank entry (online). National Center for Biotechnology Information. Retrieved From The Internet. URL: https://www.ncbi.nlm.nih.gov/protein/AAA43239.1]. Jul. 13, 2006; p. 1.
Pardi, N., et al., "mRNA vaccines—a new era in vaccinology" Nat Rev Drug Discov. Apr. 2018;17(4):261-279. doi:10.1038/nrd.2017.243. Epub Jan. 12, 2018. PMID: 29326426.
Roeffen, W., et al., "Transmission-blocking activity of antibodies to Plasmodium falciparum GLURP. 10C chimeric protein formulated in different adjuvants" Malar J 14, 443 (2015). https://doi.org/10.1186/s12936-015-0972-0.
Safety and Immunogenicity of HDT-301 Targeting a SARS-CoV-2 Variant Spike Protein, Sponsor: HDT Bio, posted 11/24/21ClinicalTrials.gov Identifier: NCT05132907 found at https://clinicaltrials.gov/ct2/show/record/NCT05132907?term=hdt+bio&draw=2&rank=1 11 pages.
Schoenmaker, L., et al. "mRNA-lipid nanoparticle COVID-19 vaccines: Structure and stability." International journal of pharmaceutics vol. 601 (2021): 120586. doi:10.1016/j.ijpharm.2021.120586.
Shu, B., et al., "Structural basis of viral RNA-dependent RNA polymerase catalysis and translocation", Proc Natl Acad Sci USA; 113(28):E4005-14, Jun. 23, 2016 doi: 10.1073/pnas.1602591113.
Singh, K., et al., "Malaria vaccine candidate based on Duffy-binding protein elicits strain transcending functional antibodies in a Phase I trial" NPJ Vaccines. Sep. 28, 2018;3:48. doi: 10.1038/s41541-018-0083-3.
Starmans, L.W.E., et al., "Iron oxide nanoparticle-micelles (ION-micelles) for sensitive (molecular) magnetic particle imaging and magnetic resonance imaging" PLoS One. 2013;8(2):e57335. doi: 10.1371/journal.pone.0057335. Epub Feb. 20, 2013.
Stokes, A., et al., "Nonclinical safety assessment of repeated administration and biodistribution of a novel rabies self-amplifying mRNA vaccine in rats" Regul Toxicol Pharmacol. Jun. 2020;113:104648. doi: 10.1016/j.yrtph.2020.104648.
Teixeira, T. et al., "Cationic nanoemulsions as nucleic acids delivery systems" Int J Pharm. Dec. 20, 2017;534(1-2):356-367. doi: 10.1016/j.ijpharm.2017.10.030.
Tregoning, J. S., et al., "Formulation, inflammation, and RNA sensing impact the immunogenicity of self-amplifying RNA vaccines" Mol Ther Nucleic Acids. Dec. 5, 2022;31:29-42. doi: 10.1016/j.omtn.2022.11.024.
Tregoning, J.S.. "LION: Taming RNA vaccine inflammation" Mol Ther. Aug. 3, 2023:S1525-0016(23)00386-6. doi: 10.1016/j.ymthe.2023.07.006.
Valdivia, L, et al., Solid Lipid Particles for Lung Metastasis Treatment. Pharmaceutics. 2021;13(1):93. Published Jan. 13, 2021. doi:10.3390/pharmaceutics13010093.
Voigt, E.A., et al., "A self-amplifying RNA vaccine against COVID-19 with long-term room-temperature stability" npj Vaccines 7, 136 (2022). https://doi.org/10.1038/s41541-022-00549-y.
Walton, T.E., et al., "Experimental infection of horses with an attenuated Venezuelan equine encephalomyelitis vaccine (strain TC-83)" Infect Immun. May 1972;5(5):750-6. doi: 10.1128/iai.5.5.750-756.1972.
Wu, F., et al., "Severe acute respiratory syndrome coronavirus 2 isolate Wuhan-Hu-1, complete genome" GenBank: MN908947.3, VRL Mar. 18, 2020, available at https://www.ncbi.nlm.nih.gov/nuccore/MN908947.
"Gennova's mRNA vaccine to come in powder form; will stay stable at 2-8° C." Business Standard. Sep. 13, 2021 02:56 IST.
Brinckerhoff, L. H., et al., "Melanoma vaccines" Current Opinion in Oncology: Mar. 2000—vol. 12—Issue 2—p. 163-173.
Brocato, R. L., et al., Protective efficacy of a SARS-CoV-2 DNA vaccine in wild-type and immunosuppressed Syrian hamsters. NPJ Vaccines 6, 16 (2021). https://doi.org/10.1038/s41541-020-00279-z.
Brown, C. M., et al. Outbreak of SARS-CoV-2 Infections, Including COVID-19 Vaccine Breakthrough Infections, Associated with Large Public Gatherings—Barnstable County, Massachusetts, Jul. 2021. MMWR Morb Mortal Wkly Rep 2021;70:1059-1062.
Corbett, K. S., et al., "Evaluation of the mRNA-1273 Vaccine against SARS-CoV-2 in Nonhuman Primates" N Engl J Med. Oct. 15, 2020;383(16):1544-1555. doi: 10.1056/NEJMoa2024671.
Corman, V. C., et al., Detection of 2019 novel coronavirus (2019-nCOV) by real-time RT-PCR. Euro Surveill. 2020;25(3), https://doi.org/10.2807/1560-7917.ES.2020.25.3.2000045.
CustomBiotech Online Development Exchange (CODE), Beyond COVID: The Future of mRNA technology, Webinar held Thursday, Nov. 11, 2021, https://dianews.roche.com/CustomBiotech-Webinar-2021.html.
Edara, V., et al., Infection and Vaccine-Induced Neutralizing-Antibody Responses to the SARS-CoV-2 B.1.617 Variants. N Engl J Med. Aug. 12, 2021;385(7):664-666. doi: 10.1056/NEJMc2107799. Epub Jul. 7, 2021. PMID: 34233096; PMCID: PMC8279090.
Erasmus, J. H., A Nanostructured Lipid Carrier for Delivery of Replicating Viral RNA Provides Single, Low-Dose Protection against Zika, Molecular Therapy, vol. 26, No. 10. pp. 2507-2522.
Erasmus, J. H., et al., "An Alphavirus-derived replicon RNA vaccine induces SARS-CoV-2 neutralizing antibody and T cell responses in mice and nonhuman primates" Science Translational Medicine, Aug. 5, 2020, vol. 12, Issue 555.
Erasmus, J.H. et al., "Single-dose Replicating RNA Vaccine Induces Neutralizing Antibodies Against SARS-CoV-2 in Nonhuman Primates", bioRxiv, 28 pages.
Erasmus, J.H., "An Alphavirus-derived replicon RNA vaccine induces SARS-CoV-2 Neutralizing Antibody and T-cell Responses in Mice and Nonhuman Primates", Science Translational Medicine, vol. 12, No. 555.

(56) References Cited

OTHER PUBLICATIONS

Erasmus, J.H., et al., Intramuscular Delivery of Replicon RNA Encoding ZIKV-117 Human Monoclonal Antibody Protects against Zika Virus Infection. Mol Ther—Methods Clin Dev. 2020;18:402-414. PMID: 32695842.
File No. BIO/CT/20/000182, CT No. CT-02/2021 Government of India Directorate General of Health Services Central Drugs Standard Control Organization (Biological Division), Form CT-06 Permission to Conduct Clinical Trial of New Drug or Investigational New Drug, Jan. 25, 2021, 3 pages.
File No. BIO/CT/21/000105, CT No. CT-28/2021 Government of India Directorate General of Health Services Central Drugs Standard Control Organization (Biological Division), Form CT-06 Permission to Conduct Clinical Trial of New Drug or Investigational New Drug, Aug. 22, 2021, 3 pages.
Fischer, Robert J., et al. "ChAdOx1 nCOV-19 (AZD1222) protects Syrian hamsters against SARS-CoV-2 B. 1.351 and B.1.1.7." bioRxiv : the preprint server for biology 2021.03.11.435000. Jun. 30, 2021, doi:10.1101/2021.03.11.435000. Preprint.
Geall, Andrew J., et al. "Nonviral delivery of self-amplifying RNA vaccines." PNAS. vol. 109. No. 36, pp. 14604-14609 (2012).
Gilchuk, P., et al., "Integrated pipeline for the accelerated discovery of antiviral antibody therapeutics" Nat Biomed Eng. 2020;4(11):1030-1043. PMID: 32747832.
Hörner , C., et al., A highly immunogenic and effective measles virus-based Th1-biased COVID-19 vaccine, Proceedings of the National Academy of Sciences Dec. 2020, 117 (51) 32657-32666; DOI: 10.1073/pnas.2014468117.
Hou, X., et al., Lipid nanoparticles for mRNA delivery. Nat Rev Mater (2021). https://doi.org/10.1038/s41578-021-00358-0.
International Search Report and Written Opinion for PCT/US2021/019103 issued Sep. 30, 2021.
Jain, T.K., et al., Iron Oxide Nanoparticles for Sustained Delivery of Anticancer Agents, Molecular Pharmaceutics, American Chemical Society, 2 (3), 194-205, 2005.
Kalnin, K.V., et al., Immunogenicity and efficacy of mRNA COVID-19 vaccine MRT5500 in preclinical animal models. npj Vaccines 6, 61 (2021). https://doi.org/10.1038/s41541-021-00324-5.
Kurup, D. et al., Inactivated rabies virus vectored SARS-CoV-2 vaccine prevents disease in a Syrian hamster model, PLOS Pathogens 17(3): e1009383. https://doi.org/10.1371/journal.ppat.1009383.
Li, Q. et al., "A Review of the Structure, Preparation, and Application of NLCs, PNPs and PLNs", Nanomaterials, vol. 7, No. 6, p. 1-25.
Limbach, P A et al. "Summary: the modified nucleosides of RNA." Nucleic acids research vol. 22,12 (1994): 2183-96. doi:10.1093/nar/22.12.2183.
Lopez Bernal, J, et al., Effectiveness of Covid-19 Vaccines against the B.1.617.2 (Delta) Variant. N Engl J Med. Aug. 12, 2021;385(7):585-594. doi: 10.1056/NEJMoa2108891. Epub Jul. 21, 2021. PMID: 34289274; PMCID: PMC8314739.
Machado, B.A.S., et al., The Importance of RNA-Based Vaccines in the Fight against COVID-19: An Overview. Vaccines (Basel). Nov. 17, 2021;9(11):1345. doi: 10.3390/vaccines9111345. PMID: 34835276; PMCID: PMC8623509.
McKay, P. F., et al., Self-amplifying RNA SARS-CoV-2 lipid nanoparticle vaccine candidate induces high neutralizing antibody titers in mice. Nat Commun. Jul. 9, 2020;11(1):3523. doi: 10.1038/s41467-020-17409-9. PMID: 32647131; PMCID: PMC7347890.
Mercado, N.B., et al., "Single-shot Ad26 vaccine protects against SARS-CoV-2 in rhesus macaques" Nature. Oct. 2020;586(7830):583-588. doi: 10.1038/s41586-020-2607-z. Epub Jul. 30, 2020. Erratum in: Nature. Feb. 2021;590(7844):E25. PMID: 32731257; PMCID: PMC7581548.
Meyer, B., et al., Characterising proteolysis during SARS-CoV-2 infection identifies viral cleavage sites and cellular targets with therapeutic potential. Nat Commun. Sep. 21, 2021;12(1):5553. doi: 10.1038/s41467-021-25796-w. PMID: 34548480; PMCID: PMC8455558.
Mohandas, S., et al., Immunogenicity and protective efficacy of BBV152, whole virion inactivated SARS-CoV-2 vaccine candidates in the Syrian hamster model. iScience. Feb. 19, 2021;24(2):102054. doi: 10.1016/j.isci.2021.102054. Epub Jan. 9, 2021. PMID: 33521604; PMCID: PMC7829205.
Planas, D., et al., Reduced sensitivity of SARS-CoV-2 variant Delta to antibody neutralization. Nature. Aug. 2021;596(7871):276-280. doi: 10.1038/s41586-021-03777-9. Epub Jul. 8, 2021. PMID: 34237773.
Rauch, S, et al., mRNA-based SARS-CoV-2 vaccine candidate CVnCoV induces high levels of virus-neutralising antibodies and mediates protection in rodents. NPJ Vaccines. Apr. 16, 2021;6(1):57. doi: 10.1038/s41541-021-00311-w. PMID: 33863911; PMCID: PMC8052455.
Sheikh, A, et al., SARS-CoV-2 Delta VOC in Scotland: demographics, risk of hospital admission, and vaccine effectiveness. Lancet. Jun. 26, 2021;397(10293):2461-2462. doi: 10.1016/S0140-6736(21)01358-1. Epub Jun. 14, 2021. PMID: 34139198; PMCID: PMC8201647.
Shen, X, et al., SARS-CoV-2 variant B.1.1.7 is susceptible to neutralizing antibodies elicited by ancestral spike vaccines. Cell Host Microbe. Apr. 14, 2021;29(4):529-539.e3. doi: 10.1016/j.chom.2021.03.002. Epub Mar. 5, 2021. PMID: 33705729; PMCID: PMC7934674.
Szurgot, I., et al., DNA-launched RNA replicon vaccines induce potent anti-SARS-CoV-2 immune responses in mice. 2021 Scientific Reports. 11. 10.1038/s41598-021-82498-5.
Van Der Lubbe, J. E. M., et al., Ad26.COV2.S protects Syrian hamsters against G614 spike variant SARS-CoV-2 and does not enhance respiratory disease. NPJ Vaccines. Mar. 19, 2021;6(1):39. doi: 10.1038/s41541-021-00301-y. PMID: 33741993; PMCID: PMC7979827.
Van Doremalen, N., et al. Immunogenicity of low dose prime-boost vaccination of mRNA vaccine CV07050101 in non-human primates. bioRxiv [Preprint]. Jul. 7, 2021:2021.07.07.451505. doi: 10.1101/2021.07.07.451505. Update in: Viruses. Aug. 19, 2021;13(8): PMID: 34268507; PMCID: PMC8282095.
Van Doremalen, N., et al., ChAdOx1 nCoV-19 vaccine prevents SARS-CoV-2 pneumonia in rhesus macaques. Nature. Oct. 2020;586(7830):578-582. doi: 10.1038/s41586-020-2608-y. Epub Jul. 30, 2020. Erratum in: Nature. Feb. 2021;590(7844):E24. PMID: 32731258; PMCID: PMC8436420.
V'Kovski, P, et al., "Coronavirus biology and replication: implications for SARS-CoV-2". Nature Reviews. (Mar. 2021). Microbiology. 19 (3): 155-170. doi:10.1038/s41579-020-00468-6. PMC 7592455. PMID 33116300.
Wang, P., et al., Antibody resistance of SARS-CoV-2 variants B.1.351 and B.1.1.7. Nature. May 2021;593(7857):130-135. doi: 10.1038/s41586-021-03398-2. Epub Mar. 8, 2021. PMID: 33684923.
Wang, Z., et al., Naturally enhanced neutralizing breadth against SARS-CoV-2 one year after infection. Nature. Jul. 2021;595(7867):426-431. doi: 10.1038/s41586-021-03696-9. Epub Jun. 14, 2021. PMID: 34126625; PMCID: PMC8277577.
Wu, C, et al. "Analysis of therapeutic targets for SARS-CoV-2 and discovery of potential drugs by computational methods," Acta Pharmaceutica Sinica (May 2020). B. 10 (5): 766-788. doi:10.1016/j.apsb.2020.02.008. PMC 7102550. PMID 32292689, the contents of which are hereby incorporated by reference in their entirety.
Yinda, C. K., et al., Prior aerosol infection with lineage A SARS-CoV-2 variant protects hamsters from disease, but not reinfection with B.1.351 SARS-CoV-2 variant. Emerg Microbes Infect. Dec. 2021;10(1):1284-1292. doi: 10.1080/22221751.2021.1943539. PMID: 34120579; PMCID: PMC8238069.
Yu, Jingyou et al. "DNA vaccine protection against SARS-CoV-2 in rhesus macaques." Science (New York, N.Y.) vol. 369,6505 (2020): 806-811. doi:10.1126/science.abc6284.
Zhang, Y., et al., A second functional furin site in the SARS-CoV-2 spike protein. Emerg Microbes Infect. Dec. 3, 2021:1-35. doi: 10.1080/22221751.2021.2014284. Epub ahead of print. PMID: 34856891.
Zhou, D., et al., Evidence of escape of SARS-CoV-2 variant B.1.351 from natural and vaccine-induced sera. Cell. Apr. 29, 2021;184(9):2348-2361.e6. doi: 10.1016/j.cell.2021.02.037. Epub Feb. 23, 2021. PMID: 33730597; PMCID: PMC7901269.

(56) References Cited

OTHER PUBLICATIONS

Zost, S.J., et al., Rapid isolation and profiling of a diverse panel of human monoclonal antibodies targeting the SARS-CoV-2 spike protein. Nat Med. 2020;26(9):1422-1427. PMID: 32651581.
Gerhardt, Alana, et al. "A thermostable, flexible RNA vaccine delivery platform for pandemic response." bioRxiv (2021): Feb. 2021.
International Search Report issued Jun. 13, 2024 in PCT/US2024/010326.
Pin, Elisa, et al. "Identification of a Novel Autoimmune Peptide Epitope of Prostein in Prostate Cancer." Journal of Proteome Research 16.1 (2017): 204-216.
Hubert, B. "Reverse Engineering the source code of the BioNTech/Pfizer SARS-CoV-2 vaccine." published Feb. 23, 2021, 15 pages and cover page, https://web.archive.org/web/20210223123219/https://berthub.com.eu/articles/posts/reverse-engineering-source-code-of-the-biontch-pfizer-vaccine/.
Vargas, Kevin M., and Young-Seok Shon. "Hybrid lipid-nanoparticle complexes for biomedical applications." Journal of Materials Chemistry B 7.5 (2019): 695-708.
Wang et al., Enterovirus D68 isolate DZH-ZJUC, complete genome, Pub. Med. Sequence submission on Sep. 17, 2019. Https://www.ncbi.nlm.nih.gov/nuccore/MK614087.1/ (printed Oct. 17, 2024).
Yates, M. in Microbiology of Waterborne Diseased, 2nd ed. In Enterovirus; Enterovirus—an overview, ScienceDirect Topics, 2014, 2 pages.
Ziegler, E., et al. "Foot-and-mouth disease virus Lb proteinase can stimulate rhinovirus and enterovirus IRES-driven translation and cleave several proteins of cellular and viral origin." Journal of Virology 69.6 (1995): 3465-3474.

* cited by examiner

VZV-FL-gE

| N-term | Glycoprotein E | TM |

FL-gI

| Glycoprotein I |

VZV-N term trunc gE

| Glycoprotein E | TM |

FL-gI-T2A-gE

| Glycoprotein I | T2A | N-term | Glycoprotein E | TM |

FL-gI-IRES-gE

| Glycoprotein I | IRES | N-term | Glycoprotein E | TM |

Secreted-gE

| Glycoprotein E |

RNA VACCINES AGAINST INFECTIOUS DISEASES

CROSS-REFERENCE

This application is a continuation of International Application No. PCT/US2022/013516, filed Jan. 24, 2022, which claims the benefit of priority to U.S. Provisional Patent Application No. 63/247,175, filed Sep. 22, 2021, and U.S. Provisional Patent Application No. 63/297,498, filed on Jan. 7, 2022, the contents of each of which are incorporated herein by reference in their entirety.

SEQUENCE LISTING

The instant application contains a Sequence Listing which has been submitted electronically in xml format and is hereby incorporated by reference in its entirety. Said xml copy, created on Jun. 6, 2024, is named 201953-714301-SL.xml and is 245,760 bytes in size.

BACKGROUND

Vaccinations can provide prophylactic protection against infectious diseases, including, but not limited to, viral, bacterial, and/or parasitic diseases. For example, influenza infections are the seventh leading cause of death in the United States with 200,000 hospitalizations and 40,000 deaths seen in the United States per year and cause about 3-5 million hospitalizations and about 300,000 to 500,000 deaths worldwide per year. Millions of people receive flu vaccines to protect them from seasonal flu each year. Vaccination can also rapidly prevent the spread of an emerging influenza pandemic. Given the ability for infectious disease agents to evolve resist vaccines, there is a need for enhanced efficiency for production of vaccines and the development of vaccines with reduced changes of being evolved around by the infectious disease agents.

BRIEF SUMMARY

The following aspects and embodiments thereof described and illustrated below are meant to be exemplary and illustrative, not limiting in scope.

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; at least one nucleic acid encoding an antigen sequence, wherein the antigen sequence comprises a sequence encoding for a viral antigen sequence, a bacterial antigen sequence, a fungal antigen sequence, or a parasitic antigen sequence, or functional variant of any of the foregoing, and wherein the viral antigen sequence is not a SARS-CoV-2 antigen sequence or functional variant thereof.

Further provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises an antigen sequence encoding for an influenza hemagglutinin protein stem region or a functional variant thereof.

Further provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises an antigen sequence encoding for a VZV protein or a functional variant thereof.

Further provided herein are compositions, wherein the compositions comprise: a lipid carrier, wherein the lipid carrier is a nanoemulsion comprising: about 30 mg/mL DOTAP chloride about 37.5 mg/mL squalene; about 37 mg/ml sorbitan monostearate; about 37 mg/ml polysorbate 80; about 10 mM sodium citrate; and about 0.2 mg Fe/ml oleic acid-coated iron oxide nanoparticles, wherein the oleic acid-coated iron oxide nanoparticle range in size from about 5 nanometers up to 25 nm, optionally, wherein the oleic acid-coated iron oxide nanoparticles are 12 nm in size; and at least one nucleic acid, wherein the at least one nucleic acid comprises a sequence at least 85% identical to SEQ ID NOS: 1-6, 38-47.

Further provided herein are compositions, wherein the compositions comprise: a lipid carrier, wherein the lipid carrier is a nanoemulsion comprising: DOTAP chloride present in an amount of about 0.75 mg; squalene present in an amount of about 0.94 mg; sorbitan monostearate present in an amount of about 0.93 mg; polysorbate 80 present in an amount of about 0.93 mg; citric acid monohydrate present in an amount of about 1.05 mg; and oleic acid-coated iron oxide nanoparticles present in an amount of about 0.005 mg; and at least one nucleic acid, wherein the at least one nucleic acid comprises a sequence at least SEQ ID NOS: 1-6, 38-47.

Further provided herein are compositions, wherein the compositions comprise (a) a lipid carrier, wherein the lipid carrier is a nanoemulsion comprising a hydrophobic core, one or more inorganic nanoparticles and one or more oils or lipids; (b) at least one nucleic acid sequence, wherein the nucleic acid sequence encodes a sequence capable of expressing an antigen, wherein the antigen is an infectious pathogen protein.

Further provided herein are dried compositions, wherein the dried compositions comprise: a lipid carrier, wherein the lipid carrier is a nanoemulsion comprising a hydrophobic core, one or more inorganic nanoparticles and one or more lipids; at least one nucleic acid sequence, wherein the nucleic acid sequence encodes a sequence capable of expressing an antigen, wherein the antigen is an infectious disease protein; and at least one cryoprotectant.

Further provided herein are vaccines comprising a composition provided herein.

Further provided herein are methods of generating an immune response in a subject, wherein the methods comprise: administering to said subject a composition provided herein. Provided herein are compositions and methods for immunoprotecting a subject comprising administering to a subject a composition provided herein.

Further provided herein are methods of reducing the severity of an infection, wherein the methods comprise: administering to a subject, prior to infection, a composition comprising: a lipid carrier, wherein the lipid carrier is a nanoemulsion comprising a hydrophobic core, one or more inorganic nanoparticles and one or more lipids; and at least one nucleic acid sequence, wherein the nucleic acid sequence encodes a sequence capable of expressing an antigen, wherein the antigen is derived from an infectious agent.

Further provided herein are kits, wherein the kits comprise a composition provided herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows an oil-in-water emulsion. FIG. 1B shows a nanostructured lipid carrier (NLC). FIG. 1C shows a nanoparticle having an inorganic nanoparticle in liquid oil.

FIG. 4A shows the first assay. FIG. 4B shows the second assay.

FIG. 5A shows the first assay. FIG. 5B shows the second assay.

FIG. 6A shows the first assay. FIG. 6B shows the second assay.

FIG. 7A shows a schematic of VZV repRNA vaccine constructs—full length glycoprotein E containing the transmembrane sequence of gE (VZV-FL-gE; black), FL-gI, gE with a truncation of the N-terminus, full length gI followed by either Thosea asigna virus 2A (T2A) ribosomal skipping peptide, or an internal ribosomal entry site (IRES) to control for co-expression of the downstream gE, and a repRNA encoding a secreted gE without the transmembrane sequence. FIG. 7B shows a Western blot and probed with anti-VZV-gE antibody. FIG. 7C shows sera antibody titers measured via ELISA against soluble VZV gE 14 days post vaccination.

Figure 1A:
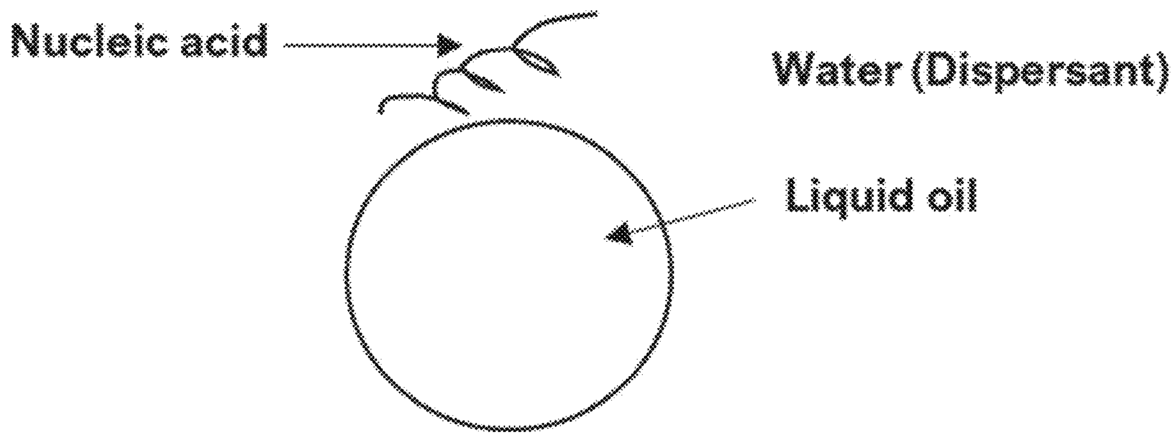
FIGS. 1A-1C show schematic representations of exemplary nanoparticle (NP) carriers.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

DETAILED DESCRIPTION

Provided herein are compositions, kits, methods, and uses thereof for inducing an immune response to an infectious microorganism. Briefly, further described herein are (1) nanoparticle carrier systems; (2) nucleic acids encoding for microbial antigens and RNA polymerases; (3) combination compositions; (4) thermally stable, dried, and lyophilized vaccines; (5) pharmaceutical compositions; (6) dosing; (7) administration; (8) therapeutic applications; and (9) kits.

Definitions

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document. All references disclosed herein, including patent references and non-patent references, are hereby incorporated by reference in their entirety as if each was incorporated individually. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein, "optional" or "optionally" means that the subsequently described circumstance may or may not occur, so that the description includes instances where the circumstance occurs and instances where it does not.

As used herein, the term “about” or “approximately” means a range of up to +20%, of a given value. Alternatively, particularly with respect to biological systems or processes, the term can mean within an order of magnitude, preferably within 2-fold, of a value. Where particular values are described in the application and claims, unless otherwise stated, the term “about” is implicit and in this context means within an acceptable error range for the particular value.

The term “effective amount” or “therapeutically effective amount” refers to an amount that is sufficient to achieve or at least partially achieve the desired effect.

Nanoparticle Carrier Systems

Provided herein are various compositions comprising a nanoparticle or a plurality of nanoparticles. Nanoparticles also referred to herein as carriers or abbreviated as NPs. Nanoparticles provided herein may be an organic, inorganic, or a combination of inorganic and organic materials that are less than about 1 micrometer (μm) in diameter. In some embodiments, nanoparticles provided herein are used as a delivery system for a bioactive agent provided herein.

Figure 1B:
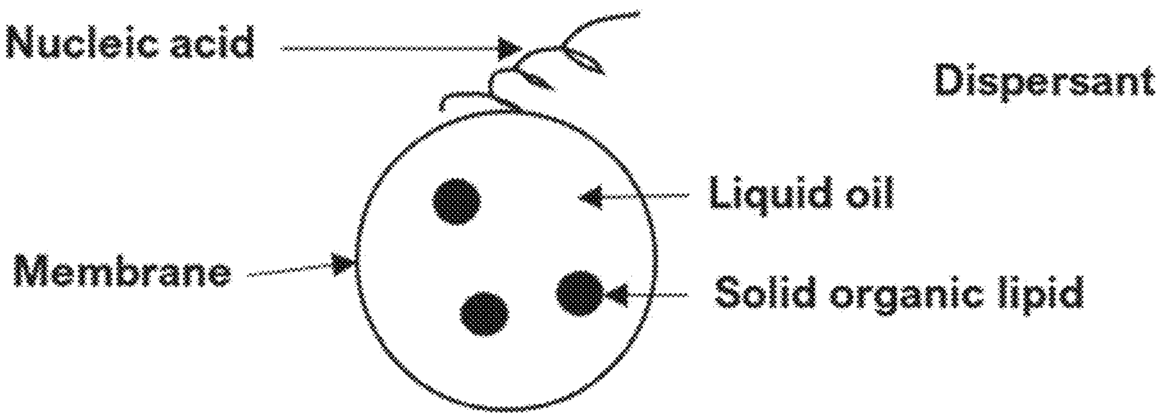
Figure 1C:
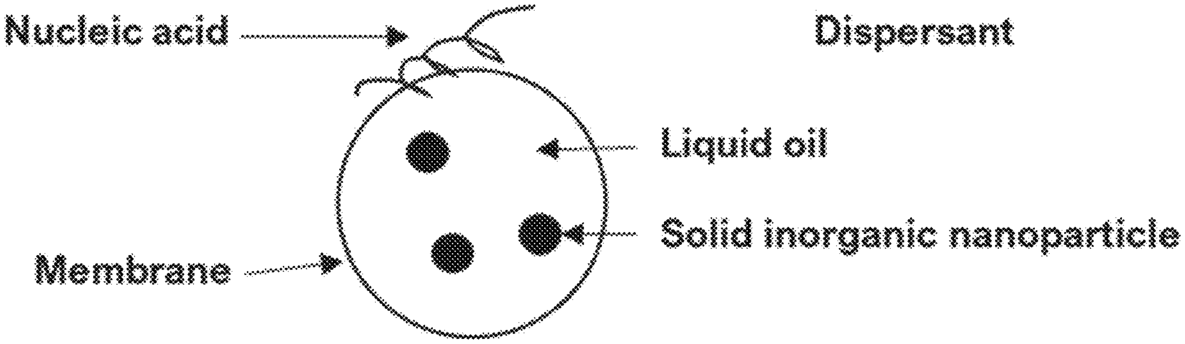

Various nanoparticles and formulations of nanoparticles (i.e., nanoemulsions) are employed. Exemplary nanoparticles are illustrated in FIGS. 1A-1C. Nanoparticles provided herein can include but are not limited to: oil in water emulsions, nanostructured lipid carriers (NLCs), cationic nanoemulsions (CNEs), vesicular phospholipid gels (VPG), polymeric nanoparticles, cationic lipid nanoparticles, liposomes, gold nanoparticles, solid lipid nanoparticles (LNPs or SLNs), mixed phase core NLCs, ionizable lipid carriers, magnetic carriers, polyethylene glycol (PEG)-functionalized carriers, cholesterol-functionalized carriers, polylactic acid (PLA)-functionalized carriers, and polylactic-co-glycolic acid (PLGA)-functionalized lipid carriers.

Oil in water emulsions, as illustrated in FIG. 1A (not to scale), are stable, immiscible fluids containing an oil droplet dispersed in water or aqueous phase. FIG. 1B (not to scale) illustrates a nanostructured lipid carrier (NLCs) which can comprise a blend of solid organic lipids (e.g., trimyristin) and liquid oil (e.g., squalene). In NLCs, the solid lipid is dispersed in the liquid oil. The entire nanodroplet is dispersed in the aqueous (water) phase. In some embodiments, the nanoparticle comprises inorganic nanoparticles, as illustrated in FIG. 1C (not to scale), as solid inorganic nanoparticles (e.g., iron oxide nanoparticles) dispersed in liquid oil. The entire nanodroplet is then dispersed as a colloid in the aqueous (water) phase. In some embodiments, the nanoparticles provided herein are dispersed in an aqueous solution. Non-limiting examples of aqueous solutions include water (e.g., sterilized, distilled, deionized, ultra-pure, RNAse-free, etc.), saline solutions (e.g., Kreb’s, Ascaris, Dent’s, Tet’s saline), or 1% (w/v) dimethyl sulfoxide (DMSO) in water.

In some embodiments, the nanoparticles provided herein comprise a hydrophilic surface. In some embodiments, the hydrophilic surface comprises a cationic lipid. In some embodiments, the hydrophilic surface comprises an ionizable lipid. In some embodiments, the nanoparticle comprises a membrane. In some embodiments, the membrane comprises a cationic lipid. In some embodiments, the nanoparticles provided herein comprise a cationic lipid. Exemplary cationic lipids for inclusion in the hydrophilic surface include, without limitation: 1,2-dioleoyloxy-3 (trimethylammonium)propane (DOTAP), 3β-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP), dipalmitoyl(C16:0)trimethyl ammonium propane (DPTAP), distearoyltrimethylammonium propane (DSTAP), N-[1-(2,3-dioleyloxy) propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3'"-(((methylazanediyl) bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; 0-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-TH-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 3β-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9'",9"",9'""-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4,1-diyl))bis(azanetriyl))tetrakis(ethane-2,1-diyl) (9Z,9'Z,9"Z,9'"Z,12Z,12'Z,12"Z,12'"Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Other examples for suitable classes of lipids include, but are not limited to, the phosphatidylcholines (PCs), phosphatidylethanolamines (PEs), phosphatidylglycerol (PGs); and PEGylated lipids including PEGylated version of any of the above lipids (e.g., DSPE-PEGs). In some embodiments, the nanoparticle provided herein comprises DOTAP.

In some embodiments, the nanoparticle provided herein comprises an oil. In some embodiments, the oil is in liquid phase. Non-limiting examples of oils that can be used include α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, solanesol, soy lecithin, soybean oil, sunflower oil, a triglyceride, or vitamin E. In some embodiments, the nanoparticle provided herein comprises a triglyceride. Exemplary triglycerides include but are not limited to: capric triglycerides, caprylic triglycerides, a caprylic and capric triglycerides, triglyceride esters, and myristic acid triglycerins.

In some embodiments, the nanoparticles provided herein comprise a liquid organic material and a solid inorganic material. In some embodiments, the nanoparticle provided herein comprises an inorganic particle. In some embodiments, the inorganic particle is a solid inorganic particle. In some embodiments, the nanoparticle provided herein comprises the inorganic particle within the hydrophobic core.

In some embodiments, the nanoparticle provided herein comprises a metal. In some embodiments, the nanoparticle provided herein comprises a metal within the hydrophobic core. The metal can be without limitation, a metal salt, a metal oxide, a metal hydroxide, or a metal phosphate. In some embodiments, the nanoparticle provided herein comprises aluminum oxide ($Al_2O_3$), aluminum oxyhydroxide, iron oxide ($Fe_3O_4$, $Fe_2O_3$, FeO, or combinations thereof), titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. The inorganic particles may be formed from one or more same or different metals (any metals including transition metal). In some embodiments, the inorganic particle is a transition metal oxide. In some embodiments, the transition metal is magnetite ($Fe_3O_4$), maghemite (y-$Fe_2O_3$), wüstite (FeO), or hematite (alpha ($\alpha$)-$Fe_2O_3$). In some embodiments, the metal is aluminum hydroxide or aluminum oxyhydroxide, and a phosphate-terminated lipid or a surfactant, such as oleic acid, oleylamine, SDS, TOPO or DSPA is used to coat the inorganic solid nanoparticle, before it is mixed with the liquid oil to form the hydrophobic core.

In some embodiments, the metal can comprise a paramagnetic, a superparamagnetic, a ferrimagnetic or a ferromagnetic compound. In some embodiments, the metal is a superparamagnetic iron oxide ($Fe_3O_4$).

In some embodiments, the nanoparticle provided herein comprises a cationic lipid, an oil, and an inorganic particle. In some embodiments, the nanoparticle provided herein comprises DOTAP; squalene and/or glyceryl trimyristate-dynasan; and iron oxide. In some embodiments, the nanoparticle provided herein further comprises a surfactant. Thus, in some embodiments, the nanoparticles provided herein comprise a cationic lipid, an oil, an inorganic particle, and a surfactant.

Surfactants are compounds that lower the surface tension between two liquids or between a liquid and a solid component of the nanoparticles provided herein. Surfactants can be hydrophobic, hydrophilic, or amphiphilic. In some embodiments, the nanoparticle provided herein comprises a hydrophobic surfactant. Exemplary hydrophobic surfactants that can be employed include but are not limited to: sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85). Suitable hydrophobic surfactants include those having a hydrophilic-lipophilic balance (HLB) value of 10 or less, for instance, 5 or less, from 1 to 5, or from 4 to 5. For instance, the hydrophobic surfactant can be a sorbitan ester having an HLB value from 1 to 5, or from 4 to 5. In some embodiments, the nanoparticle provided herein comprises a hydrophilic surfactant, also called an emulsifier.

In some embodiments, the nanoparticle provided herein comprises polysorbate. Polysorbates are oily liquids derived from ethoxylated sorbitan (a derivative of sorbitol) esterified with fatty acids. In some embodiments, the nanoparticle or lipid carrier provided herein comprises a hydrophilic surfactant. Exemplary hydrophilic surfactants that can be employed include but are not limited to: polysorbates such as Tween, Kolliphor, Scattics, Alkest, or Canarcel; polyoxyethylene sorbitan ester (polysorbate); polysorbate 80 (polyoxyethylene sorbitan monooleate, or Tween 80); polysorbate 60 (polyoxyethylene sorbitan monostearate, or Tween 60); polysorbate 40 (polyoxyethylene sorbitan monopalmitate, or Tween 40); and polysorbate 20 (polyoxyethylene sorbitan monolaurate, or Tween 20). In one embodiment, the hydrophilic surfactant is polysorbate 80.

Nanoparticles provided herein comprises a hydrophobic core surrounded by a lipid membrane (e.g., a cationic lipid such as DOTAP). In some embodiments, the hydrophobic core comprises: one or more inorganic particles; a phosphate-terminated lipid; and a surfactant.

Inorganic solid nanoparticles described herein may be surface modified before mixing with the liquid oil. For instance, if the surface of the inorganic solid nanoparticle is hydrophilic, the inorganic solid nanoparticle may be coated with hydrophobic molecules (or surfactants) to facilitate the miscibility of the inorganic solid nanoparticle with the liquid oil in the "oil" phase of the nanoemulsion particle. In some embodiments, the inorganic particle is coated with a capping ligand, the phosphate-terminated lipid, and/or the surfactant. In some embodiments the hydrophobic core comprises a phosphate-terminated lipid. Exemplary phosphate-terminated lipids that can be employed include but are not limited to: trioctylphosphine oxide (TOPO) or distearyl phosphatidic acid (DSPA). In some embodiments, the hydrophobic core comprises surfactant is a phosphorous-terminated surfactant, a carboxylate-terminated surfactant, a sulfate-terminated surfactant, or an amine-terminated surfactant. Typical carboxylate-terminated surfactants include oleic acid. Typical amine terminated surfactants include oleylamine. In some embodiments, the surfactant is distearyl phosphatidic acid (DSPA), oleic acid, oleylamine or sodium dodecyl sulfate (SDS). In some embodiments, the inorganic solid nanoparticle is a metal oxide such as an iron oxide, and a surfactant, such as oleic acid, oleylamine, SDS, DSPA, or TOPO, is used to coat the inorganic solid nanoparticle before it is mixed with the liquid oil to form the hydrophobic core.

In some embodiments, the hydrophobic core comprises: one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate.

In some embodiments, the hydrophobic core comprises: one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; a hydrophobic surfactant comprising sorbitan monostearate; and a hydrophilic surfactant comprising polysorbate 80.

In some embodiments, the hydrophobic core consists of: one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate. In some embodiments, the hydrophobic core consists of: one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; a hydrophobic surfactant comprising sorbitan monostearate; and a hydrophilic surfactant comprising polysorbate 80. In some embodiments, the nanoparticle provided herein can comprise from about 0.2% to about 40% w/v squalene, from about 0.001% to about 10% w/v iron oxide nanoparticles, from about 0.2% to about 10% w/v DOTAP, from about 0.25% to about 5% w/v sorbitan monostearate, and from about 0.5% to about 10% w/v polysorbate 80. In some embodiments the nanoparticle provided herein from about 2% to about 6% w/v squalene, from about 0.01% to about 1% w/v iron oxide nanoparticles, from about 0.2% to about 1% w/v DOTAP, from about 0.25% to about 1% w/v sorbitan monostearate, and from about 0.5%) to about 5% w/v polysorbate 80. In some embodiments, the nanoparticle provided herein can comprise from about 0.2% to about 40% w/v squalene, from about 0.001% to about 10% w/v aluminum hydroxide or aluminum oxyhydroxide nanoparticles, from about 0.2% to about 10% w/v DOTAP, from about 0.25% to about 5% w/v sorbitan monostearate, and from about 0.5% to about 10% w/v polysorbate 80. In some embodiments, the nanoparticle provided herein can comprise from about 2% to about 6% w/v squalene, from about 0.01% to about 1% w/v aluminum hydroxide or aluminum oxyhydroxide nanoparticles, from about 0.2% to about 1% w/v DOTAP, from about 0.25% to about 1% w/v sorbitan monostearate, and from about 0.5%) to about 5% w/v polysorbate 80.

In some embodiments, a composition described herein comprises at least one nanoparticle formulations as described in Table 1. In some embodiments, a composition described herein comprises any one of NP-1 to NP-30. In some embodiments, a composition described herein comprises any one of NP-1 to NP-31. In some embodiments, the nanoparticles provided herein are admixed with a nucleic acid provided herein. In some embodiments, nanoparticles provided herein are made by homogenization and ultrasonication techniques.

TABLE 1

Nanoparticle Formulations.

| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
|---|---|---|---|---|
| NP-1 [Fe-LC] (LC = lipid carrier) | 30 mg/ml 1,2-dioleoyl-3-trimethylammonium-propane (DOTAP) chloride | 37.5 mg/ml squalene | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$, Polysorbate 80 (TWEEN 80 ®) | 0.2 mg Fe/ml 12 nm oleic acid-coated iron oxide nanoparticles 10 mM sodium citrate dihydrate. |
| NP-2 [High Fe-LC] | 30 mg/ml 1,2-dioleoyl-3-trimethylammonium-propane (DOTAP) chloride | 37.5 mg/ml squalene | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$, Polysorbate 80 (TWEEN 80 ®) | 1 mg Fe/ml 15 nm oleic acid-coated iron oxide nanoparticles 10 mM sodium citrate dihydrate. |
| NP-3 [Fe-LC-Miglyol] | 30 mg/ml 1,2-dioleoyl-3-trimethylammonium-propane (DOTAP) chloride | 37.5 mg/ml Miglyol 812N (triglyceride ester of saturated coconut/palmkernel oil derived caprylic and capric fatty acids and plant derived glycerol) | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml | 0.2 mg Fe/ml 15 nm oleic acid-coated iron oxide nanoparticles 10 mM sodium citrate dihydrate. |

TABLE 1-continued

Nanoparticle Formulations.

| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
|---|---|---|---|---|
| | | | polyoxyethylene (20) sorbitan monooleate, $C_{64}H_{124}O_{26}$, Polysorbate 80 (TWEEN 80 ®) | |
| NP-4 [High Fe-LC-Miglyol] | 30 mg/ml 1,2-dioleoyl-3-trimethylammonium-propane (DOTAP) chloride | 37.5 mg/ml Miglyol 812N (triglyceride ester of saturated coconut/palmkernel oil derived caprylic and capric fatty acids and plant derived glycerol) | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$, Polysorbate 80 (TWEEN 80 ®) | 1 mg Fe/ml 15 nm oleic acid-coated iron oxide nanoparticles 10 mM sodium citrate dihydrate. |
| NP-5 [Alum-LC] | 30 mg/ml DOTAP chloride | 37.5 mg/ml squalene | 37 mg/ml sorbitan monostearate (SPAN ® 60) 37 mg/ml polysorbate 80 (TWEEN ® 80) | 1 mg/ml trioctylphosphine oxide (TOPO)-coated aluminum hydroxide (Alhydrogel ® 2%) particles 10 mM sodium citrate dihydrate. |
| NP-6 [Fe-LC-Solanesol] | 30 mg/ml DOTAP chloride | 37.5 mg/ml Solanesol (Cayman chemicals), | 37 mg/ml sorbitan monostearate (SPAN ® 60) 37 mg/ml polysorbate 80 (TWEEN ® 80) | 0.2 mg Fe/ml oleic acid-coated iron oxide nanoparticles 10 mM sodium citrate |
| NP-7 [NLC] | 30 mg/ml DOTAP chloride | 37.5 mg/ml squalene 2.4 mg/ml Dynasan 114 | 37 mg/ml sorbitan monostearate (SPAN ® 60) 37 mg/ml polysorbate 80 (TWEEN ® 80 | 10 mM sodium citrate |
| NP-8 [CNE] | 4 mg/ml DOTAP chloride | 43 mg/ml squalene | 5 mg/ml Span ® 85 5 mg/ml Tween ® 80 | 10 mM sodium citrate |
| NP-9 | 7.5 mg/ml 1,2-dioleoyl-3-trimethylammonium-propane (DOTAP) chloride | 9.4 mg/ml squalene ((6E,10E,14E,18E)-2,6,10,15,19,23-Hexamethyltetracosa-2,6,10,14,18,22-hexaene, $C_{30}H_{50}$) 0.63 mg/ml glyceryl trimyristate-dynasan (DYNASAN 114 ®) | 9.3 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 9.3 mg/ml polyoxyethylene (20) sorbitan monooleate, $C_{64}H_{124}O_{26}$, Polysorbate 80 (TWEEN 80 ®) | 0.05 mg/ml 15 nanometer superparamagnetic iron oxide ($Fe_3O_4$) 10 mM sodium citrate dihydrate |
| NP-10 | 0.4% DOTAP | 0.25% glyceryl trimyristate-dynasan (DYNASAN 114 ®) 4.75% Squalene | 0.5% sorbitan monostearate (SPAN ® 60) 0.5% polysorbate 80 (TWEEN 80 ®) | |

TABLE 1-continued

| Nanoparticle Formulations. | | | | |
|---|---|---|---|---|
| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
| NP-11 | 3.0% DOTAP | 0.25% glyceryl trimyristate-dynasan (DYNASAN 114 ®) 3.75% Squalene | 3.7% sorbitan monostearate (SPAN ® 60) 3.7% polysorbate 80 (TWEEN 80 ®) | |
| NP-12 | 0.4% DOTAP | 4.3% Squalene | 0.5% sorbitan trioleate (SPAN ® 85) 0.5% polysorbate 80 (TWEEN ® 80) | |
| NP-13 | 0.4% DOTAP | 0.25% glyceryl trimyristate-dynasan (DYNASAN 114 ®) 4.08% squalene | 2.0% polysorbate 80 (TWEEN ® 80) | |
| NP-14 | 0.4% DOTAP | 0.25% glyceryl trimyristate-dynasan (DYNASAN 114 ®) 4.08% squalene | 0.5% sorbitan trioleate (SPAN ® 85) 2.0% polysorbate 80 (TWEEN ® 80) | |
| NP-15 | 0.4% DOTAP | 0.25% glyceryl trimyristate-dynasan (DYNASAN 114 ®) 4.08% squalene | 0.25% sorbitan trioleate (SPAN ® 85) 2.0% polysorbate 80 (TWEEN ® 80) | |
| NP-16 | 0.4% DOTAP | 5% squalene | 0.5% sorbitan trioleate (SPAN ® 85) 2.0% polysorbate 80 (TWEEN ® 80) | |
| NP-17 | 0.4% DOTAP | 5% squalene | 0.5% sorbitan monostearate (SPAN ® 60) 2% polysorbate 80 (TWEEN ® 80) | |
| NP-18 | 0.4% DOTAP | 0.25% glyceryl trimyristate-dynasan (DYNASAN 114 ®) 4.08% squalene | 2% sorbitan trioleate (SPAN ® 85) 2% polysorbate 80 (TWEEN ® 80) | |
| NP-19 | 0.4% DOTAP | 0.25% glyceryl trimyristate-dynasan (DYNASAN 114 ®) 4.75% Squalene | 0.5% sorbitan monostearate (SPAN ® 60) 0.5% polysorbate 80 (TWEEN 80 ®) | 1% aluminum hydroxide |
| NP-20 | 3.0% DOTAP | 0.25% glyceryl trimyristate-dynasan (DYNASAN 114 ®) 3.75% Squalene | 3.7% sorbitan monostearate (SPAN ® 60) 3.7% polysorbate 80 (TWEEN ® 80) | 1% aluminum hydroxide |
| NP-21 | 0.4% DOTAP | 4.3% Squalene | 0.5% sorbitan trioleate (SPAN ® 85) 0.5% polysorbate 80 (TWEEN ® 80 | 1% aluminum hydroxide |
| NP-22 | 0.4% DOTAP | 0.25% glyceryl trimyristate-dynasan (DYNASAN 114 ®) 4.08% squalene | 2.0% polysorbate 80 (TWEEN ® 80) | 1% aluminum hydroxide |
| NP-23 | 0.4% DOTAP | 0.25% glyceryl trimyristate-dynasan (DYNASAN 114 ®) 4.08% squalene | 0.5% sorbitan trioleate (SPAN ® 85) 2.0% polysorbate 80 (TWEEN ® 80 | 1% aluminum hydroxide |
| NP-24 | 0.4% DOTAP | 0.25% glyceryl trimyristate-dynasan (DYNASAN 114 ®) 4.08% squalene | 0.25% sorbitan trioleate (SPAN ® 85) 2.0% polysorbate 80 (TWEEN ® 80 | 1% aluminum hydroxide |

TABLE 1-continued

Nanoparticle Formulations.

| Name | Cationic Lipid(s) %(w/v) or mg/ml | Oil(s) %(w/v) or mg/ml | Surfactant(s) %(w/v) or mg/ml | Additional Ingredients %(w/v), mg/ml, or mM |
|---|---|---|---|---|
| NP-25 | 0.4% DOTAP | 5% squalene | 0.5% sorbitan trioleate (SPAN ® 85)<br>2.0% polysorbate 80 (TWEEN ® 80 | 1% aluminum hydroxide |
| NP-26 | 0.4% DOTAP | 5% squalene | 0.5% sorbitan monostearate (SPAN ® 60)<br>2% polysorbate 80 (TWEEN ® 80) | 1% aluminum hydroxide |
| NP-27 | 0.4% DOTAP | 0.25% glyceryl trimyristate-dynasan (DYNASAN 114 ®)<br>4.08% squalene | 2% sorbitan trioleate (SPAN ® 85)<br>2% polysorbate 80 (TWEEN ® 80) | 1% aluminum hydroxide |
| NP-28 | 0.5-5.0 mg/ml DOTAP | 0.2-10% (v/v) squalene | 0.01-2.5% (v/v) polysorbate 80 (TWEEN ® 80) | |
| NP-29 | 0.4% (w/w) DOTAP | 4.3% (w/w) squalene | 0.5% (w/w) sorbitan trioleate (SPAN ® 85)<br>0.5% (w/w) polysorbate 80 (TWEEN ® 80) | |
| NP-30 [LC without inorganic core] | 30 mg/ml DOTAP chloride | 37.5 mg/ml squalene | 37 mg/ml sorbitan monostearate (SPAN ® 60)<br>37 mg/ml polysorbate 80 (TWEEN ® 80) | 10 mM sodium citrate |
| NP-31 | 30 mg/ml DOTAP chloride | 37.5 mg/ml squalene | 37 mg/ml sorbitan monostearate (SPAN ® 60)<br>37 mg/ml polysorbate 80 (TWEEN ® 80) | 0.4 mg Fe/ml 5 nm oleic acid-coated iron oxide nanoparticles<br>10 mM sodium citrate dihydrate. |

In some embodiments, nanoparticles provided herein comprise: sorbitan monostearate (e.g., SPAN-60), polysorbate 80 (e.g., TWEEN-80), DOTAP, squalene, and no solid particles. In some embodiments, nanoparticles provided herein comprise: sorbitan monostearate (e.g., SPAN-60), polysorbate 80 (e.g., TWEEN-80), DOTAP, squalene, and iron oxide particles. In some embodiments, nanoparticles provided herein comprise an immune stimulant. In some embodiments, the immune stimulant is squalene. In some embodiments, the immune stimulant is a medium chain triglyceride. In some embodiments, the immune stimulant is Miglyol 810 or Miglyol 812. In some embodiments, the immune stimulant can decrease the total amount of protein produced, but can increase the immune response to a composition provided herein (e.g., when delivered as a vaccine). In some embodiments, the immune stimulant can increase the total amount of protein produced, but can decrease the immune response to a composition provided herein.

Nanoparticles provided herein can be of various average diameters in size. In some embodiments, nanoparticles provided herein have an average diameter (z-average hydrodynamic diameter, measured by dynamic light scattering) ranging from about 20 nm to about 200 nm. In some embodiments, the z-average diameter of the nanoparticle ranges from about 20 nm to about 150 nm, from about 20 nm to about 100 nm, from about 20 nm to about 80 nm, from about 20 nm to about 60 nm. In some embodiments, the z-average diameter of the nanoparticle) ranges from about 40 nm to about 200 nm, from about 40 nm to about 150 nm, from about 40 nm to about 100 nm, from about 40 nm to about 90 nm, from about 40 nm to about 80 nm, or from about 40 nm to about 60 nm. In one embodiment, the z-average diameter of the nanoparticle is from about 40 nm to about 80 nm. In some embodiments, the z-average diameter of the nanoparticle is from about 40 nm to about 60 nm. In some embodiments, the nanoparticle is up to 100 nm in diameter. In some embodiments, the nanoparticle is 50 to 70 nm in diameter. In some embodiments, the nanoparticle is 40 to 80 nm in diameter. In some embodiments, the inorganic particle (e.g., iron oxide) within the hydrophobic core of the nanoparticle can be an average diameter (number weighted average diameter) ranging from about 3 nm to about 50 nm. For instance, the inorganic particle can have an average diameter of about 5 nm, about 10 nm, about 15 nm, about 20 nm, about 25 nm, about 30 nm, about 35 nm, about 40 nm, about 45 nm, or about 50 nm.

Nanoparticles provided herein may be characterized by the polydispersity index (PDI), which is an indication of their quality with respect to size distribution. In some embodiments, average polydispersity index (PDI) of the nanoparticles provided herein ranges from about 0.1 to about 0.5. In some embodiments, the average PDI of the nanoparticles can range from about 0.2 to about 0.5, from about 0.1 to about 0.4, from about 0.2 to about 0.4, from about 0.2 to about 0.3, or from about 0.1 to about 0.3.

In some embodiments, the nanoparticles provided herein comprise an oil-to-surfactant molar ratio ranging from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, the nanoparticles provided herein comprise a hydrophilic surfactant-to-lipid ratio ranging from about 0.1:1 to about 2:1, from about 0.2:1 to about 1.5:1, from about 0.3:1 to about 1:1, from about 0.5:1 to about 1:1, or from about 0.6:1 to about 1:1. In some embodiments, the nanoparticles provided herein comprise a hydrophobic surfactant-to-lipid ratio ranging from about 0.1:1 to about 5:1, from about 0.2:1 to about 3:1, from about 0.3:1 to about 2:1, from about 0.5:1 to about 2:1, or from about 1:1 to about 2:1. In some embodiments, the nanoparticles provided herein comprise from about 0.2% to about 40% w/v liquid oil, from about 0.001% to about 10% w/v inorganic solid nanoparticle, from about 0.2% to about 10% w/v lipid, from about 0.25% to about 5% w/v hydrophobic surfactant, and from about 0.5% to about 10% w/v hydrophilic surfactant. In some embodiments, the lipid comprises a cationic lipid, and the oil comprises squalene, and/or the hydrophobic surfactant comprises sorbitan ester. In some embodiments, nanoparticles provided herein comprise a ratio of the esters that yields a hydrophilic-lipophilic balance between 8 and 11. In some embodiments, nucleic acids provided herein are incorporated, associated with, or complexed a lipid carrier provided herein to form a lipid carrier-nucleic acid complex. In some embodiments, the lipid carrier-nucleic acid complex is formed via non-covalent interactions or via reversible covalent interactions.

Nucleic Acids for Infectious Disease Antigen Expression

Provided herein is are compositions comprising a nanoparticle and a nucleic acid. In some embodiments, the nucleic acid is in complex with the nanoparticle. In some embodiments, the nucleic acid is in complex with the membrane of the nanoparticle. In some embodiments, the nucleic acid is in complex with the hydrophilic surface of the nanoparticle. In some embodiments, the nucleic acid is within the nanoparticle. In some embodiments, the nucleic acid is within the hydrophobic core.

In some embodiments, the nucleic acid is deoxyribonucleic acid (DNA) or ribonucleic acid (RNA). The nucleic acid may be linear or include a secondary structure (e.g., a hairpin). In some embodiments, the nucleic acid is a polynucleotide comprising modified nucleotides or bases, and/or their analogs. A polynucleotide may comprise modified nucleotides, such as methylated nucleotides and their analogs. If present, modification to the nucleotide structure may be imparted before or after assembly of compositions provided herein. Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); ml1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); hoSU (5-hydroxyuridine); moSU (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-0-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Any one or any combination of these modified nucleobases may be included in the self-replicating RNA of the invention. Many of these modified nucleobases and their corresponding ribonucleosides are available from commercial suppliers. If desired, the nucleic acid can contain phosphoramidate, phosphorothioate, and/or methylphosphonate linkages. The RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap structure can provide stability and translational efficacy to the RNA molecule. The 5' cap of the RNA molecule may be further modified by a 2'-O-Methyltransferase which results in the generation of a cap 1 structure (m7Gppp [m2'-O] N), which may further increase translation efficacy. A cap 1 structure may also increase in vivo potency.

In some embodiments, compositions provided herein comprise one or more nucleic acids. In some embodiments, compositions provided herein comprise two or more nucleic acids. In some embodiments, compositions provided herein comprise at least one DNA. In some embodiments, compositions provided herein comprise at least one RNA. In some embodiments, compositions provided herein comprise at least one DNA and at least one RNA. In some embodiments, nucleic acids provided herein are present in an amount of above 5 ng to about 1 mg. In some embodiments, nucleic acids provided herein are present in an amount of up to about 25, 50, 75, 100, 150, 175 ng. In some embodiments, nucleic acids provided herein are present in an amount of up to about 1 mg. In some embodiments, nucleic acids provided herein are present in an amount of about 0.05 μg, 0.1 μg, 0.2 μg, 0.5, μg 1 μg, 5 μg, 10 μg, 12.5 μg, 15 μg, 25 μg, 40 μg, 50 μg, 100 μg, 200 μg, 300 μg, 400 μg, 500 μg, 600 μg, 700 μg, 800 μg, 900 μg, 1 mg. In some embodiments, nucleic acids provided herein are present in an amount of 0.05 μg, 0.1 μg, 0.2 μg, 0.5, μg 1 μg, 5 μg, 10 μg, 12.5 μg, 15 μg, 25 μg, 40 μg, 50 μg, 100 μg, 200 μg, 300 μg, 400 μg, 500 μg, 600 μg, 700 μg, 800 μg, 900 μg, 1 mg. In some embodiments, nucleic acids provided herein are present in an amount of about 5 μg, about 10 μg, about 25 μg, about 50 μg, or about 100 μg. In some embodiments, nucleic acids provided herein are present in an amount of up to about 5 μg, about 10 μg, about 25 μg, about 50 μg, or 100 μg. In some embodiments, the nucleic acid is at least about 200, 250, 500, 750, 1000, 2000, 3000, 4000, 5000, 6000, 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is up to about 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is about 7500, 10,000, 15,000, or 20,000 nucleotides in length.

Infectious Disease Antigens

Provided herein are infectious disease antigens for recognition by hosts. In some embodiments, the infectious disease antigen is a nucleic acid encoding for an antigen protein sequence. In some embodiments, compositions provided herein comprise at least one nucleic acid sequence comprising a sequence which encodes an antigen derived from a microorganism. In some embodiments, the microorganism is an infectious microorganism. Non-limiting examples of infectious microorganisms and infectious agents include but are not limited to: viruses such as adenoviruses, herpes simplex type 1 virus, herpes simplex type 2 virus, encephalitis virus, papillomavirus, varicella-zoster virus (VZV), Epstein-Barr virus (EBV), human cytomegalovirus (CMV), Chikungunya virus, human herpes virus type 8, human papillomavirus (HPV), BK virus, JC virus, smallpox, polio virus, hepatitis B virus, human bocavirus, parvovirus B19, human astrovirus, Norwalk virus, coxsackievirus, hepatitis A virus, poliovirus, rhinovirus, Severe acute respiratory syndrome (SARS) virus, yellow fever virus, Dengue virus, West Nile virus, rubella virus, hepatitis E virus, human immunodeficiency virus (HIV), influenza virus (influenza A or influenza B), Guanarito virus, Junin virus, Lassa virus, Machupo virus, Sabii virus, Crimean-Congo hemorrhagic fever virus, Ebola virus, Marburg virus, measles virus, mumps virus, Parainfluenza virus, respiratory syncytial virus (RSV), human metapneumovirus, Hendra virus, Nipah virus, rabies virus, hepatitis D, rotavirus, orbivirus, coltivirus, banna virus, zika virus, hanta virus, West Nile virus, Middle East Respiratory Syndrome (MERS) coronavirus, Japanese encephalitis virus, and Eastern equine encephalitis; bacteria such as *Acetobacter, Acinetobacter, Actinomyces, Agrobacterium, Anaplasma, Azorhizobia, Bacillus, Bacteroides, Bartonella, Bordetella, Borrelia, Brucella, Burkkolderia, Calymmatobacterium, Campylobacter, Chlamydia, Chlamydophila, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Moraxella, Mycobacterium, Mycoplasma, Neisseria, Pasteurella, Peptostreptococcus, Porphyromonas, Prevotella, Pseudomonas, Rhizobium, Rickettsia, Rochalimaea, Rothia, Salmonella, Shigella, Staphylococcus, Stenotrophomonas, Streptococcus, Streptococcus pneumoniae, Treponema, Vibrio, Walbachia*, and *Yersinia*; fungi such as *Aspergillus, Saccharomyces, Cryptococcus, Coccidioides, Neurospora, Histoplasma, Blastomyces*; parasites such as *Babesia* sp., *Cryptosporidium* sp., *Plasmodium* sp., *Toxoplasma* sp. *Plasmodium* sp., *Plasmodium falciparum, Plasmodium vivax, Cryptosporidium parvum, Cryptosporidium hominis, Eimeria* sp., *Eimeria tenella, Theileria* sp., *Theileria parva, Toxoplasma* sp. *Toxoplasma gondii, Trypanosoma brucei* subspecies, *Trypanosoma cruzi, Leishmania* sp., and *Leishmania major*; and yeast such as *Candida*.

In some embodiments, the antigen is derived from a microorganism that causes a severe respiratory disease in mammalian populations. In some embodiments, the antigen is a surface protein or a transmembrane protein expressed on the surface of a microbial organism.

In some embodiments, the viral antigen is an influenza virus antigen. In some embodiments, the influenza virus antigen is a hemagglutinin antigen. Hemagglutinin (abbreviated HA) is a protein present on the surface of an influenza virus. On the viral surface, the hemagglutinin protein is present in homotrimers, each monomer of which is comprised of two subunits, HA1 and HA2, linked by a disulfide bond. Structurally, hemagglutinin proteins are comprised of several domains: a globular head domain, a stalk domain (also referred to as a stem or the stem protein), a transmembrane domain, and a cytoplasmic domain. Generally, during infection of a host cell (e.g., a eukaryotic cell such as a human cell) with an influenza virus, the hemagglutinin protein recognizes and binds to sialic acid of a receptor on the surface of a host cell facilitating attachment of the virus to the host cell. Following endocytosis of the virus and acidification of the endosome, the hemagglutinin protein undergoes a pH-dependent conformational change that allows for the hemagglutinin protein to facilitate fusion of the viral envelope with the endosome membrane of host cell and entry of the viral nucleic acid into the host cell. In general, influenza viruses are classified based on the amino acid sequence of the viral hemagglutinin protein and/or the amino acid sequence of the viral neuraminidase (NA). In some embodiments, nucleic acids provided herein comprise an antigen sequence encoding for an influenza hernagglutinin protein. In some embodiments, nucleic acids provided herein comprise an antigen sequence encoding for an influenza hemagglutinin protein stem region or a functional variant thereof. In some embodiments, the hemagglutinin antigen is of the subtype H1, H2, H3, H4, H5, H6, H7, H8, H9, H10, H11, H12, H13, H14, H15, H16, H17, or H18. The differences in amino acid sequences between hemagglutinin proteins of different subtypes are largely found within the sequence of the head domain of the protein. The amino acid sequence of the stem region is considered to be more conserved between hemagglutinin subtypes compared to sequence of the head domain. In some embodiments, the hemagglutinin antigen does not comprise a head domain (HA1). In some embodiments, the hemagglutinin antigen comprises a portion of the head domain (HA1). In some embodiments, the hemagglutinin antigen does not comprise a cytoplasmic domain. In some embodiments, the hemagglutinin antigen comprises a portion of the cytoplasmic domain. In some embodiments, the truncated hemagglutinin antigen. In some embodiments, the truncated hemagglutinin protein comprises a portion of the transmembrane domain. In some embodiments, the truncated hemagglutinin protein comprises a stem region or a functional fragment thereof.

In some embodiments, the viral antigen is a Varicella-Zoster Virus (VZV) antigen. In some embodiments, the VZV antigen is a glycoprotein E (gE) antigen, a glycoprotein B (gB) antigen, a glycoprotein H (gH) antigen, a glycoprotein L (gL) antigen, a glycoprotein N (gN) antigen, a glycoprotein I (gI) antigen. In some embodiments, the viral antigen is a coronavirus antigen. In some embodiments, the coronavirus is a SARS-CoV-1 coronavirus or a Middle East Respiratory Syndrome (MERS) coronavirus antigen. In some embodiments, the coronavirus antigen is a spike (S) protein antigen. In some embodiments, the viral antigen is an Epstein-Barr virus (EBV) antigen. In some embodiments, the viral antigen is a herpes simplex virus (HSV) antigen. In some embodiments, the herpes simplex virus antigen is HSV1 or HSV2 antigen. In some embodiments, the HSV antigen is a glycoprotein B, glycoprotein E, glycoprotein L, glycoprotein M, or a glycoprotein I. In some embodiments, the viral antigen is a rabies virus antigen. In some embodiments, the rabies virus antigen is a nucleoprotein (N), a phosphoprotein (P), a matrix protein (M), a glycoprotein (G) or a polymerase (L) antigen. In some embodiments, the viral antigen is a cytomegalovirus (CMV, human betaherpesvirus 5) antigen. In some embodiments, the CMV antigen is a glycoprotein B. Non-limiting examples of viral antigens for inclusion include: Zika virus envelope protein (ZIKV E), Zika virus precursor membrane and envelope proteins (prM-ENV), SARS-CoV2 spike (S) protein and envelope (E) proteins, HIV p24 antigen and Nef protein, influenza virus hemagglutinin (HA) antigen (H2, H3, H5, H6, H7, H8 and H9), influenza virus neuraminidase, rubella E1 and E2 antigens, rotavirus VP7sc antigen, RSV M2 protein, cytomegalovirus envelope glycoprotein B, the S, M, and L proteins of hepatitis B virus, rabies glycoprotein, rabies nucleoprotein, Crimean-Congo hemorrhagic fever glycoprotein Gc and or Gn, Nipah henipavirus glycoprotein, Hendra virus glycoprotein, human papillomavirus E6 protein, human papillomavirus E7 protein, human papillomavirus L1 protein, or human papillomavirus L2 protein.

In some embodiments, the antigen is a viral antigen. In some embodiments, the antigen is a respiratory syncytial virus (RSV) antigen. In some embodiments, the antigen is an RSV glycoprotein (G), RSV-G. In some embodiments, the antigen is an RSV fusion (F) glycoprotein RSV-F. In some embodiments, the antigen is a zika virus antigen. In some embodiments, the zika virus antigen is an envelope (E) protein.

In some embodiments, the antigen is a bacterial antigen. In some embodiments, the bacterial antigen is a *Mycobacterium tuberculosis* antigen. In some embodiments, the *Mycobacterium tuberculosis* antigen is H37Rv, malate synthase, or MPT51. In some embodiments, the bacterial antigen is a *Chlamydia trachomatis* antigen. In some embodiments, the *Chlamydia trachomatis* antigen is a major outer membrane protein antigen. In some embodiments, the bacterial antigen is a *Staphylococcus aureus* antigen.

In some embodiments, nucleic acids provided herein encodes for an antigen listed in Table 2 or a fragment thereof. In some embodiments, the nucleic acid comprises at least 80%, 85%, 90%, 95%, 96%, 97%, 98%, or 99% sequence identity to a sequence which specifically binds an antigen listed in Table 2. In some embodiments, the nucleic acid provided herein comprises at least 80%, 85%, 90%, 95%, 96%, 97%, 98%, or 99% sequence similarity to an RNA sequence listed in Table 2. Percent (%) sequence identity for a given sequence relative to a reference sequence is defined as the percentage of identical residues identified after aligning the two sequences and introducing gaps if necessary, to achieve the maximum percent sequence identity. Percent identity can be calculated using alignment methods known in the art, for instance alignment of the sequences can be conducted using publicly available software such as BLAST, Align, ClustalW2. Those skilled in the art can determine the appropriate parameters for alignment, but the default parameters for BLAST are specifically contemplated. Exemplary nucleic acid sequences encoding for exemplary viral and bacterial antigens are listed in Table 2.

TABLE 2

Viral and Bacterial Antigens

| Infectious Microorganism | Antigen Protein | Nucleic Acid SEQ ID NO: | Amino Acid SEQ ID NOS: |
|---|---|---|---|
| Respiratory syncytial virus (RSV) (also referred to as Human orthopneumovirus) | RSV glycoprotein (RSV-G)<br>RSV fusion protein (RSV-F) | SEQ ID NO: 1<br>SEQ ID NO: 2 | SEQ ID NO: 7<br>SEQ ID NO: 8 (partial)<br>SEQ ID NO: 9 (full length) |

TABLE 2-continued

| Viral and Bacterial Antigens | | | |
|---|---|---|---|
| Infectious Microorganism | Antigen Protein | Nucleic Acid SEQ ID NO: | Amino Acid SEQ ID NOS: |
| Influenza virus | Haemagglutinin (HA) | SEQ ID NO: 3 | SEQ ID NO: 10 |
| Influenza A virus H3N2 (New York) variant | Influenza A Haemagglutinin (HA) | | SEQ ID NO: 11 |
| Influenza B Haemagglutinin (HA) Lee 1940 Variant | Influenza B virus HA | | SEQ ID NO: 12 |
| Varicella-Zoster Virus (VZV) (also referred to as Human alphaherpesvirus 3) | gE | SEQ ID NO: 4 | SEQ ID NO: 13 |
| | gB | | SEQ ID NO: 14 |
| | gH | | SEQ ID NO: 15 |
| | gL | | SEQ ID NO: 16 |
| | gN | | SEQ ID NO: 17 |
| | gI | SEQ ID NO: 5 | SEQ ID NO: 18 |
| severe acute respiratory syndrome coronavirus 1 (SARS-CoV-1) | spike protein | | SEQ ID NO: 19 |
| Epstein-Barr virus (EBV) (also referred to as human gammaherpesvirus 4) | envelope glycoprotein B | | SEQ ID NO: 20 |
| Human papilloma virus (HPV) | E6 oncoprotein | | SEQ ID NO: 21 |
| | E7 protein | | SEQ ID NO: 22 |
| Rabies virus | nucleoprotein N | | SEQ ID NO: 23 |
| | L protein | | SEQ ID NO: 24 |
| | transmembrane glycoprotein G | | SEQ ID NO: 25 |
| | phosphoprotein M1 | | SEQ ID NO: 26 |
| | M2 protein | | SEQ ID NO: 27 |
| Herpes simplex virus 1 (HSV1, also referred to as Human alphaherpesvirus 1) | envelope glycoprotein B | | SEQ ID NO: 28 |
| Herpes simplex virus 2 (HSV2, also referred to as Human alphaherpesvirus 2) | envelope glycoprotein G | | SEQ ID NO: 29 |
| *Mycobacterium tuberculosis* | Malate synthase | | SEQ ID NO: 30 |
| | MPT51 (H37Rv) | | SEQ ID NO: 31 |
| Zika virus | Envelope (E) protein | SEQ ID NO: 6 | SEQ ID NO: 32 |
| *Chlamydia trachomatis* | major outer membrane protein | | SEQ ID NO: 33 |

In some embodiments, compositions provided herein comprise a nucleic acid sequence comprising any one of SEQ ID NOS: 1-6. In some embodiments, compositions provided herein comprise a nucleic acid sequence encoding for the amino acid sequence of any one of SEQ ID NOS: 7-33.

In some embodiments, the antigen is a parasite antigen. In some embodiments the parasite antigen is a *Giardia lamblia* antigen, a Leishmaniasis antigen, a *Plasmodium falciparum* antigen, a *Toxoplasma gondii* antigen, a *Trichomonas vaginalis* antigen, a *Trypanosoma brucei* antigen, a *Trypanosoma cruzi* antigen, a *Schistosoma* antigen, a *Toxocara* antigen, a *Trichinella* antigen, or a *Babesia* antigen.

In some embodiments, the antigen is a fungal antigen. In some embodiments, the fungal antigen is a *Cryptococcus* antigen, an *Aspergillus* antigen, a *Coccidioides immitis* antigen, a *Coccidioides posadasii* antigen, a *Histoplasma capsulatum* antigen, a *Blastomyces dermatitidis* antigen, a *Pneumocystis jirovecii* antigen, a *Trichophyton* antigen, a *Microsporum* antigen, or a *Epidermophyton* antigen. In some embodiments, the antigen is a yeast antigen. In some embodiments, the yeast antigen is a *Candida* antigen.

Self-Replicating Nucleic Acids

Provided herein are compositions comprising a self-replicating nucleic acid. The antigens provided herein or fragment thereof can be encoded as part of a self-replicating nucleic acid construct. In some embodiments, the self-replicating nucleic acid molecule comprises at least one or more genes selected from the group consisting of viral replicases, viral proteases, viral helicases and other non-structural viral proteins, and also comprises 5'- and 3'-end cis-active replication sequences, and an antigenic sequence encoding an antigen protein. A subgenomic promoter that directs expression of the heterologous sequence(s) can be included in the self-replicating nucleotide sequence. If desired, a heterologous sequence may be fused in frame to other coding regions in the self-replicating RNA and/or may be under the control of an internal ribosome entry site (IRES).

In some embodiments, the self-replicating nucleotide sequence is a self-replicating RNA molecule. Self-replicating RNA molecules are designed so that the self-replicating RNA molecule cannot induce production of infectious viral particles. This can be achieved, for example, by omitting one or more viral genes encoding for structural proteins that are necessary for the production of viral particles in the self-replicating RNA. For example, when the self-replicating RNA molecule is based on an alpha virus, such as Sindbis virus (SIN), Semliki forest virus and Venezuelan equine encephalitis virus (VEE), one or more genes encoding for viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides an RNA-dependent RNA polymerase which then produces transcripts from the delivered RNA. Thus, the delivered RNA leads to the production of multiple daughter RNAs. These transcripts are antisense relative to the delivered RNA and may be translated themselves to provide in situ expression of encoded antigens, or may be transcribed to provide further transcripts with the same sense as the delivered RNA which are translated to provide in situ expression of the encoded antigen(s).

The self-replicating RNA molecules provided herein can contain one or more modified nucleotides and therefore have improved stability and be resistant to degradation and clearance in vivo, and other advantages. In some embodiments, self-replicating RNA molecules that contain modified nucleotides avoid or reduce stimulation of endosomal and cytoplasmic immune receptors when the self-replicating RNA is delivered into a cell. This permits self-replication, amplification and expression of protein to occur. This also reduces safety concerns relative to self-replicating RNA that does not contain modified nucleotides, because the self-replicating RNA that contains modified nucleotides reduce activation of the innate immune system and subsequent undesired consequences (e.g., inflammation at injection site, irritation at injection site, pain, and the like). RNA molecules produced as a result of self-replication are recognized as foreign nucleic acids by the cytoplasmic immune receptors. Thus, self-replicating RNA molecules that contain modified nucleotides provide for efficient amplification of the RNA in a host cell and expression of antigens provided herein, as well as adjuvant effects.

In some embodiments, self-replicating RNA molecules provided herein contain at least one modified nucleotide. Modified nucleotides that are not part of the 5' cap (e.g., in addition to the modification that are part of the 5" cap) can be used. Accordingly, the self-replicating RNA molecule can contain a modified nucleotide at a single position, can contain a particular modified nucleotide (e.g., pseudouridine, N6-methyladenosine, 5-methylcytidine, 5-methyluridine) at two or more positions, or can contain two, three, four, five, six, seven, eight, nine, ten or more modified nucleotides (e.g., each at one or more positions). Preferably, the self-replicating RNA molecules comprise modified nucleotides that contain a modification on or in the nitrogenous base, but do not contain modified sugar or phosphate moieties. In some examples, between 0.001% and 99% or 100% of the nucleotides in a self-replicating RNA molecule are modified nucleotides. For example, 0.001%-25%, 0.01%-25%, 0.1%-25%, or 1%-25% of the nucleotides in a self-replicating RNA molecule are modified nucleotides. In other examples, between 0.001% and 99% or 100% of a particular unmodified nucleotide in a self-replicating RNA molecule is replaced with a modified nucleotide. For example, about 1% of the nucleotides in the self-replicating RNA molecule that contain uridine can be modified, such as by replacement of uridine with pseudouridine. In other examples, the desired amount (percentage) of two, three, or four particular nucleotides (nucleotides that contain uridine, cytidine, guanosine, or adenine) in a self-replicating RNA molecule are modified nucleotides. For example, 0.001%-25%, 0.01%-25%, 0.1%-25%, or 1%-25% of a particular nucleotide in a self-replicating RNA molecule are modified nucleotides. In other examples, 0.001%-20%, 0.001%-15%, 0.001%-10%, 0.01%-20%, 0.01%-15%, 0.1%-25, 0.01%-10%, 1%-20%, 1%-15%, 1%-10%, or about 5%, about 10%, about 15%, about 20% of a particular nucleotide in a self-replicating RNA molecule are modified nucleotides. It is preferred that less than 100% of the nucleotides in a self-replicating RNA molecule are modified nucleotides. It is also preferred that less than 100% of a particular nucleotide in a self-replicating RNA molecule are modified nucleotides. Thus, preferred self-replicating RNA molecules comprise at least some unmodified nucleotides.

Self-replicating RNA molecules that comprise at least one modified nucleotide can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses. Suitable synthetic methods can be used alone, or in combination with one or more other methods (e.g., recombinant DNA or RNA technology), to produce a self-replicating RNA molecule that contain one or more modified nucleotides.

Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like.

In some embodiments, nucleic acids provided herein code for an RNA polymerase. In some embodiments, nucleic acids provided herein code for a viral RNA polymerase. In some embodiments, nucleic acids provided herein code for: (1) a viral RNA polymerase; and (2) a protein or functional fragment thereof. In some embodiments, compositions provided herein comprise a first nucleic acid encoding for a viral RNA polymerase; and a second nucleic acid encoding for a protein or functional fragment thereof.

Provided herein are compositions comprising a self-replicating RNA. A self-replicating RNA (also called a replicon) includes any genetic element, for example, a plasmid, cosmid, bacmid, phage or virus that is capable of replication largely under its own control. Self-replication provides a system for self-amplification of the nucleic acids provided herein in mammalian cells. In some embodiments, the self-replicating RNA is single stranded. In some embodiments, the self-replicating RNA is double stranded.

An RNA polymerase provided herein can include but is not limited to: an alphavirus RNA polymerase, an Eastern equine encephalitis virus (EEEV) RNA polymerase, a Western equine encephalitis virus (WEEV), Venezuelan equine encephalitis virus (VEEV), Also, Chikungunya virus (CHIKV), Semliki Forest virus (SFV), or Sindbis virus (SINV). In some embodiments, the RNA polymerase is a VEEV RNA polymerase. In some embodiments, the nucleic acid encoding for the RNA polymerase comprises at least 85% identity to the nucleic acid sequence of SEQ ID NO: 34. In some embodiments, the nucleic acid encoding for the RNA polymerase comprises at least 90% identity to the nucleic acid sequence of SEQ ID NO: 34. In some embodiments, the nucleic acid encoding for the RNA polymerase comprises at least 95% identity to the nucleic acid sequence of SEQ ID NO: 34. In some embodiments, the nucleic acid encoding for the RNA polymerase comprises at least 99% identity to the nucleic acid sequence of SEQ ID NO: 34. In some embodiments, the nucleic acid encoding for the RNA polymerase is SEQ ID NO: 34.

In some embodiments, the amino acid sequence for VEEV RNA polymerase comprises at least 85% identity to RELPVLDSAAFNVECFKKYACNNEYWETFKENPIRL-TEEN VVNYITKLKGP (SEQ ID NO: 35), TQM-RELPVLDSAAFNVECFKKYACNNEYWE TFKEN-PIRLTE (SEQ ID NO: 36), or SEQ ID NO: 37. In some embodiments, the amino acid sequence for VEEV RNA polymerase comprises at least 90% identity to SEQ ID NO: 35, SEQ ID NO: 36, or SEQ ID NO: 37. In some embodiments, the amino acid sequence for VEEV RNA polymerase comprises at least 95% identity to SEQ ID NO: 35, SEQ ID NO: 36, or SEQ ID NO: 37. In some embodiments, the amino acid sequence for VEEV RNA polymerase comprises at least 99% identity to SEQ ID NO: 35, SEQ ID NO: 36, or SEQ ID NO: 37. In some embodiments, the amino acid sequence for VEEV RNA polymerase comprises to SEQ ID NO: 35, SEQ ID NO: 36, or SEQ ID NO: 37.

Provided herein are compositions and methods comprising replicon RNA (repRNA) encoding for one or more structural proteins from a non-enveloped virus. In some embodiments, the repRNA encodes a protease. In some embodiments, the repRNA encodes the 3CD protease. In some embodiments, the structural protein and the protease are co-expressed. In further embodiments, the repRNA comprises one or more open reading frames. In some embodiments, the open reading frames are separated by an internal ribosomal entry site (IRES). In some embodiments, the open reading frames are separated by a ribosomal skipping peptide sequence. In some embodiments the ribosomal skipping peptide sequence is from Thosea asigna virus (T2A).

Combination Compositions

Provided herein are compositions comprising a nanoparticle described herein and a nucleic acid encoding for a coronavirus antigen. Further provided herein is a nanoemulsion comprising a plurality of nanoparticles provided herein. In some embodiments, the nucleic acid further encodes for a self-replicating RNA polymerase. In some embodiments, the nucleic acid encoding for the self-replicating RNA polymerase is on the same nucleic acid strand as the nucleic acid sequence encoding for the protein (e.g., cis). In some embodiments, the nucleic acid encoding the self-replicating RNA polymerase is on a different nucleic acid strand as the nucleic acid sequence encoding for the protein (e.g., trans). In some embodiments, the nucleic acid encoding the self-replicating RNA polymerase is a DNA molecule. In some embodiments, nucleic acid sequences encoding for an antigen provided herein are DNA or RNA molecules. In some embodiments, antigens provided herein are encoded by DNA. Nanoparticles for inclusion include, without limitation, any one of NP-1 to NP-30, or any one of NP-1 to NP-31. Nucleic acids for inclusion include, without limitation, comprise a region comprising any one of, or a plurality of, SEQ ID NOS: 1-6, 38-54 or encoding an amino acid sequence of any one of SEQ ID NOS: 7-33. In some instances, the nucleic acids further comprise a region encoding for an RNA polymerase, e.g., a region comprising a sequence of SEQ ID NO: 34.

Compositions provided herein can be characterized by an nitrogen:phosphate (N:P) molar ratio. The N:P ratio is determined by the amount of cationic lipid in the nanoparticle which contain nitrogen and the amount of nucleic acid used in the composition which contain negatively charged phosphates. A molar ratio of the lipid carrier to the nucleic acid can be chosen to increase the delivery efficiency of the nucleic acid, increase the ability of the nucleic acid-carrying nanoemulsion composition to elicit an immune response to the antigen, increase the ability of the nucleic acid-carrying nanoemulsion composition to elicit the production of antibody titers to the antigen in a subject. In some embodiments, compositions provided herein have a molar ratio of the lipid carrier to the nucleic acid can be characterized by the nitrogen-to-phosphate molar ratio, which can range from about 0.01:1 to about 1000:1, for instance, from about 0.2:1 to about 500:1, from about 0.5:1 to about 150:1, from about 1:1 to about 150:1, from about 1:1 to about 125:1, from about 1:1 to about 100:1, from about 1:1 to about 50:1, from about 1:1 to about 50:1, from about 5:1 to about 50:1, from about 5:1 to about 25:1, or from about 10:1 to about 20:1 In some embodiments, the molar ratio of the lipid carrier to the nucleic acid, characterized by the nitrogen-to-phosphate (N:P) molar ratio, ranges from about 1:1 to about 150:1, from about 5:1 to about 25:1, or from about 10:1 to about 20:1. In some embodiments, the N:P molar ratio of the nanoemulsion composition is about 15:1. In some embodiments, the nanoparticle comprises a nucleic acid provided herein covalently attached to the membrane.

Compositions provided herein can be characterized by an oil-to-surfactant molar ratio. In some embodiments, the oil-to-surfactant ratio is the molar ratio of squalene:cationic lipid, hydrophobic surfactant, and hydrophilic surfactant. In some embodiments, the oil-to-surfactant ratio is the molar ratio of squalene:DOTAP, hydrophobic surfactant, and hydrophilic surfactant. In some embodiments, the oil-to-surfactant ratio is the molar ratio of squalene:DOTAP, sorbitan monostearate, and polysorbate 80. In some embodiments, the oil-to surfactant molar ratio ranges from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, the oil-to-surfactant molar ratio is at least about 0.1:1, at least about 0.2:1, at least about 0.3:1, at least about 0.4:1, at least about 0.5:1, at least about 0.6:1, at least about 0.7:1. In some embodiments, the oil-to surfactant molar ratio is at least about 0.4:1 up to 1:1.

Compositions provided herein can be characterized by hydrophilic surfactant-to-cationic lipid ratio. In some embodiments, the hydrophilic surfactant-to-cationic lipid ratio ranges from about 0.1:1 to about 2:1, from about 0.2:1 to about 1.5:1, from about 0.3:1 to about 1:1, from about 0.5:1 to about 1:1, or from about 0.6:1 to about 1:1. Compositions provided herein can be characterized by hydrophobic surfactant-to-lipid (e.g., cationic lipid) ratio. In some embodiments, the hydrophobic surfactant-to-lipid ratio ranges from about 0.1:1 to about 5:1, from about 0.2:1 to about 3:1, from about 0.3:1 to about 2:1, from about 0.5:1 to about 2:1, or from about 1:1 to about 2:1. In some embodiments, the cationic lipid is DOTAP.

Further provided herein is a dried composition comprising a sorbitan fatty acid ester, an ethoxylated sorbitan ester, a cationic lipid, an immune stimulant, and an RNA. Further provided herein are dried compositions, wherein the dried composition comprises sorbitan monostearate (e.g., SPAN-60), polysorbate 80 (e.g., TWEEN-80), DOTAP, an immune stimulant, and an RNA.

Thermally Stable, Dried, and Lyophilized Infectious Diseases Vaccines

Provided herein are dried or lyophilized compositions and vaccines. Further provided herein are pharmaceutical compositions comprising a dried or lyophilized composition provided herein that is reconstituted in a suitable diluent and a pharmaceutically acceptable carrier. In some embodiments, the diluent is aqueous. In some embodiments, the diluent is water.

In some embodiments, a lyophilized composition is generated by a low temperature dehydration process involving the freezing of the composition, followed by a lowering of pressure, and removal of ice by sublimation. In certain cases, lyophilisation also involves the removal of bound water molecules through a desorption process. In some embodiments, compositions and vaccines provided herein are spray-dried. Spray drying is a process by which a solution is fed through an atomizer to create a spray, which is thereafter exposed to a heated gas stream to promote rapid evaporation. When sufficient liquid mass has evaporated, the remaining solid material in the droplet forms particles which are then separated from the gas stream (e.g., using a filter or a cyclone). Drying aids in the storage of the compositions and vaccines provided herein at higher temperatures (e.g., greater than 4° C.) as compared to the sub-zero temperatures needed for the storage of existing mRNA vaccines. In some embodiments, dried compositions and lyophilized compositions provided herein comprise (a) a lipid carrier, wherein the lipid carrier is a nanoemulsion comprising: (i) a hydrophobic core; (ii) one or more inorganic nanoparticles; (iii) and one or more lipids; (b) one or more nucleic acids; and (c) at least one cryoprotectant. In some embodiments, the cryoprotectant is selected from the group consisting of sucrose, maltose, trehalose, mannitol, glucose, and any combinations thereof. Additional examples of cryoprotectants include but are not limited to: dimethyl sulfoxide (DMSO), glycerol, propylene glycol, ethylene glycol, 3-O-methyl-D-glucopyranose (3-OMG), polyethylene glycol (PEG), 1,2-propanediol, acetamide, trehalose, formamide, sugars, proteins, and carbohydrates. In some embodiments, compositions and methods provided herein comprise at least one cryoprotectant. Exemplary cryoprotectants for inclusion are, but not limited to, sucrose, maltose, trehalose, mannitol, or glucose, and any combinations thereof. In some embodiments, additional or alternative cryoprotectant for inclusion is sorbitol, ribitol, erthritol, threitol, ethylene glycol, or fructose. In some embodiments, additional or alternative cryoprotectant for inclusion is dimethyl sulfoxide (DMSO), glycerol, propylene glycol, ethylene glycol, 3-O-methyl-D-glucopyranose (3-OMG), polyethylene glycol (PEG), 1,2-propanediol, acetamide, trehalose, formamide, sugars, proteins, and carbohydrates. In some embodiments, the cryoprotectant is present at about 1% w/v to at about 20% w/v, preferably about 10% w/v to at about 20% w/v, and more preferably at about 10% w/v. In certain aspects of the disclosure, the cryoprotectant is sucrose. In some aspects of the disclosure, the cryoprotectant is maltose. In some aspects of the disclosure, the cryoprotectant is trehalose. In some aspects of the disclosure, the cryoprotectant is mannitol. In some aspects of the disclosure, the cryoprotectant is glucose. In some embodiments, the cryoprotectant is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the cryoprotectant is present in an amount of about 50 to about 500 mg. In some embodiments, the cryoprotectant is present in an amount of about 200 to about 300 mg. In some embodiments, the cryoprotectant is present in an amount of about 250 mg. In some embodiments, the cryoprotectant is present in amount of a lyophilized composition by weight of at least 50, 55, 60, 65, 70, 75, 80, 85, 90, 95 or more percent. In some embodiments, the cryoprotectant is present in amount of a lyophilized composition by weight of about 95%. In some embodiments, the cryoprotectant is present in amount of a lyophilized composition by weight of 80 to 98%, 85 to 98%, 90 to 98%, or 94 to 96%. In some embodiments, the cryoprotectant is a sugar. In some embodiments, the sugar is sucrose, maltose, trehalose, mannitol, or glucose. In some embodiments, the sugar is sucrose. In some embodiments, the sucrose is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the sucrose is present in an amount of about 50 to about 500 mg. In some embodiments, the sucrose is present in an amount of about 200 to about 300 mg. In some embodiments, the sucrose is present in an amount of about 250 mg. In some embodiments, the sucrose is present in amount of a lyophilized composition by weight of at least 50, 55, 60, 65, 70, 75, 80, 85, 90, 95 or more percent. In some embodiments, the sucrose is present in amount of a lyophilized composition by weight of about 95%. In some embodiments, the sucrose is present in amount of a lyophilized composition by weight of 80 to 98%, 85 to 98%, 90 to 98%, or 94 to 96%.

In some embodiments, the cryoprotectant is sucrose. In some embodiments, the cryoprotectant is at a concentration of at least about 0.1% w/v. In some embodiments, the cryoprotectant is at a concentration of about 1% w/v to at about 20% w/v. In some embodiments, the cryoprotectant is at a concentration of about 10% w/v to at about 20% w/v. In some embodiments, the cryoprotectant is at a concentration of about 10% w/v.

In some embodiments, compositions and vaccines provided herein are thermally stable. A composition is considered thermally stable when the composition resists the action of heat or cold and maintains its properties, such as the ability to protect a nucleic acid molecule from degradation at given temperature. In some embodiments, compositions and vaccines provided herein are thermally stable at about 25° C. or standard room temperature. In some embodiments, compositions and vaccines provided herein are thermally stable at about 45° C. In some embodiments, compositions and vaccines provided herein are thermally stable at about −20° C. In some embodiments, compositions and vaccines provided herein are thermally stable at about 2° C. to about 8° C. In some embodiments, compositions and vaccines provided herein are thermally stable at a temperature of at least about −80° C., at least about −20° C., at least about 0° C., at least about 2° C., at least about 4° C., at least about 6° C., at least about 8° C., at least about 10° C., at least about 20° C., at least about 25° C., at least about 30° C., at least about 37° C., up to 45° C. In some embodiments, compositions and vaccines provided herein are thermally stable for at least about 5 day, at least about 1 week, at least about 2 weeks, at least about 1 month, up to 3 months. In some embodiments, compositions and vaccines provided herein are stored at a temperature of at least about 4° C. up to 37° C. for at least about 5 day, at least about 1 week, at least about 2 weeks, at least about 1 month, up to 3 months. In some embodiments, compositions and vaccines provided herein are stored at a temperature of at least about 20° C. up to 25° C. for at least about 5 day, at least about 1 week, at least about 2 weeks, at least about 1 month, up to 3 months.

Also provided herein are methods for preparing a lyophilized composition comprising obtaining a lipid carrier, wherein the lipid carrier is a nanoemulsion comprising a hydrophobic core, one or more inorganic nanoparticles and one or more lipids; incorporating one or more nucleic acid into the lipid carrier to form a lipid carrier-nucleic acid complex; adding at least one cryoprotectant to the lipid carrier-nucleic acid complex to form a formulation; and lyophilizing the formulation to form a lyophilized composition.

Further provided herein are methods for preparing a spray-dried composition comprising obtaining a lipid carrier, wherein the lipid carrier is a nanoemulsion comprising a hydrophobic core, one or more inorganic nanoparticles and one or more lipids; incorporating one or more nucleic acid into the lipid carrier to form a lipid carrier-nucleic acid complex; adding at least one cryoprotectant to the lipid carrier-nucleic acid complex to form a formulation; and spray drying the formulation to form a spray-dried composition.

Further provided herein are methods for reconstituting a lyophilized composition comprising: obtaining a lipid carrier, wherein the lipid carrier is a nanoemulsion comprising a hydrophobic core, one or more inorganic nanoparticles, and one or more lipids; incorporating one or more nucleic acid into the said lipid carrier to form a lipid carrier-nucleic acid complex; adding at least one cryoprotectant to the lipid carrier-nucleic acid complex to form a formulation; lyophilizing the formulation to form a lyophilized composition; and reconstituting the lyophilized composition in a suitable diluent.

Further provided herein are methods for reconstituting a spray-dried composition comprising: obtaining a lipid carrier, wherein the lipid carrier is a nanoemulsion comprising a hydrophobic core, one or more inorganic nanoparticles, and one or more lipids, incorporating one or more nucleic acid into the said lipid carrier to form a lipid carrier-nucleic acid complex; adding at least one cryoprotectant to the lipid carrier-nucleic acid complex to form a formulation; spray drying the formulation to form a spray-dried composition; and reconstituting the spray-dried composition in a suitable diluent.

Pharmaceutical Compositions

Provided herein is a pharmaceutical composition comprising a composition provided herein. In some embodiments, compositions provided herein are combined with pharmaceutically acceptable salts, excipients, and/or carriers to form a pharmaceutical composition. Pharmaceutical salts, excipients, and carriers may be chosen based on the route of administration, the location of the target issue, and the time course of delivery of the drug. A pharmaceutically acceptable carrier or excipient may include solvents, dispersion media, coatings, antibacterial and antifungal agents, isotonic and absorption delaying agents, etc., compatible with pharmaceutical administration.

In some embodiments, the pharmaceutical composition is a suspension comprising a composition provided herein. In some embodiments, suspensions provided herein comprise a plurality of nanoparticles or compositions provided herein. In some embodiments, compositions provided herein are in a suspension, optionally a homogeneous suspension. In some embodiments, compositions provided herein are in an emulsion form.

In some embodiments, the pharmaceutical composition is in the form of a solid, semi-solid, liquid or gas (aerosol). Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent. Among the acceptable vehicles and solvents that may be employed are water, Ringer's solution, U.S.P., and isotonic sodium chloride solution. In addition, sterile, fixed oils are employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Dosing

Compositions provided herein may be formulated in dosage unit form for ease of administration and uniformity of dosage. A dosage unit form is a physically discrete unit of a composition provided herein appropriate for a subject to be treated. It will be understood, however, that the total usage of compositions provided herein will be decided by the attending physician within the scope of sound medical judgment. For any composition provided herein the therapeutically effective dose can be estimated initially either in cell culture assays or in animal models, such as mice, rabbits, dogs, pigs, or non-human primates. The animal model is also used to achieve a desirable concentration range and route of administration. Such information can then be used to determine useful doses and routes for administration in humans. Therapeutic efficacy and toxicity of compositions provided herein can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies may be used in formulating a range of dosage for human use. Exemplary amounts of total nucleic acid for incorporation in a composition described herein includes about 1, 2, 2.5, 5, 7.5, 10, 12.5, 15, 20, 25, 30, 35, 40, 45, 50 micrograms (μg) or more.

Administration

Provided herein are compositions and pharmaceutical compositions for administering to a subject in need thereof. In some embodiments, pharmaceutical compositions provided here are in a form which allows for compositions provided herein to be administered to a subject.

In some embodiments, the administering is local administration or systemic administration. In some embodiments, a composition described herein is formulated for administration/for use in administration via a subcutaneous, intradermal, intramuscular, inhalation, intravenous, intraperitoneal, intracranial, sublingual, oral, or intrathecal route. In some embodiments, the administering is every 1, 2, 4, 6, 8, 12, 24, 36, or 48 hours. In some embodiments, the administering is daily, weekly, or monthly. In some embodiments, the administering is repeated at least about every 28 days or 56 days.

In some embodiments, a single dose of a composition provided herein is administered to a subject. In some embodiments, a composition or pharmaceutical composition provided herein is administered to the subject by two doses. In some embodiments, a second dose of a composition or pharmaceutical composition provided herein is administered about 28 days or 56 days after the first dose. In some embodiments, a first dose is administered, and a second dose is administered about 14 days later, or about 21 days later, or about 28 days later, or about 35 days later, or about 42 days later, or about 49 days later, or about 56 days later, or about 63 days later, or about 70 days later, or about 77 days later, or about 84 days later. In some embodiments, the second dose is administered about 10-90 days following administration of the first dose, or about 15-85 days following administration of the first dose, or about 20-80 days following administration of the first dose, or about 25-75 days following administration of the first dose, or about 30-70 days following administration of the first dose, or about 35-65 days following administration of the first dose, or about 40-60 days following administration of the first dose.

In some embodiments, a third dose of a composition or pharmaceutical composition provided herein is administered to a subject. In some embodiments, the third dose is administered about 1 month following administration of the second dose, about 2 months following administration of the second dose, about 3 months following administration of the second dose, about 4 months following administration of the second dose, about 5 months following administration of the second dose, about 6 months following administration of the second dose, about 7 months following administration of the second dose, about 8 months following administration of the second dose, about 9 months following administration of the second dose, about 10 months following administration of the second dose, about 11 months following administration of the second dose, about 12 months following administration of the second dose, about 13 months following administration of the second dose, about 14 months following administration of the second dose, about 15 months following administration of the second dose, about 16 months following administration of the second dose, about 17 months following administration of the second dose, or about 18 months following administration of the second dose.

Therapeutic Applications

Provided herein are methods of treating a disease or a disorder in a subject. Provided herein are methods of generating an immune response in a subject to an infectious microorganism. In some embodiments, the disease or disorder is an infection. In some embodiments, the infection is a viral infection, a bacterial infection, a parasitic infection, a fungal infection, or a yeast infection.

In some embodiments, the subject has, is suspected of having, or is at risk of developing a viral infection. In some embodiments, the viral infection is an RSV infection, a CMV infection, SARS, rabies, a HPV infection, chickenpox, shingles, a Herpes simplex 1 infection, a Herpes simplex 2 infection, or influenza. In some embodiments, the subject has, is suspected of having, or is at risk of developing a bacterial infection. In some embodiments, the bacterial infection is tuberculosis, chlamydia, gonorrhea, strep throat, or a *Staphylococcus aureus* infection. In some embodiments, the subject has or is suspected of having a fungal infection. In some embodiments, the subject has or is suspected of having a parasitic infection. In some embodiments, the parasitic infection is malaria. In some embodiments, the subject is at risk of developing an infectious disease or disorder. In some embodiments, the subject has contracted an infectious disease by way of contact with another infected subject. In some embodiments, the subject has contracted an infectious disease from contaminated drinking water. In some embodiments, the subject has contracted the infectious disease from a different species carrying the microorganism. In some embodiments, the subject is a mammal. In some embodiments, the mammal is a human.

Kits

Provided herein is a kit comprising a composition provided herein, a pharmaceutical composition provided herein; and optionally, a delivery system for administration to a subject. In some embodiments, the kit further comprises one or more surfactants. In some embodiments, a formulation of a composition described herein is prepared in a single container for administration. In some embodiments, a formulation of a composition described herein is prepared two containers for administration, separating the nucleic acid from the nanoparticle carrier. As used herein, "container" includes vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Examples of such containers include glass and/or plastic sealed or re-sealable tubes and ampules, including those having a rubber septum or other sealing means that is compatible with withdrawal of the contents using a needle and syringe. In some implementations, the containers are RNase free. In some embodiments, the kit comprises: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises a sequence encoding for a viral antigen sequence, a bacterial antigen sequence, a fungal antigen sequence, or a parasitic antigen sequence, or functional variant thereof, wherein the viral antigen sequence is not derived from SARS-CoV-2.

EXEMPLARY EMBODIMENTS

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; at least one nucleic acid encoding for an antigen sequence, wherein the antigen sequence comprises a sequence encoding for a viral antigen sequence, a bacterial antigen sequence, a fungal antigen sequence, or a parasitic antigen sequence, or functional variant of any of the foregoing, and wherein the viral antigen sequence is not a SARS-CoV-2 antigen sequence or functional variant thereof. Further provided herein are compositions, wherein the viral antigen sequences are derived from an influenza virus, a varicella-zoster virus (VZV), a severe acute respiratory syndrome coronavirus 1 (SARS-CoV-1), a human gammaherpesvirus 4, a human papilloma virus (HPV), a rabies virus, a human alphaherpesvirus 1, a human immunodeficiency virus (HIV), or a human alphaherpesvirus 2. Further provided herein are compositions, wherein the bacterial antigen sequences are derived from a *Mycobacterium* bacterium, a *Streptococcus* bacterium, a *Pseudomonas* bacterium, a *Salmonella* bacterium, a *Staphylococcus* bacterium, a *Neisseria* bacterium, a *Clostridium* bacterium, or a *Chlamydia* bacterium. Further provided herein are compositions, wherein the fungi antigen sequences are derived from a *Aspergillus* fungi, a *Saccharomyces* fungi, a *Cryptococcus* fungi, a *Coccidioides* fungi, a *Neurospora* fungi, a *Histoplasma* fungi, or a *Blastomyces* fungi. Further provided herein are compositions, wherein the parasitic antigen sequences are a derived from a *Plasmodium* parasite. Further provided herein are compositions, wherein the at least one nucleic acid comprises a sequence at least 85% identical to SEQ ID NOS: 1-6, 43-47. Further provided herein are compositions, wherein the at least one nucleic acid comprises a sequence encoding for an amino acid sequence of any one of SEQ ID NOS: 7-33. Further provided herein are compositions, wherein the nucleic acid is in complex with the lipid carrier. Further provided herein are compositions, wherein the nucleic acid further encodes for an RNA polymerase. Further provided herein are compositions, wherein the RNA polymerase is a Venezuelan equine encephalitis virus (VEEV) RNA polymerase. Further provided herein are compositions, wherein the nucleic acid encoding for the RNA polymerase comprises the nucleic acid sequence of SEQ ID NO: 34. Further provided herein are compositions, wherein the liquid oil is α-tocopherol, coconut oil, grapeseed oil, lauroyl polyoxylglyceride, mineral oil, monoacylglycerol, palmkemal oil, olive oil, paraffin oil, peanut oil, propolis, squalene, squalane, solanesol, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein the lipid carrier comprises a hydrophobic core. Further provided herein are compositions, wherein the lipid carrier comprises an inorganic particle. Further provided herein are compositions, wherein the inorganic particle is within the hydrophobic core. Further provided herein are compositions, wherein the inorganic particle comprises a metal. Further provided herein are compositions, wherein the metal comprises a metal salt, a metal oxide, a metal hydroxide, or a metal phosphate. Further provided herein are compositions, wherein the metal oxide comprises aluminum oxide, aluminum oxyhydroxide, iron oxide, titanium dioxide, or silicon dioxide. Further provided herein are compositions, wherein the hydrophobic surfactant is sorbitan monolaurate, sorbitan monopalmitate, sorbitan monostearate, sorbitan monooleate, or sorbitan trioleate. Further provided herein are compositions, wherein the hydrophilic surfactant is a polysorbate. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the composition is lyophilized.

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises an antigen sequence encoding for an influenza hemagglutinin protein stem region or a functional variant thereof. Further provided herein are compositions, wherein the nucleic acid comprises a sequence at least 85% identical to SEQ ID NO: 3 or a functional fragment thereof. Further provided herein are compositions, wherein the nucleic acid encodes an amino acid sequence at least 85% identical to any one of SEQ ID NOS: 10-12. Further provided herein are compositions, wherein the nucleic acid is in complex with the lipid carrier. Further provided herein are compositions, wherein the nucleic acid further encodes for an RNA polymerase. Further provided herein are compositions, wherein the RNA polymerase is a Venezuelan equine encephalitis virus (VEEV) RNA polymerase. Further provided herein are compositions, wherein the nucleic acid encoding for the RNA polymerase comprises the nucleic acid sequence of SEQ ID NO: 34. Further provided herein are compositions, wherein the liquid oil is α-tocopherol, coconut oil, grapeseed oil, lauroyl polyoxylglyceride, mineral oil, monoacylglycerol, palmkemal oil, olive oil, paraffin oil, peanut oil, propolis, squalene, squalane, solanesol, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein the lipid carrier comprises a hydrophobic core. Further provided herein are compositions, wherein the lipid carrier comprises an inorganic particle. Further provided herein are compositions, wherein the inorganic particle is within the hydrophobic core. Further provided herein are compositions, wherein the inorganic particle comprises a metal. Further provided herein are compositions, wherein the metal comprises a metal salt, a metal oxide, a metal hydroxide, or a metal phosphate. Further provided herein are compositions, wherein the metal oxide comprises aluminum oxide, aluminum oxyhydroxide, iron oxide, titanium dioxide, or silicon dioxide. Further provided herein are compositions, wherein the hydrophobic surfactant is sorbitan monolaurate, sorbitan monopalmitate, sorbitan monostearate, sorbitan monooleate, or sorbitan trioleate. Further provided herein are compositions, wherein the hydrophilic surfactant is a polysorbate. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are lyophilized.

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises an antigen sequence encoding for a VZV protein or a functional variant thereof. Further provided herein are compositions, wherein the VZV protein or functional variant thereof is a glycoprotein E (gE), gI, gB, gH, μL, a gN or a functional fragment thereof. Further provided herein are compositions, wherein the antigen sequence encoding for a VZV protein is at least 85% identical to any one of SEQ ID NOS: 4, 5, 38-43. Further provided herein are compositions, wherein the nucleic acid is in complex with the lipid carrier. Further provided herein are compositions, wherein the nucleic acid further encodes for an RNA polymerase. Further provided herein are compositions, wherein the RNA polymerase is a Venezuelan equine encephalitis virus (VEEV) RNA polymerase. Further provided herein are compositions, wherein the nucleic acid encoding for the RNA polymerase comprises the nucleic acid sequence of SEQ ID NO: 34. Further provided herein are compositions, wherein the liquid oil is α-tocopherol, coconut oil, grapeseed oil, lauroyl polyoxylglyceride, mineral oil, monoacylglycerol, palmkemal oil, olive oil, paraffin oil, peanut oil, propolis, squalene, squalane, solanesol, soy lecithin, soybean oil, sunflower oil, a triglyceride, or vitamin E. Further provided herein are compositions, wherein the triglyceride is capric triglyceride, caprylic triglyceride, a caprylic and capric triglyceride, a triglyceride ester, or myristic acid triglycerin. Further provided herein are compositions, wherein the lipid carrier comprises a hydrophobic core. Further provided herein are compositions, wherein the lipid carrier comprises an inorganic particle. Further provided herein are compositions, wherein the inorganic particle is within the hydrophobic core. Further provided herein are compositions, wherein the inorganic particle comprises a metal. Further provided herein are compositions, wherein the metal comprises a metal salt, a metal oxide, a metal hydroxide, or a metal phosphate. Further provided herein are compositions, wherein the metal oxide comprises aluminum oxide, aluminum oxyhydroxide, iron oxide, titanium dioxide, or silicon dioxide. Further provided herein are compositions, wherein the hydrophobic surfactant is sorbitan monolaurate, sorbitan monopalmitate, sorbitan monostearate, sorbitan monooleate, or sorbitan trioleate. Further provided herein are compositions, wherein the hydrophilic surfactant is a polysorbate. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the compositions are lyophilized.

Provided herein are compositions, wherein the compositions comprise: a lipid carrier, wherein the lipid carrier is a nanoemulsion comprising: about 30 mg/mL DOTAP chloride about 37.5 mg/mL squalene; about 37 mg/ml sorbitan monostearate; about 37 mg/ml polysorbate 80; about 10 mM sodium citrate; and about 0.2 mg Fe/ml oleic acid-coated iron oxide nanoparticles, wherein the oleic acid-coated iron oxide nanoparticle range in size from about 5 nanometers up to 25 nm; and at least one nucleic acid, wherein the at least one nucleic acid comprises a sequence at least 85% identical to SEQ ID NOS: 1-6, 38-47. Further provided herein are compositions, wherein the oleic acid-coated iron oxide nanoparticles range in size from about 5 to about 25 nanometers in size. Further provided herein are compositions, wherein the oleic acid-coated iron oxide nanoparticles are 12 nanometers in size. Further provided herein are compositions, wherein the composition comprises sucrose. Further provided herein are compositions, wherein the sucrose is present in an about of about 50 mg. Further provided herein are compositions, wherein the nucleic acid is in complex with the lipid carrier. Further provided herein are compositions, wherein the nucleic acid further encodes for an RNA polymerase. Further provided herein are compositions, wherein the RNA polymerase is a Venezuelan equine encephalitis virus (VEEV) RNA polymerase. Further provided herein are compositions, wherein the nucleic acid encoding for the RNA polymerase comprises the nucleic acid sequence of SEQ ID NO: 34. Further provided herein are compositions, wherein the lipid carrier comprises a hydrophobic core. Further provided herein are compositions, wherein the oleic acid-coated iron oxide nanoparticles are within the hydrophobic core. Further provided herein are compositions, wherein the compositions are lyophilized.

Provided herein are compositions, wherein the compositions comprise: a lipid carrier, wherein the lipid carrier is a nanoemulsion comprising: DOTAP chloride present in an amount of about 0.75 mg; squalene present in an amount of about 0.94 mg; sorbitan monostearate present in an amount of about 0.93 mg; polysorbate 80 present in an amount of about 0.93 mg; citric acid monohydrate present in an amount of about 1.05 mg; and oleic acid-coated iron oxide nanoparticles present in an amount of about 0.005 mg; and at least one nucleic acid, wherein the at least one nucleic acid comprises a sequence at least SEQ ID NOS: 1-6, 38-47. Further provided herein are compositions, wherein the at least one nucleic acid sequence is present in an amount of up to about 100 micrograms (μg). Further provided herein are compositions, wherein the at least one nucleic acid sequence is present in an amount of up to about 5, about 10, about 25, about 50, or about 100 micrograms (μg). Further provided herein are compositions, wherein the at least one nucleic acid sequence is present in an amount of up to about 25 μg. Further provided herein are compositions, wherein the composition comprises sucrose. Further provided herein are compositions, wherein the sucrose is present in an about of about 50 milligrams (mg). Further provided herein are compositions, wherein the nucleic acid is in complex with the lipid carrier. Further provided herein are compositions, wherein the nucleic acid further encodes for an RNA polymerase. Further provided herein are compositions, wherein the RNA polymerase is a Venezuelan equine encephalitis virus (VEEV) RNA polymerase. Further provided herein are compositions, wherein the nucleic acid encoding for the RNA polymerase comprises the nucleic acid sequence of SEQ ID NO: 34. Further provided herein are compositions, wherein the lipid carrier comprises a hydrophobic core. Further provided herein are compositions, wherein the oleic acid-coated iron oxide nanoparticles are within the hydrophobic core. Further provided herein are compositions, wherein the compositions are lyophilized.

Provided herein are compositions, wherein the compositions comprise: a lipid carrier, wherein the lipid carrier is a nanoemulsion comprising a hydrophobic core, one or more inorganic nanoparticles and one or more oils or lipids; at least one nucleic acid sequence, wherein the nucleic acid sequence encodes a sequence capable of expressing an antigen, wherein the antigen is an infectious pathogen protein. Further provided herein are compositions, wherein the composition comprises a nucleic acid polymerase or a nucleic acid encoding for a sequence capable of expressing a nucleic acid polymerase. Further provided herein are compositions, wherein the nucleic acid sequence is an RNA nucleic acid sequence. Further provided herein are compositions, wherein the RNA polymerase or a nucleic acid sequence capable of expressing an RNA polymerase. Further provided herein are compositions, wherein the composition comprises a nucleic acid sequence comprising any one of SEQ ID NOS: 1-6, 34-54. Further provided herein are compositions, wherein the host cell is capable of expressing an antigen from a nucleic acid sequence, wherein the antigen is derived from an infectious agent. Further provided herein are compositions, wherein infectious agent is respiratory syncytial virus (RSV). Further provided herein are compositions, wherein the antigen comprises an RSV attachment (G) glycoprotein (RSV-G). Further provided herein are compositions, wherein the antigen comprises an RSV fusion (F) glycoprotein (RSV-F). Further provided herein are compositions, wherein the infectious agent is not SARS-COV-2. Further provided herein are compositions, wherein the infectious agent is a Zika virus. Further provided herein are compositions, wherein the infectious agent is an influenza virus. Further provided herein are compositions, wherein the hydrophobic core comprises an oil. Further provided herein are compositions, wherein the oil comprises at least one of α-tocopherol, lauroyl polyoxylglyceride, monoacylglycerol, propolis, squalene, squalene, miglyol, dehydroisosqualene (DHIS), mineral oil, grapeseed oil, olive oil, paraffin oil, peanut oil, soybean oil, sunflower oil, soy lecithin, triglyceride, vitamin E, and a medium chain triglyceride. Further provided herein are compositions, wherein the one or more inorganic nanoparticles is selected from the group consisting of a metal salt, metal oxide, metal hydroxide, metal phosphate, and any combinations thereof. Further provided herein are compositions, wherein the one or more lipids is selected from the group consisting of cationic lipids, anionic lipids, neutral lipids, and any combinations thereof. Further provided herein are compositions, wherein the one or more lipids is a cationic lipid. Further provided herein are compositions, wherein the cationic lipid is selected from the group consisting of 1,2-dioleoyloxy-3-(trimethylammonium)propane (DOTAP); 30-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:O)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis (2-hydroxydodecyl)amino)ethyl) (2-hydroxydodecyl) amino)ethyl)piperazin-1-yl)ethyl)azanediyl)bis(dodecan-2-ol) (C12-200), and any combinations thereof. Further provided herein are compositions, wherein the lipid carrier optionally comprises one or more surfactants. Further provided herein are compositions, wherein the one or more surfactants is selected from the group consisting of hydrophobic surfactant, hydrophilic surfactant, and any combinations thereof. Further provided herein are compositions, wherein the hydrophobic surfactant comprises a sorbitan ester selected from the group consisting of sorbitan monostearate, sorbitan monooleate, and sorbitan trioleate; and the hydrophilic surfactant comprises a polysorbate. Further provided herein are compositions, wherein the lipid carrier have a z-average hydrodynamic diameter ranging from about 40 nm to about 150 nm, with an average polydispersity index ranging from about 0.1 to about 0.4. Further provided herein are compositions, wherein the one or more nucleic acids is incorporated or complexed with the lipid carrier to form a lipid carrier-nucleic acid complex. Further provided herein are compositions, wherein the lipid carrier-RNA complex is formed via non-covalent interactions or via reversible covalent interactions. Further provided herein are compositions, wherein the molar ratio of the lipid carrier to the one or more nucleic acids, characterized by the nitrogen-to-phosphate (N:P) molar ratio, ranges from about 1:1 to about 150:1. Further provided herein are compositions, wherein the compositions are lyophilized. Further provided herein are compositions, wherein the compositions are stable at 2 to 8 degrees Celsius. Further provided herein are compositions, wherein the compositions are in the form of a suspension. Further provided herein are compositions, wherein the compositions are lyophilized. Further provided herein are vaccines comprising a composition provided herein.

Further provided herein are dried compositions, wherein the dried compositions comprise: a lipid carrier, wherein the lipid carrier is a nanoemulsion comprising a hydrophobic core, one or more inorganic nanoparticles and one or more lipids; at least one nucleic acid sequence, wherein the nucleic acid sequence encodes a sequence capable of expressing an antigen, wherein the antigen is an infectious disease protein; and at least one cryoprotectant.

Further provided herein are pharmaceutical compositions, wherein the pharmaceutical compositions comprise a composition provided herein; and a pharmaceutically acceptable excipient.

Provided herein are methods of generating an immune response in a subject, the methods comprise administering to said subject a composition provided herein. Provided herein are methods of generating an immune response in a subject, the methods comprise administering to said subject a composition provided herein, thereby generating an immune response to an antigen. Provided herein are compositions and methods for immunoprotecting a subject comprising administering to a subject a composition provided herein. Provided herein are methods of augmenting an immune response in a subject, the method comprising: administering to a subject the composition provided herein, thereby augmenting an immune response to an antigen. Provided herein are methods of treating an influenza infection, the method comprising: administering to a subject the composition provided herein thereby treating the influenza infection. Provided herein are methods of treating a VZV infection in a subject, the method comprising: administering to a subject the composition provided herein, thereby treating the VZV infection. Further provided herein are methods, wherein the compositions are administered to the subject by two doses. Further provided herein are methods, wherein the second dose is administered at about 14 days after the first dose.

Further provided herein are methods, wherein the second dose is administered at about 28 days after the first dose. Further provided herein are methods, wherein the second dose is administered at about 42 days after the first dose. Further provided herein are methods, wherein the second dose is administered at about 56 days after the first dose. Further provided herein are methods, wherein the second dose is administered at about 70 days after the first dose. Further provided herein are methods, wherein the methods further comprise administering a third dose of said composition to said subject. Further provided herein are methods, wherein 5 micrograms of said composition is administered to said subject. Further provided herein are methods, wherein 10 micrograms of said composition is administered to said subject. Further provided herein are methods, wherein 25 micrograms of said composition is administered to said subject. Further provided herein are methods, wherein 30 micrograms of the compositions are administered to said subject. Further provided herein are methods, wherein 35 micrograms of the compositions are administered to said subject. Further provided herein are methods, wherein 40 micrograms of the compositions are administered to said subject. Further provided herein are methods, wherein 45 micrograms of the compositions are administered to said subject. Further provided herein are methods, wherein 50 micrograms of the compositions are administered to said subject. Further provided herein are methods, wherein 55 micrograms of the compositions are administered to said subject. Further provided herein are methods, wherein 60 micrograms of the compositions are administered to said subject. Further provided herein are methods, wherein 65 micrograms of the compositions are administered to said subject. Further provided herein are methods, wherein 70 micrograms of the compositions are administered to said subject. Further provided herein are methods, wherein 75 micrograms of the compositions are administered to said subject. Further provided herein are methods, wherein 80 micrograms of the compositions are administered to said subject. Further provided herein are methods, wherein 85 micrograms of the compositions are administered to said subject. Further provided herein are methods, wherein 90 micrograms of the compositions are administered to said subject. Further provided herein are methods, wherein 95 micrograms of the compositions are administered to said subject. Further provided herein are methods, wherein 100 micrograms of the compositions are administered to said subject. Further provided herein are methods, wherein the subject is a mammal. Further provided herein are methods, wherein the mammal is a human. Further provided herein are methods, wherein the compositions are administered intramuscularly. Further provided herein are methods, wherein the compositions are administered intranasally. the subject has, is suspected of having, or is at risk of developing a viral infection. Further provided herein are methods, wherein the viral infection is an influenza infection, a VZV infection, a severe acute respiratory syndrome infection, a human gammaherpesvirus 4 infection, a human papilloma virus (HPV) infection, a rabies virus infection, a human alphaherpesvirus 1 infection, or a human alphaherpesvirus 2 infection. Further provided herein are methods, wherein the subject has, is suspected of having, or is at risk of developing a bacterial infection. Further provided herein are methods, wherein the bacterial infection is a *Mycobacterium* infection, a *Streptococcus* infection, a *Pseudomonas* infection, a *Salmonella* infection, a *Staphylococcus* infection, a *Neisseria* infection, a *Clostridium* infection, or a *Chlamydia* infection. Further provided herein are methods, wherein the subject has, is suspected of having, or is at risk of developing a parasitic infection, a fungal infection, or a yeast infection. Further provided herein are methods, wherein the immune response comprises increasing the titer of neutralizing antibodies to the antigen as compared to a subject that has not been administered the composition. Further provided herein are methods, wherein the immune response comprises increasing the amount of CD4+ and/or CD8+ positive T cells as compared to a subject that has not been administered the composition. Further provided herein are methods, wherein the subject is immunocompromised or immunosuppressed.

Provided here are dried compositions comprising: a lipid carrier, wherein the lipid carrier is a nanoemulsion comprising a hydrophobic core, and one or more lipids; one or more nucleic acid; and at least one sugar present in amount of (i) at least about 50% by weight of the dried composition, or (ii) present in an amount of least 50 mg. Further provided herein are compositions wherein the composition is lyophilized. Further provided herein are compositions wherein the composition is thermally stable at about 25 degrees Celsius. Further provided herein are compositions wherein the composition is thermally stable at about 45 degrees Celsius. Further provided herein are compositions wherein the composition is thermally stable at about −20 degrees Celsius. Further provided herein are compositions wherein the composition is thermally stable at about 2 degrees Celsius to about 8 degrees Celsius. Further provided herein are compositions wherein the composition is thermally stable for at least 1 week, at least 2 weeks, and/or at least 1 month. Further provided herein are compositions wherein the hydrophobic core comprises an oil. Further provided herein are compositions wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a caprylic/capric triglyceride, a triglyceride ester of saturated coconut/palmkernel oil derived caprylic and capric fatty acids and plant derived glycerol, dihydroisosqualene (DHIS), famesene and squalane. Further provided herein are compositions wherein the one or more lipids is selected from the group consisting of cationic lipids, anionic lipids, neutral lipids, and any combinations thereof. Further provided herein are compositions wherein the one or more lipids comprises a cationic lipid. Further provided herein are compositions wherein the cationic lipid is selected from the group consisting of 1,2-dioleoyloxy-3-(trimethylammonium)propane (DOTAP); 30-[N—(N',N'-dimethylaminoethane)-carbamoyl] cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N, Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis(2-hydroxydodecyl)amino)ethyl) (2-hydroxydodecyl)amino)ethyl)piperazin-1-yl)ethyl)azanediyl) bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein are compositions wherein the lipid carrier comprises at least one surfactant. Further provided herein are compositions wherein the at least one surfactant is selected from the group consisting of a hydrophobic surfactant, a hydrophilic surfactant, and any combinations thereof. Further provided herein are compositions wherein the hydrophobic surfactant comprises a sorbitan ester selected from the group consisting of sorbitan monolaurate, sorbitan monopalmitate, sorbitan monostearate, sorbitan tristearate, sorbitan monooleate, and sorbitan trioleate; and the hydrophilic surfactant comprises a polysorbate. Further provided herein are compositions wherein the lipid carrier has a z-average hydrodynamic diameter ranging from about 40 nm to about 150 nm, with an average polydispersity index ranging from about 0.1 to about 0.4. Further provided herein are compositions wherein the one or more nucleic acid is a DNA. Further provided herein are compositions wherein the one or more nucleic acid is a RNA. Further provided herein are compositions wherein the RNA is a self-replicating RNA. Further provided herein, are compositions wherein the hydrophobic core comprises one or more inorganic nanoparticles. Further provided herein are compositions, wherein the one or more inorganic nanoparticles is selected from the group consisting of a metal salt, metal oxide, metal hydroxide, metal phosphate, and any combinations thereof. Further provided herein are compositions wherein the one or more nucleic acid is incorporated or complexed with the lipid carrier to form a lipid carrier-nucleic acid complex. Further provided herein are compositions wherein the lipid carrier-nucleic acid complex is formed via non-covalent interactions or via reversible covalent interactions. Further provided herein are compositions wherein a molar ratio of the lipid carrier to the one or more nucleic acids, characterized by the nitrogen-to-phosphate (N:P) molar ratio, ranges from about 1:1 to about 150:1. Further provided herein are compositions wherein the at least one sugar is selected from the group consisting of sucrose, maltose, trehalose, mannitol, glucose, and any combinations thereof. Further provided herein are compositions wherein the at least one sugar is present in an amount of at least about 50, 60, 70, 80, 90, 100, 110, 120, 130, 140, 150, 160, 170, 180, 190, 200, 210, 220, 230, 240, 250, 260, 270, 280, 290, 300 or more mg. Further provided herein are compositions wherein the at least one sugar is present in an amount of 50 mg to 250 mg. Further provided herein are compositions wherein the at least one sugar is present in an amount of at least about 250 mg. Further provided herein are compositions wherein the sugar is present in amount of the composition by weight of at least 50, 55, 60, 65, 70, 75, 80, 85, 90, 95% or more. Further provided herein are compositions wherein the sugar is present in amount of the composition by weight of 80 to 98%, optionally 94 to 96%. Further provided herein are compositions wherein the sugar is present in amount of the composition by weight of about 95%. Further provided herein are compositions wherein the at least one sugar comprises sucrose. Further provided herein are pharmaceutical compositions, comprising a dried composition disclosed herein reconstituted in a suitable diluent and a pharmaceutically acceptable carrier. Further provided herein are pharmaceutical compositions wherein the diluent is aqueous. Further provided herein are pharmaceutical compositions wherein the diluent is water.

Further provided herein are kits, wherein the kits comprise a composition provided herein. Further provided herein are kits, wherein the kits comprise one or more surfactants.

EXAMPLES

Example 1. Immunogenicity of RSV Replicons

In order to determine the bioactivity of lipid carrier complexed with RSV repRNA and measure the in vivo generation of anti-RSV IgG, an assay was designed to first immunize 6-8 week old C57BL/6 and BALB/c female mice with the RSV repRNA and then analyze the anti-RSV target IgG levels in serum.

Initially, the formulation was prepared by combining the repRNA encoding RSV-F and G proteins (approximately 10 ng/μL, −80 degrees Celsius) and lipid carrier formulation (30 mg DOTAP/mL, 4° C.). 144 microliters of formulation was then mixed with 180 μL 40% sucrose and 36 μL 100 mM citrate and split into 2 mL tubes and inverted ten times to mix thoroughly.

Fifty microliters of the solution was injected intramuscularly into each mouse strain to yield an RNA dose of 2.5 μg on day 0, and blood was collected by retro-orbital eye bleed at day 14, 28, and 75. After collection, the blood was allowed to clot and the serum was collected and stored at −80 degrees Celsius until evaluation.

The blood collections were assessed with ELISA, using three recombinant proteins (1 μg/mL)—F Protein and G Protein with C-term His-Tag from Respiratory Syncytial Virus, B1, recombinant from RSV, and G Protein from RSV purified from HEp-2 cells. Data indicated that RSV-G protein-specific responses were induced in both C57BL/6 and BALB/c mice, while RSV-G A2 strain protein-specific responses were induced in only BALB/c mice (FIGS. 1 and 2A-2B). RSV-G B1 strain protein-specific responses were not observed, though this could have been due to an issue related to ELISA coating of RSV-G B1. RSV-G A2 protein responses were detected on the same ELISA plate, so a lack of response was not due to ELISA reagent failure.

Example 2: Lipid Carrier Innate Immune Response in Macrophages

Various repRNA/lipid carrier formulations were prepared and analyzed in order to assess lipid carrier's innate immune response in macrophages. repRNA/lipid carrier formulations studied include Fe-lipid carrier, High Fe-lipid carrier, Fe-lipid carrier miglyol, High Fe-lipid carrier miglyol, Alum-Lipid Carrier, Fe-lipid carrier solanesol (SLN), NLC and CNE. Protein expression and stimulation of TNF production in THP-1 macrophages were studied. ELISA assay was performed to evaluate the TNF-alpha protein level in the media using the Human TNF-alpha DuoSet ELISA by R&D Systems according to the manufacturer's protocol. The 96-well microplate was coated with anti-TNF capture antibody. The plate was blocked and then media samples were added directly without dilution. After addition of the biotinylated detection antibody, SA-HRP, and substrate, the absorbance was read at 450 nm on a Spectramax i3 plate reader.

Initially, the THP-1 monocytes were differentiated into macrophages using phorbol 12-myristate 13-acetate (PMA). The cells were then transfected with various formulations with Nano Luciferase encoding replicon RNA or a PAMP. The cell culture media was then assessed for NanoLuc expression via luciferase assay and TNF expression via ELISA. The formulations used in the study are described in Table 3.

TABLE 3

| Materials for Lipid Carrier Innate Immune Response Study | | |
|---|---|---|
| Description | Concentration | Location |
| repRNA encoding NanoLuc | 909 ng/ul | −80 degrees C. |
| NP-1: Fe-Lipid carrier | 30 mg DOTAP/ml | +4 degrees C. |
| NP-2: High Fe-Lipid carrier | 30 mg DOTAP/ml | +4 degrees C. |
| NP-3: Fe-Lipid carrier miglyol | 30 mg DOTAP/ml | +4 degrees C. |
| NP-4: High Fe-Lipid carrier miglyol | 30 mg DOTAP/ml | +4 degrees C. |
| NP-5: Alum-Lipid carrier | 30 mg DOTAP/ml | +4 degrees C. |
| NP-6: Fe-Lipid carrier solanesol (SLN) | 30 mg DOTAP/ml | +4 degrees C. |
| NP-7: NLC | 30 mg DOTAP/ml | +4 degrees C. |
| NP-8: CNE | 4 mg DOTAP/ml | +4 degrees C. |

Eleven treatment groups were prepared. Eight of those groups were NanoLuc repRNA groups, with 600 ng repRNA dose per well was prepared using the Fe-Lipid carrier, High Fe-Lipid carrier, Fe-Lipid carrier miglyol, High Fe-Lipid carrier miglyol, Alum-Lipid carrier, Fe-Lipid carrier solanesol (SLN), NLC, and CNE formulations. Two of those groups were PAMP groups, with 200 ng dose per well prepared using the Fe-Lipid carrier and Fe-Lipid carrier miglyol formulations. The untreated group did not have NanoLuc repRNA or the PAMP.

The various formulations were prepared by diluting NanoLuc repRNA to 8 ng/μL in 2.2 mL of RNAse-free water and diluting PAMP RNA to 2.67 ng/μL in 600 μL of water. The Lipid Carrier and RNA master mix was complexed by adding 250 μL of each diluted formulation with 250 μL of diluted RNA and mixed by pipetting up and down.

Cell transfections were carried out by seeding $7\times10^5$ THP-1s per well in a 24 well plate. 80 μM of PMA per well was added and incubated at 37 degrees Celsius. The next day, the PMA-containing media was removed and replaced with cRPMI for an hour before transfection. The samples were then serially diluted in Opti-MEM to make a 10-point 1.5-fold dilution series starting at 0.45 ng/μL. The culture media was then removed from the plates by pipetting. 450 μL of Opti-MEM and 150 μL of the complexed formulation was added to the plate in duplicate. The empty wells were given 450 μL of Opti-MEM only. After four hours, the samples were removed from the plate by pipetting and replaced with 500 μL of growth media. The plate was then incubated overnight at 37 degrees Celsius. The growth media was harvested the next day and stored at −80 degrees Celsius. Downstream assays were conducted.

The luciferase assay was performed by first diluting the Nano-Glo luciferase assay reagent 1:50 in buffer. 25 μL of supernatant was removed and mixed with 25 μL of Nano-Glo reagent in a 96-well plate and incubated at room temperature for 3 minutes. The luminescence was read.

ELISA assay was performed to evaluate the TNF-alpha protein level in the media using the Human TNF-alpha DuoSet ELISA by R&D Systems according to the manufacturer's protocol. The 96-well microplate was coated with anti-TNF capture antibody. The plate was blocked and then media samples were added directly without dilution. After addition of the biotinylated detection antibody, SA-HRP, and substrate, the absorbance was read at 450 nm on a Spectramax i3 plate reader.

Figure 4A:
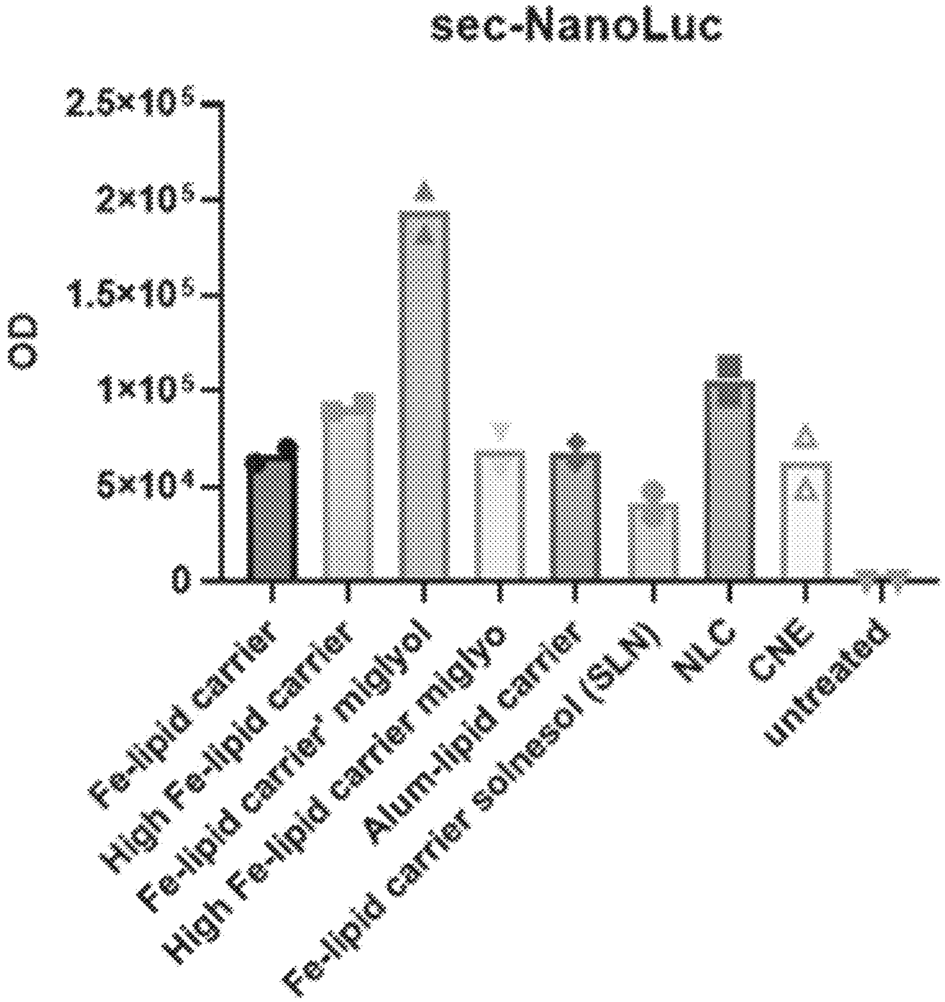
FIGS. 4A-4B show the increased protein production induced by the Miglyol lipid carrier formulation, NP-3.
Figure 4B:
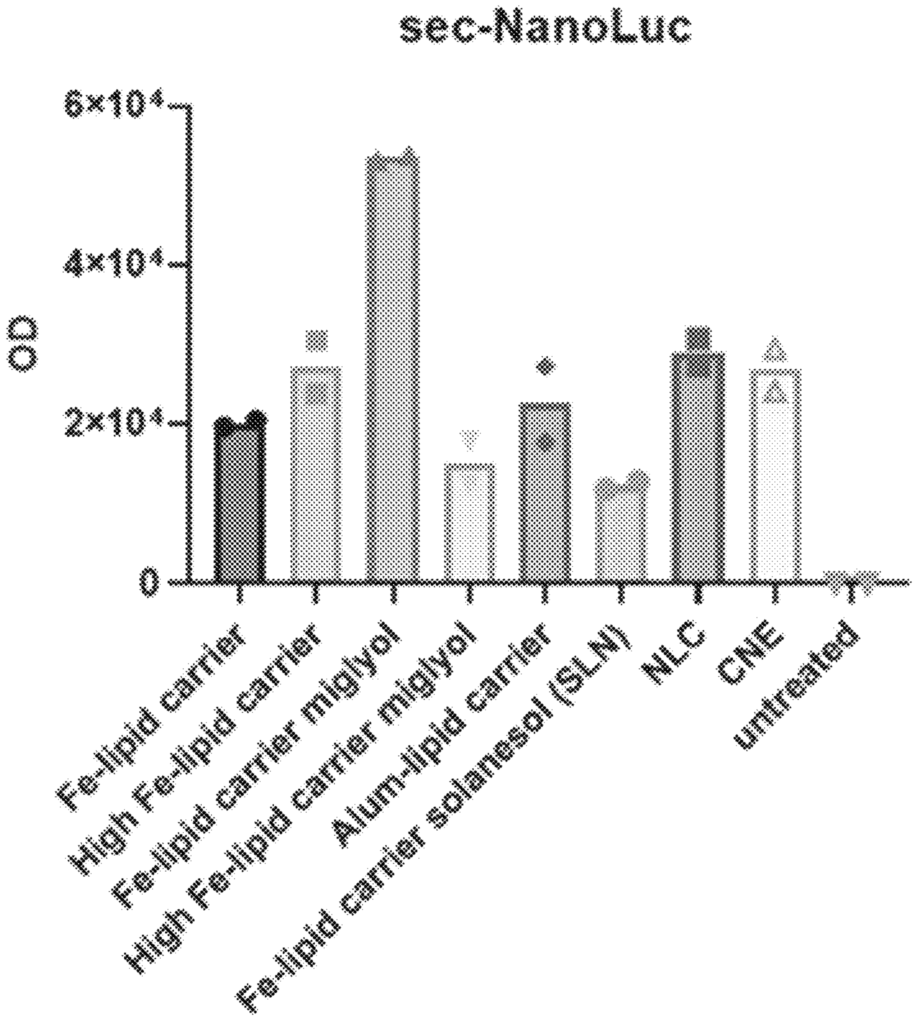

The studies described in herein demonstrate that Miglyol lipid carrier formulation induced higher protein production off the replicon, as shown in the first assay in FIG. 4A and in the second assay in FIG. 4B. A reduced innate immune response was detected, as measured by TNF-alpha secretion and is shown in the first assay in FIG. 5A and in the second assay in FIG. 5B.

Protein expression levels from the first assay in FIG. 4A and the second assay in FIG. 4B were performed using a luciferase assay by first diluting the Nano-Glo luciferase assay reagent 1:50 in buffer. 25 μL of supernatant was removed and mixed with 25 μL of Nano-Glo reagent in a 96-well plate and incubated at room temperature for 3 minutes. The luminescence was read using a luminometer.

Figure 5A:
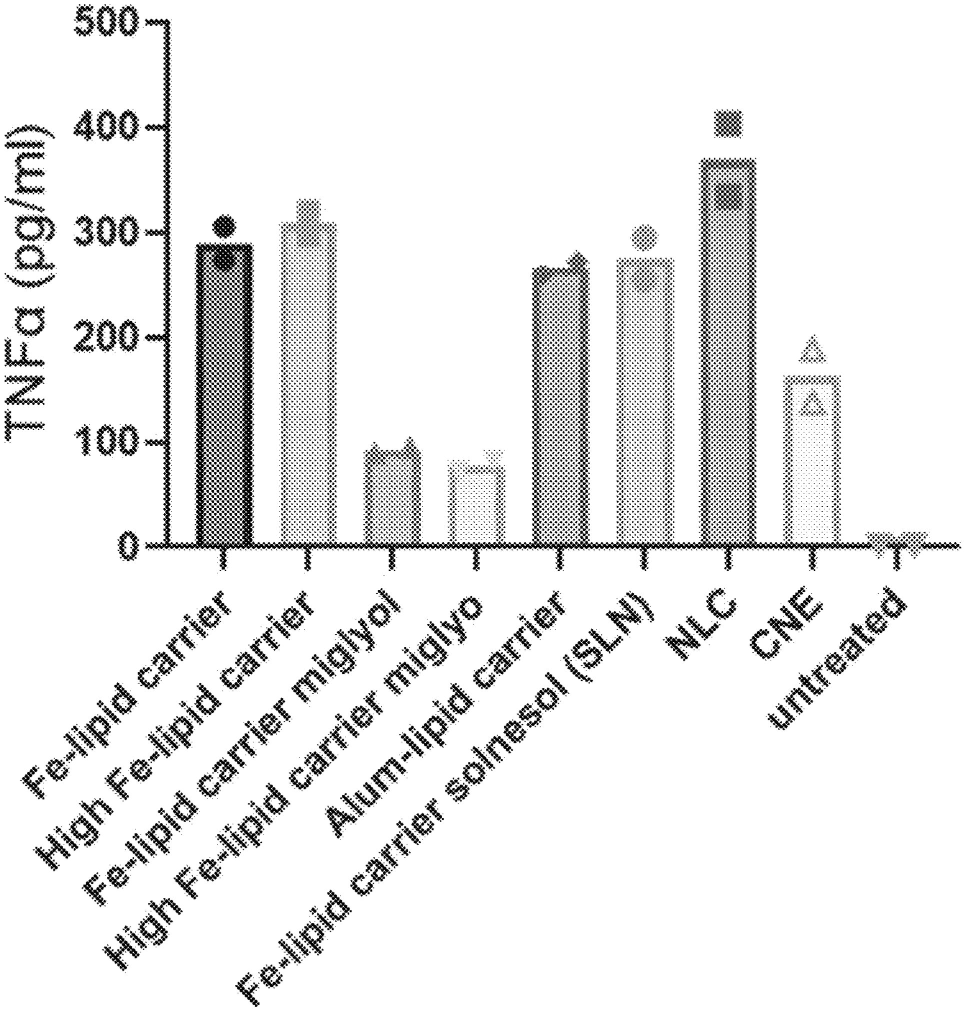
FIGS. 5A-5B show the decreased immune response induced by the Miglyol lipid carrier formulation, NP-3.
Figure 5B:
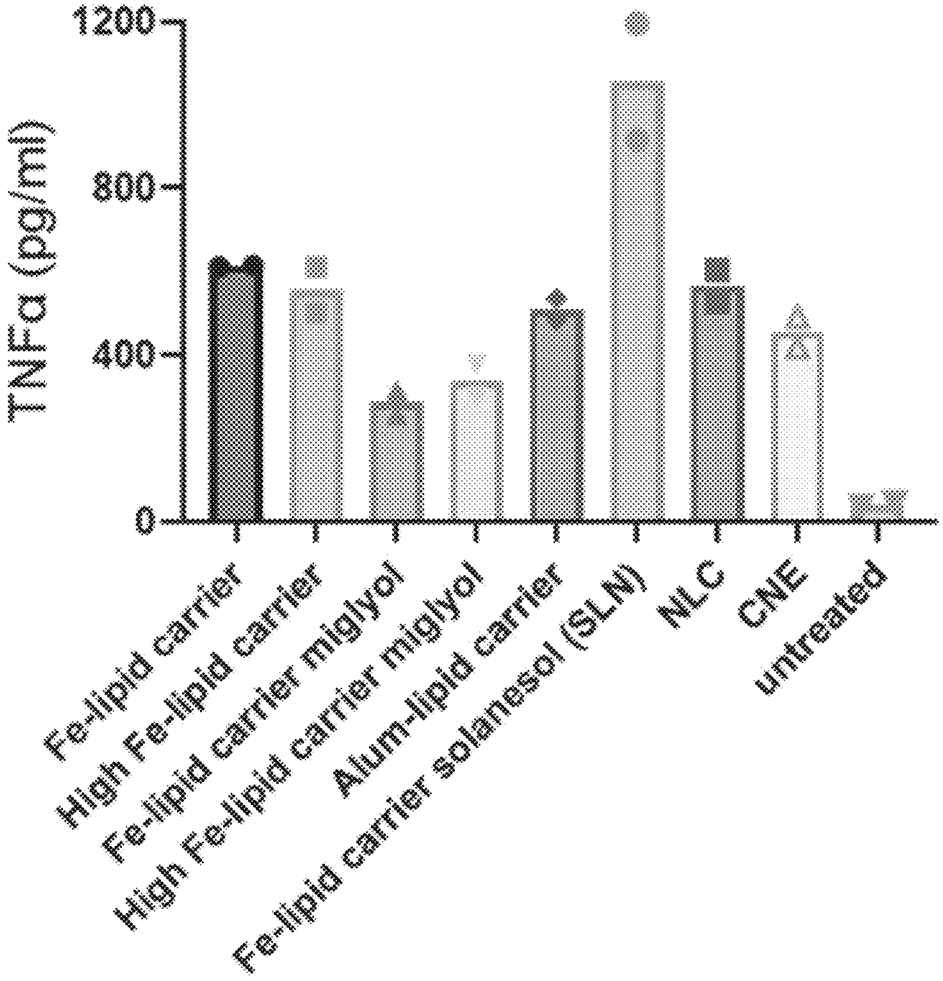
Figure 6A:
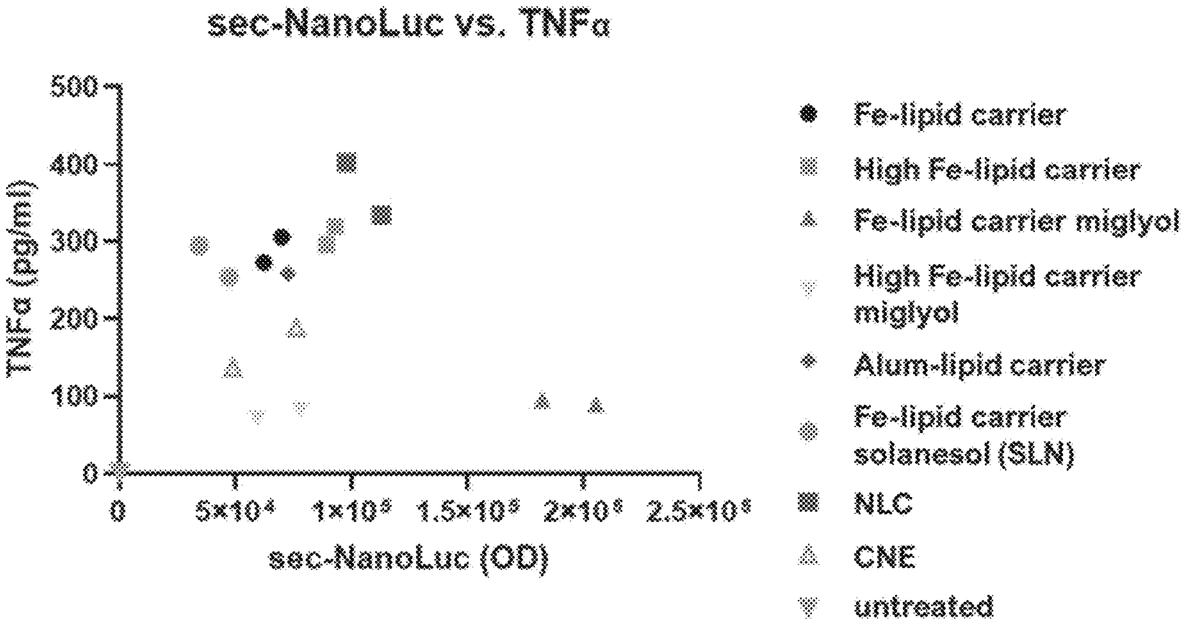
FIGS. 6A-6B show the correlation between enhanced protein production and low TNF (e.g., TNF alpha) stimulation observed with NP-3 as a result of the first and second assays.
Figure 6B:
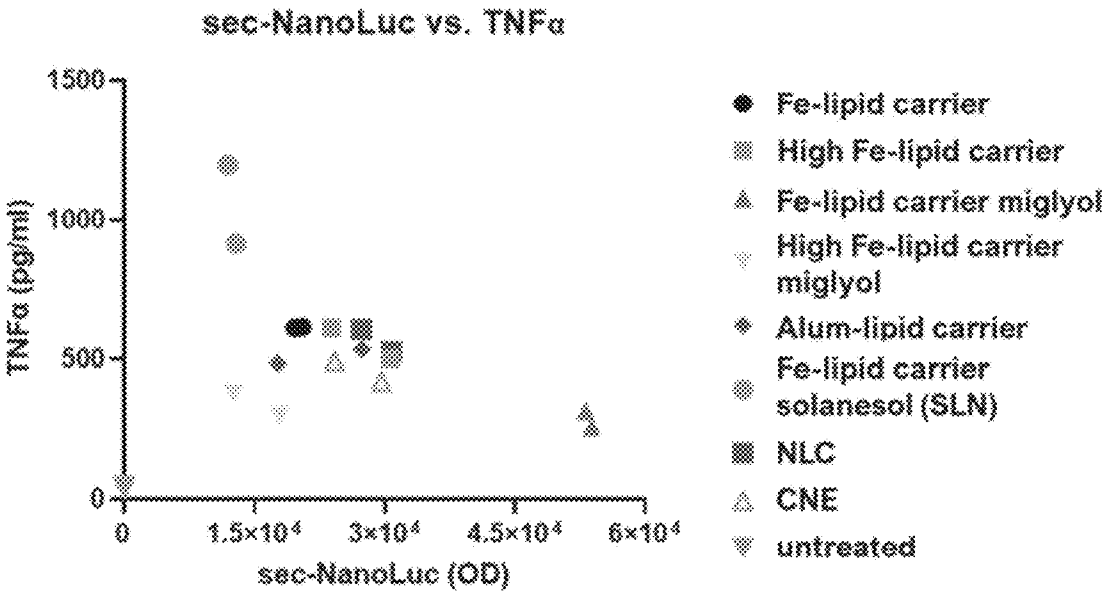

TNF-alpha protein levels in the media from the first assay in FIG. 5A and the second assay in FIG. 5B were determined using the Human TNF-alpha DuoSet ELISA by R&D Systems according to the manufacturer's protocol. The 96-well microplate was coated with anti-TNF capture antibody. The plate was blocked and then media samples were added directly without dilution. After addition of the biotinylated detection antibody, SA-HRP, and substrate, the absorbance was read at 450 nm on a Spectramax i3 plate reader. The correlation between enhanced protein production and low TNF-alpha stimulation was observed with Miglyol lipid carrier formulation, as shown in the first assay in FIG. 6A and in the second assay in FIG. 6B. The solanesol induced slightly lower protein production, but potentially higher TNF production, shown in the first assay in FIG. 6A and in the second assay in FIG. 6B. The correlation data from Assay 1 shown in FIG. 6A are derived from the data represented in FIG. 4A and FIG. 5A, and the correlation data from Assay 2 shown in FIG. 6B are derived from the data represented in FIG. 4B and FIG. 5B.

Example 3: Manufacture and Stability of NP-1

Manufacture of NP-1. NP-1 particles comprise 37.5 mg/ml squalene (SEPPIC), 37 mg/ml Span® 60 (Millipore Sigma), 37 mg/ml Tween® 80 (Fisher Chemical), 30 mg/ml DOTAP chloride (LIPOID), 0.2 mg Fe/ml 12 nm oleic acid-coated iron oxide nanoparticles (ImagionBio) and 10 mM sodium citrate dihydrate (Fisher Chemical). 1 ml of 20 mg Fe/ml 12 nm diameter oleic acid-coated iron oxide nanoparticles in chloroform (ImagionBio, lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams span 60, and 3 grams DOTAP were added to produce the oil phase. The oil phase was sonicated for 45 minutes in a 65° C. water bath. Separately, the aqueous phase was prepared by dissolving 19.5 grams Tween 80 in 500 ml of 10 mM sodium citrate buffer prepared in nuclease free water. 92 ml of the aqueous phase was transferred to a separate glass bottle and heated to 65° C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.25 polydispersity index (PDI). The microfluidized NP-1 was terminally filtered with a 200 nm pore-size polyethersulfone (PES) filter and stored at 2-8 degrees C. Iron concentration was determined by ICP-OES. DOTAP and Squalene concentration were measured by RP-HPLC.

Manufacture of NP-3. NP-3 particles comprise 37.5 mg/ml Miglyol 812 N (IOI Oleo GmbH), 37 mg/ml Span® 60 (Millipore Sigma), 37 mg/ml Tween® 80 (Fisher Chemical), 30 mg/ml DOTAP chloride (LIPOID), 0.2 mg Fe/ml 15 nm oleic acid-coated iron oxide nanoparticles (ImagionBio) and 10 mM sodium citrate dihydrate (Fisher Chemical). 1 ml of 20 mg Fe/ml 15 nm diameter oleic acid-coated iron oxide nanoparticles in chloroform (ImagionBio, Lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams span 60, and 3 grams DOTAP were added to produce the oil phase. The oil phase was sonicated for 45 minutes in a 65 degree C. water bath. Separately, the aqueous phase was prepared by dissolving 19.5 grams Tween 80 in 500 ml of 10 mM sodium citrate buffer prepared in nuclease free water. 92 ml of the aqueous phase was transferred to a separate glass bottle and heated to 65° C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized NP-1 was terminally filtered with a 200 nm pore-size polyethersulfone (PES) filter and stored at 2-8° C. Iron concentration was determined by ICP-OES. DOTAP concentration was measured by RP-HPLC.

iii. Manufacture of NP-30. A lipid carrier without providing inorganic core particles in the core was generated having 37.5 mg/ml squalene (SEPPIC), 37 mg/ml Span® 60 (Millipore Sigma), 37 mg/ml Tween® 80 (Fisher Chemical), 30 mg/ml DOTAP chloride (LIPOID) and 10 mM sodium citrate. To a 200 ml beaker 3.75 grams squalene, 3.7 grams span 60, and 3.0 grams DOTAP were added to produce the oil phase. The oil phase was sonicated for 45 minutes in a 65 degrees Celsius water bath. Separately, the aqueous phase was prepared by dissolving 19.5 grams Tween 80 in 500 ml of 10 mM sodium citrate buffer prepared in nuclease free water. 96 ml of the aqueous phase was transferred to a separate glass bottle and heated to 65 degrees Celsius for 30 minutes. The oil phase was mixed with the 96 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized NP-30 without inorganic core formulation was terminally filtered with a 200 nm pore-size polyethersulfone (PES) filter and stored at 2-8 degrees C. DOTAP and Squalene concentration were measured by RP-HPLC.

Figure 2:
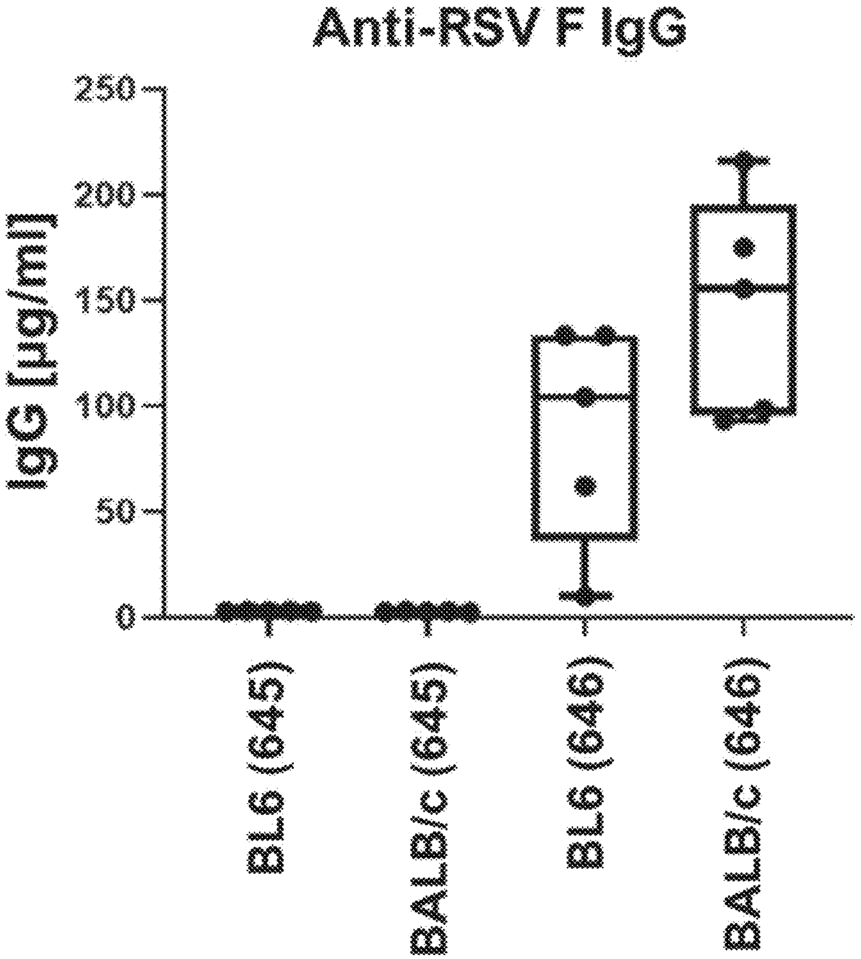
FIG. 2 shows anti RSV-F IgG levels in C57Bl/6 and BALB/c mice injected IM with 2.5 μg RSV repRNA formulated with a lipid carrier. Blood was collected 28 days after immunization, serum prepared and assessed by ELISA. Replicon number is indicated in parentheses (645 encodes for RSV-G and 646 encodes for RSV-F). Each point represents data from an individual animal, with the whiskers representing minimum to maximum, the box representing the interquartile range and the horizontal bar depicting the median. X-axis: repRNA RSV antigen. Y-axis: Immunoglobulin G (IgG) concentration (micrograms/milliliter).
Figure 3A:
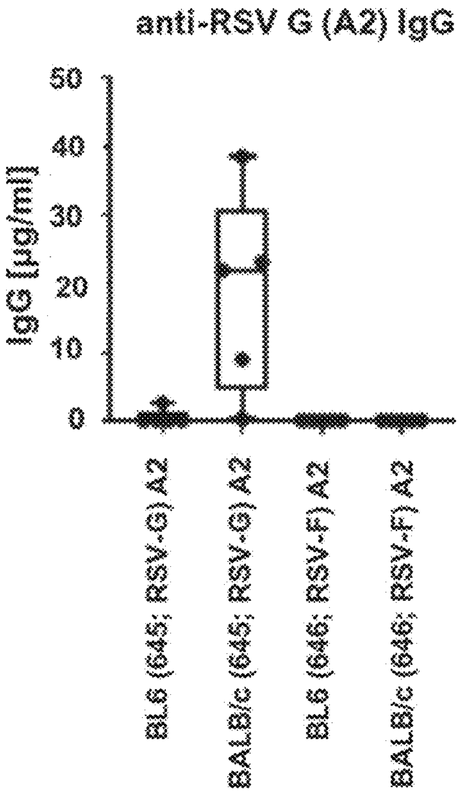
FIGS. 3A-3B show anti-G IgG levels in C57Bl/6 and BALB/c mice injected IM with 2.5 μg RSV repRNA formulated with lipid carrier. Blood was collected 28 days after immunization, serum prepared and assessed by ELISA. Replicon number is indicated in parentheses. Each point represents data from an individual animal, with the whiskers representing minimum to maximum, the box representing the interquartile range and the horizontal bar depicting the median. X-axis: repRNA RSV antigen. Y-axis: Immunoglobulin G (IgG) concentration (micrograms/milliliter).
Figure 3B:
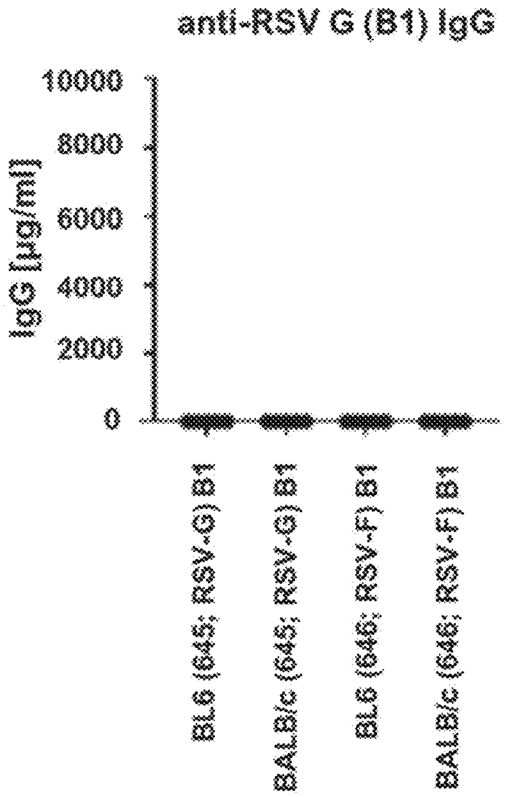

Stability. A nanoparticle according to NP-1 was placed into a stability chamber at the indicated temperatures. The stability was determined by particle size measurement using dynamic light scattering. The results show that the NP-1 formulation formed a stable colloid when stored at 4, 25 and 42 degrees Celsius. Time measurements were taken over 4 weeks. As shown in FIG. 2, the range of nanoparticle size was about 50-100 nm in diameter, and closer to 40-60 nm in diameter for the 4 and 25 degrees Celsius conditions over time.

Example 4: Additional Nanoparticle Formulations

Additional nanoparticle formulations are produced according to the following tables (Table 4 and Table 5). The mRNA comprises a sequence encoding for an influenza viral antigen or a VZV viral antigen (SEQ ID NOS: 3-5, and 38-43, 47).

TABLE 4 mRNA Vaccine Formulation

| | Dosage form: Solution for Injection for IM route of administration | | |
|---|---|---|---|
| | Each 0.5 ml Vial Contains: | Quantity | Concentration (mg/ml) |
| Composition: | mRNA | 25 mcg | 0.05 |
| | DOTAP | 0.75 mg | 1.5 |
| | Iron Oxide Nanoparticles | 0.005 mg | 0.01 |
| | Squalene | 0.94 mg | 1.88 |
| | Sorbitan Monostearate | 0.93 mg | 1.86 |
| | Polysorbate 80 | 0.93 mg | 1.86 |
| | Sucrose IP | 50 mg | 100 |
| | Citric Acid Monohydrate | 1.05 mg | 2.1 |
| | Water for Injection | q.s. to 0.5 ml | |

TABLE 5

Lyophilized mRNA Vaccine Formulation

| | Dosage form: Lyophilized powder | | | |
|---|---|---|---|---|
| | Each 5 dose vial contains: | Quantity | Concentration (mg/ml) | Approximate dry weight % |
| Composition: | mRNA | 50 mcg | 0.02 | 0.02 |
| | DOTAP | 1.5 mg | 0.6 | 0.57 |
| | Squalene | 1.88 mg | 0.752 | 0.72 |
| | Sorbitan Monostearate | 1.86 mg | 0.744 | 0.71 |
| | Polysorbate 80 | 1.86 mg | 0.744 | 0.71 |
| | Sucrose IP | 250 mg | 100 | 95.3 |
| | Citric Acid Monohydrate | 5.25 mg | 2.1 | 2 |
| | Water for Injection (for reconstitution) | 2.5 ml | | |

Example 5: Self-Replicating mRNA Construct

A plasmid encoding a T7 promoter followed by the 5' and 3' UTRs and nonstructural genes of Venezuelan equine encephalitis virus (VEEV) strain TC-83 was generated using standard DNA synthesis and cloning methods. The VEEV replicon mRNA backbone is set forth in SEQ ID NO: 34.

Example 6: Varicella-Zoster Virus (VZV) RNA Vaccine Compositions

Six constructs were designed for self-replicating (repRNA) vaccines against Varicella-Zoster virus (VZV) encoding various combinations of glycoprotein E (gE) and glycoprotein I (gI). VZV gI was designed to include either Thosea asigna virus 2A (T2A) ribosomal skipping peptide or an internal ribosomal entry site (IRES) to control for co-expression of the downstream gE. Each self-replicating RNA construct is summarized in Table 6 and illustrated in FIG. 7A.

TABLE 6

VZV-repRNA constructs

| repRNA Construct Name | Description | RNA Sequence (SEQ ID NO:) |
|---|---|---|
| VZV-FL-gE | full length glycoprotein E containing the transmembrane sequence of gE | SEQ ID NO: 38 |
| FL-gI | Full length glycoprotein I | SEQ ID NO: 39 |
| VZV-N term trunc gE | gE with a truncation of the N-terminus | SEQ ID NO: 40 |
| FL-gI-T2A-gE | full length gI-Thosea asigna virus 2A (T2A)-gE | SEQ ID NO: 41 |
| FL-gI-IRES-gE | full length gI-ribosomal skipping peptide or an internal ribosomal entry site (IRES)-gE | SEQ ID NO: 42 |
| Secreted-gE | gE without the transmembrane sequence | SEQ ID NO: 43 |

Baby hamster kidney epithelial cells (BHKs) were transfected with 4 micrograms (μg) of each corresponding RNA using lipofectamine 2000 as a delivery vehicle. Cell lysates and cell supernatants were tested via Western blot and probed with anti-VZV-gE antibody at a 1:2000 dilution (FIG. 7B). Supernatants from BHKs transfected with Secreted-gE, VZV-FL-gE, and VZV-N term trunc gE expressed anti-VZV-gE antibodies.

Figure 7A:
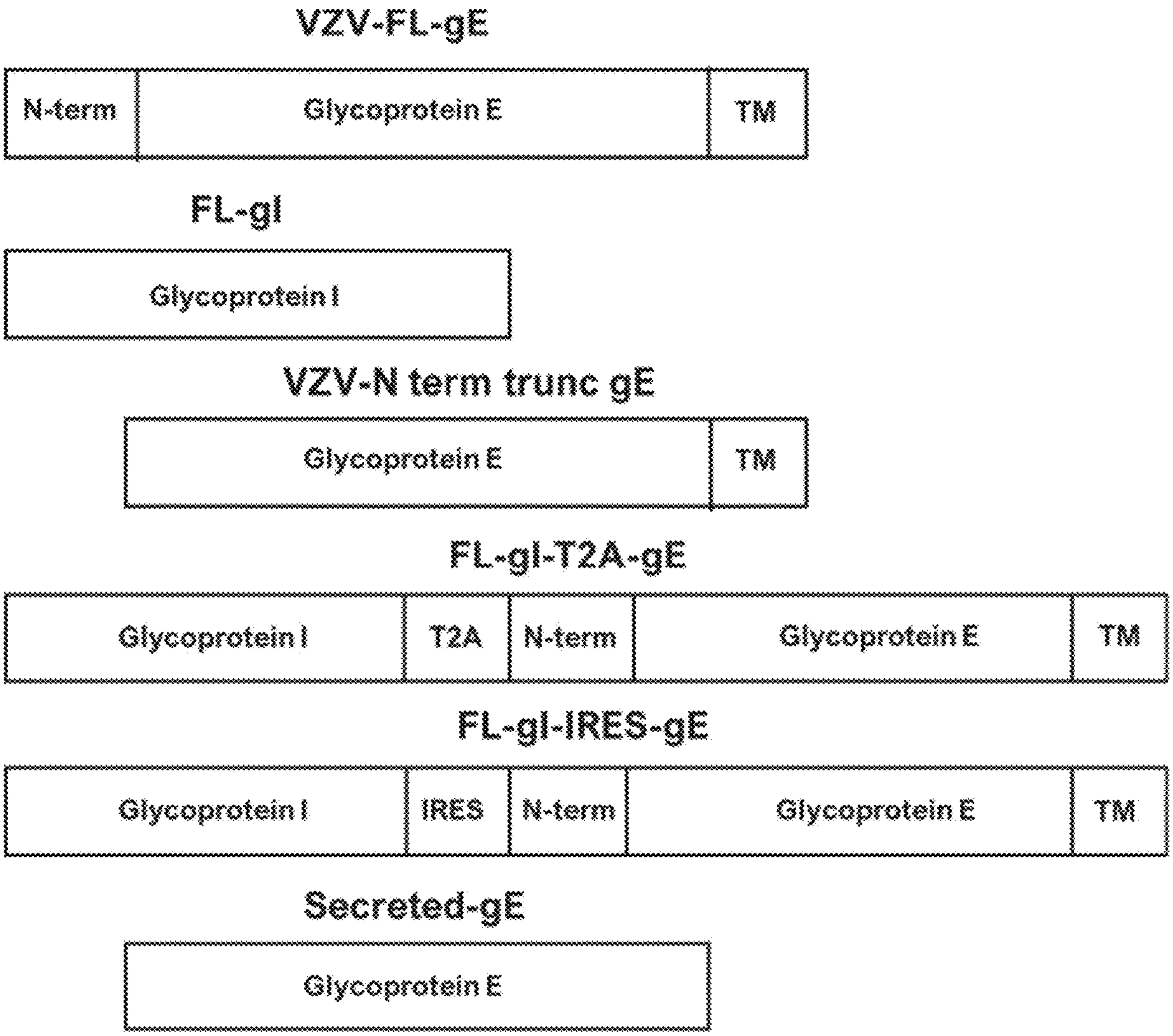
FIGS. 7A-7C show the effect of VZV repRNAs on antibody titers and expression.
Figure 7B:
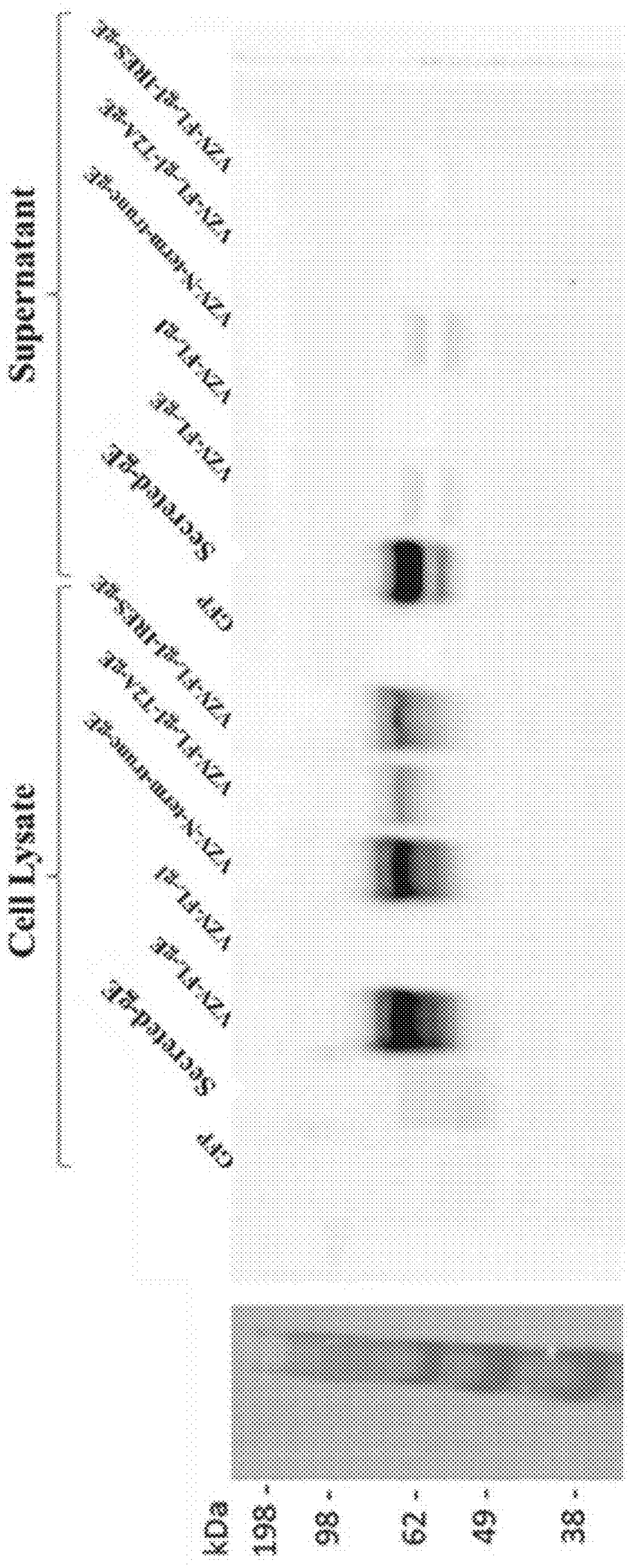
Figure 7C:
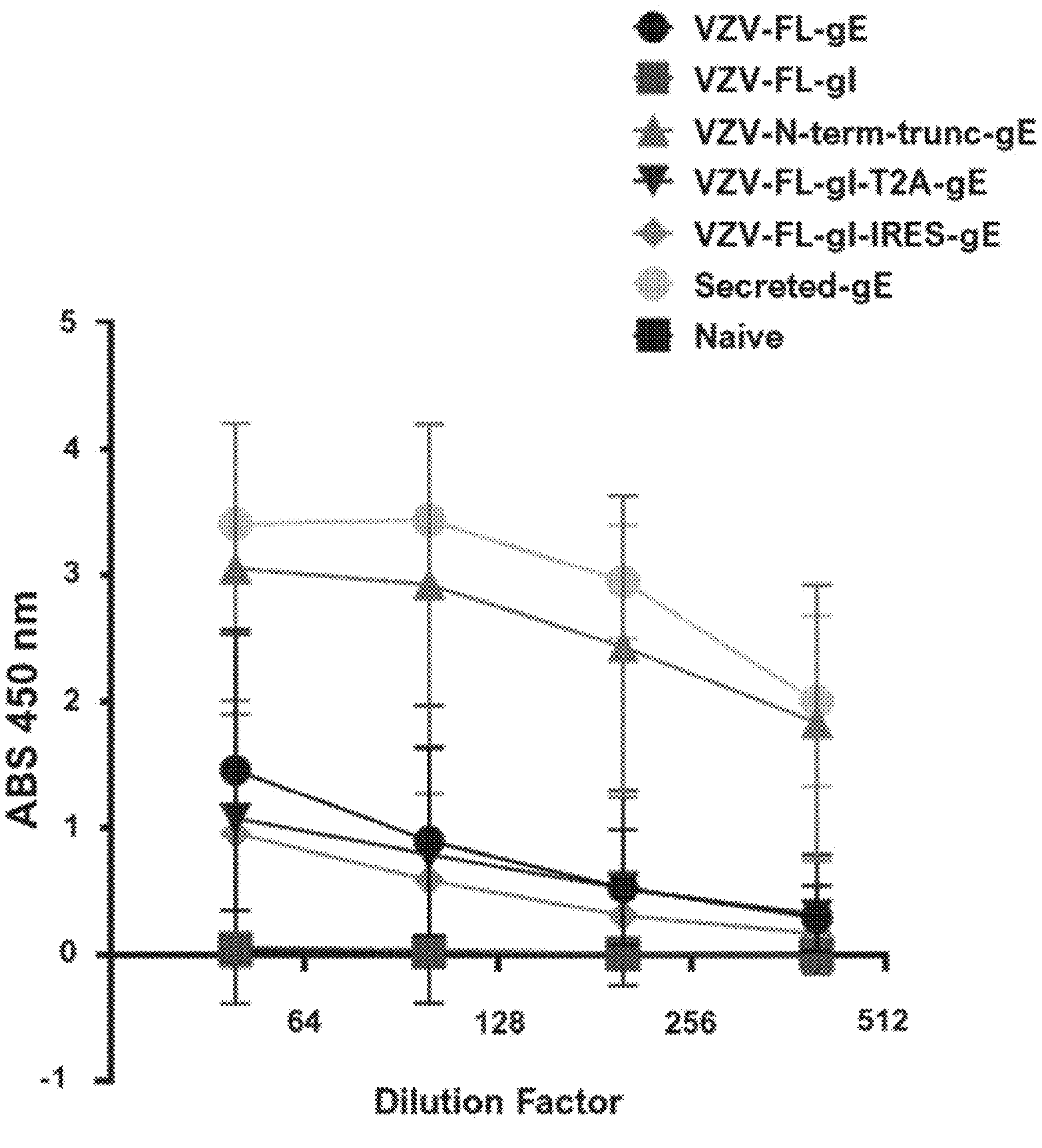

Six-week-old female C57BL/6 mice (n=5 mice per group) were immunized intramuscularly in the hind leg with 10 μg of repRNA encoding for a Varicella-Zoster virus (VZV) antigen (Table 6, FIG. 7A). Sera was collected 14 days post vaccination. Additionally, mice were immunized with a positive control containing repRNA encoding the gE without the transmembrane sequence, resulting in only soluble gE. Sera antibody titers were measured via ELISA against soluble VZV gE post vaccination (FIG. 7C). Mice treated with RNA encoding gE with a truncation of the N-terminus (VZV-N term trunc gE) produced increased antibody titers as compared with control mice or those immunized with the full length gE.

```
SEQUENCES
RSV-G Antigen Encoding RNA Sequence
                                                                 SEQ ID NO: 1
auguccaaaaauaaagaccagcgaacggccaagacucuggagaggacuugggauacccugaaucaucuguuguuuau uucaaguugccuuuauaaauugaaucucaaauccgucgcgcaaaucacgcugagcauacucgcaaugauuaucucaa cuuccuugauaauugccgccauaaucuucauugcaagugcaaaucauaaagugacuccuacaaccgcaauaauacag gacgcgaccagccaaauuaagaacacgacucccacguaucucacccaaaauccccaacucggaauuagcccaaguaa uccgucagagauuacuucacaaaucaccaccauacuggcgagcacaacuccaggcguaaaauccacccuccaaucua cuaccgucaagacuaaaaauaccacuacuacucagacacaaccuaguaaaccuacgacuaagcagcgccagaauaaa cccccaagcaaaccaaacaacgacuuccauuuugaaguuucaacuucgugccuuguucuaucugcucuaauaaucc aacaugcugggccaucugcaagcgcauuccgaauaagaaacccgguaagaaaacuacaacgaaaccuaccaagaagc cuacccugaaaacgacaaagaaagacccgaaaccgcaaacaaccaaaaguaaagaagugcccacaacuaaacccaca gaagaaccaacgauaaacacgaccaaaaccaacauaauaacuacgcugcuuaccagcaacacgacaggcaacccgga auugaccagucagauggaaacuuuucauucaaccagcagcgaagguaauccaaguccuagucaggugucuacgacau cugaauauccaucucagccuaguuccccuccgaacacgccgcgccagugauaa RSV-F Antigen Encoding RNA Sequence
                                                                 SEQ ID NO: 2
auggagcugcucauccuuaaagcgaaugcuauaacuacuauacuuacagcuguaaccuuuugcuucgccucuggcca aaacauuacugaggaguuuuaucaauccacuugcagcgcagucucaaaggauaucugucagcauugcgcaccgggu gguacaccagcguuaucacuaucgagcuuuccaacauuaaagagaauaaguguaacggcacagacgcgaaagucaaa cucauuaagcaagaacuugauaaauacaaaaaugcaguuacugaacuucaguugcucaugcaaucaaccccagcaac gaacaauagggccaggagagaauugccgagguuuaugaacuacacacuuaauaacgcuaaaaagacuaacguuacgc ucucuaagaagcggaagcgcagguuucucggguuccuucugggguuggcagugcaauagcauccggcgucgcggua ucaaaggugcuucaucuugaaggagaaguuaacaaaaucaaaagcgccuugcuuucaacuaauaaggcaguaguauc auugucuaacggugucagcgucuugacuuccaagguuuuggauuugaaaaacuauaucgacaaacaacuucucccga
```

-continued ucguuaacaagcagucaugcaguaucuccaacaucgaaaccgucaucgaauuccaacagaaaaacaauagacugcuu gaaauuacuagagaguuuucagugaacgcuggcguuaccacuccgguauccacuuauaugcucacuaauagcgaacu gcugucucugauaaaugacaugccaauaacuaacgaccagaagaaacuuaugaguaacaacguccagaucgugagac agcaaucauauagcauuaugagcauaauuaaggaggagguccuugcauacguaguccagcucccacuguacgggguu aucgacacgccauguuggaagcuucauacuucccccuugugcaccacgaacacgaaggaagggucuaacauuugucu cacgcgcacugaucggggggugguacugugacaacgccgggucagugucauuuuucccucaggccgagaccugcaagg uccaaucaaaccggguauucugugauacuaugaacucccugacucugccuucugaaguuaaccuguguaauguagau auauucaauccuaaauacgacugcaagauaaugaccagcaaaaccgacguguccucaucugucaucacuucccuugg ugcuauaguaagcugcuauggcaaaacgaaaugcaccgcgaguaauaaaaaucgcgguaucaucaagacauuuagua acggcugcgauuauguuuccaacaaagguguugacaccguaucuguggggaauacccuguauuacguaaauaagcag gaagggaaaucucucuacgugaaggggaaccgauaaucaacuuuuaugacccgcugguuuuuccguccgacgaauu ugacgcgaguaucucccaagucaacgagaaaauuaaccaaagccucgcguucauaagaaaauccgaugagcugcugc auaauguaaacgcgggcaaaucaacuaccaacaucaugauuacaacaauaaucaucgugauaaucgugauccugcuu ucacuuaucgcugucgggcuucuucucuauuguaaggcccggaguacucccgugaccuugucuaaggaucagcucuc agguaucaacaauauugcauucagcaauuga Influenza H3 Antigen Encoding RNA Sequence

SEQ ID NO: 3

Augaaaacaauuaucgcucucaguuauauuuucugccuuccuuuggggcaagacuugccgggcaaugauaauaguac agcgacucucugucucggacaccacgcaguaccgaacggcacacuugugaagacaaucacagacgaucaaaucgaag ugacgaaugcaacagagcuuguucaaucaucaucuaccggcaaaaucugcaauaauccgcauagaauccuugaugga aucgacugcacccugauugacgcacuguugggagauccucauugcgauguguuucagaaugagacaugggaccuuuu ugucgagaggagcaaagcguuuuccaacugcuacccguaugacgugccugauuacgcgucacuccgcucacuuguag caucaagcgguacucuggaguucaucaccgaaggauucaccuggacgggcguaacucagaacggcgguucuaacgca uguaagagggggccaggguccggcuucuucucacggcucaacugguugacuaagucugguucaacauacccgguccu uaacguuacaaugccgaauaaugacaacuuugauaaacucuacaucuggggcauucaccauccauccacaaaucaag aacagacaaguuuguacguucaggcgucagggcgcguuaccgugaguacaagaagaucacagcaaacaauuauaccc aauauugggucccgacccuggguaagaggacuguccucucgcaucuccauauacuggaccauugucaaaccgggcga cguccugguuaucaauaguaauggaaaccuuauugcuccgcgcggcuauuucaaaaugcgaacuggaaagucaagua uaaugcgcucagacgcaccgaucgauacuuguaucagugaaugcaucaccccuaacggguccauaccgaacgauaag cccuuccagaaugugaauaaaaucacguauggagcaugccccaaauacgugaagcaaaacacccucaaguuggcuac ggguaugcgcaacgucccagaaaaacaaacgcgaggcuuguuuggggcgauagcagguuuuaucgagaacggcuggg aaggaaugaucgauggguggu acggcuuucgccaucaaaacucagaaggaacugggcaggccgcagaucuuaagucu acgcaagcggcgauagaucaaauuaauggcaaguugaauagggugauagagaagacgaacgagaaguuccaucaaau agagaaagaauucagugaaguagaggggcgaauucaggauuuggaaaaauaugucgaggauacuaagaucgaccugu ggagcuauaacgcagagcuucugguagcacuugagaaccagcauacuauugaucucaccgauuccgagaugaacaag cuuuuugagaagaccaggagacaguugcgcgagaaugccgaagaaaugggguaacgguuguuuuaagauuuaucacaa augugacaacgcguguauugaguccauuaggaaugguacauaugaucacgauguguaucgcgaugaagcacuuaaca aucgguuccaaauaaagggcguggagcucaagagugggguauaaagauuggauccucuggaucucauucgcgauuucc ugcuuccuccugugcguugucuugcugggcuuuauuaugugggcaugucagagagguaacauccggugcaacauaug uaucugauaa -continued Varicella-Zoster Virus (VZV) Ig E Antigen Encoding RNA Sequence

SEQ ID NO: 4 cgccaccauguucuaugaagcuuugaaggccgaacuuguauacacccgagccgugcaugguuuccgcccgagagcgaac ugcgucguacugucagauuacauccccagagucgcgugcaacaugguacgguuaauaagcccgugguggggugcuga uggguuuugggauaaucaccggaacucugcgcaucacaaauccuguaagagcgucagugcugagguaugacgauuucca cauagacgaggacaagcuggauaccaauuccguuuacgaaccauauuaucacuccgaucacgccgaauccagcugggua aaucgaggagaguccucacggaaggcauacgaccauaacuccccauauauauggccucgcaaugauuaugacggauucc uggaaaacgcccaugagcaccacggcguuuauaaccagggucgcgguaucgauucuggggaaagguugaugcaaccaac ucagauguccgcucaggaagauuuggggaugacaccggaauccaugugauaccuacacucaauggugaugaucgacac aaaauuguaaacguggaccagaggcaauacggggacguuuuuaagggagaccugaauccaaaaccacaaggacaacgac ucaucgagguuucuguagaagaaaaccauccguuuacgcuccgcgcccccauacagcgcauauauggcgugcgcuauac ggagaccuggucuuuucuccccagucugacaugcacuggugaugcagcuccagcaauucagcacauaugucucaagcau accaccuguuuccaagauguaguaguggauguggauugcgccgaaaacacgaaagaagaccagcuugccgagauuucau accgguuucaaggaaaaaaagaagccgaccagccguggauaguagugaauacguccacgcucuucgaugaacuggaauu ggacccuccugaaauugaacccggaguccugaaaguuuugcggacugagaaacaguaucucggugugacaucuggaau augaggggcagugauggaacaagcacauacgcgaccuuucuggugacauggaaaggugacgaaaagacuagaaacccaa ccccagcagugacccccccaaccuagaggugcugaguuccacauguggaauuaccacucccauguauucucugucggaga caccuucagcuuggcgaugcaccuccaauacaagauccaugaagccccguucgaccucuuguuggaguggcucuacgua ccaauagacccuaccugucaaccaaugaggcuuuacucuacaugccuuuaccacccaaacgcaccacaaugucuuucuc auaugaauagcgguuguacauuuacaucuccccaucucgcgcaaagagucgcgaguacaguuuaccaaaauugugagca ugcggacaauuacacagcauauugucuugggaucucccacauggagcccucuuuugggcuuauacuucacgacggggu acaacgcuuaaguucgucgauacgccagaaucccucucuggcuuguauguauucgugguuuauuuuaacggucacguug aggcuguggccuauacuguuguuagcacuguagaccacuuuguuaacgccauagaagagagggguucccgcccaccgc uggccagccaccggccacaacgaagccuaaagagauuacgccggugaaucccggcacaaguccccuuauccgguacgcc gcauggacaggaggacuggcggccgucguccuccuuugucugguuauauuccuuauaugcacggcaaagcgaaugcggg uuaaggcuuaccgaguggauaaaucuccauauaaucagagcauguauuacgcagggcucccuguggacgacuuugagga uagcgaguccacggauacagaagaggaauuuggaaacgccaucggugggagccauggagggucaucuuacaccguuuac auugacaaaacuagauga Varicella-Zoster Virus (VZV) Ig I Antigen Encoding RNA Sequence

SEQ ID NO: 5 cgccaccauguuccuuauucaaugccucauauccgcagucaucuucuauauucaaguuacuaaugcacuuaucuucaag ggcgaucaugucagccugcaagugaauucaagucuuacguccauuuugauuccaaugcagaaugauaacuauaccgaaa uuaagggacagcugguuuuuauuggagaacaacugccgaccgguacaaacuacagcgggacccucgagcugcuuuacgc agacacuguggcauucugcuuucggucaguacaaguuaucagauacgacggaugcccacgcauuaggacaucugccuuc auuucuugccgauacaagcauaguuggcauuacggaaacucuaccgauagaauuucaacugaaccagaugccgguguga ugcucaagauaaccaaaccugggaucaacgacgcagggguguauguccucuuggugagauuggaccauucaaggaguac ggacggguuuauacugggcgugaacgucuauaccgcaggaagucaucauaacauucacggugucauuuauaccagcccc agucuccagaaugggguacagcacucgagcccuguuccagcaagcaagauugugugaccuuccagccacuccuaagggau caggcacaagucuuuuucaacauauguuggaucucagagcagggaaaagucuugaggacaacccguggcuccaugaaga cgugguuacuacugaaacaaagucagugggucaaggagggaaucgagaaccauguguacccaacugacaugagcacgcug ccugaaaaaucacugaacgacccaccagagaaucugcugauaauaauaccuauuguagcgaguguuaugauuuugaccg caauggucauaguuauuguaauaagcgugaaaaggagacgaaucaaaaaacauccgauauacaggccgaauacgaagac -continued aagaagagggauucagaacgcgacuccggagagugauguaaugcucgaagcagccaucgcucaacuugccaccauucgc gaagaaagcccuccgcauuccgucguaaauccuuuugucaaguga Zika Envelope Protein Antigen Encoding RNA Sequence

SEQ ID NO: 6 augcggagaggagcagacacauccgugggaaucguggg ccugcugcugaccacagcaauggcagccgaggugaccagga gaggcagcgccuacuauauguaccuggacagaaaugaugccggcgaggccaucuccuuucccaccacacugggcaugaa caagugcuacauccagaucauggaccugggccacaugugcgaugccaccaugagcuaugaguguccaaugcuggacgag ggcguggagcccgacgauguggauugcugguguaauaccacaucuacauggguggu guacggcaccugucaccacaaga agggagaggcacggcgcagcaggagagcagugacacugccuucccacucuaccaggaagcugcagacaagaagccagac cuggcuggaguccagggaguauacaaagcaccugaucaggguggagaacuggaucuuuagaaauccaggauucgcacug gcugccgccgccaucgcauggcugcugggcagcuccaccagccagaaagugaucuaccuggucaugauccugcugaucg ccccugccuauucuauccggugcaucggcgugagcaauagggacuucguggagggaauguccggaggcaccuggugga ugguggugcuggagcacggcggcugcgugacagugauggcccaggacaagccaaccguggauaucgagcuggugaccaca accguguccaacauggccgaggugaggucuuacugcuaugaggccagcaucuccgacauggccucugauagcagauguc ccacccagggcgaggccuaccuggacaagcaguccgauacacaguacgugugcaagcggacccugguggacaggggaug gggaaauggauguggccuguuuggcaagggcucucuggugacaugcgccaaguucgccuguagcaagaagaugaccggc aaguccauccagccagagaaccuggaguaccggaucaugcugucugugcacggcucccagcacucuggcaugaucguga acgacacaggccacgagacagaugagaaucgggccaagguggagaucacaccuaacuccccacgcgccgaggccacccu gggaggauuuggcucucugggccuggacugcgagccuaggacaggccuggacuucuccgaucuguacuaucugaccaug aacaauaagcacuggcuggugcacaaggagugguuucacgacaucccacugccauggcacgcaggagcagauacaggca ccccacacuggaacaauaaggaggcccugguggaguucaaggacgcccacgccaagcggcagacagugguggugcuggg cagccaggagggagcagugcacaccgcccuggcaggcgcccuggaggccgagauggacggagcaaagggccgccugucu agcggccaccugaagugcaggcugaagauggauaagcugagacugaagggcguguccuacucucugugcacagccgccu ucaccuucaccaagaucccugccgagacacugcacggcacagugaccguggaggugcaguaugccggcacagacggccc cuguaaggugccugcccagauggccguggauaugcagacacugaccccugugggcaggcugaucaccgccaauccagug aucacagagucuaccgagaacagcaagaugaugcuggagcuggacccccuuucggcgauagcuauaucgugaucggcg ugggcgagaagaagaucacacaccacuggcacagaagcggcuccacaaucggcaaggccuuugaggcaaccgugcgggg agcaaagaggauggccgugcugggcgacaccgcaugggauuucggaucugugggaggcgcccugaacagccugggcaag ggcauccaccagaucuucggcgccgccuuuaagucccuguucggcggcaugagcugguuuucccagauccugaucggca cacugcugauguggcugggccugaacaccaagaauggcucuaucagccugaugugccuggcccugggaggcgugcugau cuuccuguccaccgccgugucugcc RSV-G Amino Acid Sequence
Human respiratory syncytial virus A (strain A2) attachment glycoprotein [Human orthopneumovirus] NCBI Reference Sequence: YP_009518856.1

SEQ ID NO: 7

MSKNKDQRTAKTLERTWDTLNHLLFISSCLYKLNLKSVAQITLSILAMIISTSLIIAAIIFIASANHKVTPTTAIIQD

ATSQIKNTTPTYLTQNPQLGISPSNPSEITSQITTILASTTPGVKSTLQSTTVKTKNTTTTQTQPSKPTTKQRQNKPP

SKPNNDFHFEVFNFVPCSICSNNPTCWAICKRIPNKKPGKKTTTKPTKKPTLKTTKKDPKPQTTKSKEVPTTKPTEEP

TINTTKTNIITTLLTSNTTGNPELTSQMETFHSTSSEGNPSPSQVSTTSEYPSQPSSPPNTPRQ

RSV-F Partial Amino Acid Sequence-F protein, partial
[Human respiratory syncytial virus B] NCBI GenBank: CBW45391.1

SEQ ID NO: 8

MELLIHRSSAIFLTLAINALYLTSSQNITEEFYQSTCSAVSRGYLSALRTGWYTSVITIELSNIKETKCNGTDTKVKL

IKQELDKYKNAVTELQLLMQNTPAANNRARREAPQYMNYTINTTKNLNVSISKKRKRRFLGFLLGVGSAIASGIAVSK

VLHLEGEVNK

-continued

RSV-F Full Length Amino Acid Sequence
[Human respiratory syncytial virus B] NCBI GenBank: QED08852.1

SEQ ID NO: 9

```
  1 mellihrssa ifltlainal yltssqnite efyqstcsav srgylsalrt gwytsvitie
 61 lsniketkcn gtdtkvklik qeldkyknav telqllmqnt pavnnrarre apqymnytin
121 ttknlnvsis kkrkrrflgf llgvgsaias giavskvlhl egevnkikna lqstnkavvs
181 lsngvsvlts kvldlknyin nqllpivnkq scrisnietv iefqqknsrl leitrefsvn
241 agvttplsty mltnsellsl indmpitndq kklmssnvqi vrqqsysims iikeevlayv
301 vqlpiygvid tpcwklhtsp lcttnikegs nicltrtdrg wycdnagsvs ffpqadtckv
361 qsnrvfcdtm nsltlpsevs lcntdifnsk ydckimtskt disssvitsl gaivscygkt
421 kctasnknrg iiktfsngcd yvsnkgvdtv svgntlyyvn klegknlyvk gepiinyydp
481 lvfpsdefda sisqvnekin qslafirrsd ellhnvntgk sttnimitai iiviivvlls
541 liaiglllyc kakntpvtls kdqlsginni afsk
```

Influenza Virus Haemagglutinin (HA) Amino Acid Sequence
hemagglutinin [Influenza A virus (A/Aichi/2/1968(H3N2))] GenBank: AAA43239.1

SEQ ID NO: 10

MKTIIALSYIFCLPLGQDLPGNDNSTATLCLGHHAVPNGTLVKTITDDQIEVTNATELVQSSSTGKICNNPHRILDGI

DCTLIDALLGDPHCDVFQNETWDLFVERSKAFSNCYPYDVPDYASLRSLVASSGTLEFITEGFTWTGVTQNGGSNACK

RGPGSGFFSRLNWLTKSGSTYPVLNVTMPNNDNFDKLYIWGIHHPSTNQEQTSLYVQASGRVTVSTRRSQQTIIPNIG

SRPWVRGLSSRISIYWTIVKPGDVLVINSNGNLIAPRGYFKMRTGKSSIMRSDAPIDTCISECITPNGSIPNDKPFQN

VNKITYGACPKYVKQNTLKLATGMRNVPEKQTRGLFGAIAGFIENGWEGMIDGWYGFRHQNSEGTGQAADLKSTQAAI

DQINGKLNRVIEKTNEKFHQIEKEFSEVEGRIQDLEKYVEDTKIDLWSYNAELLVALENQHTIDLTDSEMNKLFEKTR

RQLRENAEEMGNGCFKIYHKCDNACIESIRNGTYDHDVYRDEALNNRFQIKGVELKSGYKDWILWISFAISCFLLCVV

LLGFIMWACQRGNIRCNICI

Influenza A Haemagglutinin Amino Acid Sequence
hemagglutinin [Influenza A virus (A/New York/392/2004(H3N2))] NCBI Reference Sequence:
YP_308839.1

SEQ ID NO: 11

MKTIIALSYILCLVFAQKLPGNDNSTATLCLGHHAVPNGTIVKTITNDQIEVTNATELVQSSSTGGICDSPHQILDGE

NCTLIDALLGDPQCDGFQNKKWDLFVERSKAYSNCYPYDVPDYASLRSLVASSGTLEFNNESFNWTGVTQNGTSSACK

RRSNNSFFSRLNWLTHLKFKYPALNVTMPNNEKFDKLYIWGVHHPGTDNDQISLYAQASGRITVSTKRSQQTVIPSIG

SRPRIRDVPSRISIYWTIVKPGDILLINSTGNLIAPRGYFKIRSGKSSIMRSDAPIGKCNSECITPNGSIPNDKPFQN

VNRITYGACPRYVKQNTLKLATGMRNVPEKQTRGIFGAIAGFIENGWEGMVDGWYGFRHQNSEGTGQAADLKSTQAAI

NQINGKLNRLIGKTNEKFHQIEKEFSEVEGRIQDLEKYVEDTKIDLWSYNAELLVALENQHTIDLTDSEMNKLFERTK

KQLRENAEDMGNGCFKIYHKCDNACIGSIRNGTYDHDVYRDEALNNRFQIKGVELKSGYKDWILWISFAISCFLLCVA

LLGFIMWACQKGNIRCNICI

Influenza B Haemagglutinin Amino Acid Sequence
hemagglutinin [Influenza B virus (B/Lee/1940)] NCBI Reference Sequence: NP_056660.1

SEQ ID NO: 12

MKAIIVLLMVVTSNADRICTGITSSNSPHVVKTATQGEVNVTGVIPLTTTPTKSHFANLKGTQTRGKLCPNCFNCTDL

DVALGRPKCMGNTPSAKVSILHEVKPATSGCFPIMHDRTKIRQLPNLLRGYENIRLSTSNVINTETAPGGPYKVGTSG

SCPNVANGNGFFNTMAWVIPKDNNKTAINPVTVEVPYICSEGEDQITVWGFHSDDKTQMERLYGDSNPQKFTSSANGV

TTHYVSQIGGFPNQTEDEGLKQSGRIVVDYMVQKPGKTGTIVYQRGILLPQKVWCASGRSKVIKGSLPLIGEADCLHE

KYGGLNKSKPYYTGEHAKAIGNCPIWVKTPLKLANGTKYRPPAKLLKERGFFGAIAGFLEGGWEGMIAGWHGYTSHGA

HGVAVAADLKSTQEAINKITKNLNYLSELEVKNLQRLSGAMNELHDEILELDEKVDDLRADTISSQIELAVLLSNEGI

INSEDEHLLALERKLKKMLGPSAVEIGNGCFETKHKCNQTCLDRIAAGTFNAGDFSLPTFDSLNITAASLNDDGLDNH

TILLYYSTAASSLAVTLMIAIFIVYMVSRDNVSCSICL

-continued

VZV envelope glycoprotein E [Human alphaherpesvirus 3] GenBank: AQT34120.1

SEQ ID NO: 13

MFYEALKAELVYTRAVHGFRPRANCVVLSDYIPRVACNMGTVNKPVVGVLMGFGIITGTLRITNPVRASVLRYDDFHI

DEDKLDTNSVYEPYYHSDHAESSWVNRGESSRKAYDHNSPYIWPRNDYDGFLENAHEHHGVYNQGRGIDSGERLMQPT

QMSAQEDLGDDTGIHVIPTLNGDDRHKIVNVDQRQYGDVFKGDLNPKPQGQRLIEVSVEENHPFTLRAPIQRIYGVRY

TETWSFLPSLTCTGDAAPAIQHICLKHTTCFQDVVVDVDCAENTKEDQLAEISYRFQGKKEADQPWIVVNTSTLFDEL

ELDPPEIEPGVLKVLRTEKQYLGVYIWNMRGSDGTSTYATFLVTWKGDEKTRNPTPAVTPQPRGAEFHMWNYHSHVFS

VGDTFSLAMHLQYKIHEAPFDLLLEWLYVPIDPTCQPMRLYSTCLYHPNAPQCLSHMNSGCTFTSPHLAQRVASTVYQ

NCEHADNYTAYCLGISHMEPSFGLILHDGGTTLKFVDTPESLSGLYVFVVYFNGHVEAVAYTVVSTVDHFVNAIEERG

FPPTAGQPPATTKPKEITPVNPGTSPLIRYAAWTGGLAAVVLLCLVIFLICTAKRMRVKAYRVDKSPYNQSMYYAGLP

VDDFEDSESTDTEEEFGNAIGGSHGGSSYTVYIDKTR

VZV envelope glycoprotein B [Human alphaherpesvirus 3] NCBI Reference Sequence: NP_040154.2

SEQ ID NO: 14

MSPCGYYSKWRNRDRPEYRRNLRFRRFFSSIHPNAAAGSGFNGPGVFITSVTGVWLCFLCIFSMFVTAVVSVSPSSFY

ESLQVEPTQSEDITRSAHLGDGDEIREAIHKSQDAETKPTFYVCPPPTGSTIVRLEPTRTCPDYHLGKNFTEGIAVVY

KENIAAYKFKATVYYKDVIVSTAWAGSSYTQITNRYADRVPIPVSEITDTIDKFGKCSSKATYVRNNHKVEAFNEDKN

PQDMPLIASKYNSVGSKAWHTTNDTYMVAGTPGTYRTGTSVNCIIEEVEARSIFPYDSFGLSTGDIIYMSPFFGLRDG

AYREHSNYAMDRFHQFEGYRQRDLDTRALLEPAARNFLVTPHLTVGWNWKPKRTEVCSLVKWREVEDVVRDEYAHNFR

FTMKTLSTTFISETNEFNLNQIHLSQCVKEEARAIINRIYTTRYNSSHVRTGDIQTYLARGGFVVVFQPLLSNSLARL

YLQELVRENTNHSPQKHPTRNTRSRRSVPVELRANRTITTTSSVEFAMLQFTYDHIQEHVNEMLARISSSWCQLQNRE

RALWSGLFPINPSALASTILDQRVKARILGDVISVSNCPELGSDTRIILQNSMRVSGSTTRCYSRPLISIVSLNGSGT

VEGQLGTDNELIMSRDLLEPCVANHKRYFLFGHHYVYYEDYRYVREIAVHDVGMISTYVDLNLTLLKDREFMPLQVYT

RDELRDTGLLDYSEIQRRNQMHSLRFYDIDKVVQYDSGTAIMQGMAQFFQGLGTAGQAVGHVVLGATGALLSTVHGFT

TFLSNPFGALAVGLLVLAGLVAAFFAYRYVLKLKTSPMKALYPLTTKGLKQLPEGMDPFAEKPNATDTPIEEIGDSQN

TEPSVNSGFDPDKFREAQEMIKYMTLVSAAERQESKARKKNKTSALLTSRLTGLALRNRRGYSRVRTENVTGV

VZV envelope glycoprotein H [Human alphaherpesvirus 3] GenBank: QXN54893.1

SEQ ID NO: 15

MFALVLAVVILPLWTTANKSYVTPTPATRSIGHMSALLREYSDRNMSLKLEAFYPTGFDEELIKSLHWGNDRKHVFLV

IVKVNPTTHEGDVGLVIFPTYLLSPYHFKAEHRAPFPAGRFGFLSHPVTPDVSFFDSSFAPYLTTQHLVAFTTFPPNP

LVWHLERAETAATAERPFGVSLLPARPTVPKNTILEHKAHFATWDALARHTFFSAEAIITNSTLRIHVPLFGSVWPIR

YWATGSVLLTSDSGRVEVNIGVGFMSSLISLSSGLPIELIVVPHTVKLNAVTSDTTWFQLNPPGPDPGPSYRVYLLGR

GLDMNFSKHATVDICAYPEESLDYRYHLSMAHTEALRMTTKADQHDINEESYYHIAARIATSIMGRTTEYFLLDEIVD

VQYQLKFLNYILMRIGAGAHPNTISGTSDLIFADPSQLHDELSLLFGQVKPANVDYFISYDEARDQLKTAYALSRGQD

HVNALSLARRVIMSIYKGLLVKQNLNATERQALFFASMILLNFREGLENSSRVLDGRTTLLLMTSMCTAAHATQAALN

IQEGLAYLNPSKHMFTIPNVYSPCMGSLRTDLTEEIHVMNLLSAIPTRPGLNEVLHTQLDESEIFDAAFKTMMIFTTW

TAKDLHILHTHVPEVFTCQDAAARNGEYVLILPAVQGHSYVITRNKPQRGLVYSLADVDVYNPISVVYLSKDTCVSEH

GVIETVALPHPDNLKECLYCGSVFLRYLTTGAIMDIIIIDSKDTERQLAAMGNSTIPPFNPDMHGDDSKAVLLFPNGT

VVTLLGFERRQAIRMSGQYLGASLGGAFLAVVGFGIIGWMLCGNSRLREYNKIPLT

VZV glycoprotein gL [Human alphaherpesvirus 3] GenBank: ABE03078.1

SEQ ID NO: 16

MASHKWLLQMIVFLKTITIAYCLHLQDDTPLFFGAKPLSDVSLIITEPCVSSVYEAWDYAAPPVSNLSEALSGIVVKT

KCPVPEVILWFKDKQMAYWTNPYVTLKGLAQSVGEEHKSGDIRDALLDALSGVWVDSTPSSTNIPENGCVWGADRLFQ

RVCQ

-continued

VZV envelope glycoprotein N [Human alphaherpesvirus 3] GenBank: QXN54863.1

SEQ ID NO: 17

MGSITASFILITMQILFFCEDSSGEPNFAERNFWHASCSARGVYIDGSMITTLFFYASLLGVCVALISLAYHACFRLF

TRSVLRSTW

VZV envelope glycoprotein I [Human alphaherpesvirus 3] Genbank: QXN54922.1

SEQ ID NO: 18

MFLIQCLISAVIFYIQVTNALIFKGDHVSLQVNSSLTSILIPMQNDNYTEIKGQLVFIGEQLPTGTNYSGTLELLYAD

TVAFCFRSVQVIRYDGCPRIRTSAFISCRYKHSWHYGNSTDRISTEPDAGVMLKITKPGINDAGVYVLLVRLDHSRST

DGFILGVNVYTAGSHHNIHGVIYTSPSLQNGYSTRALFQQARLCDLPATPKGSGTSLFQHMLDLRAGKSLEDNPWLHE

DVVTTETKSVVKEGIENHVYPTDMSTLPEKSINDPPENLLIIIPIVASVMILTAMVIVIVISVKRRRIKKHPIYRPNT

KTRRGIQNATPESDVMLEAAIAQLATIREESPPHSVVNPFVK spike glycoprotein [Severe acute respiratory syndrome-related coronavirus-1] GenBank: ABD73002.1

SEQ ID NO: 19

MFIFLLFLTLTSGSDLDRCTTFDDVQAPNYTQHTSSMRGVYYPDEIFRSDTLYLTQDLFLPFYSNVTGFHTINHTFGN

PVIPFKDGIYFAATEKSNVVRGWVFGSTMNNKSQSVIIINNSTNVVIRACNFELCDNPFFAVSKPMGTQTHTMIFDNA

FNCTFEYISDAFSLDVSEKSGNFKHLREFVFKNKDGFLYVYKGYQPIDVVRDLPSGFNTLKPIFKLPLGINITNFRAI

LTAFSPAQDIWGTSAAAYFVGYLKPTTFMLKYDENGTITDAVDCSQNPLAELKCSVKSFEIDKGIYQTSNFRVVPSGD

VVRFPNITNLCPFGEVFNATKFPSVYAWERKKISNCVADYSVLYNSTFFSTFKCYGVSATKLNDLCFSNVYADSFVVK

GDDVRQIAPGQTGVIADYNYKLPDDFMGCVLAWNTRNIDATSTGNYNYKYRYLRHGKLRPFERDISNVPFSPDGKPCT

PPALNCYWPLNDYGFYTTTGIGYQPYRVVVLSFELLNAPATVCGPKLSTDLIKNQCVNFNFNGLTGTGVLTPSSKRFQ

PFQQFGRDVSDFTDSVRDPKTSEILDISPCSFGGVSVITPGTNASSEVAVLYQDVNCTDVSTAIHADQLTPAWRIYST

GNNVFQTQAGCLIGAEHVDTSYECDIPIGAGICASYHTVSLLRSTSQKSIVAYTMSLGADSSIAYSNNTIAIPTNFSI

SITTEVMPVSMAKTSVDCNMYICGDSTECANLLLQYGSFCTQLNRALSGIAAEQDRNTREVFAQVKQMYKTPTLKYFG

GFNFSQILPDPLKPTKRSFIEDLLFNKVTLADAGFMKQYGECLGDINARDLICAQKFNGLTVLPPLLTDDMIAAYTAA

LVSGTATAGWTFGAGAALQIPFAMQMAYRFNGIGVTQNVLYENQKQIANQFNKAISQIQESLTTTSTALGKLQDVVNQ

NAQALNTLVKQLSSNFGAISSVLNDILSRLDKVEAEVQIDRLITGRLQSLQTYVTQQLIRAAEIRASANLAATKMSEC

VLGQSKRVDFCGKGYHLMSFPQAAPHGVVFLHVTYVPSQERNFTTAPAICHEGKAYFPREGVFVFNGTSWFITQRNFF

SPQIITTDNTFVSGNCDVVIGIINNTVYDPLQPELDSFKEELDKYFKNHTSPDVDLGDISGINASVVNIQKEIDRLNE

VAKNLNESLIDLQELGKYEQYIKWPWYVWLGFIAGLIVIVMVTILLCCMTSCCSCLKGACSCGSCCKFDEDDSEPVLK

GVKLHYT envelope glycoprotein B [Human gammaherpesvirus 4] GenBank: QXN54824.1

SEQ ID NO: 20

MTRRRVLSVVVLLAALACRLGAQTPEQPAPPATTVQPTATRQQTSFPFRVCELSSHGDLFRFSSDIQCPSFGTRENHT

EGLLMVFKDNIIPYSFKVRSYTKIVTNILIYNGWYADSVTNRHEEKFSVDSYETDQMDTIYQCYNAVKMTKDGLTRVY

VDRDGVNITVNLKPTGGLANGVRRYASQTELYDAPGWLIWTYRTRTTVNCLITDMMAKSNSPFDFFVTTTGQTVEMSP

FYDGKNKETFHERADSFHVRTNYKIVDYDNRGTNPQGERRAFLDKGTYTLSWKLENRTAYCPLQHWQTFDSTIATETG

KSIHFVTDEGTSSFVTNTTVGIELPDAFKCIEEQVNKTMHEKYEAVQDRYTKGQEAITYFITSGGLLLAWLPLTPRSL

ATVKNLTELTTPTSSPPSSPSPPAPSAARGSTPAAVLRRRRRDAGNATTPVPPTAPGKSLGTLNNPATVQIQFAYDSL

RRQINRMLGDLARAWCLEQKRQNMVLRELTKINPTTVMSSIYGKAVAAKRLGDVISVSQCVPVNQATVTLRKSMRVPG

SETMCYSRPLVSFSFINDTKTYEGQLGTDNEIFLTKKMTEVCQATSQYYFQSGNEIHVYNDYHHFKTIELDGIATLQT

FISLNTSLIENIDFASLELYSRDEQRASNVFDLEGIFREYNFQAQNIAGLRKDLDNAVSNGRNQFVDGLGELMDSLGS

VGQSITNLVSTVGGLFSSLVSGFISFFKNPFGGMLILVLVAGVVILVISLTRRTRQMSQQPVQMLYPGIDELAQQHAS

GEGPGINPISKTELQAIMLALHEQNQEQKRAAQRAAGPSVASRALQAARDRFPGLRRRRYHDPETAAALLGEAETEF

E6 oncoprotein [Human papillomavirus] GenBank: QNJ45009.1
SEQ ID NO: 21

MHQKRTAMFQDPQERPRKLPQLCTELQTTIHDIILECVYCKQQLLRREVYDFAFRDLCIVYRDGNPYAVCDKCLKFYS

KISEYRHYCYSVYGTTLEQQYNKPLCDLLIRCINCQKPLCPEEKQRHLDKKQRFHNIRGRWTGRCMSCCRSSRTRRET

QL

E7, partial [Human papillomavirus] GenBank: QIQ28214.1
SEQ ID NO: 22

SQPLKQHYQIVTCCCGCDSNVRLVVQCTETDIREVQQLLLGTLNIVCPICA nucleo protein N [Rabies lyssavirus] GenBank: AFR56624.1
SEQ ID NO: 23

MDADKIVFKVNNQVVSLKPEIIVDQYEYKYPAIKDLKKPCITLGKAPDLNKAYKSVLSCMSAAKLDPDDVCSYLAAAM

QFFEGTCPEDWTSYGILIARKGDKITPGSLVEIKRTDVEGNWALTGGMELTRDPTVPEHASLVGLLLSLYRLSKISGQ

NTGNYKTNIADRIEQIFETAPFVKIVEHHTLMTTHKMCANWSTIPNFRFLAGTYDMFFSRIEHLYSAIRVGTVVTAYE

DCSGLVSFTGFIKQINLTAREAILYFFHKNFEEEIRRMFEPGQETAVPHSYFIHFRSLGLSGKSPYSSNAVGHVENLI

HFVGCYMGQVRSLNATVIAACAPHEMSVLGGYLGEEFFGKGTFERRFFRDEKELQEYEAAELTKTDVALADDGTVNSD

DEDYFSGETRSPEAVYTRIIMNGGRLKRSHIRRYVSVSSNHQARPNSFAEFLNKTYSSDS

L protein, partial [Rabies lyssavirus] NCBI Ref: ABH03115.1
SEQ ID NO: 24

MIDPGEVYDDP transmembrane glycoprotein G [Rabies lyssavirus] NCBI Ref: AFR56627.1

SEQ ID NO: 25

MVPQALLFVPLLVFPLCFGKFPIYTIPDKLGPWSPIDIHHLSCPNNLVVEDEGCTNLSGFSYMELKVGYISAIKINGF

TCTGVVTEAETYTNFVGYVTTTFKRKHFRPTPDACRAAYNWKMAGDPRYEESLHNPYPDYHWLRTVKTTKESLVIISP

SVADLDPYDRSLHSRVFPGGNCSGVAVSSTYCSTNHDYTIWMPENPRLGMSCDIFTNSRGKRASKGSETCGFVDERGL

YKSLKGACKLKLCGVLGLRLMDGTWVAMQTSNETKWCPPGQLVNLHDFRSDEIEHLVVEELVKKREECLDALESIMTT

KSVSFRRLSHLRKLVPGFGKAYTIFNKTLMEADAHYKSVRTWNEIIPSKGCLRVGGRCHPHVNGVFFNGIILGPDGNV

LIPEMQSSLLQQHMELLVSSVIPLMHPMADPSTVFKNGDEAEDFVEVHLPDVHERISGVDLGLPNWGKYVLLSAGALT

ALMLIIFLMTCWRRVNRSEPTQHNLRGTGREVSVTPQSGKIISSWESYKSGGETGL phosphoprotein M1 [Rabies lyssavirus] NCBI Ref: AFR56625.1

SEQ ID NO: 26

MSKIFVNPSAIRAGLADLEMAEETVDLINRNIEDNQAHLQGEPIEVDNLPEDMGRLHLDDGKSPNPGEMAKVGEGKYR

EDFQMDEGEDPSLLFQSYLDNVGVQIVRQIRSGERFFKIWSQTVEEIISYVAVNFPNPPGKSSEDKSTQTTGRELKKE

TTPTPSQRESQSSKARMAAQTASGPPALEWSATNEEDDLSVEAEIAHQIAESFSKKYKFPSRSSGILLYNFEQLKMNL

DDIVKEAKNVPGVTRLARDGSKLPLRCVLGWVALANSKKFQLLVESNKLSKIMQDDLNRYTSC

M2 protein [Rabies lyssavirus] NCBI Ref: AFR56626.1

SEQ ID NO: 27

MNFLRKIVKNCRDEDTQKPSPVSAPLDDDDLWLPPPEYVPLKELTSKKNRRNFCINGGVKVCSPNGYSFGILRHILRS

FDEIYSGNHRMIGLVKVVIGLALSGAPVPEGMNWVYKLRRTLIFQWADSRGPLEGEELEYSQEITWDDDTEFVGLQIR

VSAKQCHIRGRIWCINMNSRAGQLWSDMSLQTQRSEEDKDSSLLLE envelope glycoprotein B [Human alphaherpesvirus 1] NCBI Ref: YP_009137102.1

SEQ ID NO: 28

MRQGAPARGRRWFVVWALLGLTLGVLVASAAPSSPGTPGVAAATQAANGGPATPAPPAPGAPPTGDPKPKKNKKPKPP

KPPRPAGDNATVAAGHATLREHLRDIKAENTDANFYVCPPPTGATVVQFEQPRRCPTRPEGQNYTEGIAVVFKENIAP

YKFKATMYYKDVTVSQVWFGHRYSQFMGIFEDRAPVPFEEVIDKINAKGVCRSTAKYVRNNLETTAFHRDDHETDMEL

KPANAATRTSRGWHTTDLKYNPSRVEAFHRYGTTVNCIVEEVDARSVYPYDEFVLATGDFVYMSPFYGYREGSHTEHT

SYAADRFKQVDGFYARDLTTKARATAPTTRNLLTTPKFTVAWDWVPKRPSVCTMTKWQEVDEMLRSEYGGSFRFSSDA

ISTTFTTNLTEYPLSRVDLGDCIGKDARDAMDRIFARRYNATHIKVGQPQYYLANGGFLIAYQPLLSNTLAELYVREH

LREQSRKPPNPTPPPPGASANASVERIKTTSSIEFARLQFTYNHIQRHVNDMLGRVAIAWCELQNHELTLWNEARKLN

PNAIASATVGRRVSARMLGDVMAVSTCVPVAADNVIVQNSMRISSRPGACYSRPLVSFRYEDQGPLVEGQLGENNELR

-continued

LTRDAIEPCTVGHRRYFTFGGGYVYFEEYAYSHQLSRADITTVSTFIDLNITMLEDHEFVPLEVYTRHEIKDSGLLDY

TEVQRRNQLHDLRFADIDTVIHADANAAMFAGLGAFFEGMGDLGRAVGKVVMGIVGGVVSAVSGVSSFMSNPFGALAV

GLLVLAGLAAAFFAFRYVMRLQSNPMKALYPLTTKELKNPTNPDASGEGEEGGDFDEAKLAEAREMIRYMALVSAMER

TEHKAKKKGTSALLSAKVTDMVMRKRRNTNYTQVPNKDGDADEDDL glycoprotein G [Human alphaherpesvirus 2] NCBI Ref: ABU45441.1

SEQ ID NO: 29

MHAIAPRLLLLFVLSGLPGTRGGSGVPGPINPPNNDVVFPGGSPVAQYCYAYPRLDDPGPLGSADAGRQDLPRRVVRH

EPLGRSFLTGGLVLLAPPVRGFGAPNATYAARVTYYRLTRACRQPILLRQYGGCRGGEPPSPKTCGSYTYTYQGGGPP

TRYALVNASLLVPIWDRAAETFEYQIELGGELHVGLLWVEVGGEGPGPTAPPQAARAEGGPCVPPVPAGRPWRSVPPV

WYSAPNPGFRGLRFRERCLPPQTPAAPSDLPRVAFAPQSLLVGITGRTFIRMARPTEDVGVLPPHWAPGALDDGPYAP

FPPRPRFRRALRTDPEGVDPDVRAPLTGRRLMALTEDASSDSPTSAPEKTPLPVSATAMAPSVDPSAEPTAPATTTPP

DEMATQAATVAVTPEETAVASPPATASVESSPLPAAAATPGAGHTNTSSAPAAKTPPTTPAPTTPPPTSTHATPRPTT

PGPQTTPPGPATPGPVGASAAPTADSPLTASPPATAPGPSAANVSVAATTATPGTRGTARTPPTDPKTHPHGPADAPP

GSPAPPPPEHRGGPEEFEGAGDGEPPDDDDSATGLAFRTPNPNKPPPARPGPIRPTLPPGILGPLAPNTPRPPAQAPA

KDMPSGPTPQHIPLFWFLTASPALDILFIISTTIHTAAFVCLVALAAQLWRGRAGRRRYAHPSVRYVCLPPERD

Malate synthase [*Mycobacterium tuberculosis*] NCBI Ref: QJF21868.1

SEQ ID NO: 30

MTDRVSVGNLRIARVLYDFVNNEALPGTDIDPDSFWAGVDKVVADLTPQNQALLNARDELQAQIDKWHRRRVIEPIDM

DAYRQFLTEIGYLLPEPDDFTITTSGVDAEITTTAGPQLVVPVLNARFALNAANARWGSLYDALYGTDVIPETDGAEK

GPTYNKVRGDKVIAYARKFLDDSVPLSSGSFGDATGFTVQDGQLVVALPDKSTGLANPGQFAGYTGAAESPTSVLLIN

HGLHIEILIDPESQVGTTDRAGVKDVILESAITTIMDFEDSVAAVDAADKVLGYRNWLGLNKGDLAAAVDKDGTAFLR

VLNRDRNYTAPGGGQFTLPGRSLMFVRNVGHLMTNDAIVDTDGSEVFEGIMDALFTGLIAIHGLKASDVNGPLINSRT

GSIYIVKPKMHGPAEVAFTCELFSRVEDVLGLPQNTMKIGIMDEERRTTVNLKACIKAAADRVVFINTGFLDRTGDEI

HTSMEAGPMVRKGTMKSQPWILAYEDHNVDAGLAAGFSGRAQVGKGMWTMTELMADMVETKIAQPRAGASTAWVPSPT

AATLHALHYHQVDVAAVQQGLAGKRRATIEQLLTIPLAKELAWAPDEIREEVDNNCQSILGYVVRWVDQGVGCSKVPD

IHDVALMEDRATLRISSQLLANWLRHGVITSADVRASLERMAPLVDRQNAGDVAYRPMAPNFDDSIAFLAAQELILSG

AQQPNGYTEPILHRRRREFKARAAEKPAPSDRAGDDAAR

MPT51 [*Mycobacterium tuberculosis* H37Rv] NCBI Ref: CAA05211.1

SEQ ID NO: 31

MKGRSALLRALWIAALSFGLGGVAVAAEPTAKAAPYENLMVPSPSMGRDIPVAFLAGGPHAVYLLDAFNAGPDVSNWV

TAGNAMNTLAGKGISVVAPAGGAYSMYTNWEQDGSKQWDTFLSAELPDWLAANRGLAPGGHAAVGAAQGGYGAMALAA

FHPDRFGFAGSMSGFLYPSNTTTNGAIAAGMQQFGGVDTNGMWGAPQLGRWKWHDPWVHASLLAQNNTRVWVWSPTNP

GASDPAAMIGQTAEAMGNSRMFYNQYRSVGGHNGHFDFPASGDNGWGSWAPQLGAMSGDIVGAIR

Zika Virus E Antigen Amino Acid Sequence
polyprotein, partial [Zika virus] GenBank: ART29827.1

SEQ ID NO: 32

MKNPKKKSGGFRIVNMLKRGVARVSPFGGLKRLPAGLLLGHGPIRMVLAILAFLRFTAIKPSLGLINRWGSVGKKEAM

EIIKKFKKDLAAMLRIINARKEKKRRGADTSVGIVGLLLTTAMAAEVTRRGSAYYMYLDRNDAGEAISFPTTLGMNKC

YIQIMDLGHMCDATMSYECPMLDEGVEPDDVDCWCNTTSTWVVYGTCHHKKGEARRSRRAVTLPSHSTRKLQTRSQTW

LESREYTKHLIRVENWIFRNPGFALAAAAIAWLLGSSTSQKVIYLVMILLIAPAYSIRCIGVSNRDFVEGMSGGTWVD

VVLEHGGCVTVMAQDKPTVDIELVTTTVSNMAEVRSYCYEASISDMASDSRCPTQGEAYLDKQSDTQYVCKRTLVDRG

WGNGCGLFGKGSLVTCAKFACSKKMTGKSIQPENLEYRIMLSVHGSQHSGMIVNDTGHETDENRAKVEITPNSPRAEA

TLGGFGSLGLDCEPRTGLDFSDLYYLTMNNKHWLVHKEWFHDIPLPWHAGADTGTPHWNNKEALVEFKDAHAKRQTVV

VLGSQEGAVHTALAGALEAEMDGAKGRLSSGHLKCRLKMDKLRLKGVSYSLCTAAFTFTKIPAETLHGTVTVEVQYAG

TDGPCKVPAQMAVDMQTLTPVGRLITANPVITESTENSKMMLELDPPFGDSYIVIGVGEKKITHHWHRSGSTIGKAFE

-continued

ATVRGAKRMAVLGDTAWDFGSVGGALNSLGKGIHQIFGAAFKSLFGGMSWFSQILIGTLLMWLGLNTKNGSISLMCLA

LGGVLIFLSTAVSADVGCSVDFSKKETRCGTGVFVYNDVEAWRDRYKYHPDSPRRLAAAVKQAWEDGICGISSVSRME

NIMWRSVEGELNAILEENGVQLTVVVGSVKNPMWRAPQRLPVPVNELPHGWKAWGKSYFVRAAKTNNSFVVDGDTLKE

CPLKHRAWNSFLVEDHGFGVFHTSVWLKVREDYSLECDPAVIGTAVKGKEAVHSDLGYWIESEKNDTWRLKRAHLIEM

KTCEWPKSHTLWTDGIEESDLIIPTSLAGPLSHHNTREGYRTQMKGPWHSEELEIRFEECPGTKVHVEETCGTRGPSL

RSTTASGRVIEEWCCRECTMPPLSFRAKDGCWYGMEIRPRKEPESNLVRSMVTAGSTDHMDHFSLGVLVILLMVQEGL

KKRMTTKIIISTSMAVLVAMILGGFSMSDLAKLAILMGATFAEMNTGGDVAHLALIAAFKVRPALLVSFIFRANWTPR

ESMLLALASCLLQTAISALEGDLMVLINGFALAWLAIRAMVVPRTDNITLAILAALTPLARGTLLVAWRAGLATCGGF

MLLSLKGKGSVKKNLPFVMALGLTAVRLVDPINVVGLLLLTRSGKRSWPPSEVLTAVGLICALAGGFAKADIEMAGPM

AAVGLLIVSYVVSGKSVDMYIERAGDITWEKDAEVTGNSPRLDVALDESGDFSLVEDDGPPMREIILKVVLMTICGMN

PIAIPFAAGAWYVYVKTWKRSGALWDVPASKEVKKGETTDGVYRVMTRRLLGSTQVGVGIMQEGVFHTMWHVTKGSAL

RSGEGRLDPYWGDVKQDLVSYCGPWKLDAAWDGHSEVQLLAVPPGERARNIQTLPGIFKTKDGDIGAVALDYPAGTSG

SPILDKCGRVIGLYGNGVVIKNGSYVSAITQGRREEETPVECFEPSMLKKKQLTVLDLHPGAGKTRRVLPEIVREAIK

TRLRTVILAPTRVVAAEMEEALRGLPVRYMTTAVNVTHSGTEIVDLMCHATFTSRLLQPIRVPNYNLYIMDEAHFTDP

SSIAARGYISTRVEMGEAAAIFMTATPPGTRDAFPDSNSPIMDTEVEVPERAWSSGFDWVTDHSGKTVWFVPSVRNGN

EIAACLTKAGKRVIQLSRKTFETEFQKTKHQEWDFVVTTDISEMGANFKADRVIDSRRCLKPVILDGERVILAGPMPV

THASAAQRRGRIGRNPNKPGDEYLYGGGCAETDEDHAHWLEARMLLDNIYLQDGLIASLYRPEADKVAAIEGEFKLRT

EQRKTFVELMKRGDLPVWLAYQVASAGITYTDRRWCFDGTTNNTILEDSVPAEVWTRHGEKRVLKPRWMDARVCSDHA

ALKSFKEFAAGKRGAAFGVMEALGTLPGHMTERFQEAIDNLAVLMRAEIGSRPYKAAAAQLPETLETIMLLGLLGTVS

LGIFFVLMRNKGIGKMGFGMVTLGASAWLMWLSEIEPARIACVLIVVFLLLVVLIPEPEKQRSPQDNQMAIIIMVAVG

LLGLITANELGWLERTKSDLSHLMGRREEGATIGFSMDIDLRPASAWAIYAALTTFITPAVQHAVTTSYNNYSLMAMA

TQAGVLFGMGKGMPFYAWDFGVPLLMIGCYSQLTPLTLIVAIILLVAHYMYLIPGLQAAAARAAQKRTAAGIMKNPVV

DGIVVTDIDTMTIDPQVEKKMGQVLLIAVAVSSAILSRTAWGWGEAGALITAATSTLWEGSPNKYWNSSTATSLCNIF

RGSYLAGASLIYTVTRNAGLVKRRGGGTGETLGEKWKARLNQMSALEFYSYKKSGITEVCREEARRALKDGVATGGHA

VSRGSAKLRWLVERGYLQPYGKVIDLGCGRGGWSYYAATIRKVQEVKGYTKGGPGHEEPVLVQSYGWNIVRLKSGVDV

FHMAAEPCDTLLCDIGESSSSPEVEEARTLRVLSMVGDWLEKRPGAFCIKVLCPYTSTMMETLERLQRRYGGGLVRVP

LSRNSTHEMYWVSGAKSNTIKSVSTTSQLLLGRMDGPRRPVKYEEDVNLGSGTRAVVSCAEAPNMKIIGNRIERIRSE

HAETWFFDENHPYRTWAYHGSYEAPTQGSASSLINGVVRLLSKPWDVVTGVTGIAMTDTTPYGQQRVFKEKVDTRVPD

PQEGTRQVMSMVSSWLWKELGKHKRPRVCTKEEFINKVRSNAALGAIFEEEKEWKTAVEAVNDPRFWALVDKEREHHL

RGECQSCVYNMMGKREKKQGEFGKAKGSRAIWYMWLGARFLEFEALGFLNEDHWMGRENSGGGVEGLGLQRLGYVLEE

MSCIPGGRMYADDTAGWDTRISRFDLENEALITNQMEKGHRALALAIIKYTYQNKVVKVLRPAEKGKTVMDIISRQDQ

RGSGQVVTYALNTFTNLVVQLIRNMEAEEVLEMQDLWLLRRSEKVTNWLQSNGWDRLKRMA major outer membrane protein precursor [*Chlamydia trachomatis*] NCBI Ref: AAA23156.1

SEQ ID NO: 33

MKKLLKSVLVFAALSSASSLQALPVGNPAEPSLMIDGILWEGFGGDPCDPCTTWCDAISMRVGYYGDFVFDRVLKTDV

NKEFQMGAAPTTSDVAGLQNDPTINVARPNPAYGKHMQDAEMFTNAAYMALNIWDRFDVFCTLGATTGYLKGNSASFN

LVGLFGTKTQSSSFNTAKLIPNTALNEAVVELYINTTFAWSVGARAALWECGCATLGASFQYAQSKPKVEELNVLCNA

SEFTINKPKGYVGAEFPLNITAGTEAATGTKDASIDYHEWQASLALSYRLNMFTPYIGVKWSRVSFDADTIRIAQPKL

AEAILDVTTLNRTTAGKGSVVSAGTDNELADTMQIVSLQLNKMKSRKSCGIAVGTTIVDADKYAVTVEARLIDERAAH

VNAQFRF

-continued

VEEV RNA Sequence

SEQ ID NO: 34

AUAGGCGGCGCAUGAGAGAAGCCCAGACCAAUUACCUACCCAAAAUGGAGAAAGUUCACGUUGACAUCGAGGAAGACA

GCCCAUUCCUCAGAGCUUUGCAGCGGAGCUUCCCGCAGUUUGAGGUAGAAGCCAAGCAGGUCACUGAUAAUGACCAUG

CUAAUGCCAGAGCGUUUUCGCAUCUGGCUUCAAAACUGAUCGAAACGGAGGUGGACCCAUCCGACACGAUCCUUGACA

UUGGAAGUGCGCCCGCCCGCAGAAUGUAUUCUAAGCACAAGUAUCAUUGUAUCUGUCCGAUGAGAUGUGCGGAAGAUC

CGGACAGAUUGUAUAAGUAUGCAACUAAGCUGAAGAAAAACUGUAAGGAAAUAACUGAUAAGGAAUUGGACAAGAAAA

UGAAGGAGCUGGCCGCCGUCAUGAGCGACCCUGACCUGGAAACUGAGACUAUGUGCCUCCACGACGACGAGUCGUGUC

GCUACGAAGGGCAAGUCGCUGUUUACCAGGAUGUAUACGCGGUUGACGGACCGACAAGUCUCUAUCACCAAGCCAAUA

AGGGAGUUAGAGUCGCCUACUGGAUAGGCUUUGACACCACCCCUUUUAUGUUUAAGAACUUGGCUGGAGCAUAUCCAU

CAUACUCUACCAACUGGGCCGACGAAACCGUGUUAACGGCUCGUAACAUAGGCCUAUGCAGCUCUGACGUUAUGGAGC

GGUCACGUAGAGGGAUGUCCAUUCUUAGAAAGAAGUAUUUGAAACCAUCCAACAAUGUUCUAUUCUCUGUUGGCUCGA

CCAUCUACCACGAGAAGAGGGACUUACUGAGGAGCUGGCACCUGCCGUCUGUAUUUCACUUACGUGGCAAGCAAAAUU

ACACAUGUCGGUGUGAGACUAUAGUUAGUUGCGACGGGUACGUCGUUAAAAGAAUAGCUAUCAGUCCAGGCCUGUAUG

GGAAGCCUUCAGGCUAUGCUGCUACGAUGCACCGCGAGGGAUUCUUGUGCUGCAAAGUGACAGACACAUUGAACGGGG

AGAGGGUCUCUUUUCCCGUGUGCACGUAUGUGCCAGCUACAUUGUGUGACCAAAUGACUGGCAUACUGGCAACAGAUG

UCAGUGCGGACGACGCGCAAAAACUGCUGGUUGGGCUCAACCAGCGUAUAGUCGUCAACGGUCGCACCCAGAGAAACA

CCAAUACCAUGAAAAAUUACCUUUUGCCCGUAGUGGCCCAGGCAUUUGCUAGGUGGGCAAAGGAAUAUAAGGAAGAUC

AAGAAGAUGAAAGGCCACUAGGACUACGAGAUAGACAGUUAGUCAUGGGGUGUUGUUGGGCUUUUAGAAGGCACAAGA

UAACAUCUAUUUAUAAGCGCCCGGAUACCCAAACCAUCAUCAAAGUGAACAGCGAUUUCCACUCAUUCGUGCUGCCCA

GGAUAGGCAGUAACACAUUGGAGAUCGGGCUGAGAACAAGAAUCAGGAAAAUGUUAGAGGAGCACAAGGAGCCGUCAC

CUCUCAUUACCGCCGAGGACGUACAAGAAGCUAAGUGCGCAGCCGAUGAGGCUAAGGAGGUGCGUGAAGCCGAGGAGU

UGCGCGCAGCUCUACCACCUUUGGCAGCUGAUGUUGAGGAGCCCACUCUGGAGGCAGACGUCGACUUGAUGUUACAAG

AGGCUGGGGCCGGCUCAGUGGAGACACCUCGUGGCUUGAUAAAGGUUACCAGCUACGAUGGCGAGGACAAGAUCGGCU

CUUACGCUGUGCUUUCUCCGCAGGCUGUACUCAAGAGUGAAAAAUUAUCUUGCAUCCACCCUCUCGCUGAACAAGUCA

UAGUGAUAACACACUCUGGCCGAAAAGGGCGUUAUGCCGUGGAACCAUACCAUGGUAAAGUAGUGGUGCCAGAGGGAC

AUGCAAUACCCGUCCAGGACUUUCAAGCUCUGAGUGAAAGUGCCACCAUUGUGUACAACGAACGUGAGUUCGUAAACA

GGUACCUGCACCAUAUUGCCACACAUGGAGGAGCGCUGAACACUGAUGAAGAAUAUUACAAAACUGUCAAGCCCAGCG

AGCACGACGGCGAAUACCUGUACGACAUCGACAGGAAACAGUGCGUCAAGAAAGAACUAGUCACUGGGCUAGGGCUCA

CAGGCGAGCUGGUGGAUCCUCCCUUCCAUGAAUUCGCCUACGAGAGUCUGAGAACACGACCAGCCGCUCCUUACCAAG

UACCAACCAUAGGGGUGUAUGGCGUGCCAGGAUCAGGCAAGUCUGGCAUCAUUAAAAGCGCAGUCACCAAAAAAGAUC

UAGUGGUGAGCGCCAAGAAAGAAAACUGUGCAGAAAUUAUAAGGGACGUCAAGAAAAUGAAAGGGCUGGACGUCAAUG

CCAGAACUGUGGACUCAGUGCUCUUGAAUGGAUGCAAACACCCCGUAGAGACCCUGUAUAUUGACGAAGCUUUUGCUU

GUCAUGCAGGUACUCUCAGAGCGCUCAUAGCCAUUAUAAGACCUAAAAAGGCAGUGCUCUGCGGGGAUCCCAAACAGU

GCGGUUUUUUUAACAUGAUGUGCCUGAAAGUGCAUUUUAACCACGAGAUUUGCACACAAGUCUUCCACAAAAGCAUCU

CUCGCCGUUGCACUAAAUCUGUGACUUCGGUCGUCUCAACCUUGUUUUACGACAAAAAAAUGAGAACGACGAAUCCGA

AAGAGACUAAGAUUGUGAUUGACACUACCGGCAGUACCAAACCUAAGCAGGACGAUCUCAUUCUCACUUGUUUCAGAG

GGUGGGUGAAGCAGUUGCAAAUAGAUUACAAAGGCAACGAAAUAAUGACGGCAGCUGCCUCUCAAGGGCUGACCCGUA

AAGGUGUGUAUGCCGUUCGGUACAAGGUGAAUGAAAAUCCUCUGUACGCACCCACCUCAGAACAUGUGAACGUCCUAC

UGACCCGCACGGAGGACCGCAUCGUGUGGAAAACACUAGCCGGCGACCCAUGGAUAAAAACACUGACUGCCAAGUACC

CUGGGAAUUUCACUGCCACGAUAGAGGAGUGGCAAGCAGAGCAUGAUGCCAUCAUGAGGCACAUCUUGGAGAGACCGG

-continued

ACCCUACCGACGUCUUCCAGAAUAAGGCAAACGUGUGUUGGGCCAAGGCUUUAGUGCCGGUGCUGAAGACCGCUGGCA

UAGACAUGACCACUGAACAAUGGAACACUGUGGAUUAUUUUGAAACGGACAAAGCUCACUCAGCAGAGAUAGUAUUGA

ACCAACUAUGCGUGAGGUUCUUUGGACUCGAUCUGGACUCCGGUCUAUUUUCUGCACCCACUGUUCCGUUAUCCAUUA

GGAAUAAUCACUGGGAUAACUCCCCGUCGCCUAACAUGUACGGGCUGAAUAAAGAAGUGGUCCGUCAGCUCUCUCGCA

GGUACCCACAACUGCCUCGGGCAGUUGCCACUGGAAGAGUCUAUGACAUGAACACUGGUACACUGCGCAAUUAUGAUC

CGCGCAUAAACCUAGUACCUGUAAACAGAAGACUGCCUCAUGCUUUAGUCCUCCACCAUAAUGAACACCCACAGAGUG

ACUUUUCUUCAUUCGUCAGCAAAUUGAAGGGCAGAACUGUCCUGGUGGUCGGGGAAAAGUUGUCCGUCCCAGGCAAAA

UGGUUGACUGGUUGUCAGACCGGCCUGAGGCUACCUUCAGAGCUCGGCUGGAUUUAGGCAUCCCAGGUGAUGUGCCCA

AAUAUGACAUAAUAUUUGUUAAUGUGAGGACCCCAUAUAAAUACCAUCACUAUCAGCAGUGUGAAGACCAUGCCAUUA

AGCUUAGCAUGUUGACCAAGAAAGCUUGUCUGCAUCUGAAUCCCGGCGGAACCUGUGUCAGCAUAGGUUAUGGUUACG

CUGACAGGGCCAGCGAAAGCAUCAUUGGUGCUAUAGCGCGGCAGUUCAAGUUUUCCCGGGUAUGCAAACCGAAAUCCU

CACUUGAAGAGACGGAAGUUCUGUUUGUAUUCAUUGGGUACGAUCGCAAGGCCCGUACGCACAAUCCUUACAAGCUUU

CAUCAACCUUGACCAACAUUUAUACAGGUUCCAGACUCCACGAAGCCGGAUGUGCACCCUCAUAUCAUGUGGUGCGAG

GGGAUAUUGCCACGGCCACCGAAGGAGUGAUUAUAAAUGCUGCUAACAGCAAAGGACAACCUGGCGGAGGGGUGUGCG

GAGCGCUGUAUAAGAAAUUCCCGGAAAGCUUCGAUUUACAGCCGAUCGAAGUAGGAAAAGCGCGACUGGUCAAAGGUG

CAGCUAAACAUAUCAUUCAUGCCGUAGGACCAAACUUCAACAAAGUUUCGGAGGUUGAAGGUGACAAACAGUUGGCAG

AGGCUUAUGAGUCCAUCGCUAAGAUUGUCAACGAUAACAAUUACAAGUCAGUAGCGAUUCCACUGUUGUCCACCGGCA

UCUUUUCCGGGAACAAAGAUCGACUAACCCAAUCAUUGAACCAUUUGCUGACAGCUUUAGACACCACUGAUGCAGAUG

UAGCCAUAUACUGCAGGGACAAGAAAUGGGAAAUGACUCUCAAGGAAGCAGUGGCUAGGAGAGAAGCAGUGGAGGAGA

UAUGCAUAUCCGACGACUCUUCAGUGACAGAACCUGAUGCAGAGCUGGUGAGGGUGCAUCCGAAGAGUUCUUUGGCUG

GAAGGAAGGGCUACAGCACAAGCGAUGGCAAAACUUUCUCAUAUUUGGAAGGGACCAAGUUUCACCAGGCGGCCAAGG

AUAUAGCAGAAAUUAAUGCCAUGUGGCCCGUUGCAACGGAGGCCAAUGAGCAGGUAUGCAUGUAUAUCCUCGGAGAAA

GCAUGAGCAGUAUUAGGUCGAAAUGCCCCGUCGAAGAGUCGGAAGCCUCCACACCACCUAGCACGCUGCCUUGCUUGU

GCAUCCAUGCCAUGACUCCAGAAAGAGUACAGCGCCUAAAAGCCUCACGUCCAGAACAAAUUACUGUGUGCUCAUCCU

UUCCAUUGCCGAAGUAUAGAAUCACUGGUGUGCAGAAGAUCCAAUGCUCCCAGCCUAUAUUGUUCUCACCGAAAGUGC

CUGCGUAUAUUCAUCCAAGGAAGUAUCUCGUGGAAACACCACCGGUAGACGAGACUCCGGAGCCAUCGGCAGAGAACC

AAUCCACAGAGGGGACACCUGAACAACCACCACUUAUAACCGAGGAUGAGACCAGGACUAGAACGCCUGAGCCGAUCA

UCAUCGAAGAGGAAGAAGAGGAUAGCAUAAGUUUGCUGUCAGAUGGCCCGACCCACCAGGUGCUGCAAGUCGAGGCAG

ACAUUCACGGGCCGCCCUCUGUAUCUAGCUCAUCCUGGUCCAUUCCUCAUGCAUCCGACUUUGAUGUGGACAGUUUAU

CCAUACUUGACACCCUGGAGGGAGCUAGCGUGACCAGCGGGGCAACGUCAGCCGAGACUAACUCUUACUUCGCAAAGA

GUAUGGAGUUUCUGGCGCGACCGGUGCCUGCGCCUCGAACAGUAUUCAGGAACCCUCCACAUCCCGCUCCGCGCACAA

GAACACCGUCACUUGCACCCAGCAGGGCCUGCUCGAGAACCAGCCUAGUUUCCACCCCGCCAGGCGUGAAUAGGGUGA

UCACUAGAGAGGAGCUCGAGGCGCUUACCCCGUCACGCACUCCUAGCAGGUCGGUCUCGAGAACCAGCCUGGUCUCCA

ACCCGCCAGGCGUAAAUAGGGUGAUUACAAGAGAGGAGUUUGAGGCGUUCGUAGCACAACAACAAUGACGGUUUGAUG

CGGGUGCAUACAUCUUUUCCUCCGACACCGGUCAAGGGCAUUUACAACAAAAAUCAGUAAGGCAAACGGUGCUAUCCG

AAGUGGUGUUGGAGAGGACCGAAUUGGAGAUUUCGUAUGCCCCGCGCCUCGACCAAGAAAAAGAAGAAUUACUACGCA

AGAAAUUACAGUUAAAUCCCACACCUGCUAACAGAAGCAGAUACCAGUCCAGGAAGGUGGAGAACAUGAAAGCCAUAA

CAGCUAGACGUAUUCUGCAAGGCCUAGGGCAUUAUUUGAAGGCAGAAGGAAAAGUGGAGUGCUACCGAACCCUGCAUC

CUGUUCCUUUGUAUUCAUCUAGUGUGAACCGUGCCUUUUCAAGCCCCAAGGUCGCAGUGGAAGCCUGUAACGCCAUGU

UGAAAGAGAACUUUCCGACUGUGGCUUCUUACUGUAUUAUUCCAGAGUACGAUGCCUAUUUGGACAUGGUUGACGGAG

CUUCAUGCUGCUUAGACACUGCCAGUUUUUGCCCUGCAAAGCUGCGCAGCUUUCCAAAGAAACACUCCUAUUUGGAAC

-continued

CCACAAUACGAUCGGCAGUGCCUUCAGCGAUCCAGAACACGCUCCAGAACGUCCUGGCAGCUGCCACAAAAAGAAAUU

GCAAUGUCACGCAAAUGAGAGAAUUGCCCGUAUUGGAUUCGGCGGCCUUUAAUGUGGAAUGCUUCAAGAAAUAUGCGU

GUAAUAAUGAAUAUUGGGAAACGUUUAAAGAAAACCCCAUCAGGCUUACUGAAGAAAACGUGGUAAAUUACAUUACCA

AAUUAAAAGGACCAAAAGCUGCUGCUCUUUUUGCGAAGACACAUAAUUUGAAUAUGUUGCAGGACAUACCAAUGGACA

GGUUUGUAAUGGACUUAAAGAGAGACGUGAAAGUGACUCCAGGAACAAAACAUACUGAAGAACGGCCCAAGGUACAGG

UGAUCCAGGCUGCCGAUCCGCUAGCAACAGCGUAUCUGUGCGGAAUCCACCGAGAGCUGGUUAGGAGAUUAAAUGCGG

UCCUGCUUCCGAACAUUCAUACACUGUUUGAUAUGUCGGCUGAAGACUUUGACGCUAUUAUAGCCGAGCACUUCCAGC

CUGGGGAUUGUGUUCUGGAAACUGACAUCGCGUCGUUUGAUAAAAGUGAGGACGACGCCAUGGCUCUGACCGCGUUAA

UGAUUCUGGAAGACUUAGGUGUGGACGCAGAGCUGUUGACGCUGAUUGAGGCGGCUUUCGGCGAAAUUUCAUCAAUAC

AUUUGCCCACUAAAACUAAAUUUAAAUUCGGAGCCAUGAUGAAAUCUGGAAUGUUCCUCACACUGUUUGUGAACACAG

UCAUUAACAUUGUAAUCGCAAGCAGAGUGUUGAGAGAACGGCUAACCGGAUCACCAUGUGCAGCAUUCAUUGGAGAUG

ACAAUAUCGUGAAAGGAGUCAAAUCGGACAAAUUAAUGGCAGACAGGUGCGCCACCUGGUUGAAUAUGGAAGUCAAGA

UUAUAGAUGCUGUGGUGGGCGAGAAAGCGCCUUAUUUCUGUGGAGGGUUUAUUUUGUGUGACUCCGUGACCGGCACAG

CGUGCCGUGUGGCAGACCCCCUAAAAAGGCUGUUUAAGCUUGGCAAACCUCUGGCAGCAGACGAUGAACAUGAUGAUG

ACAGGAGAAGGGCAUUGCAUGAAGAGUCAACACGCUGGAACCGAGUGGGUAUUCUUUCAGAGCUGUGCAAGGCAGUAG

AAUCAAGGUAUGAAACCGUAGGAACUUCCAUCAUAGUUAUGGCCAUGACUACUCUAGCUAGCAGUGUUAAAUCAUUCA

GCUACCUGAGAGGGGCCCCUAUAACUCUCUACGGCUAACCUGAAUGGACUACGACAUAGUCUAGUCCGCCAAG

VEEV RNA polymerase Amino Acid Sequence (NCBI Accession: AXP98866.1)

SEQ ID NO: 35

RELPVLDSAAFNVECFKKYACNNEYWETFKENPIRLTEENVVNYITKLKGP

VEEV RNA polymerase Amino Acid Sequence (NCBI Accession: AXP98867.1)

SEQ ID NO: 36

TQMRELPVLDSAAFNVECFKKYACNNEYWETFKENPIRLTE

Polyprotein Amino Acid Sequence [Venezuelan equine encephalitis virus] (GenBank: ALE15116.1)

SEQ ID NO: 37

MKAITARRILQGLGHYLKAEGKVECYRTLHPVPLYSSSVNRAFSSPKVAVEACNAMLKENFPTVASYCIIPEYDAYLD

MIDGASCCLDTASFCPAKLRSFPKKHSYLEPTIRSAVPSAIQNTLQNVLAAATKRNCNVTQMRELPVLDSAAFNVECF

KKYACNNEYWKTFKENPIRLTEENVINYITKLKGPKAAALYAKTHNLNMLQDIPMDRFVMDLKRDVKVTPGTKHTEER

PKVQVIQAADPLATAYLCGIHRELVRRLNAVLLPNIHTLFDMSAEDFDAIIAEHFQPGDCVLETDIASFDKSEDDAMA

LTAMMILEDLGVDAELLTLIEAAFGEISSIHLPTKTKFKFGAMMKSGMFLTLFVNTVINIVIASRVLRERLTGSPCAA

FIGDDNIVKGVKSDKLMADRCATWLNMEVKIIDAVVGEKAPYFCGGFILCDSVTGTACRVADPLKRLFKLGKPLAADD

EHDDDRRRALHEESTRWNRVGILPELCKAVESRYETVGTSVIVMAMATLASSVKSFSYLRGAPITLYG

The following sequences (SEQ ID NOS: 38-43) are formatted to signify vector backbone and antigen open reading frames as follows: lower case letters signify the vector backbone sequence; and UPPER CASE letters signify the VZV antigen open reading frame.

VEEV-kozak-VZV-FL-gE

SEQ ID NO: 38 auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa -continued ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucaugggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uaguggugagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucgugugggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaagugguccgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa -continued ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggagggggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauaggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg -continued uccugcuuccgaacauucauacacuguuugauaugucggcugaagacuuugacgcuauuauagccgagcacuuccagc
cuggggauuguguucuggaaacugacaucgcgucguuugauaaaagugaggacgacgccauggcucugaccgcguuaa
ugauucuggaagacuuagguguggacgcagagcuguugacgcugauugaggcggcuuucggcgaaauuucaucaauac
auuugcccacuaaaacuaaauuuaaauucggagccaugaugaaaucuggaauguuccucacacuguuugugaacacag
ucauuaacauuguaaucgcaagcagaguguugagagaacggcuaaccggaucaccaugugcagcauucauuggagaug
acaauaucgugaaaggagucaaaucggacaaauuaauggcagacaggugcgccaccugguugaauauggaagucaaga
uuauagaugcugugguggggcgagaaagcgccuuauuucuguggagggguuuauuuugugugacuccgugaccggcacag
cgugccguguggcagaccccuaaaaaggcuguuuaagcuuggcaaaccucuggcagcagacgaugaacaugaugaug
acaggagaagggcauugcaugaagagucaacacgcuggaaccgaguggguauucuuucagagcugugcaaggcaguag
aaucaagguaugaaaccguaggaacuuccaucauaguuauggccaugacuacucuagcuagcaguguuaaaucauuca
gcuaccugagaggggccccuauaacucucuacggcuaaccugaauggacuacgacauagucuaguccgcCGCCACCAU
GUUCUAUGAAGCUUUGAAGGCCGAACUUGUAUACACCCGAGCCGUGCAUGGUUUCCGCCCGAGAGCGAACUGCGUCGU
ACUGUCAGAUUACAUCCCCAGAGUCGCGUGCAACAUGGGUACGGUUAAUAAGCCCGUGGUGGGGGUGCUGAUGGGUUU
UGGGAUAAUCACCGGAACUCUGCGCAUCACAAAUCCUGUAAGAGCGUCAGUGCUGAGGUAUGACGAUUUCCACAUAGA
CGAGGACAAGCUGGAUACCAAUUCCGUUUACGAACCAUAUUAUCACUCCGAUCACGCCGAAUCCAGCUGGGUAAAUCG
AGGAGAGUCCUCACGGAAGGCAUACGACCAUAACUCCCCAUAUAUAUGGCCUCGCAAUGAUUAUGACGGAUUCCUGGA
AAACGCCCAUGAGCACCACGGCGUUUAUAACCAGGGUCGCGGUAUCGAUUCUGGGGAAAGGUUGAUGCAACCAACUCA
GAUGUCCGCUCAGGAAGAUUUGGGGGAUGACACCGGAAUCCAUGUGAUACCUACACUCAAUGGUGAUGAUCGACACAA
AAUUGUAAACGUGGACCAGAGGCAAUACGGGGACGUUUUUAAGGGAGACCUGAAUCCAAAACCACAAGGACAACGACU
CAUCGAGGUUUCUGUAGAAGAAAACCAUCCGUUUACGCUCCGCGCCCCCAUACAGCGCAUAUAUGGCGUGCGCUAUAC
GGAGACCUGGUCUUUUCUCCCCAGUCUGACAUGCACUGGUGAUGCAGCUCCAGCAAUUCAGCACAUAUGUCUCAAGCA
UACCACCUGUUUCCAAGAUGUAGUAGUGGAUGUGGAUUGCGCCGAAAACACGAAAGAAGACCAGCUUGCCGAGAUUUC
AUACCGGUUUCAAGGAAAAAAAGAAGCCGACCAGCCGUGGAUAGUAGUGAAUACGUCCACGCUCUUCGAUGAACUGGA
AUUGGACCCUCCUGAAAUUGAACCCGGAGUCCUGAAAGUUUUGCGGACUGAGAAACAGUAUCUCGGUGUGUACAUCUG
GAAUAUGAGGGGCAGUGAUGGAACAAGCACAUACGCGACCUUUCUGGUGACAUGGAAAGGUGACGAAAAGACUAGAAA
CCCAACCCCAGCAGUGACCCCCCAACCUAGAGGUGCUGAGUUCCACAUGUGGAAUUACCACUCCCAUGUAUUCUCUGU
CGGAGACACCUUCAGCUUGGCGAUGCACCUCCAAUACAAGAUCCAUGAAGCCCCGUUCGACCUCUUGUUGGAGUGGCU
CUACGUACCAAUAGACCCUACCUGUCAACCAAUGAGGCUUUACUCUACAUGCCUUUACCACCCAAACGCACCACAAUG
UCUUUCUCAUAUGAAUAGCGGUUGUACAUUUACAUCUCCCCAUCUCGCGCAAAGAGUCGCGAGUACAGUUUACCAAAA
UUGUGAGCAUGCGGACAAUUACACAGCAUAUUGUCUUGGGAUCUCCCACAUGGAGCCCUCUUUUGGGCUUAUACUUCA
CGACGGGGGUACAACGCUUAAGUUCGUCGAUACGCCAGAAUCCCUCUCUGGCUUGUAUGUAUUCGUGGUUUAUUUUAA
CGGUCACGUUGAGGCUGUGGCCUAUACUGUUGUUAGCACUGUAGACCACUUUGUUAACGCCAUAGAAGAGAGGGGGUU
CCCGCCCACCGCUGGCCAGCCACCGGCCACAACGAAGCCUAAAGAGAUUACGCCGGUGAAUCCCGGCACAAGUCCCCU
UAUCCGGUACGCCGCAUGGACAGGAGGACUGGCGGCCGUCGUCCUCCUUUGUCUGGUUAUAUUCCUUAUAUGCACGGC
AAAGCGAAUGCGGGUUAAGGCUUACCGAGUGGAUAAAUCUCCAUAUAAUCAGAGCAUGUAUUACGCAGGGCUCCCUGU
GGACGACUUUGAGGAUAGCGAGUCCACGGAUACAGAAGAGGAAUUUGGAAACGCCAUCGGUGGGAGCCAUGGAGGGUC
AUCUUACACCGUUUACAUUGACAAAACUAGAUGAuaaccgcggugucaaaaaccgcguggacgugguuaacaucccug
cugggaggaucagccguaauuauuauaauuggcuuggugcuggcuacuauuguggccauguacgugcugaccaaccag
aaacauaauugaauacagcagcaauuggcaagcugcuuacauagaacucgcggcgauuggcaugccgccuuaaaauuu
uuauuuuauuuuuucuuuucuuuuccgaaucggauuuuguuuuuaauauuucaaaaaaaaaaaaaaaaaaaaaaaaaa
aaaaaaaaaaaaaaaaaa -continued VEEV-kozak-FL-gI

SEQ ID NO: 39 auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucgguguggagacuauaguuaguugcgacggguacgucguuaaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uagugguggagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuucccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugcccucucaagggcugacccgua aaggugugcuaugccguucgguacaaggugaaugaaaauccucuguacgcacccaccucagaacaugugaacguccuac ugacccgcacggaggaccgcaucgugugggaaaacacuagccggcgacccauggauaaaaacacugacugccaaguacc cugggaauuucacugccacgauagaggaguggcaagcagagcaugaugccaucaugaggcacaucuuggagagaccgg -continued acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga acccuaccgacgucuuccagaauaaggcaaacguguguugggccaaggcuuuagugccggugcugaagaccgcuggca ggaauaaucacugggauaacuccccgucgccuaacauguacgggcugaauaaagaagugguccgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccgguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggaggggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagcaguuuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauagggug a ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac -continued ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggggcgagaaagcgccuuauuucuguggaggguuuauuuugugugacuccgugaccggcacag cgugccguguggcagaccccccuaaaaaggcuguuuaagcuuggcaaaccucuggcagcagacgaugaacaugaugaug acaggagaagggcauugcaugaagagucaacacgcuggaaccgaguggguauucuuucagagcugugcaaggcaguag aaucaagguaugaaaccguaggaacuuccaucauaguuauggccaugacuacucuagcuagcaguguuaaaucauuca gcuaccugagagggggccccuauaacucucuacggcuaaccugaauggacuacgacauagucuaguccgcCGCCACCAU

GUUCCUUAUUCAAUGCCUCAUAUCCGCAGUCAUCUUCUAUAUUCAAGUUACUAAUGCACUUAUCUUCAAGGGCGAUCA

UGUCAGCCUGCAAGUGAAUUCAAGUCUUACGUCCAUUUUGAUUCCAAUGCAGAAUGAUAACUAUACCGAAAUUAAGGG

ACAGCUGGUUUUUAUUGGAGAACAACUGCCGACCGGUACAAACUACAGCGGGACCCUCGAGCUGCUUUACGCAGACAC

UGUGGCAUUCUGCUUUCGGUCAGUACAAGUUAUCAGAUACGACGGAUGCCCACGCAUUAGGACAUCUGCCUUCAUUUC

UUGCCGAUACAAGCAUAGUUGGCAUUACGGAAACUCUACCGAUAGAAUUUCAACUGAACCAGAUGCCGGUGUGAUGCU

CAAGAUAACCAAACCUGGGAUCAACGACGCAGGGGUGUAUGUCCUCUUGGUGAGAUUGGACCAUUCAAGGAGUACGGA

CGGGUUUAUACUGGGCGUGAACGUCUAUACCGCAGGAAGUCAUCAUAACAUUCACGGUGUCAUUUAUACCAGCCCCAG

UCUCCAGAAUGGGUACAGCACUCGAGCCCUGUUCCAGCAAGCAAGAUUGUGUGACCUUCCAGCCACUCCUAAGGGAUC

AGGCACAAGUCUUUUUCAACAUAUGUUGGAUCUCAGAGCAGGGAAAAGUCUUGAGGACAACCCGUGGCUCCAUGAAGA

CGUGGUUACUACUGAAACAAAGUCAGUGGUCAAGGAGGGAAUCGAGAACCAUGUGUACCCAACUGACAUGAGCACGCU

GCCUGAAAAAUCACUGAACGACCCACCAGAGAAUCUGCUGAUAAUAAUACCUAUUGUAGCGAGUGUUAUGAUUUUGAC

CGCAAUGGUCAUAGUUAUUGUAAUAAGCGUGAAAAGGAGACGAAUCAAAAAACAUCCGAUAUACAGGCCGAAUACGAA

GACAAGAAGAGGGAUUCAGAACGCGACUCCGGAGAGUGAUGUAAUGCUCGAAGCAGCCAUCGCUCAACUUGCCACCAU

UCGCGAAGAAAGCCCUCCGCAUUCCGUCGUAAAUCCUUUUGUCAAGUGAuaaccgcggugucaaaaaccgcguggacg ugguuaacaucccugcugggaggaucagccguaauuauuauaauuggcuuggugcuggcuacuauuguggccauguac gugcugaccaaccagaaacauaauugaauacagcagcaauuggcaagcugcuuacauagaacucgcggcgauuggcau gccgccuuaaaauuuuuauuuuauuuuuucuuuucuuuuccgaaucggauuuuguuuuuaauauuucaaaaaaaaaaa aaaaaaaaaaaaaaaaaaaaaaaaaaaaaaaaa VZV-N term trunc gE

SEQ ID NO: 40 auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc -continued cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucaugggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uagugguggagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucgugugggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaaguggucgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug -continued acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauuggguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggagggggugugcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauagggu ga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg -continued ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcuguggugggcgagaaagcgccuuauuucuguggaggguuuauuuugugugacuccgugaccggcacag cgugccguguggcagacccccuaaaaaggcuguuuaagcuuggcaaaccucuggcagcagacgaugaacaugaugaug acaggagaagggcauugcaugaagagucaacacgcuggaaccgagugggguauucuuucagagcugugcaaggcaguag aaucaagguaugaaaccguaggaacuuccaucauaguuauggccaugacuacucuagcuagcaguguuaaaucauuca gcuaccugagaggggccccuauaacucucuacggcuaaccugaauggacuacgacauagucuaguccgcCGCCACCAU

GGGUACGGUUAAUAAGCCCGUGGUGGGGGUGCUGAUGGGUUUUGGGAUAAUCACCGGAACUCUGCGCAUCACAAAUCC

UGUAAGAGCGUCAGUGCUGAGGUAUGACGAUUUCCACAUAGACGAGGACAAGCUGGAUACCAAUUCCGUUUACGAACC

AUAUUAUCACUCCGAUCACGCCGAAUCCAGCUGGGUAAAUCGAGGAGAGUCCUCACGGAAGGCAUACGACCAUAACUC

CCCAUAUAUAUGGCCUCGCAAUGAUUAUGACGGAUUCCUGGAAAACGCCCAUGAGCACCACGGCGUUUAUAACCAGGG

UCGCGGUAUCGAUUCUGGGGAAAGGUUGAUGCAACCAACUCAGAUGUCCGCUCAGGAAGAUUUGGGGGAUGACACCGG

AAUCCAUGUGAUACCUACACUCAAUGGUGAUGAUCGACACAAAAUUGUAAACGUGGACCAGAGGCAAUACGGGGACGU

UUUUAAGGGAGACCUGAAUCCAAAACCACAAGGACAACGACUCAUCGAGGUUUCUGUAGAAGAAAACCAUCCGUUUAC

GCUCCGCGCCCCCAUACAGCGCAUAUAUGGCGUGCGCUAUACGGAGACCUGGUCUUUUCUCCCCAGUCUGACAUGCAC

UGGUGAUGCAGCUCCAGCAAUUCAGCACAUAUGUCUCAAGCAUACCACCUGUUUCCAAGAUGUAGUAGUGGAUGUGGA

UUGCGCCGAAAACACGAAAGAAGACCAGCUUGCCGAGAUUUCAUACCGGUUUCAAGGAAAAAAAGAAGCCGACCAGCC

GUGGAUAGUAGUGAAUACGUCCACGCUCUUCGAUGAACUGGAAUUGGACCCUCCUGAAAUUGAACCCGGAGUCCUGAA

AGUUUUGCGGACUGAGAAACAGUAUCUCGGUGUGUACAUCUGGAAUAUGAGGGGCAGUGAUGGAACAAGCACAUACGC

GACCUUUCUGGUGACAUGGAAAGGUGACGAAAAGACUAGAAACCCAACCCCAGCAGUGACCCCCCAACCUAGAGGUGC

UGAGUUCCACAUGUGGAAUUACCACUCCCAUGUAUUCUCUGUCGGAGACACCUUCAGCUUGGCGAUGCACCUCCAAUA

CAAGAUCCAUGAAGCCCCGUUCGACCUCUUGUUGGAGUGGCUCUACGUACCAAUAGACCCUACCUGUCAACCAAUGAG

GCUUUACUCUACAUGCCUUUACCACCCAAACGCACCACAAUGUCUUUCUCAUAUGAAUAGCGGUUGUACAUUUACAUC

UCCCCAUCUCGCGCAAAGAGUCGCGAGUACAGUUUACCAAAAUUGUGAGCAUGCGGACAAUUACACAGCAUAUUGUCU

UGGGAUCUCCCACAUGGAGCCCUCUUUUGGGCUUAUACUUCACGACGGGGGUACAACGCUUAAGUUCGUCGAUACGCC

AGAAUCCCUCUCUGGCUUGUAUGUAUUCGUGGUUUAUUUUAACGGUCACGUUGAGGCUGUGGCCUAUACUGUUGUUAG

CACUGUAGACCACUUUGUUAACGCCAUAGAAGAGAGGGGGUUCCCGCCCACCGCUGGCCAGCCACCGGCCACAACGAA

GCCUAAAGAGAUUACGCCGGUGAAUCCCGGCACAAGUCCCCUUAUCCGGUACGCCGCAUGGACAGGAGGACUGGCGGC

CGUCGUCCUCCUUUGUCUGGUUAUAUUCCUUAUAUGCACGGCAAAGCGAAUGCGGGUUAAGGCUUACCGAGUGGAUAA

AUCUCCAUAUAAUCAGAGCAUGUAUUACGCAGGGCUCCCUGUGGACGACUUUGAGGAUAGCGAGUCCACGGAUACAGA

AGAGGAAUUUGGAAACGCCAUCGGUGGGAGCCAUGGAGGGUCAUCUUACACCGUUUACAUUGACAAAACUAGAUGAua accgcggugucaaaaaccgcguggacgugguuaacaucccugcugggaggaucagccguaauuuuauaauuuugcuug gugcuggcuacuauuguggccauguacgugcugaccaaccagaaacauaauugaauacagcagcaauuggcaagcugc uuacauagaacucgcggcgauuggcaugccgccuuaaaauuuuuauuuuauuuuuucuuuucuuuuccgaaucggauu uuguuuuuaauauuucaaaaaaaaaaaaaaaaaaaaaaaaaaaaaaaaaaaaaaaaaaaaaaaa -continued FL-gI-T2A-gE

SEQ ID NO: 41 auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uagugguga gcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucgugugggaaaacacuagccggcgacccauggauaaaaacacugacugccaaguacc cugggaauuucacugccacgauagaggaguggcaagcagagcaugaugccaucaugaggcacaucuuggagagaccgg -continued acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaagugguccgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccgguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucauguggugcgag gggauauugccacggccaccgaaggagugauuauaaaugcugcuaacagcaaaggacaaccuggcggagggguguggcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuccaccccgccaggcgugaauaggguga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac -continued ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugguggugggcgagaaagcgccuuauuucuguggagggguuuauuuugugugacuccgugaccggcacag cgugccguguggcagacccccuaaaaaggcuguuuaagcuuggcaaaccucuggcagcagacgaugaacaugaugaug acaggagaagggcauugcaugaagagucaacacgcuggaaccgagugguauucuuucagagcugugcaaggcaguag aaucaagguaugaaaccguaggaacuuccaucauaguuauggccaugacuacucuagcuagcaguguuaaaucauuca gcuaccugagaggggccccuauaacucucuacggcuaaccugaauggacuacgacauagucuaguccgcCGCCACCAU

GUUCCUUAUUCAAUGCCUCAUAUCCGCAGUCAUCUUCUAUAUUCAAGUUACUAAUGCACUUAUCUUCAAGGGCGAUCA

UGUCAGCCUGCAAGUGAAUUCAAGUCUUACGUCCAUUUUGAUUCCAAUGCAGAAUGAUAACUAUACCGAAAUUAAGGG

ACAGCUGGUUUUUAUUGGAGAACAACUGCCGACCGGUACAAACUACAGCGGGACCCUCGAGCUGCUUUACGCAGACAC

UGUGGCAUUCUGCUUUCGGUCAGUACAAGUUAUCAGAUACGACGGAUGCCCACGCAUUAGGACAUCUGCCUUCAUUUC

UUGCCGAUACAAGCAUAGUUGGCAUUACGGAAACUCUACCGAUAGAAUUUCAACUGAACCAGAUGCCGGUGUGAUGCU

CAAGAUAACCAAACCUGGGAUCAACGACGCAGGGGUGUAUGUCCUCUUGGUGAGAUUGGACCAUUCAAGGAGUACGGA

CGGGUUUAUACUGGGCGUGAACGUCUAUACCGCAGGAAGUCAUCAUAACAUUCACGGUGUCAUUUAUACCAGCCCCAG

UCUCCAGAAUGGGUACAGCACUCGAGCCCUGUUCCAGCAAGCAAGAUUGUGUGACCUUCCAGCCACUCCUAAGGGAUC

AGGCACAAGUCUUUUUCAACAUAUGUUGGAUCUCAGAGCAGGGAAAAGUCUUGAGGACAACCCGUGGCUCCAUGAAGA

CGUGGUUACUACUGAAACAAAGUCAGUGGUCAAGGAGGGAAUCGAGAACCAUGUGUACCCAACUGACAUGAGCACGCU

GCCUGAAAAAUCACUGAACGACCCACCAGAGAAUCUGCUGAUAAUAAUACCUAUUGUAGCGAGUGUUAUGAUUUUGAC

CGCAAUGGUCAUAGUUAUUGUAAUAAGCGUGAAAAGGAGACGAAUCAAAAAACAUCCGAUAUACAGGCCGAAUACGAA

GACAAGAAGAGGGAUUCAGAACGCGACUCCGGAGAGUGAUGUAAUGCUCGAAGCAGCCAUCGCUCAACUUGCCACCAU

UCGCGAAGAAAGCCCUCCGCAUUCCGUCGUAAAUCCUUUUGUCAAGCGGAGGAAAAGGGGAUCCGGGGAAGGCCGGGG

UAGUUUGCUGACGUGCGGAGAUGUUGAAGAGAACCCAGGGCCGAUGUUCUAUGAAGCUUUGAAGGCCGAACUUGUAUA

CACCCGAGCCGUGCAUGGUUUCCGCCCGAGAGCGAACUGCGUCGUACUGUCAGAUUACAUCCCCAGAGUCGCGUGCAA

CAUGGGUACGGUUAAUAAGCCCGUGGUGGGGGUGCUGAUGGGUUUUGGGAUAAUCACCGGAACUCUGCGCAUCACAAA

UCCUGUAAGAGCGUCAGUGCUGAGGUAUGACGAUUUCCACAUAGACGAGGACAAGCUGGAUACCAAUUCCGUUUACGA

ACCAUAUUAUCACUCCGAUCACGCCGAAUCCAGCUGGGUAAAUCGAGGAGAGUCCUCACGGAAGGCAUACGACCAUAA

CUCCCCAUAUAUAUGGCCUCGCAAUGAUUAUGACGGAUUCCUGGAAAACGCCCAUGAGCACCACGGCGUUUAUAACCA

GGGUCGCGGUAUCGAUUCUGGGGAAAGGUUGAUGCAACCAACUCAGAUGUCCGCUCAGGAAGAUUUGGGGGAUGACAC

CGGAAUCCAUGUGAUACCUACACUCAAUGGUGAUGAUCGACACAAAAUUGUAAACGUGGACCAGAGGCAAUACGGGGA

CGUUUUUAAGGGAGACCUGAAUCCAAAACCACAAGGACAACGACUCAUCGAGGUUUCUGUAGAAGAAAACCAUCCGUU

-continued

UACGCUCCGCGCCCCCAUACAGCGCAUAUAUGGCGUGCGCUAUACGGAGACCUGGUCUUUUCUCCCCAGUCUGACAUG

CACUGGUGAUGCAGCUCCAGCAAUUCAGCACAUAUGUCUCAAGCAUACCACCUGUUUCCAAGAUGUAGUAGUGGAUGU

GGAUUGCGCCGAAAACACGAAAGAAGACCAGCUUGCCGAGAUUUCAUACCGGUUUCAAGGAAAAAAAGAAGCCGACCA

GCCGUGGAUAGUAGUGAAUACGUCCACGCUCUUCGAUGAACUGGAAUUGGACCCUCCUGAAAUUGAACCCGGAGUCCU

GAAAGUUUUGCGGACUGAGAAACAGUAUCUCGGUGUGUACAUCUGGAAUAUGAGGGGCAGUGAUGGAACAAGCACAUA

CGCGACCUUUCUGGUGACAUGGAAAGGUGACGAAAAGACUAGAAACCCAACCCCAGCAGUGACCCCCCAACCUAGAGG

UGCUGAGUUCCACAUGUGGAAUUACCACUCCCAUGUAUUCUCUGUCGGAGACACCUUCAGCUUGGCGAUGCACCUCCA

AUACAAGAUCCAUGAAGCCCCGUUCGACCUCUUGUUGGAGUGGCUCUACGUACCAAUAGACCCUACCUGUCAACCAAU

GAGGCUUUACUCUACAUGCCUUUACCACCCAAACGCACCACAAUGUCUUUCUCAUAUGAAUAGCGGUUGUACAUUUAC

AUCUCCCCAUCUCGCGCAAAGAGUCGCGAGUACAGUUUACCAAAAUUGUGAGCAUGCGGACAAUUACACAGCAUAUUG

UCUUGGGAUCUCCCACAUGGAGCCCUCUUUUGGGCUUAUACUUCACGACGGGGGUACAACGCUUAAGUUCGUCGAUAC

GCCAGAAUCCCUCUCUGGCUUGUAUGUAUUCGUGGUUUAUUUUAACGGUCACGUUGAGGCUGUGGCCUAUACUGUUGU

UAGCACUGUAGACCACUUUGUUAACGCCAUAGAAGAGAGGGGGUUCCCGCCCACCGCUGGCCAGCCACCGGCCACAAC

GAAGCCUAAAGAGAUUACGCCGGUGAAUCCCGGCACAAGUCCCCUUAUCCGGUACGCCGCAUGGACAGGAGGACUGGC

GGCCGUCGUCCUCCUUUGUCUGGUUAUAUUCCUUAUAUGCACGGCAAAGCGAAUGCGGGUUAAGGCUUACCGAGUGGA

UAAAUCUCCAUAUAAUCAGAGCAUGUAUUACGCAGGGCUCCCUGUGGACGACUUUGAGGAUAGCGAGUCCACGGAUAC

AGAAGAGGAAUUUGGAAACGCCAUCGGUGGGAGCCAUGGAGGGUCAUCUUACACCGUUUACAUUGACAAAACUAGAUG

Auaaccgcggugucaaaaaccgcguggacgugguuaacaucccugcugggaggaucagccguaauuauuauaauuggc uuggugcuggcuacuauuguggccauguacgugcugaccaaccagaaacauaauugaauacagcagcaauuggcaagc ugcuuacauagaacucgcggcgauuggcaugccgccuuaaaauuuuuauuuuauuuuuucuuuucuuuuccgaaucgg auuuuguuuuuaauauuucaaaaaaaaaaaaaaaaaaaaaaaaaaaaaaaaaaaaaaaaaaaaa FL-gI-IRES-gE

SEQ ID NO: 42 auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac -continued cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uagugguggagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu gcgguuuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aagguguguaugccguucgguacaaggugaaugaaaauccucuguacgcacccaccucagaacaugugaacguccuac ugacccgcacggaggaccgcaucgugugggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacgugugguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaaguggucgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuucccggguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucauguggugcgag gggauauugccacggccaccgaaggagugauuauaaaugcugcuaacagcaaaggacaaccuggcggagggguguggcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcugguggagggugcauccgaagaguucuuuggcug -continued gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauagggu ga ucacuagagaggagcucgaggcgcuuaccccgucacgcacuccuagcaggucggucucgagaaccagccuggucucca acccgccaggcguaaauagggugauuacaagagaggaguuugaggcguucguagcacaacaacaaugacgguuugaug cgggugcauacaucuuuucccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuagguguggacgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggcgagaaagcgccuuauuucuguggaggguuuauuuuguguggacuccgugaccggcacag cgugccguguggcagaccccccuaaaaaggcuguuuaagcuuggcaaaccucuggcagcagacgaugaacaugaugaug acaggagaaggcauugcaugaagagucaacacgcuggaaccgaguggguauucuuucagagcugugcaaggcaguag aaucaagguaugaaaccguaggaacuuccaucauaguuauggccaugacuacucuagcuagcaguguuaaaucauuca gcuaccugagaggggccccuauaacucucuacggcuaaccugaauggacuacgacauagucuaguccgcCGCCACCAU

GUUCCUUAUUCAAUGCCUCAUAUCCGCAGUCAUCUUCUAUAUUCAAGUUACUAAUGCACUUAUCUUCAAGGGCGAUCA

UGUCAGCCUGCAAGUGAAUUCAAGUCUUACGUCCAUUUUGAUUCCAAUGCAGAAUGAUAACUAUACCGAAAUUAAGGG

ACAGCUGGUUUUUAUUGGAGAACAACUGCCGACCGGUACAAACUACAGCGGGACCCUCGAGCUGCUUUACGCAGACAC

-continued

UGUGGCAUUCUGCUUUCGGUCAGUACAAGUUAUCAGAUACGACGGAUGCCCACGCAUUAGGACAUCUGCCUUCAUUUC

UUGCCGAUACAAGCAUAGUUGGCAUUACGGAAACUCUACCGAUAGAAUUUCAACUGAACCAGAUGCCGGUGUGAUGCU

CAAGAUAACCAAACCUGGGAUCAACGACGCAGGGGUGUAUGUCCUCUUGGUGAGAUUGGACCAUUCAAGGAGUACGGA

CGGGUUUAUACUGGGCGUGAACGUCUAUACCGCAGGAAGUCAUCAUAACAUUCACGGUGUCAUUUAUACCAGCCCCAG

UCUCCAGAAUGGGUACAGCACUCGAGCCCUGUUCCAGCAAGCAAGAUUGUGUGACCUUCCAGCCACUCCUAAGGGAUC

AGGCACAAGUCUUUUUCAACAUAUGUUGGAUCUCAGAGCAGGGAAAAGUCUUGAGGACAACCCGUGGCUCCAUGAAGA

CGUGGUUACUACUGAAACAAAGUCAGUGGUCAAGGAGGGAAUCGAGAACCAUGUGUACCCAACUGACAUGAGCACGCU

GCCUGAAAAAUCACUGAACGACCCACCAGAGAAUCUGCUGAUAAUAAUACCUAUUGUAGCGAGUGUUAUGAUUUUGAC

CGCAAUGGUCAUAGUUAUUGUAAUAAGCGUGAAAAGGAGACGAAUCAAAAAACAUCCGAUAUACAGGCCGAAUACGAA

GACAAGAAGAGGGAUUCAGAACGCGACUCCGGAGAGUGAUGUAAUGCUCGAAGCAGCCAUCGCUCAACUUGCCACCAU

UCGCGAAGAAAGCCCUCCGCAUUCCGUCGUAAAUCCUUUUGUCAAGUGACCCCUCUCCCUCCCCCCCCCCUAACGUUA

CUGGCCGAAGCCGCUUGGAAUAAGGCCGGUGUGCGUUUGUCUAUAUGUUAUUUUCCACCAUAUUGCCGUCUUUUGGCA

AUGUGAGGGCCCGGAAACCUGGCCCUGUCUUCUUGACGAGCAUUCCUAGGGGUCUUUCCCCUCUCGCCAAAGGAAUGC

AAGGUCUGUUGAAUGUCGUGAAGGAAGCAGUUCCUCUGGAAGCUUCUUGAAGACAAACAACGUCUGUAGCGACCCUUU

GCAGGCAGCGGAACCCCCCACCUGGCGACAGGUGCCUCUGCGGCCAAAAGCCACGUGUAUAAGAUACACCUGCAAAGG

CGGCACAACCCCAGUGCCACGUUGUGAGUUGGAUAGUUGUGGAAAGAGUCAAAUGGCUCUCCUCAAGCGUAUUCAACA

AGGGGCUGAAGGAUGCCCAGAAGGUACCCCAUUGUAUGGGAUCUGAUCUGGGGCCUCGGUGCACAUGCUUUACAUGUG

UUUAGUCGAGGUUAAAAAACGUCUAGGCCCCCCGAACCACGGGGACGUGGUUUUCCUUUGAAAAACACGAUGAUAAUA

UGGCCACAACCAUGUUCUAUGAAGCUUUGAAGGCCGAACUUGUAUACACCCGAGCCGUGCAUGGUUUCCGCCCGAGAG

CGAACUGCGUCGUACUGUCAGAUUACAUCCCCAGAGUCGCGUGCAACAUGGGUACGGUUAAUAAGCCCGUGGUGGGGG

UGCUGAUGGGUUUUGGGAUAAUCACCGGAACUCUGCGCAUCACAAAUCCUGUAAGAGCGUCAGUGCUGAGGUAUGACG

AUUUCCACAUAGACGAGGACAAGCUGGAUACCAAUUCCGUUUACGAACCAUAUUAUCACUCCGAUCACGCCGAAUCCA

GCUGGGUAAAUCGAGGAGAGUCCUCACGGAAGGCAUACGACCAUAACUCCCCAUAUAUAUGGCCUCGCAAUGAUUAUG

ACGGAUUCCUGGAAAACGCCCAUGAGCACCACGGCGUUUAUAACCAGGGUCGCGGUAUCGAUUCUGGGGAAAGGUUGA

UGCAACCAACUCAGAUGUCCGCUCAGGAAGAUUUGGGGGAUGACACCGGAAUCCAUGUGAUACCUACACUCAAUGGUG

AUGAUCGACACAAAAUUGUAAACGUGGACCAGAGGCAAUACGGGGACGUUUUUAAGGGAGACCUGAAUCCAAAACCAC

AAGGACAACGACUCAUCGAGGUUUCUGUAGAAGAAAACCAUCCGUUUACGCUCCGCGCCCCCAUACAGCGCAUAUAUG

GCGUGCGCUAUACGGAGACCUGGUCUUUUCUCCCCAGUCUGACAUGCACUGGUGAUGCAGCUCCAGCAAUUCAGCACA

UAUGUCUCAAGCAUACCACCUGUUUCCAAGAUGUAGUAGUGGAUGUGGAUUGCGCCGAAAACACGAAAGAAGACCAGC

UUGCCGAGAUUUCAUACCGGUUUCAAGGAAAAAAAGAAGCCGACCAGCCGUGGAUAGUAGUGAAUACGUCCACGCUCU

UCGAUGAACUGGAAUUGGACCCUCCUGAAAUUGAACCCGGAGUCCUGAAAGUUUUGCGGACUGAGAAACAGUAUCUCG

GUGUGUACAUCUGGAAUAUGAGGGGCAGUGAUGGAACAAGCACAUACGCGACCUUUCUGGUGACAUGGAAAGGUGACG

AAAAGACUAGAAACCCAACCCCAGCAGUGACCCCCCAACCUAGAGGUGCUGAGUUCCACAUGUGGAAUUACCACUCCC

AUGUAUUCUCUGUCGGAGACACCUUCAGCUUGGCGAUGCACCUCCAAUACAAGAUCCAUGAAGCCCCGUUCGACCUCU

UGUUGGAGUGGCUCUACGUACCAAUAGACCCUACCUGUCAACCAAUGAGGCUUUACUCUACAUGCCUUUACCACCCAA

ACGCACCACAAUGUCUUUCUCAUAUGAAUAGCGGUUGUACAUUUACAUCUCCCCAUCUCGCGCAAAGAGUCGCGAGUA

CAGUUUACCAAAAUUGUGAGCAUGCGGACAAUUACACAGCAUAUUGUCUUGGGAUCUCCCACAUGGAGCCCUCUUUUG

GGCUUAUACUUCACGACGGGGGUACAACGCUUAAGUUCGUCGAUACGCCAGAAUCCCUCUCUGGCUUGUAUGUAUUCG

UGGUUUAUUUUAACGGUCACGUUGAGGCUGUGGCCUAUACUGUUGUUAGCACUGUAGACCACUUUGUUAACGCCAUAG

AAGAGAGGGGGUUCCCGCCCACCGCUGGCCAGCCACCGGCCACAACGAAGCCUAAAGAGAUUACGCCGGUGAAUCCCG

-continued

GCACAAGUCCCCUUAUCCGGUACGCCGCAUGGACAGGAGGACUGGCGGCCGUCGUCCUCCUUUGUCUGGUUAUAUUCC

UUAUAUGCACGGCAAAGCGAAUGCGGGUUAAGGCUUACCGAGUGGAUAAAUCUCCAUAUAAUCAGAGCAUGUAUUACG

CAGGGCUCCCUGUGGACGACUUUGAGGAUAGCGAGUCCACGGAUACAGAAGAGGAAUUUGGAAACGCCAUCGGUGGGA

GCCAUGGAGGGUCAUCUUACACCGUUUACAUUGACAAAACUAGAUGAuaaccgcggugucaaaaaccgcguggacgug guuaacaucccugcugggaggaucagccguaauuauuauaauuggcuuggugcuggcuacuauuguggccauguacgu gcugaccaaccagaaacauaauugaauacagcagcaauuggcaagcugcuuacauagaacucgcggcgauuggcaugc cgccuuaaaauuuuuauuuuauuuuuucuuuucuuuuccgaaucggauuuuguuuuuaauauuucaaaaaaaaaaaaa aaaaaaaaaaaaaaaaaaaaaaaaaaaaaaaa Secreted-gE

SEQ ID NO: 43 auaggcggcgcaugagagaagcccagaccaauuaccuacccaaaauggagaaaguucacguugacaucgaggaagaca gcccauuccucagagcuuugcagcggagcuucccgcaguuugagguagaagccaagcaggucacugauaaugaccaug cuaaugccagagcguuuucgcaucuggcuucaaaacugaucgaaacggagguggacccauccgacacgauccuugaca uuggaagugcgcccgcccgcagaauguauucuaagcacaaguaucauuguaucuguccgaugagaugugcggaagauc cggacagauuguauaaguaugcaacuaagcugaagaaaaacuguaaggaaauaacugauaaggaauuggacaagaaaa ugaaggagcuggccgccgucaugagcgacccugaccuggaaacugagacuaugugccuccacgacgacgagucguguc gcuacgaagggcaagucgcuguuuaccaggauguauacgcgguugacggaccgacaagucucuaucaccaagccaaua agggaguuagagucgccuacuggauaggcuuugacaccaccccuuuuauguuuaagaacuuggcuggagcauauccau cauacucuaccaacugggccgacgaaaccguguuaacggcucguaacauaggccuaugcagcucugacguuauggagc ggucacguagagggauguccauucuuagaaagaaguauuugaaaccauccaacaauguucuauucucuguuggcucga ccaucuaccacgagaagagggacuuacugaggagcuggcaccugccgucuguauuucacuuacguggcaagcaaaauu acacaugucggugugagacuauaguuaguugcgacggguacgucguuaaaagaauagcuaucaguccaggccuguaug ggaagccuucaggcuaugcugcuacgaugcaccgcgagggauucuugugcugcaaagugacagacacauugaacgggg agagggucucuuuucccgugugcacguaugugccagcuacauugugugaccaaaugacuggcauacuggcaacagaug ucagugcggacgacgcgcaaaaacugcugguugggcucaaccagcguauagucgucaacggucgcacccagagaaaca ccaauaccaugaaaaauuaccuuuugcccguaguggcccaggcauuugcuaggugggcaaaggaauauaaggaagauc aagaagaugaaaggccacuaggacuacgagauagacaguuagucauggggguguuguugggcuuuuagaaggcacaaga uaacaucuauuuauaagcgcccggauacccaaaccaucaucaaagugaacagcgauuuccacucauucgugcugccca ggauaggcaguaacacauuggagaucgggcugagaacaagaaucaggaaaauguuagaggagcacaaggagccgucac cucucauuaccgccgaggacguacaagaagcuaagugcgcagccgaugaggcuaaggaggugcgugaagccgaggagu ugcgcgcagcucuaccaccuuuggcagcugauguugaggagcccacucuggaggcagacgucgacuugauguuacaag aggcuggggccggcucaguggagacaccucguggcuugauaaagguuaccagcuacgauggcgaggacaagaucggcu cuuacgcugugcuuucuccgcaggcuguacucaagagugaaaaauuaucuugcauccacccucucgcugaacaaguca uagugauaacacacucuggccgaaaagggcguuaugccguggaaccauaccaugguaaaguaguggugccagagggac augcaauacccguccaggacuuucaagcucugagugaaagugccaccauuguguacaacgaacgugaguucguaaaca gguaccugcaccauauugccacacauggaggagcgcugaacacugaugaagaauauuacaaaacugucaagcccagcg agcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaag uaccaaccauagggguguauggcgugccaggaucaggcaagucuggcaucauuaaaagcgcagucaccaaaaaagauc uaguggugagcgccaagaaagaaaacugugcagaaauuauaagggacgucaagaaaaugaaagggcuggacgucaaug ccagaacuguggacucagugcucuugaauggaugcaaacaccccguagagacccuguauauugacgaagcuuuugcuu gucaugcagguacucucagagcgcucauagccauuauaagaccuaaaaaggcagugcucugcggggaucccaaacagu -continued gcgguuuuuuaacaugaugugccugaaagugcauuuuaaccacgagauuugcacacaagucuuccacaaaagcaucu cucgccguugcacuaaaucugugacuucggucgucucaaccuuguuuuacgacaaaaaaaugagaacgacgaauccga aagagacuaagauugugauugacacuaccggcaguaccaaaccuaagcaggacgaucucauucucacuuguuucagag ggugggugaagcaguugcaaauagauuacaaaggcaacgaaauaaugacggcagcugccucucaagggcugacccgua aaggugugugaugccguucgguacaaggugaaugaaaauccucuguacgcacccaccucagaacaugugaacguccuac ugacccgcacggaggaccgcaucguguggaaaacacuagccggcgacccauggauaaaaacacugacugccaaguacc cugggaauuucacugccacgauagaggaguggcaagcagagcaugaugccaucaugaggcacaucuuggagagaccgg acccuaccgacgucuuccagaauaaggcaaacguguguugggccaaggcuuuagugccggugcugaagaccgcuggca uagacaugaccacugaacaauggaacacuguggauuauuuugaaacggacaaagcucacucagcagagauaguauuga accaacuaugcgugagguucuuuggacucgaucuggacuccggucuauuuucugcacccacuguuccguuauccauua ggaauaaucacugggauaacuccccgucgccuaacauguacgggcugaauaaagaaguggucgucagcucucucgca gguacccacaacugccucgggcaguugccacuggaagagucuaugacaugaacacugguacacugcgcaauuaugauc cgcgcauaaaccuaguaccuguaaacagaagacugccucaugcuuuaguccuccaccauaaugaacacccacagagug acuuuucuucauucgucagcaaauugaagggcagaacuguccugguggucggggaaaaguuguccgucccaggcaaaa ugguugacugguugucagaccggccugaggcuaccuucagagcucggcuggauuuaggcaucccaggugaugugccca aauaugacauaauauuuguuaaugugaggaccccauauaaauaccaucacuaucagcagugugaagaccaugccauua agcuuagcauguugaccaagaaagcuugucugcaucugaaucccggcggaaccugugucagcauagguuaugguuacg cugacagggccagcgaaagcaucauuggugcuauagcgcggcaguucaaguuuucccggguaugcaaaccgaaauccu cacuugaagagacggaaguucuguuuguauucauugguacgaucgcaaggcccguacgcacaauccuuacaagcuuu caucaaccuugaccaacauuuauacagguuccagacuccacgaagccggaugugcacccucauaucaugguggugcgag gggauauugccacggccaccgaaggagugauuauaaaugcugcuaacagcaaaggacaaccuggcggagggguguggcg gagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcag aggcuuaugaguccaucgcuaagauugucaacgauaacaauuacaagucaguagcgauuccacuguuguccaccggca ucuuuuccgggaacaaagaucgacuaacccaaucauugaaccauuugcugacagcuuuagacaccacugaugcagaug uagccauauacugcagggacaagaaaugggaaaugacucucaaggaagcaguggcuaggagagaagcaguggaggaga uaugcauauccgacgacucuucagugacagaaccugaugcagagcuggugagggugcauccgaagaguucuuuggcug gaaggaagggcuacagcacaagcgauggcaaaacuuucucauauuuggaagggaccaaguuucaccaggcggccaagg auauagcagaaauuaaugccauguggcccguugcaacggaggccaaugagcagguaugcauguauauccucggagaaa gcaugagcaguauuaggucgaaaugccccgucgaagagucggaagccuccacaccaccuagcacgcugccuugcuugu gcauccaugccaugacuccagaaagaguacagcgccuaaaagccucacguccagaacaaauuacugugugcucauccu uuccauugccgaaguauagaaucacuggugugcagaagauccaaugcucccagccuauauuguucucaccgaaagugc cugcguauauucauccaaggaaguaucucguggaaacaccaccgguagacgagacuccggagccaucggcagagaacc aauccacagaggggacaccugaacaaccaccacuuauaaccgaggaugagaccaggacuagaacgccugagccgauca ucaucgaagaggaagaagaggauagcauaaguuugcugucagauggcccgacccaccaggugcugcaagucgaggcag acauucacgggccgcccucuguaucuagcucauccugguccauuccucaugcauccgacuuugauguggacaguuuau ccauacuugacacccuggagggagcuagcgugaccagcggggcaacgucagccgagacuaacucuuacuucgcaaaga guauggaguuucuggcgcgaccggugccugcgccucgaacaguauucaggaacccuccacaucccgcuccgcgcacaa gaacaccgucacuugcacccagcagggccugcucgagaaccagccuaguuuccaccccgccaggcgugaauagggguga ucacuagagaggagcucgaggcgcuuaccccgucacgcacuccuagcaggucggucucgagaaccagccuggucucca -continued acccgccaggcguaaauagggugauuacaagagaggaguuugaggcguucguagcacaacaacaaugacgguuugaug cgggugcauacaucuuuuccuccgacaccggucaagggcauuuacaacaaaaaucaguaaggcaaacggugcuauccg aagugguguuggagaggaccgaauuggagauuucguaugccccgcgccucgaccaagaaaaagaagaauuacuacgca agaaauuacaguuaaaucccacaccugcuaacagaagcagauaccaguccaggaagguggagaacaugaaagccauaa cagcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaugu ugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgu guaauaaugaauauugggaaacguuuaaagaaaaccccaucaggcuuacugaagaaaacgugguaaauuacauuacca aauuaaaaggaccaaaagcugcugcucuuuuugcgaagacacauaauuugaauauguugcaggacauaccaauggaca gguuuguaauggacuuaaagagagacgugaaagugacuccaggaacaaaacauacugaagaacggcccaagguacagg ugauccaggcugccgauccgcuagcaacagcguaucugugcggaauccaccgagagcugguuaggagauuaaaugcgg uccugcuuccgaacauucauacacuguuugauaugucggcugaagacuuugacgcuauuauagccgagcacuuccagc cuggggauuguguucuggaaacugacaucgcgucguuugauaaaagugaggacgacgccauggcucugaccgcguuaa ugauucuggaagacuuaggugugg acgcagagcuguugacgcugauugaggcggcuuucggcgaaauuucaucaauac auuugcccacuaaaacuaaauuuaaauucggagccaugaugaaaucuggaauguuccucacacuguuugugaacacag ucauuaacauuguaaucgcaagcagaguguugagagaacggcuaaccggaucaccaugugcagcauucauuggagaug acaauaucgugaaaggagucaaaucggacaaauuaauggcagacaggugcgccaccugguugaauauggaagucaaga uuauagaugcugugguggggcgagaaagcgccuuauuucuguggaggguuuauuuugugugacuccgugaccggcacag cgugccguguggcagaccccc uaaaaaggcuguuuaagcuuggcaaaccucuggcagcagacgaugaacaugaugaug acaggagaagggcauugcaugaagagucaacacgcuggaaccgaguggguauucuuucagagcugugcaaggcaguag aaucaagguaugaaaccguaggaacuuccaucauaguuauggccaugacuacucuagcuagcaguguuaaaucauuca gcuaccugagaggggccccuauaacucucuacggcuaaccugaauggacuacgacauagucuaguccgccaagAUGGG

UACCGUAAAUAAGCCCGUUGUCGGUGUCUUGAUGGGCUUUGGAAUCAUUACUGGAACUUUGAGGAUUACGAACCCUGU

CAGAGCCUCUGUUCUUCGGUACGACGACUUCCACAUUGACGAAGACAAGUUGGAUACCAACUCCGUAUACGAGCCGUA

UUACCACUCAGAUCAUGCCGAAUCAUCAUGGGUCAAUCGAGGCGAAUCUUCCCGAAAGGCGUACGAUCAUAACAGUCC

CUACAUAUGGCCCAGAAACGAUUACGACGGCUUUCUCGAGAACGCGCAUGAGCAUCAUGGGGUGUAUAAUCAAGGGAG

AGGCAUAGAUUCUGGUGAACGCUUGAUGCAACCAACUCAGAUGUCCGCACAAGAAGAUCUUGGGGACGACACAGGAAU

ACACGUCAUCCCUACACUGAACGGCGAUGAUCGGCAUAAGAUCGUAAAUGUGGAUCAACGGCAAUAUGGCGACGUGUU

UAAGGGGGACCUUAAUCCCAAGCCCCAGGGACAACGGUUGAUUGAGGUAUCUGUUGAGGAAAACCACCCCUUUACGCU

GCGGGCGCCGAUUCAGCGCAUCUACGGUGUUCGCUAUACGGAGACGUGGAGUUUCCUGCCAUCUCUCACAUGUACCGG

GGACGCUGCACCGGCAAUUCAACAUAUUUGCCUGAAACACACGACAUGCUUUCAAGACGUUGUAGUGGAUGUGGACUG

UGCGGAGAAUACCAAAGAGGACCAACUUGCGGAAAUAAGCUACCGAUUCCAAGGGAAGAAGGAGGCCGACCAGCCAUG

GAUUGUUGUUAAUACAUCUACACUUUUUGAUGAACUCGAACUUGACCCACCCGAGAUUGAACCUGGCGUUUUGAAAGU

CCUUAGAACAGAAAAACAAUACCUUGGUGUAUAUAUAUGGAACAUGAGGGGGUCCGACGGCACGUCUACCUAUGCCAC

CUUUCUGGUCACAUGGAAAGGAGAUGAAAAGACUCGCAAUCCUACCCCGGCGGUCACUCCUCAACCCAGAGGCGCUGA

GUUCCAUAUGUGGAAUUAUCAUUCACAUGUCUUCUCCGUUGGCGACACUUUUAGCUUGGCGAUGCAUCUGCAGUACAA

AAUACAUGAGGCGCCGUUCGACCUUCUCCUUGAAUGGCUCUAUGUGCCCAUUGAUCCUACUUGUCAACCGAUGAGGCU

UUACUCUACGUGCCUCUACCACCCGAAUGCGCCUCAAUGCCUGUCCCAUAUGAAUUCCGGGUGUACCUUUACAUCCCC

-continued

UCAUCUUGCUCAGCGAGUUGCUAGCACGGUUUACCAGAACUGCGAGCAUGCGGACAAUUAUACAGCCUACUGUCUUGG

CAUAAGUCACAUGGAACCUAGCUUCGGCCUGAUUCUCCAUGAUGGAGGAACAACGCUUAAAUUCGUAGACACCCCCGA

AUCAUUGAGCGGUUUGUAUGUUUUUGUAGUUUAUUUCAAUGGGCAUGUGGAGGCGGUAGCUUACACCGUCGUGUCAAC

AGUUGACCAUUUUGUCAACGCCAUCGAAGAAAGAGGAUUUCCGCCGACCGCGGGUCAGCCGCCCGCUACUACCAAACC

UAAGGAAAUUACUCCCGUGAACCCCGGCACCAGUCCGCUGAUAAGAUAUGCGGCUUGGACGGGAGGCUUGGCGugagg cgcgccauacagcagcaauuggcaagcugcuuacauagaacucgcggcgauuggcaugccgccuuaaaauuuuuauuu uauuuuuucuuuucuuuuccgaaucggauuuuguuuuuaauauuucaaaaaaaaaaaaaaaaaaaaaaaaaaaaaaaa aaaaaaaaaaaaa The following sequences (SEQ ID NOS: 44-47) are formatted to signify vector backbone and antigen open reading frames as follows: lower case letters signify the VEEV replicon backbone sequence; and UPPER CASE letters signify antigen open reading frame.

VEEV + Zika Envelope Protein Antigen Encoding RNA Sequence

SEQ ID NO: 44 auaggcggcgcaugagagaagcccagaccaauuaccuacccaaaauggagaaaguucacguugacaucgaggaagacag cccauuccucagagcuuugcagcggagcuucccgcaguuugagguagaagccaagcaggucacugauaaugaccaugcu aaugccagagcguuuucgcaucuggcuucaaaacugaucgaaacggagguggacccauccgacacgauccuugacauug gaagugcgcccgcccgcagaauguauucuaagcacaaguaucauuguaucuguccgaugagaugugcggaagauccgga cagauuguauaaguaugcaacuaagcugaagaaaaacuguaaggaaauaacugauaaggaauuggacaagaaaaugaag gagcuggccgccgucaugagcgacccugaccuggaaacugagacuaugugccuccacgacgacgagucgugucgcuacg aagggcaagucgcuguuuaccaggauguauacgcgguugacggaccgacaagucucuaucaccaagccaauaagggagu uagagucgccuacuggauaggcuuugacaccaccccuuuuauguuuaagaacuuggcuggagcauauccaucauacucu accaacugggccgacgaaaccguguuaacggcucguaacauaggccuaugcagcucugacguuauggagcggucacgua gagggauguccauucuuagaaagaaguauuugaaaccauccaacaauguucuauucucuguuggcucgaccaucuacca cgagaagagggacuuacugaggagcuggcaccugccgucuguauuucacuuacguggcaagcaaaauuacacaugucgg ugugagacuauaguuaguugcgacggguacgucguuaaaagaauagcuaucaguccaggccuguaugggaagccuucag gcuaugcugcuacgaugcaccgcgagggauucuugugcugcaaagugacagacacauugaacggggagagggucucuuu ucccgugugcacguaugugccagcuacauugugugaccaaaugacuggcauacuggcaacagaugucagugcggacgac gcgcaaaaacugcugguugggcucaaccagcguauagucgucaacggucgcacccagagaaacaccaauaccaugaaaa auuaccuuuugcccguaguggcccaggcauuugcuaggugggcaaaggaauauaaggaagaucaagaagaugaaaggcc acuaggacuacgagauagacaguuagucauggggguguuguugggcuuuuagaaggcacaagauaacaucuauuuauaag cgcccggauacccaaaccaucaucaaagugaacagcgauuuccacucauucgugcugcccaggauaggcaguaacacau uggagaucgggcugagaacaagaaucaggaaaauguuagaggagcacaaggagccgucaccucucauuaccgccgagga cguacaagaagcuaagugcgcagccgaugaggcuaaggaggugcgugaagccgaggaguugcgcgcagcucuaccaccu uuggcagcugauguugaggagcccacucuggaggcagacgucgacuugauguuacaagaggcuggggccggcucagugg agacaccucguggcuugauaaagguuaccagcuacgauggcgaggacaagaucggcucuuacgcugugcuuucuccgca ggcuguacucaagagugaaaaauuaucuugcauccacccucucgcugaacaagucauagugauaacacacucuggccga aaagggcguuaugccguggaaccauaccaugguaaaguagugguggccagagggacaugcaauacccguccaggacuuuc aagcucugagugaaagugccaccauuguguacaacgaacgugaguucguaaacagguaccugcaccauauugccacaca uggaggagcgcugaacacugaugaagaauauuacaaaacugucaagcccagcgagcacgacggcgaauaccuguacgac aucgacaggaaacagugcgucaagaaagaacuagucacugggcuagggcucacaggcgagcugguggauccucccuucc -continued augaauucgccuacgagagucugagaacacgaccagccgcuccuuaccaaguaccaaccauaggggguguauggcgugcc
aggaucaggcaagucuggcaucauuaaaagcgcagucaccaaaaaagaucuaguggugagcgccaagaaagaaaacugu
gcagaaauuauaagggacgucaagaaaaugaaagggcuggacgucaaugccagaacuguggacucagugcucuugaaug
gaugcaaacaccccguagagacccuguauauugacgaagcuuuugcuugucaugcagguacucucagagcgcucauagc
cauuauaagaccuaaaaaggcagugcucugcggggaucccaaacagugcgguuuuuuuaacaugaugugccugaaagug
cauuuuaaccacgagauuugcacacaagucuuccacaaaagcaucucucgccguugcacuaaaucugugacuucggucg
ucucaaccuuguuuuacgacaaaaaaaugagaacgacgaauccgaaagagacuaagauugugauugacacuaccggcag
uaccaaaccuaagcaggacgaucucauucucacuuguuucagagggugggugaagcaguugcaaauagauuacaaaggc
aacgaaauaaugacggcagcugccucucaagggcugacccguaaaggugugugaugccguucgguacaaggugaaugaaa
auccucuguacgcacccaccucagaacaugugaacguccuacugacccgcacggaggaccgcaucguguggaaaacacu
agccggcgacccauggauaaaaacacugacugccaaguacccugggaauuucacugccacgauagaggaguggcaagca
gagcaugaugccaucaugaggcacaucuuggagagaccggacccuaccgacgucuuccagaauaaggcaaacguguguu
gggccaaggcuuuagugccggugcugaagaccgcuggcauagacaugaccacugaacaauggaacacuguggauuauuu
ugaaacggacaaagcucacucagcagagauaguauugaaccaacuaugcgugagguucuuuggacucgaucuggacucc
ggucuauuuucugcacccacuguuccguuauccauuaggaauaaucacugggauaacuccccgucgccuaacauguacg
ggcugaauaaagaaguggucccgucagcucucucgcagguacccacaacugccucgggcaguugccacuggaagagucua
ugacaugaacacugguacacugcgcaauuaugauccgcgcauaaaccuaguaccuguaaacagaagacugccucaugcu
uuaguccuccaccauaaugaacacccacagagugacuuuucuucauucgucagcaaauugaagggcagaacuguccugg
uggucggggaaaaguuguccgucccaggcaaaaugguugacugguugucagaccggccugaggcuaccuucagagcucg
gcuggauuuaggcaucccaggugaugugcccaaauaugacauaauauuuguuaaugugaggaccccauauaaauaccau
cacuaucagcagugugaagaccaugccauuaagcuuagcauguugaccaagaaagcuugucugcaucugaaucccggcg
gaaccugugucagcauagguuaugguuacgcugacagggccagcgaaagcaucauugggugcuauagcgcggcaguucaa
guuuucccggguaugcaaaccgaaauccucacuugaagagacggaaguucuguuuguauucauuggguacgaucgcaag
gcccguacgcacaauccuuacaagcuuucaucaaccuugaccaacauuuauacagguuccagacuccacgaagccggau
gugcacccucauaucauguggugcgaggggauauugccacggccaccgaaggagugauuauaaaugcugcuaacagcaa
aggacaaccuggcggaggggugugcggagcgcuguauaagaaauucccggaaagcuucgauuuacagccgaucgaagua
ggaaaagcgcgacuggucaaaggugcagcuaaacauaucauucaugccguaggaccaaacuucaacaaaguuucggagg
uugaaggugacaaacaguuggcagaggcuuaugaguccaucgcuaagauugucaacgauaacaauuacaagucaguagc
gauuccacuguuguccaccggcaucuuuuccgggaacaaagaucgacuaacccaaucauugaaccauuugcugacagcu
uuagacaccacugaugcagauguagccauauacugcagggacaagaaaugggaaaugacucucaaggaagcaguggcua
ggagagaagcaguggaggagauaugcauauccgacgacucuucagugacagaaccugaugcagagcuggugagggugca
uccgaagaguucuuuggcuggaaggaagggcuacagcacaagcgauggcaaaacuuucucauauuuggaagggaccaag
uuucaccaggcggccaaggauauagcagaaauuaaugccauguggcccguugcaacggaggccaaugagcagguaugca
uguauauccucggagaaagcaugagcaguauuaggucgaaaugccccgucgaagagucggaagccuccacaccaccuag
cacgcugccuugcuugugcauccaugccaugacuccagaaagaguacagcgccuaaaagccucacguccagaacaaauu
acugugugcucauccuuuccauugccgaaguauagaaucacuggugugcagaagauccaaugcucccagccuauauugu
ucucaccgaaagugccugcguauauucauccaaggaaguaucucguggaaacaccaccgguagacgagacuccggagcc
aucggcagagaaccaauccacagaggggacaccugaacaaccaccacuuauaaccgaggaugagaccaggacuagaacg
ccugagccgaucaucaucgaagaggaagaagaggauagcauaaguuugcugucagauggcccgacccaccaggugcugc
aagucgaggcagacauucacgggccgcccucuguaucuagcucauccugguccauuccucaugcauccgacuuugaugu -continued ggacaguuuauccauacuugacacccuggagggagcuagcgugaccagcggggcaacgucagccgagacuaacucuuac uucgcaaagaguauggaguuucuggcgcgaccggugccugcgccucgaacaguauucaggaacccuccacaucccgcuc cgcgcacaagaacaccgucacuugcacccagcagggccugcucgagaaccagccuaguuuccaccccgccaggcgugaa uagggugaucacuagagaggagcucgaggcgcuuaccccgucacgcacuccuagcaggucggucucgagaaccagccug gucuccaacccgccaggcguaaauagggugauuacaagagaggaguuugaggcguucguagcacaacaacaaugacggu uugaugcgggugcauacaucuuuuccuccgacaccggucaagggcauuuacaacaaaaaucaguaaggcaaacggugcu auccgaagugguguuggagaggaccgaauuggagauuucguaugccccgcgccucgaccaagaaaaagaagaauuacua cgcaagaaauuacaguuaaaucccacaccugcuaacagaagcagauaccaguccaggaagguggagaacaugaaagcca uaacagcuagacguauucugcaaggccuagggcauuauuugaaggcagaaggaaaaguggagugcuaccgaacccugca uccuguuccuuuguauucaucuagugugaaccgugccuuuucaagccccaaggucgcaguggaagccuguaacgccaug uugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaacc cacaauacgaucggcagugccuucagcgauccagaacacgcuccagaacguccuggcagcugccacaaaaagaaauugc aaugucacgcaaaugagagaauugcccguauuggauucggcggccuuuaauguggaaugcuucaagaaauaugcgugua auaaugaauauugggaaacguuuaaagaaaaccccaucaggcuuacugaagaaaacgugguaaauuacauuaccaaauu aaaaggaccaaaagcugcugcucuuuuugcgaagacacauaauuugaauauguugcaggacauaccaauggacagguuu guaauggacuuaaagagagacgugaaagugacuccaggaacaaaacauacugaagaacggcccaagguacaggugaucc aggcugccgauccgcuagcaacagcguaucugugcggaauccaccgagagcugguuaggagauuaaaugcgguccugcu uccgaacauucauacacuguuugauaugucggcugaagacuuugacgcuauuauagccgagcacuuccagccuggggau uguguucuggaaacugacaucgcgucguuugauaaaagugaggacgacgccauggcucugaccgcguuaaugauucugg aagacuuagguguggacgcagagcuguugacgcugauugaggcggcuuucggcgaaauuucaucaauacauuugcccac uaaaacuaaauuuaaauucggagccaugaugaaaucuggaauguuccucacacuguuugugaacacagucauuaacauu guaaucgcaagcagaguguugagagaacggcuaaccggaucaccaugugcagcauucauuggagaugacaauaucguga aaggagucaaaucggacaaauuaauggcagacaggugcgccaccugguugaauauggaagucaagauuauagaugcugu ggugggcgagaaagcgccuuauuucuguggaggguuuauuuugugugacuccgugaccggcacagcgugccguguggca gacccccuaaaaaggcuguuuaagcuuggcaaaccucuggcagcagacgaugaacaugaugaugacaggagaagggcau ugcaugaagagucaacacgcuggaaccgagugggguauucuuucagagcugugcaaggcaguagaaucaagguaugaaac cguaggaacuuccaucauaguuauggccaugacuacucuagcuagcaguguuaaaucauucagcuaccugagaggggcc ccuauaacucucuacggcuaaccugaauggacuacgacauagucuaguccgccaagAUGCGGAGAGGAGCAGACACAUC

CGUGGGAAUCGUGGGCCUGCUGCUGACCACAGCAAUGGCAGCCGAGGUGACCAGGAGAGGCAGCGCCUACUAUAUGUAC

CUGGACAGAAAUGAUGCCGGCGAGGCCAUCUCCUUUCCCACCACACUGGGCAUGAACAAGUGCUACAUCCAGAUCAUGG

ACCUGGGCCACAUGUGCGAUGCCACCAUGAGCUAUGAGUGUCCAAUGCUGGACGAGGGCGUGGAGCCCGACGAUGUGGA

UUGCUGGUGUAAUACCACAUCUACAUGGGUGGUGUACGGCACCUGUCACCACAAGAAGGGAGAGGCACGGCGCAGCAGG

AGAGCAGUGACACUGCCUUCCCACUCUACCAGGAAGCUGCAGACAAGAAGCCAGACCUGGCUGGAGUCCAGGGAGUAUA

CAAAGCACCUGAUCAGGGUGGAGAACUGGAUCUUUAGAAAUCCAGGAUUCGCACUGGCUGCCGCCGCCAUCGCAUGGCU

GCUGGGCAGCUCCACCAGCCAGAAAGUGAUCUACCUGGUCAUGAUCCUGCUGAUCGCCCCUGCCUAUUCUAUCCGGUGC

AUCGGCGUGAGCAAUAGGGACUUCGUGGAGGGAAUGUCCGGAGGCACCUGGGUGGAUGUGGUGCUGGAGCACGGCGGCU

GCGUGACAGUGAUGGCCCAGGACAAGCCAACCGUGGAUAUCGAGCUGGUGACCACAACCGUGUCCAACAUGGCCGAGGU

GAGGUCUUACUGCUAUGAGGCCAGCAUCUCCGACAUGGCCUCUGAUAGCAGAUGUCCCACCCAGGGCGAGGCCUACCUG

GACAAGCAGUCCGAUACACAGUACGUGUGCAAGCGGACCCUGGUGGACAGGGGAUGGGGAAAUGGAUGUGGCCUGUUUG

GCAAGGGCUCUCUGGUGACAUGCGCCAAGUUCGCCUGUAGCAAGAAGAUGACCGGCAAGUCCAUCCAGCCAGAGAACCU

-continued

GGAGUACCGGAUCAUGCUGUCUGUGCACGGCUCCCAGCACUCUGGCAUGAUCGUGAACGACACAGGCCACGAGACAGAU

GAGAAUCGGGCCAAGGUGGAGAUCACACCUAACUCCCCACGCGCCGAGGCCACCCUGGGAGGAUUUGGCUCUCUGGGCC

UGGACUGCGAGCCUAGGACAGGCCUGGACUUCUCCGAUCUGUACUAUCUGACCAUGAACAAUAAGCACUGGCUGGUGCA

CAAGGAGUGGUUUCACGACAUCCCACUGCCAUGGCACGCAGGAGCAGAUACAGGCACCCCACACUGGAACAAUAAGGAG

GCCCUGGUGGAGUUCAAGGACGCCCACGCCAAGCGGCAGACAGUGGUGGUGCUGGGCAGCCAGGAGGGAGCAGUGCACA

CCGCCCUGGCAGGCGCCCUGGAGGCCGAGAUGGACGGAGCAAAGGGCCGCCUGUCUAGCGGCCACCUGAAGUGCAGGCU

GAAGAUGGAUAAGCUGAGACUGAAGGGCGUGUCCUACUCUCUGUGCACAGCCGCCUUCACCUUCACCAAGAUCCCUGCC

GAGACACUGCACGGCACAGUGACCGUGGAGGUGCAGUAUGCCGGCACAGACGGCCCCUGUAAGGUGCCUGCCCAGAUGG

CCGUGGAUAUGCAGACACUGACCCCUGUGGGCAGGCUGAUCACCGCCAAUCCAGUGAUCACAGAGUCUACCGAGAACAG

CAAGAUGAUGCUGGAGCUGGACCCCCCUUUCGGCGAUAGCUAUAUCGUGAUCGGCGUGGGCGAGAAGAAGAUCACACAC

CACUGGCACAGAAGCGGCUCCACAAUCGGCAAGGCCUUUGAGGCAACCGUGCGGGGAGCAAAGAGGAUGGCCGUGCUGG

GCGACACCGCAUGGGAUUUCGGAUCUGUGGGAGGCGCCCUGAACAGCCUGGGCAAGGGCAUCCACCAGAUCUUCGGCGC

CGCCUUUAAGUCCCUGUUCGGCGGCAUGAGCUGGUUUUCCCAGAUCCUGAUCGGCACACUGCUGAUGUGGCUGGGCCUG

AACACCAAGAAUGGCUCUAUCAGCCUGAUGUGCCUGGCCCUGGGAGGCGUGCUGAUCUUCCUGUCCACCGCCGUGUCUG

CCugaccgcggugucaaaaaccgcguggacgugguuaacaucccugcugggaggaucagccguaauuauuauaauuggc uuggugcuggcuacuauuguggccauguacgugcugaccaaccagaaacauaauugaauacagcagcaauuggcaagcu gcuuacauagaacucgcggcgauuggcaugccgccuuaaaauuuuuauuuuauuuuuucuuuucuuuuccgaaucggau uuuguuuuuaauauuucaaaaaaaaaaaaaaaaaaaaaaaaaaaaaaaaaaaaaaaaaaa Full-length VEEV + RSV-F Antigen Encoding RNA Sequence

SEQ ID NO: 45 auaggcggcgcaugagagaagcccagaccaauuaccuacccaaaauggagaaaguucacguugacaucgaggaagac agcccauuccucagagcuuugcagcggagcuucccgcaguuugagguagaagccaagcaggucacugauaaugacca ugcuaaugccagagcguuuucgcaucuggcuucaaaacugaucgaaacggagguggacccauccgacacgauccuug acauuggaagugcgcccgcccgcagaauguauucuaagcacaaguaucauuguaucuguccgaugagaugugcggaa gauccggacagauuguauaaguaugcaacuaagcugaagaaaaacuguaaggaaauaacugauaaggaauuggacaa gaaaaugaaggagcuggccgccgucaugagcgacccugaccuggaaacugagacuaugugccuccacgacgacgagu cgugucgcuacgaagggcaagucgcuguuuaccaggauguauacgcgguugacggaccgacaagucucuaucaccaa gccaauaagggaguuagagucgccuacuggauaggcuuugacaccaccccuuuuauguuuaagaacuuggcuggagc auauccaucauacucuaccaacugggccgacgaaaccguguuaacggcucguaacauaggccuaugcagcucugacg uuauggagcggucacguagagggauguccauucuuagaaagaaguauuugaaaccauccaacaauguucuauucucu guuggcucgaccaucuaccacgagaagagggacuuacugaggagcuggcaccugccgucuguauuucacuuacgugg caagcaaaauuacacaugucggugugagacuauaguuaguugcgacggguacgucguuaaaagaauagcuaucaguc caggccuguaugggaagccuucaggcuaugcugcuacgaugcaccgcgagggauucuugugcugcaaagugacagac acauugaacggggagagggucucuuuucccgugugcacguaugugccagcuacauugugugaccaaaugacuggcau acuggcaacagaugucagugcggacgacgcgcaaaaacugcugguugggcucaaccagcguauagucgucaacgguc gcacccagagaaacaccaauaccaugaaaaauuaccuuuugcccguaguggcccaggcauuugcuaggugggcaaag gaauauaaggaagaucaagaagaugaaaggccacuaggacuacgagauagacaguuagucaugggguguuguugggc uuuuagaaggcacaagauaacaucuauuuauaagcgcccggauacccaaaccaucaucaaagugaacagcgauuucc acucauucgugcugcccaggauaggcaguaacacauuggagaucgggcugagaacaagaaucaggaaaauguuagag gagcacaaggagccgucaccucucauuaccgccgaggacguacaagaagcuaagugcgcagccgaugaggcuaagga ggugcgugaagccgaggaguugcgcgcagcucuaccaccuuuggcagcugauguugaggagcccacucuggaggcag -continued acgucgacuugauguuacaagaggcuggggccggcucaguggagacaccucguggcuugauaaagguuaccagcuac gauggcgaggacaagaucggcucuuacgcugugcuuucuccgcaggcuguacucaagagugaaaaauuaucuugcau ccacccucucgcugaacaagucauagugauaacacacucuggccgaaaagggcguuaugccguggaaccauaccaug guaaaguaguggugccagagggacaugcaauacccguccaggacuuucaagcucugagugaaagugccaccauugug uacaacgaacgugaguucguaaacagguaccugcaccauauugccacacauggaggagcgcugaacacugaugaaga auauuacaaaacugucaagcccagcgagcacgacggcgaauaccuguacgacaucgacaggaaacagugcgucaaga aagaacuagucacugggcuagggcucacaggcgagcugguggauccucccuuccaugaauucgccuacgagagucug agaacacgaccagccgcuccuuaccaaguaccaaccauagggguguauggcgugccaggaucaggcaagucuggcau cauuaaaagcgcagucaccaaaaaagaucuaguggugagcgccaagaaagaaaacugugcagaaauuauaagggacg ucaagaaaaugaaagggcuggacgucaaugccagaacuguggacucagugcucuugaauggaugcaaacaccccgua gagacccuguauauugacgaagcuuuugcuugucaugcagguacucucagagcgcucauagccauuauaagaccuaa aaaggcagugcucugcggggaucccaaacagugcgguuuuuuuaacaugaugugccugaaagugcauuuuaaccacg agauuugcacacaagucuuccacaaaagcaucucucgccguugcacuaaaucugugacuucggucgucucaaccuug uuuuacgacaaaaaaaugagaacgacgaauccgaaagagacuaagauugugauugacacuaccggcaguaccaaacc uaagcaggacgaucucauucucacuuguuucagagggugggugaagcaguugcaaauagauuacaaaggcaacgaaa uaaugacggcagcugccucucaagggcugacccguaaagguguguaugccguucgguacaaggugaaugaaaauccu cuguacgcacccaccucagaacaugugaacguccuacugacccgcacggaggaccgcaucgugugga aaacacuagc cggcgacccauggauaaaaacacugacugccaaguacccugggaauuucacugccacgauagaggaguggcaagcag agcaugaugccaucaugaggcacaucuuggagagaccggacccuaccgacgucuuccagaauaaggcaaacgugugu ugggccaaggcuuuagugccggugcugaagaccgcuggcauagacaugaccacugaacaauggaacacuguggauua uuuugaaacggacaaagcucacucagcagagauaguauugaaccaacuaugcgugagguucuuuggacucgaucugg acuccggucuauuuucugcacccacuguuccguuauccauuaggaauaaucacugggauaacuccccgucgccuaac auguacgggcugaauaaagaagugguccgucagcucucucgcagguacccacaacugccucgggcaguugccacugg aagagucuaugacaugaacacugguacacugcgcaauuaugauccgcgcauaaaccuaguaccuguaaacagaagac ugccucaugcuuuaguccuccaccauaaugaacacccacagagugacuuuucuucauucgucagcaaauugaagggc agaacuguccugguggucggggaaaaguuguccgucccaggcaaaaugguugacugguugucagaccggccugaggc uaccuucagagcucggcuggauuuaggcaucccaggugaugugcccaaauaugacauaauauuuguuaaugugagga ccccauauaaauaccaucacuaucagcagugugaagaccaugccauuaagcuuagcauguugaccaagaaagcuugu cugcaucugaaucccggcggaaccugugucagcauagguuaugguuacgcugacagggccagcgaaagcaucauugg ugcuauagcgcggcaguucaaguuuucccggguaugcaaaccgaaauccucacuugaagagacggaaguucuguuug uauucauugguacgaucgcaaggcccguacgcacaauccuuacaagcuuucaucaaccuugaccaacauuuauaca gguuccagacuccacgaagccggaugugcacccucauaucaugguggugcgaggggauauugccacggccaccgaagg agugauuauaaaugcugcuaacagcaaaggacaaccuggcggagggguguguggagcgcuguauaagaaauucccgg aaagcuucgauuuacagccgaucgaaguaggaaaagcgcgacuggucaaaggugcagcuaaacauaucauucaugcc guaggaccaaacuucaacaaaguuucggagguugaaggugacaaacaguuggcagaggcuuaugaguccaucgcuaa gauugucaacgauaacaauuacaagucaguagcgauuccacuguuguccaccggcaucuuuuccgggaacaaagauc gacuaacccaaucauugaaccauuugcugacagcuuuagacaccacugaugcagauguagccauauacugcagggac aagaaaugggaaaugacucucaaggaagcaguggcuaggagagaagcaguggaggagauaugcauauccgacgacuc uucagugacagaaccugaugcagagcuggugagggugcauccgaagaguucuuuggcuggaaggaagggcuacagca caagcgauggcaaaacuuucucauauuuggaagggaccaaguuucaccaggcggccaaggauauagcagaaauuaau gccauguggcccguugcaacggaggccaaugagcagguaugcauguauauccucggagaaagcaugagcaguauuag -continued gucgaaaugccccgucgaagagucggaagccuccacaccaccuagcacgcugccuugcuugugcauccaugccauga
cuccagaaagaguacagcgccuaaaagccucacguccagaacaaauuacugugugcucauccuuuccauugccgaag
uauagaaucacuggugugcagaagauccaaugcucccagccuauauuguucucaccgaaagugccugcguauauuca
uccaaggaaguaucucguggaaacaccaccgguagacgagacuccggagccaucggcagagaaccaauccacagagg
ggacaccugaacaaccaccacuuauaaccgaggaugagaccaggacuagaacgccugagccgaucaucaucgaagag
gaagaagaggauagcauaaguuugcugucagauggcccgacccaccaggugcugcaagucgaggcagacauucacgg
gccgcccucuguaucuagcucauccugguccauuccucaugcauccgacuuugauguggacaguuuauccauacuug
acacccuggagggagcuagcgugaccagcggggcaacgucagccgagacuaacucuuacuucgcaaagaguauggag
uuucuggcgcgaccggugccugcgccucgaacaguauucaggaacccuccacaucccgcuccgcgcacaagaacacc
gucacuugcacccagcagggccugcucgagaaccagccuaguuuccaccccgccaggcgugaauagggugaucacua
gagaggagcucgaggcgcuuaccccgucacgcacuccuagcaggucggucucgagaaccagccuggucucccaacccg
ccaggcguaaauagggugauuacaagagaggaguuugaggcguucguagcacaacaacaaugacgguuugaugcggg
ugcauacaucuuuuccuccgacaccggucaagggcauuuacaacaaaaaucaguaaggcaaacggugcuauccgaag
ugguguuggagaggaccgaauuggagauuucguaugccccgcgccucgaccaagaaaaagaagaauuacuacgcaag
aaauuacaguuaaaucccacaccugcuaacagaagcagauaccaguccaggaagguggagaacaugaaagccauaac
agcuagacguauucugcaaggccuagggcauuauuugaaggcagaaggaaaaguggagugcuaccgaacccugcauc
cuguuccuuuguauucaucuagugugaaccgugccuuuucaagccccaaggucgcaguggaagccuguaacgccaug
uugaaagagaacuuuccgacuguggcuucuuacuguauuauuccagaguacgaugccuauuuggacaugguugacgg
agcuucaugcugcuuagacacugccaguuuuugcccugcaaagcugcgcagcuuuccaaagaaacacuccuauuugg
aacccacaauacgaucggcagugccuucagcgauccagaacacgcuccagaacguccuggcagcugccacaaaaaga
aauugcaaugucacgcaaaugagagaauugcccguauuggauucggcggccuuuaauguggaaugcuucaagaaaua
ugcguguaauaaugaauauugggaaacguuuaaagaaaaccccaucaggcuuacugaagaaaacgugguaaauuaca
uuaccaaauuaaaaggaccaaaagcugcugcucuuuuugcgaagacacauaauuugaauauguugcaggacauacca
auggacagguuuguaaggacuuaaagagagacgugaaagugacuccaggaacaaaacauacugaagaacggcccaa
gguacaggugauccaggcugccgauccgcuagcaacagcguaucugugcggaauccaccgagagcugguuaggagau
uaaaugcgguccugcuuccgaacauucauacacuguuugauaugucggcugaagacuuugacgcuauuauagccgag
cacuuccagccuggggauuguguucuggaaacugacaucgcgucguuugauaaaagugaggacgacgccauggcucu
gaccgcguuaaugauucuggaagacuuaggugugggacgcagagcuguugacgcugauugaggcggcuuucggcgaaa
uuucaucaauacauuugcccacuaaaacuaaauuuaaauucggagccaugaugaaaucuggaauguuccucacacug
uuugugaacacagucauuaacauuguaaucgcaagcagaguguugagagaacggcuaaccggaucaccaugugcagc
auucauuggagaugacaauaucgugaaaggagucaaaucggacaaauuaauggcagacaggugcgccaccugguuga
auauggaagucaagauuauagaugcuguggugggcgagaaagcgccuuauuucuguggaggguuuauuuugugugac
uccgugaccggcacagcgugccguguggcagacccccuaaaaaggcuguuuaagcuuggcaaacccucuggcagcaga
cgaugaacaugaugaugacaggagaagggcauugcaugaagagucaacacgcuggaaccgaguggguauucuuucag
agcugugcaaggcaguagaaucaagguaugaaaccguaggaacuuccaucauaguuauggccaugacuacucuagcu
agcaguguuaaaucauucagcuaccugagagggggccccuauaacucucuacggcuaaccugaauggacuacgacaua
gucuaguccgccaagAUGGAGCUGCUCAUCCUUAAAGCGAAUGCUAUAACUACUAUACUUACAGCUGUAACCUUUUG
CUUCGCCUCUGGCCAAAACAUUACUGAGGAGUUUUAUCAAUCCACUUGCAGCGCAGUCUCAAAAGGAUAUCUGUCAG
CAUUGCGCACCGGGUGGUACACCAGCGUUAUCACUAUCGAGCUUUCCAACAUUAAAGAGAAUAAGUGUAACGGCACA
GACGCGAAAGUCAAACUCAUUAAGCAAGAACUUGAUAAAUACAAAAAUGCAGUUACUGAACUUCAGUUGCUCAUGCA -continued

AUCAACCCCAGCAACGAACAAUAGGGCCAGGAGAGAAUUGCCGAGGUUUAUGAACUACACACUUAAUAACGCUAAAA

AGACUAACGUUACGCUCUCUAAGAAGCGGAAGCGCAGGUUUCUCGGGUUCCUUCUGGGGGUUGGCAGUGCAAUAGCA

UCCGGCGUCGCGGUAUCAAAGGUGCUUCAUCUUGAAGGAGAAGUUAACAAAAUCAAAAGCGCCUUGCUUUCAACUAA

UAAGGCAGUAGUAUCAUUGUCUAACGGUGUCAGCGUCUUGACUUCCAAGGUUUUGGAUUUGAAAAACUAUAUCGACA

AACAACUUCUCCCGAUCGUUAACAAGCAGUCAUGCAGUAUCUCCAACAUCGAAACCGUCAUCGAAUUCCAACAGAAA

AACAAUAGACUGCUUGAAAUUACUAGAGAGUUUUCAGUGAACGCUGGCGUUACCACUCCGGUAUCCACUUAUAUGCU

CACUAAUAGCGAACUGCUGUCUCUGAUAAAUGACAUGCCAAUAACUAACGACCAGAAGAAACUUAUGAGUAACAACG

UCCAGAUCGUGAGACAGCAAUCAUAUAGCAUUAUGAGCAUAAUUAAGGAGGAGGUCCUUGCAUACGUAGUCCAGCUC

CCACUGUACGGGGUUAUCGACACGCCAUGUUGGAAGCUUCAUACUUCCCCCUUGUGCACCACGAACACGAAGGAAGG

GUCUAACAUUUGUCUCACGCGCACUGAUCGGGGGUGGUACUGUGACAACGCCGGGUCAGUGUCAUUUUUCCCUCAGG

CCGAGACCUGCAAGGUCCAAUCAAACCGGGUAUUCUGUGAUACUAUGAACUCCCUGACUCUGCCUUCUGAAGUUAAC

CUGUGUAAUGUAGAUAUAUUCAAUCCUAAAUACGACUGCAAGAUAAUGACCAGCAAAACCGACGUGUCCUCAUCUGU

CAUCACUUCCCUUGGUGCUAUAGUAAGCUGCUAUGGCAAAACGAAAUGCACCGCGAGUAAUAAAAAUCGCGGUAUCA

UCAAGACAUUUAGUAACGGCUGCGAUUAUGUUUCCAACAAAGGUGUUGACACCGUAUCUGUGGGGAAUACCCUGUAU

UACGUAAAUAAGCAGGAAGGGAAAUCUCUCUACGUGAAGGGGGAACCGAUAAUCAACUUUUAUGACCCGCUGGUUUU

UCCGUCCGACGAAUUUGACGCGAGUAUCUCCCAAGUCAACGAGAAAAUUAACCAAAGCCUCGCGUUCAUAAGAAAAU

CCGAUGAGCUGCUGCAUAAUGUAAACGCGGGCAAAUCAACUACCAACAUCAUGAUUACAACAAUAAUCAUCGUGAUA

AUCGUGAUCCUGCUUUCACUUAUCGCUGUCGGGCUUCUUCUCUAUUGUAAGGCCCGGAGUACUCCCGUGACCUUGUC

UAAGGAUCAGCUCUCAGGUAUCAACAAUAUUGCAUUCAGCAAUUGAggcgcgccauacagcagcaauuggcaagcug cuuacauagaacucgcggcgauuggcaugccgccuuaaaauuuuuauuuuauuuuuucuuuucuuuuccgaaucgga uuuuguuuuuaauauuucaaaaaaaaaaaaaaaaaaaaaaaaaaaaaaaaaaaaaaaaaaaaaa Full-length VEEV + RSV-G Antigen Encoding RNA Sequence

SEQ ID NO: 46 auaggcggcgcaugagagaagcccagaccaauuaccuacccaaaauggagaaaguucacguugacaucgaggaagac agcccauuccucagagcuuugcagcggagcuucccgcaguuugagguagaagccaagcaggucacugauaaugacca ugcuaaugccagagcguuuucgcaucuggcuucaaaacugaucgaaacggagguggacccauccgacacgauccuug acauuggaagugcgcccgcccgcagaauguauucuaagcacaaguaucauuguaucuguccgaugagaugugcggaa gauccggacagauuguauaaguaugcaacuaagcugaagaaaaacuguaaggaaauaacugauaaggaauuggacaa gaaaaugaaggagcuggccgccgucaugagcgacccugaccuggaaacugagacuaugugccuccacgacgacgagu cgugucgcuacgaagggcaagucgcuguuuaccaggauguauacgcgguugacggaccgacaagucucuaucaccaa gccaauaagggaguuagagucgccuacuggauaggcuuugacaccaccccuuuuauguuuaagaacuuggcuggagc auauccaucauacucuaccaacugggccgacgaaaccguguuaacggcucguaacauaggccuaugcagcucugacg uuauggagcggucacguagagggauguccauucuuagaaagaaguauuugaaaccauccaacaauguucuauucucu guuggcucgaccaucuaccacgagaagagggacuuacugaggagcuggcaccugccgucuguauuucacuuacgugg caagcaaaauuacacaugucggugugagacuauaguuaguugcgacggguacgucguuaaaagaauagcuaucaguc caggccuguaugggaagccuucaggcuaugcugcuacgaugcaccgcgagggauucuugugcugcaaagugacagac acauugaacggggagagggucucuuucccgugugcacguaugugccagcuacauugugugaccaaaugacuggcau acuggcaacagaugucagugcggacgacgcgcaaaaacugcugguugggcucaaccagcguauagucgucaacgguc gcacccagagaaacaccaauaccaugaaaaauuaccuuuugcccguaguggcccaggcauuugcuaggugggcaaag gaauauaaggaagaucaagaagaugaaaggccacuaggacuacgagauagacaguuagucauggggguguuguugggc uuuuagaaggcacaagauaacaucuauuuauaagcgcccggauacccaaaccaucaucaaagugaacagcgauuucc acucauucgugcugcccaggauaggcaguaacacauuggagaucgggcugagaacaagaaucaggaaaauguuagag -continued gagcacaaggagccgucaccucucauuaccgccgaggacguacaagaagcuaagugcgcagccgaugaggcuaagga ggugcgugaagccgaggaguugcgcgcagcucuaccaccuuuggcagcugauguugaggagcccacucuggaggcag acgucgacuugauguuacaagaggcuggggccggcucaguggagacaccucguggcuugauaaagguuaccagcuac gauggcgaggacaagaucggcucuuacgcugugcuuucuccgcaggcuguacucaagagugaaaaauuaucuugcau ccacccucucgcugaacaagucauagugauaacacacucuggccgaaaagggcguuaugccguggaaccauaccaug guaaaguaguggugccagagggacaugcaauacccguccaggacuuucaagcucugagugaaagugccaccauugug uacaacgaacgugaguucguaaacagguaccugcaccauauugccacacauggaggagcgcugaacacugaugaaga auauuacaaaacugucaagcccagcgagcacgacggcgaauaccuguacgacaucgacaggaaacagugcgucaaga aagaacuagucacugggcuagggcucacaggcgagcugguggauccucccuuccaugaauucgccuacgagagucug agaacacgaccagccgcuccuuaccaaguaccaaccauagggguguauggcgugccaggaucaggcaagucuggcau cauuaaaagcgcagucaccaaaaaagaucuaguggugagcgccaagaaagaaaacugugcagaaauuauaagggacg ucaagaaaaugaaagggcuggacgucaaugccagaacuguggacucagugcucuugaauggaugcaaacaccccgua gagacccuguauauugacgaagcuuuugcuugucaugcagguacucucagagcgcucauagccauuauaagaccuaa aaaggcagugcucugcggggaucccaaacagugcgguuuuuuuaacaugaugugccugaaagugcauuuuaaccacg agauuugcacacaagucuuccacaaaagcaucucucgccguugcacuaaaucugugacuucggucgucucaaccuug uuuuacgacaaaaaaaugagaacgacgaauccgaaagagacuaagauugugauugacacuaccggcaguaccaaacc uaagcaggacgaucucauucucacuuguuucagagggugggugaagcaguugcaaauagauuacaaaggcaacgaaa uaaugacggcagcugccucucaagggcugacccguaaaggugugugaugccguucgguacaaggugaaugaaaauccu cuguacgcacccaccucagaacaugugaacguccuacugacccgcacggaggaccgcaucgugugggaaaacacuagc cggcgacccauggauaaaaacacugacugccaaguacccugggaauuucacugccacgauagaggaguggcaagcag agcaugaugccaucaugaggcacaucuuggagagaccggacccuaccgacgucuuccagaauaaggcaaacgugugu ugggccaaggcuuuagugccggugcugaagaccgcuggcauagacaugaccacugaacaauggaacacuguggauua uuuugaaacggacaaagcucacucagcagagauaguauugaaccaacuaugcgugagguucuuuggacucgaucugg acuccggucuauuuucugcacccacuguuccguuauccauuaggaauaaucacugggauaacuccccgucgccuaac auguacgggcugaauaaagaaguggucgucagcucucucgcagguacccacaacugccucgggcaguugccacugg aagagucuaugacaugaacacugguacacugcgcaauuaugauccgcgcauaaaccuaguaccuguaaacagaagac ugccucaugcuuuaguccuccaccauaaugaacacccacagagugacuuuucuucauucgucagcaaauugaagggc agaacuguccugguggucggggaaaaguuguccgucccaggcaaaaugguugacugguugucagaccggccugaggc uaccuucagagcucggcuggauuuaggcaucccaggugaugugcccaaauaugacauaauauuuguuaaugugagga ccccauauaaauaccaucacuaucagcagugugaagaccaugccauuaagcuuagcauguugaccaagaaagcuugu cugcaucugaaucccggcggaaccugugucagcauagguuaugguuacgcugacagggccagcgaaagcaucauugg ugcuauagcgcggcaguucaaguuuucccggguaugcaaaccgaaauccucacuugaagagacggaaguucuguuug uauucauugguacgaucgcaaggcccguacgcacaauccuuacaagcuuucaucaaccuugaccaacauuuauaca gguuccagacuccacgaagccggaugugcacccucauaucaugguggugcgaggggauauugccacggccaccgaagg agugauuauaaaugcugcuaacagcaaaggacaaccuggcggagggguguggggagcgcuguauaagaaauucccgg aaagcuucgauuuacagccgaucgaaguaggaaaagcgcgacuggucaaaggugcagcuaaacauaucauucaugcc guaggaccaaacuucaacaaaguuucggagguugaaggugacaaacaguuggcagaggcuuaugaguccaucgcuaa gauugucaacgauaacaauuacaagucaguagcgauuccacuguuguccaccggcaucuuuuccgggaacaaagauc gacuaacccaaucauugaaccauuugcugacagcuuuagacaccacugaugcagauguagccauauacugcagggac aagaaaugggaaaugacucucaaggaagcaguggcuaggagagaagcaguggaggagauaugcauauccgacgacuc -continued uucagugacagaaccugaugcagagcuggugagggugcauccgaagaguucuuuggcuggaaggaagggcuacagca caagcgauggcaaaacuuucucauauuuggaagggaccaaguuucaccaggcggccaaggauauagcagaaauuaau gccauguggcccguugcaacggaggccaaugagcagguaugcauguauauccucggagaaagcaugagcaguauuag gucgaaaugccccgucgaagagucggaagccuccacaccaccuagcacgcugccuugcuugugcauccaugccauga cuccagaaagaguacagcgccuaaaagccucacguccagaacaaauuacugugugcucauccuuuccauugccgaag uauagaaucacuggugugcagaagauccaaugcucccagccuauauuguucucaccgaaagugccugcguauauuca uccaaggaaguaucucguggaaacaccaccgguagacgagacuccggagccaucggcagagaaccaauccacagagg ggacaccugaacaaccaccacuuauaaccgaggaugagaccaggacuagaacgccugagccgaucaucaucgaagag gaagaagaggauagcauaaguuugcugucagauggcccgacccaccaggugcugcaagucgaggcagacauucacgg gccgcccucuguaucuagcucauccugguccauuccucaugcauccgacuuugauguggacaguuuauccauacuug acacccuggagggagcuagcgugaccagcggggcaacgucagccgagacuaacucuuacuucgcaaagaguauggag uuucuggcgcgaccggugccugcgccucgaacaguauucaggaacccuccacaucccgcuccgcgcacaagaacacc gucacuugcacccagcagggccugcucgagaaccagccuaguuccaccccgccaggcgugaauagggugaucacua gagaggagcucgaggcgcuuaccccgucacgcacuccuagcaggucggucucgagaaccagccuggucuccaacccg ccaggcguaaauagggugauuacaagagaggaguuugaggcguucguagcacaacaacaaugacgguuugaugcggg ugcauacaucuuuuccuccgacaccggucaagggcauuuacaacaaaaaucaguaaggcaaacggugcuauccgaag ugguguuggagaggaccgaauuggagauuucguaugccccgcgccucgaccaagaaaaagaagaauuacuacgcaag aaauuacaguuaaaucccacaccugcuaacagaagcagauaccaguccaggaagguggagaacaugaaagccauaac agcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaug uugaaagagaacuuuccgacuguggcuucuuacuguauuauuccagaguacgaugccuauuuggacaugguugacgg agcuucaugcugcuuagacacugccaguuuuugcccugcaaagcugcgcagcuuuccaaagaaacacuccuauuugg aacccacaauacgaucggcagugccuucagcgauccagaacacgcuccagaacguccuggcagcugccacaaaaaga aauugcaaugucacgcaaaugagagaauugcccguauuggauucggcggccuuuaauguggaaugcuucaagaaaua ugcguguaauaaugaauauugggaaacguuuaaagaaaaccccaucaggcuuacugaagaaaacgugguaaauuaca uuaccaaauuaaaaggaccaaaagcugcugcucuuuuugcgaagacacauaauuugaauauguugcaggacauacca auggacagguuuguaauggacuuaaagagagacgugaaagugacuccaggaacaaaacauacugaagaacggcccaa gguacaggugauccaggcugccgauccgcuagcaacagcguaucugugcggaauccaccgagagcugguuaggagau uaaaugcgguccugcuuccgaacauucauacacuguuugauaugucggcugaagacuuugacgcuauuauagccgag cacuuccagccuggggauuguguucuggaaacugacaucgcgucguuugauaaaagugaggacgacgccauggcucu gaccgcguuaaugauucuggaagacuuaggugugggacgcagagcuguugacgcugauugaggcggcuuucggcgaaa uuucaucaauacauuugcccacuaaaacuaaauuuaaauucggagccaugaugaaaucuggaauguuccucacacug uuugugaacacagucauuaacauuguaaucgcaagcagaguguugagagaacggcuaaccggaucaccaugugcagc auucauuggagaugacaauaucgugaaaggagucaaaucggacaaauuaauggcagacaggugcgccaccugguuga auauggaagucaagauuauagaugcugugguggggcgagaaagcgccuuauuucuguggaggguuuauuuugugugac uccgugaccggcacagcgugccguguggcagaccccuaaaaaggcuguuuaagcuuggcaaaccucuggcagcaga cgaugaacaugaugaugacaggagaagggcauugcaugaagagucaacacgcuggaaccgagugguauucuuucag agcugugcaaggcaguagaaucaagguaugaaaccguaggaacuuccaucauaguuauggccaugacuacucuagcu agcaguguuaaaucauucagcuaccugagaggggccccuauaacucucuacggcuaaccugaauggacuacgacaua gucuaguccgccaagAUGUCCAAAAAUAAAGACCAGCGAACGGCCAAGACUCUGGAGAGGACUUGGGAUACCCUGAA

UCAUCUGUUGUUUAUUUCAAGUUGCCUUUAUAAAUUGAAUCUCAAAUCCGUCGCGCAAAUCACGCUGAGCAUACUCG

-continued

CAAUGAUUAUCUCAACUUCCUUGAUAAUUGCCGCCAUAAUCUUCAUUGCAAGUGCAAAUCAUAAAGUGACUCCUACA

ACCGCAAUAAUACAGGACGCGACCAGCCAAAUUAAGAACACGACUCCCACGUAUCUCACCCAAAAUCCCCAACUCGG

AAUUAGCCCAAGUAAUCCGUCAGAGAUUACUUCACAAAUCACCACCAUACUGGCGAGCACAACUCCAGGCGUAAAAU

CCACCCUCCAAUCUACUACCGUCAAGACUAAAAAUACCACUACUACUCAGACACAACCUAGUAAACCUACGACUAAG

CAGCGCCAGAAUAAACCCCCAAGCAAACCAAACAACGACUUCCAUUUUGAAGUUUUCAACUUCGUGCCUUGUUCUAU

CUGCUCUAAUAAUCCAACAUGCUGGGCCAUCUGCAAGCGCAUUCCGAAUAAGAAACCCGGUAAGAAAACUACAACGA

AACCUACCAAGAAGCCUACCCUGAAAACGACAAAGAAAGACCCGAAACCGCAAACAACCAAAAGUAAAGAAGUGCCC

ACAACUAAACCCACAGAAGAACCAACGAUAAACACGACCAAAACCAACAUAAUAACUACGCUGCUUACCAGCAACAC

GACAGGCAACCCGGAAUUGACCAGUCAGAUGGAAACUUUUCAUUCAACCAGCAGCGAAGGUAAUCCAAGUCCUAGUC

AGGUGUCUACGACAUCUGAAUAUCCAUCUCAGCCUAGUUCCCCUCCGAACACGCCGCGCCAGUGAUAAccgcggugu caaaaaccgcguggacgugguuaacaucccugcugggaggaucagccguaauuauuauaauuggcuuggugcuggcu acuauuguggccauguacgugcugaccaaccagaaacauaauugaauacagcagcaauuggcaagcugcuuacauag aacucgcggcgauuggcaugccgccuuaaaauuuuuauuuuauuuuuucuuuucuuuuccgaaucggauuuuguuuu uaauauuucaaaaaaaaaaaaaaaaaaaaaaaaaaaaaaaaaaaaaaaa Full Length VEEV + Influenza H3 Antigen Encoding RNA Sequence

SEQ ID NO: 47 auaggcggcgcaugagagaagcccagaccaauuaccuacccaaaauggagaaaguucacguugacaucgaggaagac agcccauuccucagagcuuugcagcggagcuucccgcaguuugagguagaagccaagcaggucacugauaaugacca ugcuaaugccagagcguuuucgcaucuggcuucaaaacugaucgaaacggagguggacccauccgacacgauccuug acauuggaagugcgcccgcccgcagaauguauucuaagcacaaguaucauuguaucuguccgaugagaugugcggaa gauccggacagauuguauaaguaugcaacuaagcugaagaaaaacuguaaggaaauaacugauaaggaauuggacaa gaaaaugaaggagcuggccgccgucaugagcgacccugaccuggaaacugagacuaugugccuccacgacgacgagu cgugucgcuacgaagggcaagucgcuguuuaccaggauguauacgcgguugacggaccgacaagucucuaucaccaa gccaauaagggaguuagagucgccuacuggauaggcuuugacaccaccccuuuuauguuuaagaacuuggcuggagc auauccaucauacucuaccaacugggccgacgaaaccguguuaacggcucguaacauaggccuaugcagcucugacg uuauggagcggucacguagagggauguccauucuuagaaagaaguauuugaaaccauccaacaauguucuauucucu guuggcucgaccaucuaccacgagaagagggacuuacugaggagcuggcaccugccgucuguauuucacuuacgugg caagcaaaauuacacaugucggugugagacuauaguuaguugcgacggguacgucguuaaaagaauagcuaucaguc caggccuguaugggaagccuucaggcuaugcugcuacgaugcaccgcgagggauucuugugcugcaaagugacagac acauugaacggggagagggucucuuuucccgugugcacguaugugccagcuacauugugugaccaaaugacuggcau acuggcaacagaugucagugcggacgacgcgcaaaaacugcugguugggcucaaccagcguauagucgucaacgguc gcacccagagaaacaccaauaccaugaaaaauuaccuuuugcccguaguggcccaggcauuugcuaggugggcaaag gaauauaaggaagaucaagaagaugaaaggccacuaggacuacgagauagacaguuagucaugggguguuguugggc uuuuagaaggcacaagauaacaucuauuuauaagcgcccggauacccaaaccaucaucaaagugaacagcgauuucc acucauucgugcugcccaggauaggcaguaacacauuggagaucgggcugagaacaagaaucaggaaaauguuagag gagcacaaggagccgucaccucucauuaccgccgaggacguacaagaagcuaagugcgcagccgaugaggcuaagga ggugcgugaagccgaggaguugcgcgcagcucuaccaccuuuggcagcugauguugaggagcccacucuggaggcag acgucgacuugauguuacaagaggcuggggccggcucaguggagacaccucguggcuugauaaagguuaccagcuac gauggcgaggacaagaucggcucuuacgcugugcuuucuccgcaggcuguacucaagagugaaaaauuaucuugcau ccacccucucgcugaacaagucauagugauaacacacucuggccgaaaagggcguuaugccguggaaccauaccaug guaaaguagugguggccagagggacaugcaauacccguccaggacuuucaagcucugagugaaagugccaccauugug -continued uacaacgaacgugaguucguaaacagguaccugcaccauauugccacacauggaggagcgcugaacacugaugaaga auauuacaaaacugucaagcccagcgagcacgacggcgaauaccuguacgacaucgacaggaaacagugcgucaaga aagaacuagucacugggcuagggcucacaggcgagcugguggauccucccuuccaugaauucgccuacgagagucug agaacacgaccagccgcuccuuaccaaguaccaaccauagggguguauggcgugccaggaucaggcaagucuggcau cauuaaaagcgcagucaccaaaaaagaucuaguggugagcgccaagaaagaaaacugugcagaaauuauaagggacg ucaagaaaaugaaagggcuggacgucaaugccagaacuguggacucagugcucuugaauggaugcaaacaccccgua gagacccuguauauugacgaagcuuuugcuugucaugcagguacucucagagcgcucauagccauuauaagaccuaa aaaggcagugcucugcggggaucccaaacagugcgguuuuuuuaacaugaugugccugaaagugcauuuuaaccacg agauuugcacacaagucuuccacaaaagcaucucucgccguugcacuaaaucugugacuucggucgucucaaccuug uuuuacgacaaaaaaaugagaacgacgaauccgaaagagacuaagauugugauugacacuaccggcaguaccaaacc uaagcaggacgaucucauucucacuuguuucagaggugggugaagcaguugcaaauagauuacaaaggcaacgaaa uaaugacggcagcugccucucaagggcugacccguaaaggugugaugccguucgguacaaggugaaugaaaauccu cuguacgcacccaccucagaacaugugaacguccuacugacccgcacggaggaccgcaucguguggaaaacacuagc cggcgacccauggauaaaaacacugacugccaaguacccugggaauuucacugccacgauagaggaguggcaagcag agcaugaugccaucaugaggcacaucuuggagagaccggacccuaccgacgucuuccagaauaaggcaaacgugugu ugggccaaggcuuuagugccggugcugaagaccgcuggcauagacaugaccacugaacaauggaacacuguggauua uuuugaaacggacaaagcucacucagcagagauaguauugaaccaacuaugcgugagguucuuuggacucgaucugg acuccggucuauuuucugcacccacuguuccguuauccauuaggaauaaucacugggauaacuccccgucgccuaac auguacgggcugaauaaagaaguggucgucagcucucucgcagguacccacaacugccucgggcaguugccacugg aagagucuaugacaugaacacugguacacugcgcaauuaugauccgcgcauaaaccuaguaccuguaaacagaagac ugccucaugcuuuaguccuccaccauaaugaacacccacagagugacuuuucuucauucgucagcaaauugaagggc agaacuguccugguggucggggaaaaguuguccgucccaggcaaaaugguugacugguugucagaccggccugaggc uaccuucagagcucggcuggauuuaggcaucccaggugaugugcccaaauaugacauaauauuuguuaaugugagga ccccauauaaauaccaucacuaucagcagugugaagaccaugccauuaagcuuagcauguugaccaagaaagcuugu cugcaucugaaucccggcggaaccugugucagcauagguuaugguuacgcugacagggccagcgaaagcaucauugg ugcuauagcgcggcaguucaaguuuucccggguaugcaaaccgaaauccucacuugaagagacggaaguucuguuug uauucauuggguacgaucgcaaggcccguacgcacaauccuuacaagcuuucaucaaccuugaccaacauuuauaca gguuccagacuccacgaagccggaugugcacccucauaucauguggugcgaggggauauugccacggccaccgaagg agugauuauaaaugcugcuaacagcaaaggacaaccuggcggaggggugugcggagcgcuguauaagaaauucccgg aaagcuucgauuuacagccgaucgaaguaggaaaagcgcgacuggucaaaggugcagcuaaacauaucauucaugcc guaggaccaaacuucaacaaaguuucggagguugaaggugacaaacaguuggcagaggcuuaugaguccaucgcuaa gauugucaacgauaacaauuacaagucaguagcgauuccacuguuguccaccggcaucuuuuccgggaacaaagauc gacuaacccaaucauugaaccauuugcugacagcuuuagacaccacugaugcagauguagccauauacugcagggac aagaaaugggaaaugacucucaaggaagcaguggcuaggagagaagcaguggaggagauaugcauauccgacgacuc uucagugacagaaccugaugcagagcuggugagggugcauccgaagaguucuuuggcuggaaggaagggcuacagca caagcgauggcaaaacuuucucauauuuggaagggaccaaguuucaccaggcggccaaggauauagcagaaauuaau gccauguggcccguugcaacggaggccaaugagcagguaugcauguauauccucggagaaagcaugagcaguauuag gucgaaaugccccgucgaagagucggaagccuccacaccaccuagcacgcugccuugcuugugcauccaugccauga cuccagaaagaguacagcgccuaaaagccucacguccagaacaaauuacugugugcucauccuuuccauugccgaag uauagaaucacuggugugcagaagauccaaugcucccagccuauauuguucucaccgaaagugccugcguauauuca uccaaggaaguaucucguggaaacaccaccgguagacgagacuccggagccaucggcagagaaccaauccacagagg -continued ggacaccugaacaaccaccacuuauaaccgaggaugagaccaggacuagaacgccugagccgaucaucaucgaagag gaagaagaggauagcauaaguuugcugucagauggcccgacccaccaggugcugcaagucgaggcagacauucacgg gccgcccucuguaucuagcucauccugguccauucccucaugcauccgacuuugauguggacaguuuauccauacuug acacccuggagggagcuagcgugaccagcggggcaacgucagccgagacuaacucuuacuucgcaaagaguauggag uuucuggcgcgaccggugccugcgccucgaacaguauucaggaacccuccacaucccgcuccgcgcacaagaacacc gucacuugcacccagcagggccugcucgagaaccagccuaguuuccaccccgccaggcgugaauagggugaucacua gagaggagcucgaggcgcuuaccccgucacgcacuccuagcaggucggucucgagaaccagccuggucuccaacccg ccaggcguaaauagggugauuacaagagaggaguuugaggcguucguagcacaacaacaaugacgguuugaugcggg ugcauacaucuuuuccuccgacaccggucaagggcauuuacaacaaaaaucaguaaggcaaacggugcuauccgaag ugguguuggagaggaccgaauuggagauuucguaugccccgcgccucgaccaagaaaaagaagaauuacuacgcaag aaauuacaguuaaaucccacaccugcuaacagaagcagauaccaguccaggaagguggagaacaugaaagccauaac agcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaug uugaaagagaacuuuccgacuguggcuucuuacuguauuauuccagaguacgaugccuauuuggacaugguugacgg agcuucaugcugcuuagacacugccaguuuuugcccugcaaagcugcgcagcuuuccaaagaaacacuccuauuugg aacccacaauacgaucggcagugccuucagcgauccagaacacgcuccagaacguccuggcagcugccacaaaaaga aauugcaaugucacgcaaaugagagaauugcccguauuggauucggcggccuuuaauguggaaugcuucaagaaaua ugcguguaauaaugaauauugggaaacguuuaaagaaaaccccaucaggcuuacugaagaaaacgugguaaauuaca uuaccaaauuaaaaggaccaaaagcugcugcucuuuuugcgaagacacauaauuugaauauguugcaggacauacca auggacagguuuguaauggacuuaaagagagacgugaaagugacuccaggaacaaaacauacugaagaacggcccaa gguacaggugauccaggcugccgauccgcuagcaacagcguaucugugcggaauccaccgagagcugguuaggagau uaaaugcgguccugcuuccgaacauucauacacuguuugauaugucggcugaagacuuugacgcuauuauagccgag cacuuccagccuggggauuguguucuggaaacugacaucgcgucguuugauaaaaagugaggacgacgccauggcucu gaccgcguuaaugauucuggaagacuuaggugugggacgcagagcuguugacgcugauugaggcggcuuucggcgaaa uuucaucaauacauuugcccacuaaaacuaaauuuaaauucggagccaugaugaaaucuggaauguuccucacacug uuugugaacacagucauuaacauuguaaucgcaagcagaguguugagagaacggcuaaccggaucaccaugugcagc auucauuggagaugacaauaucgugaaaggagucaaaucggacaaauuaauggcagacaggugcgccaccugguuga auauggaagucaagauuauagaugcugugguggggcgagaaagcgccuuauuucuguggaggguuuauuuugugugac uccgugaccggcacagcgugccguguggcagaccccccuaaaaaggcuguuuaagcuuggcaaaccucuggcagcaga cgaugaacaugaugaugacaggagaagggcauugcaugaagagucaacacgcuggaaccgagugggguauucuuucag agcugugcaaggcaguagaaucaagguaugaaaccguaggaacuuccaucauaguuauggccaugacuacucuagcu agcaguguuaaaucauucagcuaccugagaggggccccuauaacucucuacggcuaaccugaauggacuacgacaua gucuaguccgccaagAUGAAAACAAUUAUCGCUCUCAGUUAUAUUUUCUGCCUUCCUUUGGGGCAAGACUUGCCGGG

CAAUGAUAAUAGUACAGCGACUCUCUGUCUCGGACACCACGCAGUACCGAACGGCACACUUGUGAAGACAAUCACAG

ACGAUCAAAUCGAAGUGACGAAUGCAACAGAGCUUGUUCAAUCAUCAUCUACCGGCAAAAUCUGCAAUAAUCCGCAU

AGAAUCCUUGAUGGAAUCGACUGCACCCUGAUUGACGCACUGUUGGGAGAUCCUCAUUGCGAUGUGUUUCAGAAUGA

GACAUGGGACCUUUUUGUCGAGAGGAGCAAAGCGUUUUCCAACUGCUACCCGUAUGACGUGCCUGAUUACGCGUCAC

UCCGCUCACUUUGUAGCAUCAAGCGGUACUCUGGAGUUCAUCACCGAAGGAUUCACCUGGACGGGCGUAACUCAGAAC

GGCGGUUCUAACGCAUGUAAGAGGGGGCCAGGGUCCGGCUUCUUCUCACGGCUCAACUGGUUGACUAAGUCUGGUUC

AACAUACCCGGUCCUUAACGUUACAAUGCCGAAUAAUGACAACUUUGAUAAACUCUACAUCUGGGGCAUUCACCAUC

-continued

CAUCCACAAAUCAAGAACAGACAAGUUUGUACGUUCAGGCGUCAGGGCGCGUUACCGUGAGUACAAGAAGAUCACAG

CAAACAAUUAUACCCAAUAUUGGGUCCCGACCCUGGGUAAGAGGACUGUCCUCUCGCAUCUCCAUAUACUGGACCAU

UGUCAAACCGGGCGACGUCCUGGUUAUCAAUAGUAAUGGAAACCUUAUUGCUCCGCGCGGCUAUUUCAAAAUGCGAA

CUGGAAAGUCAAGUAUAAUGCGCUCAGACGCACCGAUCGAUACUUGUAUCAGUGAAUGCAUCACCCCUAACGGGUCC

AUACCGAACGAUAAGCCCUUCCAGAAUGUGAAUAAAAUCACGUAUGGAGCAUGCCCCAAAUACGUGAAGCAAAACAC

CCUCAAGUUGGCUACGGGUAUGCGCAACGUCCCAGAAAAACAAACGCGAGGCUUGUUUGGGGCGAUAGCAGGUUUUA

UCGAGAACGGCUGGGAAGGAAUGAUCGAUGGGUGGUACGGCUUUCGCCAUCAAAACUCAGAAGGAACUGGGCAGGCC

GCAGAUCUUAAGUCUACGCAAGCGGCGAUAGAUCAAAUUAAUGGCAAGUUGAAUAGGGUGAUAGAGAAGACGAACGA

GAAGUUCCAUCAAAUAGAGAAAGAAUUCAGUGAAGUAGAGGGGCGAAUUCAGGAUUUGGAAAAAUAUGUCGAGGAUA

CUAAGAUCGACCUGUGGAGCUAUAACGCAGAGCUUCUGGUAGCACUUGAGAACCAGCAUACUAUUGAUCUCACCGAU

UCCGAGAUGAACAAGCUUUUUGAGAAGACCAGGAGACAGUUGCGCGAGAAUGCCGAAGAAAUGGGUAACGGUUGUUU

UAAGAUUUAUCACAAAUGUGACAACGCGUGUAUUGAGUCCAUUAGGAAUGGUACAUAUGAUCACGAUGUGUAUCGCG

AUGAAGCACUUAACAAUCGGUUCCAAAUAAAGGGCGUGGAGCUCAAGAGUGGGUAUAAAGAUUGGAUCCUCUGGAUC

UCAUUCGCGAUUUCCUGCUUCCUCCUGUGCGUUGUCUUGCUGGGCUUUAUUAUGUGGGCAUGUCAGAGAGGUAACAU

CCGGUGCAACAUAUGUAUCUGAUAAccgcggugucaaaaaccgcguggacgugguuaacaucccugcugggaggauc agccguaauuauuauaauuggcuuggugcuggcuacuauuguggccauguacgugcugaccaaccagaaacauaauu uuuuucuuuucuuuuccgaaucggauuuuguuuuuaauauuucaaaaaaaaaaaaaaaaaaaaaaaaaaaaaaaaa aaaaaaaaaaa Vector Backbone RNA Sequence 1

SEQ ID NO: 48 auaggcggcgcaugagagaagcccagaccaauuaccuacccaaaauggagaaaguucacguugacaucgaggaagacagcc cauuccucagagcuuugcagcggagcuucccgcaguuugagguagaagccaagcaggucacugauaaugaccaugcuaaug ccagagcguuuucgcaucuggcuucaaaacugaucgaaacggagguggacccauccgacacgauccuugacauuggaagug cgcccgcccgcagaauguauucuaagcacaaguaucauuguaucuguccgaugagaugugcggaagauccggacagauugu auaaguaugcaacuaagcugaagaaaaacuguaaggaaauaacugauaaggaauuggacaagaaaaugaaggagcuggccg ccgucaugagcgacccugaccuggaaacugagacuaugugccuccacgacgacgagucgugucgcuacgaagggcaagucg cuguuuaccaggauguauacgcgguugacggaccgacaagucucuaucaccaagccaauaagggaguuagagucgccuacu ggauaggcuuugacaccaccccuuuuauguuuaagaacuuggcuggagcauauccaucauacucuaccaacugggccgacg aaaccguguuaacggcucguaacauaggccuaugcagcucugacguuauggagcggucacguagagggauguccauucuua gaaagaaguauuugaaaccauccaacaauguucuauucucuguuggcucgaccaucuaccacgagaagagggacuuacuga ggagcuggcaccugccgucuguauuucacuuacguggcaagcaaaauuacacaugucggugugagacuauaguuaguugcg acggguacgucguuaaaagaauagcuaucaguccaggccuguaugggaagccuucaggcuaugcugcuacgaugcaccgcg agggauucuugugcugcaaagugacagacacauugaacggggagagggucucuuucccgugugcacguaugugccagcua cauugugugaccaaaugacuggcauacuggcaacagaugucagugcggacgacgcgcaaaaacugcugguugggcucaacc agcguauagucgucaacggucgcacccagagaaacaccaauaccaugaaaaauuaccuuuugcccguaguggcccaggcau uugcuaggugggcaaaggaauauaaggaagaucaagaagaugaaaggccacuaggacuacgagauagacaguuagucaugg gguguuguugggcuuuuagaaggcacaagauaacaucuauuuauaagcgcccggauacccaaaccaucaucaaagugaaca gcgauuuccacucauucgugcugcccaggauaggcaguaacacauuggagaucgggcugagaacaagaaucaggaaaaugu uagaggagcacaaggagccgucaccucucauuaccgccgaggacguacaagaagcuaagugcgcagccgaugaggcuaagg aggugcgugaagccgaggaguugcgcgcagcucuaccaccuuuggcagcugauguugaggagcccacucuggaggcagacg ucgacuugauguuacaagaggcuggggccggcucaguggagacaccucguggcuugauaaagguuaccagcuacgauggcg aggacaagaucggcucuuacgcugugcuuucuccgcaggcuguacucaagagugaaaaauuaucuugcauccacccucucg -continued cugaacaagucauagugauaacacacucuggccgaaaagggcguuaugccguggaaccauaccaugguaaaguaguggugc cagagggacaugcaauacccguccaggacuuucaagcucugagugaaagugccaccauuguguacaacgaacgugaguucg uaaacagguaccugcaccauauugccacacauggaggagcgcugaacacugaugaagaauauuacaaaacugucaagccca gcgagcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaaguac caaccauagggguguauggcgugccaggaucaggcaagucuggcaucauuaaaagcgcagucaccaaaaaagaucuagugg ugagcgccaagaaagaaaacugugcagaaauuauaagggacgucaagaaaaugaaagggcuggacgucaaugccagaacug uggacucagugcucuugaauggaugcaaacaccccguagagacccuguauauugacgaagcuuuugcuugucaugcaggua cucucagagcgcucauagccauuauaagaccuaaaaaggcagugcucugcggggaucccaaacagugcgguuuuuuuaaca ugaugugccugaaagugcauuuuaaccacgagauuugcacacaagucuuccacaaaagcaucucucgccguugcacuaaau cugugacuucggucgucucaaccuuguuuuacgacaaaaaaaugagaacgacgaauccgaaagagacuaagauugugauug acacuaccggcaguaccaaaccuaagcaggacgaucucauucucacuuguuucagaggguggugaagcaguugcaaauag auuacaaaggcaacgaaauaaugacggcagcugccucucaagggcugacccguaaagguguguaugccguucgguacaagg ugaaugaaaauccucuguacgcacccaccucagaacaugugaacguccuacugacccgcacggaggaccgcaucgugugga aaacacuagccggcgacccauggauaaaaacacugacugccaaguacccugggaauuucacugccacgauagaggaguggc aagcagagcaugaugccaucaugaggcacaucuuggagagaccggacccuaccgacgucuuccagaauaaggcaaacgugu guugggccaaggcuuuagugccggugcugaagaccgcuggcauagacaugaccacugaacaauggaacacuguggauuauu uugaaacggacaaagcucacucagcagagauaguauugaaccaacuaugcgugagguucuuuggacucgaucuggacuccg gucuauuuucugcacccacuguuccguuauccauuaggaauaaucacugggauaacuccccgucgccuaacauguacgggc ugaauaaagaagugguccgucagcucucucgcagguacccacaacugccucgggcaguugccacuggaagagucuaugaca ugaacacugguacacugcgcaauuaugauccgcgcauaaaccuaguaccuguaaacagaagacugccucaugcuuuagucc uccaccauaaugaacacccacagagugacuuuucuucauucgucagcaaauugaagggcagaacuguccugguggucgggg aaaaguuguccgucccaggcaaaaugguugacugguugucagaccggccugaggcuaccuucagagcucggcuggauuuag gcaucccaggugaugugcccaaauaugacauaauauuuguuaaugugaggaccccauauaaauaccaucacuaucagcagu gugaagaccaugccauuaagcuuagcauguugaccaagaaagcuugucugcaucugaaucccggcggaaccugugucagca uagguuaugguuacgcugacagggccagcgaaagcaucauuggugcuauagcgcggcaguucaaguuucccggguaugca aaccgaaauccucacuugaagagacggaaguucuguuuguauucauuggguacgaucgcaaggcccguacgcacaauccuu acaagcuuucaucaaccuugaccaacauuuauacagguuccagacuccacgaagccggaugugcacccucauaucaugugg ugcgaggggauauugccacggccaccgaaggagugauuauaaaugcugcuaacagcaaaggacaaccuggcggaggggugu gcggagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcagagg cuuaugaguccaucgcuaagauugucaacgauaacaauuacaagucaguagcgauuccacuguuguccaccggcaucuuuu ccgggaacaaagaucgacuaacccaaucauugaaccauuugcugacagcuuuagacaccacugaugcagauguagccauau acugcagggacaagaaaugggaaaugacucucaaggaagcaguggcuaggagagaagcaguggaggagauaugcauauccg acgacucuucagugacagaaccugaugcagagcuggugagggugcauccgaagaguucuuuggcuggaaggaagggcuaca gcacaagcgauggcaaaacuuucucauauuggaagggaccaaguuucaccaggcggccaaggauauagcagaaauuaaug ccauguggcccguugcaacggaggccaaugagcagguaugcauguauauccucggagaaagcaugagcaguauuaggucga aaugccccgucgaagagucggaagccuccacaccaccuagcacgcugccuugcuugugcauccaugccaugacuccagaaa gaguacagcgccuaaaagccucacguccagaacaaauuacugugugcucauccuuuccauugccgaaguauagaaucacug gugugcagaagauccaaugcucccagccuauauuguucucaccgaaagugccugcguauauucauccaaggaaguaucucg -continued uggaaacaccaccgguagacgagacuccggagccaucggcagagaaccaauccacagaggggacaccugaacaaccaccac uuauaaccgaggaugagaccaggacuagaacgccugagccgaucaucaucgaagaggaagaagaggauagcauaaguuugc ugucagauggcccgacccaccaggugcugcaagucgaggcagacauucacgggccgcccucuguaucuagcucauccuggu ccauuccucaugcauccgacuuugauguggacaguuuauccauacuugacacccuggagggagcuagcgugaccagcgggg caacgucagccgagacuaacucuuacuucgcaaagaguauggaguuucuggcgcgaccggugccugcgccucgaacaguau ucaggaacccuccacaucccgcuccgcgcacaagaacaccgucacuugcacccagcagggccugcucgagaaccagccuag uuuccaccccgccaggcgugaauagggugaucacuagagaggagcucgaggcgcuuaccccgucacgcacuccuagcaggu cggucucgagaaccagccuggucuccaacccgccaggcguaaauagggugauuacaagagaggaguuugaggcguucguag cacaacaacaaugacgguuugaugcgggugcauacaucuuuuccuccgacaccggucaagggcauuuacaacaaaaaucag uaaggcaaacggugcuauccgaagugguguuggagaggaccgaauuggagauuucguaugccccgcgccucgaccaagaaa aagaagaauuacuacgcaagaaauuacaguuaaaucccacaccugcuaacagaagcagauaccaguccaggaagguggaga acaugaaagccauaacagcuagacguauucugcaaggccuagggcauuauuugaaggcagaaggaaaaguggagugcuacc gaacccugcauccuguuccuuuguauucaucuagugugaaccgugccuuuucaagccccaaggucgcaguggaagccugua acgccauguugaaagagaacuuuccgacuguggcuucuuacuguauuauuccagaguacgaugccuauuuggacaugguug acggagcuucaugcugcuuagacacugccaguuuuugcccugcaaagcugcgcagcuuuccaaagaaacacuccuauuugg aacccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgugua auaaugaauauugggaaacguuuaaagaaaaccccaucaggcuuacugaagaaaacgugguaaauuacauuaccaaauuaa aaggaccaaaagcugcugcucuuuuugcgaagacacauaauuugaauauguugcaggacauaccaauggacagguuuguaa uggacuuaaagagagacgugaaagugacuccaggaacaaaacauacugaagaacggcccaagguacaggugauccaggcug ccgauccgcuagcaacagcguaucugugcggaauccaccgagagcugguuaggagauuaaaugcgguccugcuuccgaaca uucauacacuguuugauaugucggcugaagacuuugacgcuauuauagccgagcacuuccagccuggggauuguguucugg aaacugacaucgcgucguuugauaaaagugaggacgacgccauggcucugaccgcguuaaugauucuggaagacuuaggug uggacgcagagcuguugacgcugauugaggcggcuuucggcgaaauuucaucaauacauuugcccacuaaaacuaaauuua aauucggagccaugaugaaaucuggaauguuccucacacuguuugugaacacagucauuaacauuguaaucgcaagcagag uguugagagaacggcuaaccggaucaccaugugcagcauucauuggagaugacaauaucgugaaaggagucaaaucggaca aauuaauggcagacaggugcgccaccugguugaauauggaagucaagauuauagaugcugugguggcgagaaagcgccuu auuucuguggaggguuuauuuugugugacuccgugaccggcacagcgugccguguggcagaccccccuaaaaaggcuguuua agcuuggcaaaccucuggcagcagacgaugaacaugaugaugacaggagaagggcauugcaugaagagucaacacgcugga accgagugggguauucuuucagagcugugcaaggcaguagaaucaagguaugaaaccguaggaacuuccaucauaguuaugg ccaugacuacucuagcuagcaguguuaaaucauucagcuaccugagagggggccccuauaacucucuacggcuaaccugaau ggacuacgacauagucuaguccgccaagnugauaaccgcggugucaaaaaccgcguggacgugguuaacaucccugcuggg aggaucagccguaauuauuauaauuggcuuggugcuggcuacuauuguggccauguacgugcugaccaaccagaaacauaa uugaauacagcagcaauuggcaagcugcuuacauagaacucgcggcgauuggcaugccgccuuaaaauuuuuauuuuauuu uuucuuuucuuuuccgaaucggauuuuguuuuuaauauuucaaaaaaaaaaaaaaaaaaaaaaaaaaaaaaaaaaaaaaaaa aaaaa Vector Backbone RNA Sequence 2

SEQ ID NO: 49 auaggcggcgcaugagagaagcccagaccaauuaccuacccaaaauggagaaaguucacguugacaucgaggaagacagcc cauuccucagagcuuugcagcggagcuucccgcaguuugagguagaagccaagcaggucacugauaaugaccaugcuaaug ccagagcguuuucgcaucuggcuucaaaacugaucgaaacggagguggacccauccgacacgauccuugacauuggaagug cgcccgcccgcagaauguauucuaagcacaaguaucauuguaucuguccgaugagaugugcggaagauccggacagauugu -continued auaaguaugcaacuaagcugaagaaaaacuguaaggaaauaacugauaaggaauuggacaagaaaaugaaggagcuggccg ccgucaugagcgacccugaccuggaaacugagacuaugugccuccacgacgacgagucgugucgcuacgaagggcaagucg cuguuuaccaggauguauacgcgguugacggaccgacaagucucuaucaccaagccaauaagggaguuagagucgccuacu ggauaggcuuugacaccaccccuuuuauguuuaagaacuuggcuggagcauauccaucauacucuaccaacugggccgacg aaaccguguuaacggcucguaacauaggccuaugcagcucugacguuauggagcggucacguagagggauguccauucuua gaaagaaguauuugaaaccauccaacaauguucuauucucuguuggcucgaccaucuaccacgagaagagggacuuacuga ggagcuggcaccugccgucuguauuucacuuacguggcaagcaaaauuacacaugucggugugagacuauaguuaguugcg acggguacgucguuaaaagaauagcuaucaguccaggccuguaugggaagccuucaggcuaugcugcuacgaugcaccgcg agggauucuugugcugcaaagugacagacacauugaacggggagagggucucuuuucccgugugcacguaugugccagcua cauugugugaccaaaugacuggcauacuggcaacagaugucagugcggacgacgcgcaaaaacugcugguugggcucaacc agcguauagucgucaacggucgcacccagagaaacaccaauaccaugaaaaauuaccuuuugcccguaguggcccaggcau uugcuaggugggcaaaggaauauaaggaagaucaagaagaugaaaggccacuaggacuacgagauagacaguuagucaugg gguguuguugggcuuuuagaaggcacaagauaacaucuauuuauaagcgcccggauacccaaaccaucaucaaagugaaca gcgauuuccacucauucgugcugcccaggauaggcaguaacacauuggagaucgggcugagaacaagaaucaggaaaaugu uagaggagcacaaggagccgucaccucucauuaccgccgaggacguacaagaagcuaagugcgcagccgaugaggcuaagg aggugcgugaagccgaggaguugcgcgcagcucuaccaccuuuggcagcugauguugaggagcccacucuggaggcagacg ucgacuugauguuacaagaggcuggggccggcucaguggagacaccucguggcuugauaaagguuaccagcuacgauggcg aggacaagaucggcucuuacgcugugcuuucuccgcaggcuguacucaagagugaaaaauuaucuugcauccacccucucg cugaacaagucauagugauaacacacucuggccgaaaagggcguuaugccguggaaccauaccaugguaaaguaguggugc cagagggacaugcaauacccguccaggacuuucaagcucugagugaaagugccaccauuguguacaacgaacgugaguucg uaaacagguaccugcaccauauugccacacauggaggagcgcugaacacugaugaagaauauuacaaaacugucaagccca gcgagcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaaguac caaccauagggguguauggcgugccaggaucaggcaagucuggcaucauuaaaagcgcagucaccaaaaaagaucuagugg ugagcgccaagaaagaaaacugugcagaaauuauaagggacgucaagaaaaugaaagggcuggacgucaaugccagaacug uggacucagugcucuugaauggaugcaaacaccccguagagacccuguauauugacgaagcuuuugcuugucaugcaggua cucucagagcgcucauagccauuauaagaccuaaaaaggcagugcucugcggggaucccaaacagugcgguuuuuuuaaca ugaugugccugaaagugcauuuuaaccacgagauuugcacacaagucuuccacaaaagcaucucucgccguugcacuaaau cugugacuucggucgucucaaccuuguuuuacgacaaaaaaaugagaacgacgaauccgaaagagacuaagauugugauug acacuaccggcaguaccaaaccuaagcaggacgaucucauucucacuuguuucagagggugggugaagcaguugcaaauag auuacaaaggcaacgaaauaaugacggcagcugccucucaagggcugacccguaaagguguguaugccguucgguacaagg ugaaugaaaauccucuguacgcacccaccucagaacaugugaacguccuacugacccgcacggaggaccgcaucgugugga aaacacuagccggcgacccauggauaaaaacacugacugccaaguacccugggaauuucacugccacgauagaggaguggc aagcagagcaugaugccaucaugaggcacaucuuggagagaccggacccuaccgacgucuuccagaauaaggcaaacgugu guugggccaaggcuuuagugccggugcugaagaccgcuggcauagacaugaccacugaacaauggaacacuguggauuauu uugaaacggacaaagcucacucagcagagauaguauugaaccaacuaugcgugagguucuuuggacucgaucuggacuccg gucuauuuucugcacccacuguuccguuauccauuaggaauaaucacugggauaacuccccgucgccuaacauguacgggc ugaauaaagaaguggucgucagcucucucgcagguacccacaacugccucgggcaguugccacuggaagagucuaugaca ugaacacugguacacugcgcaauuaugauccgcgcauaaaccuaguaccuguaaacagaagacugccucaugcuuuagucc uccaccauaaugaacacccacagagugacuuuucuucauucgucagcaaauugaagggcagaacuguccugguggucgggg -continued aaaaguuguccgucccaggcaaaaugguugacugguugucagaccggccugaggcuaccuucagagcucggcuggauuuag gcaucccaggugaugugcccaaauaugacauaauauuuguuaaugugaggaccccauauaaauaccaucacuaucagcagu gugaagaccaugccauuaagcuuagcauguugaccaagaaagcuugucugcaucugaaucccggcggaaccugugucagca uagguuaugguuacgcugacagggccagcgaaagcaucauuggugcuauaggccggcaguucaaguuucccgggu augca aaccgaaauccucacuugaagagacggaaguucuguuuguauucauuggguacgaucgcaaggcccguacgcacaaccuuu acaagcuuucaucaaccuugaccaacauuuauacagguuccagacuccacgaagccggaugugcacccucauaucaugugg ugcgaggggauauugccacggccaccgaaggagugauuauaaaugcugcuaacagcaaaggacaaccuggcggagggggugu gcggagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcagagg cuuaugaguccaucgcuaagauugucaacgauaacaauuacaagucaguagcgauuccacuguuguccaccggcaucuuuu ccgggaacaaagaucgacuaacccaaucauugaaccauuugcugacagcuuuagacaccacugaugcagauguagccauau acugcagggacaagaaaugggaaaugacucucaaggaagcaguggcuaggagagaagcaguggaggagauaugcauauccg acgacucuucagugacagaaccugaugcagagcuggugagggugcauccgaagaguucuuuggcuggaaggaagggcuaca gcacaagcgauggcaaaacuuucucauauuuggaagggaccaaguuucaccaggcggccaaggauauagcagaaauuaaug ccauguggcccguugcaacggaggccaaugagcagguaugcauguauauccucggagaaagcaugagcaguauuaggucga aaugccccgucgaagagucggaagccuccacaccaccuagcacgcugccuugcuugugcauccaugccaugacuccagaaa gaguacagcgccuaaaagccucacguccagaacaaauuacugugugcucauccuuuccauugccgaaguauagaaucacug gugugcagaagauccaaugcucccagccuauauuguucucaccgaaagugccugcguauauucauccaaggaaguaucucg uggaaacaccaccgguagacgagacuccggagccaucggcagagaaccaauccacagaggggacaccugaacaaccaccac uuauaaccgaggaugagaccaggacuagaacgccugagccgaucaucaucgaagaggaagaagaggauagcauaaguuugc ugucagauggcccgacccaccaggugcugcaagucgaggcagacauucacgggccgcccucuguaucuagcucauccuggu ccauuccucaugcauccgacuuugauguggacaguuuauccauacuugacacccuggagggagcuagcgugaccagcgggg caacgucagccgagacuaacucuuacuucgcaaagaguauggaguuucuggcgcgaccggugccugcgccucgaacaguau ucaggaacccuccacaucccgcuccgcgcacaagaacaccgucacuugcacccagcagggccugcucgagaaccagccuag uuuccaccccgccaggcgugaauagggugaucacuagagaggagcucgaggcgcuuaccccgucacgcacuccuagcaggu cggucucgagaaccagccuggucuccaacccgccaggcguaaauagggugauuacaagagaggaguuugaggcguucguag cacaacaacaaugacgguuugaugcgggugcauacaucuuuuccuccgacaccggucaagggcauuuacaacaaaaaucag uaaggcaaacggugcuauccgaagugguguuggagaggaccgaauuggagauuucguaugccccgcgccucgaccaagaaa aagaagaauuacuacgcaagaaauuacaguuaaaucccacaccugcuaacagaagcagauaccaguccaggaagguggaga acaugaaagccauaacagcuagacguauucugcaaggccuagggcauuauuugaaggcagaaggaaaaguggagugcuacc gaacccugcauccuguuccuuuguauucaucuagugugaaccgugccuuuucaagccccaaggucgcaguggaagccugua acgccauguugaaagagaacuuuccgacuguggcuucuuacuguauuauuccagaguacgaugccuauuuggacaugguug acggagcuucaugcugcuuagacacugccaguuuuugcccugcaaagcugcgcagcuuuccaaagaaacacuccuauuugg aacccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgugua auaaugaauauugggaaacguuuaaagaaaaccccaucaggcuuacugaagaaaacgugguaaauuacauuaccaaauuaa aaggaccaaaagcugcugcucuuuuugcgaagacacauaauuugaauauguugcaggacauaccaauggacagguuuguaa uggacuuaaagagagacgugaaagugacuccaggaacaaaacauacugaagaacggcccaagguacaggugauccaggcug ccgauccgcuagcaacagcguaucugugcggaauccaccgagagcugguuaggagauuaaaugcgguccugcuuccgaaca uucauacacuguuugauaugucggcugaagacuuugacgcuauuauagccgagcacuuccagccuggggauuguguucugg aaacugacaucgcgucguuugauaaaagugaggacgacgccauggcucugaccgcguuaaugauucuggaagacuuaggug -continued uggacgcagagcuguugacgcugauugaggcggcuuucggcgaaauuucaucaauacauuugcccacuaaaacuaaaauuua aauucggagccaugaugaaaucuggaauguucccucacacuguuugugaacacagucauuaacauuguaaucgcaagcagag uguugagagaacggcuaaccggaucaccaugugcagcauucauuggagaugacaauaucgugaaaggagucaaaucggaca aauuaauggcagacaggugcgccaccugguugaauauggaagucaagauuauagaugcugugguggggcgagaaagcgccuu auuucuguggaggguuuauuuuguguacucccgugaccggcacagcgugccguguggcagacccccuaaaaaggcuguuua agcuuggcaaaccucuggcagcagacgaugaacaugaugaugacaggagaagggcauugcaugaagagucaacacgcugga accgaguggguauucuuucagagcugugcaaggcaguagaaucaagguaugaaaccguaggaacuucccaucauaguuaugg ccaugacuacucuagcuagcaguguuaaaucauucagcuaccugagagggggccccuauaaacucucuacggcuaaccugaau ggacuacgacauagucuaguccgccaagnugauaaccgcggugucaaaaaccgcguggacgugguuaacaucccugcuggg aggaucagccguaauuauuauaauuggcuuggugcuggcuacuauuguggccauguacgugcugaccaaccagaaacauaa uugaauacagcagcaauuggcaaagcugcuuacaugaacucgcggcgauuggcaugccgccuuaaaauuuuuauuuuauuu uuucuuuucuuuuccgaaucggauuuuguuuuuaauauuucaaaaaaaaaaaaaaaaaaaaaaaaaaaaaaaaaaaaaaaaaa aaaaa Vector Backbone RNA Sequence 3

SEQ ID NO: 50 auaggcggcgcaugagagaagcccagaccaauuaccuacccaaaauggagaaaguucacguugacaucgaggaagacagcc cauuccucagagcuuugcagcggagcuucccgcaguuugagguagaagccaagcaggucacugauaaugaccaugcuaaug ccagagcguuuucgcaucuggcuucaaaacugaucgaaacggagguggacccauccgacacgauccuugacauuggaagug cgcccgcccgcagaauguauucuaagcacaaguaucauuguaucuguccgaugagaugugcggaagauccggacagauugu auaaguaugcaacuaagcugaagaaaaacuguaaggaaauaacugauaaggaauuggacaagaaaaugaaggagcuggccg ccgucaugagcgacccugaccuggaaacugagacuaugugccuccacgacgacgagucgugucgcuacgaagggcaagucg cuguuuaccaggauguauacgcgguugacggaccgacaagucucuaucaccaagccaauaagggaguuagagucgccuacu ggauaggcuuugacaccaccccuuuuauguuuaagaacuuggcuggagcauauccaucauacucuaccaacugggccgacg aaaccguguuaacggcucguaacauaggccuaugcagcucugacguuauggagcggucacguagagggauguccauucuua gaaagaaguauuugaaaccauccaacaauguucuauucucuguuggcucgaccaucuaccacgagaagagggacuuacuga ggagcuggcaccugccgucuguauuucacuuacguggcaagcaaaauuacacaugucggugugagacuauaguuaguugcg acggguacgucguuaaaagaauagcuaucaguccaggccuguaugggaagccuucaggcuaugcugcuacgaugcaccgcg agggauucuugugcugcaaagugacagacacauugaacggggagagggucucuuuucccgugugcacguaugugccagcua cauugugugaccaaaugacuggcauacuggcaacagaugucagugcggacgacgcgcaaaaacugcugguugggcucaacc agcguauagucgucaacggucgcacccagagaaacaccaauaccaugaaaaauuaccuuuugcccguaguggcccaggcau uugcuaggugggcaaaggaauauaaggaagaucaagaagaugaaaggccacuaggacuacgagauagacaguuagucaugg gguguuguugggcuuuuagaaggcacaagauaacaucuauuuauaagcgcccggauacccaaaccaucaucaaagugaaca gcgauuuccacucauucgugcugcccaggauaggcaguaacacauuggagaucgggcugagaacaagaaucaggaaaaugu uagaggagcacaaggagccgucaccucucauuaccgccgaggacguacaagaagcuaagugcgcagccgaugaggcuaagg aggugcgugaagccgaggaguugcgcgcagcucuaccaccuuuggcagcugauguugaggagcccacucuggaggcagacg ucgacuugauguuacaagaggcuggggccggcucaguggagacaccucguggcuugauaaagguuaccagcuacgauggcg aggacaagaucggcucuuacgcugugcuuucuccgcaggcuguacucaagagugaaaaauuaucuugcauccacccucucg cugaacaagucauagugauaacacacucuggccgaaaagggcguuaugccguggaaccauaccaugguaaaguaguggugc cagagggacaugcaauacccguccaggacuuucaagcucugagugaaagugccaccauuguguacaacgaacgugaguucg uaaacagguaccugcaccauauugccacacauggaggagcgcugaacacugaugaagaauauuacaaaacugucaagccca gcgagcacgacggcgaauaccuguacgacaucgacaggaaacagugcgucaagaaagaacuagucacugggcuagggcuca -continued caggcgagcugguggauccucccuuccaugaauucgccuacgagagucugagaacacgaccagccgcuccuuaccaaguac caaccauagggguguauggcgugccaggaucaggcaagucuggcaucauuaaaagcgcagucaccaaaaaagaucuagugg ugagcgccaagaaagaaaacugugcagaaauuauaagggacgucaagaaaaugaaagggcuggacgucaaugccagaacug uggacucagugcucuugaauggaugcaaacaccccguagagacccuguauauugacgaagcuuuugcuugucaugcaggua cucucagagcgcucauagccauuauaagaccuaaaaaggcagugcucugcggggaucccaaacagugcgguuuuuuuaaca ugaugugccugaaagugcauuuuaaccacgagauuugcacacaagucuuccacaaaagcaucucucgccguugcacuaaau cugugacuucggucgucucaaccuuguuuuacgacaaaaaaaugagaacgacgaauccgaaagagacuaagauugugauug acacuaccggcaguaccaaaccuaagcaggacgaucucauucucacuuguuucagagggugggugaagcaguugcaaauag auuacaaaggcaacgaaauaaugacggcagcugccucucaagggcugacccguaaaggugugua ugccguucgguacaagg ugaaugaaaauccucuguacgcacccaccucagaacaugugaacguccuacugacccgcacggaggaccgcaucgugugga aaacacuagccggcgacccauggauaaaaacacugacugccaaguacccugggaauuucacugccacgauagaggaguggc aagcagagcaugaugccaucaugaggcacaucuuggagagaccggacccuaccgacgucuuccagaauaaggcaaacgugu guugggccaaggcuuuagugccggugcugaagaccgcuggcauagacaugaccacugaacaauggaacacuguggauuauu uugaaacggacaaagcucacucagcagagauaguauugaaccaacuaugcgugagguucuuuggacucgaucuggacuccg gucuauuuucugcacccacuguuccguuauccauuaggaauaaucacugggauaacuccccgucgccuaacauguacgggc ugaauaaagaaguggucc gucagcucucucgcagguacccacaacugccucgggcaguugccacuggaagagucuaugaca ugaacacugguacacugcgcaauuaugauccgcgcauaaaccuaguaccuguaaacagaagacugccucaugcuuuagucc uccaccauaaugaacacccacagagugacuuuucuucauucgucagcaaauugaagggcagaacuguccugguggucgggg aaaaguuguccgucccaggcaaaaugguugacugguugucagaccggccugaggcuaccuucagagcucggcuggauuuag gcaucccaggugaugugcccaaauaugacauaauauuuguuaaugugaggaccccauauaaauaccaucacuaucagcagu gugaagaccaugccauuaagcuuagcauguugaccaagaaagcuugucugcaucugaaucccggcggaaccugugucagca uagguuaugguuacgcugacagggccagcgaaagcaucauuggugcuauagcgcggcaguucaaguuucccggguaugca aaccgaaauccucacuugaagagacggaaguucuguuuguauucauuggguacgaucgcaaggcccguacgcacaauccuu acaagcuuucaucaaccuugaccaacauuuauacagguuccagacuccacgaagccggaugugcacccucauaucaugugg ugcgaggggauauugccacggccaccgaaggagugauuauaaaugcugcuaacagcaaaggacaaccuggcggaggggugu gcggagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcagagg cuuaugaguccaucgcuaagauugucaacgauaacaauuacaagucaguagcgauuccacuguuguccaccggcaucuuuu ccgggaacaaagaucgacuaacccaaucauugaaccauuugcugacagcuuuagacaccacugaugcagauguagccauau acugcagggacaagaaaugggaaaugacucucaaggaagcaguggcuaggagagaagcaguggaggagauaugcauauccg acgacucuucagugacagaaccugaugcagagcuggugagggugcauccgaagaguucuuuggcuggaaggaagggcuaca gcacaagcgauggcaaaacuuucucauauuuggaagggaccaaguuucaccaggcggccaaggauauagcagaaauuaaug ccauguggcccguugcaacggaggccaaugagcagguaugcauguauauccucggagaaagcaugagcaguauuaggucga aaugccccgucgaagagucggaagccuccacaccaccuagcacgcugccuugcuugugcauccaugccaugacuccagaaa gaguacagcgccuaaaagccucacguccagaacaaauuacugugugcucauccuuuccauugccgaaguauagaaucacug gugugcagaagauccaaugcucccagccuauauuguucucaccgaaagugccugcguauauucauccaaggaaguaucucg uggaaacaccaccgguagacgagacuccggagccaucggcagagaaccaauccacagaggggacaccugaacaaccaccac uuauaaccgaggaugagaccaggacuagaacgccugagccgaucaucaucgaagaggaagaagaggauagcauaaguuugc ugucagauggcccgacccaccaggugcugcaagucgaggcagacauucacgggccgcccucuguaucuagcucauccuggu ccauuccucaugcauccgacuuugauguggacaguuuauccauacuugacacccuggagggagcuagcgugaccagcgggg caacgucagccgagacuaacucuuacuucgcaaagaguauggaguuucuggcgcgaccggugccugcgccucgaacaguau -continued ucaggaacccuccacaucccgcuccgcgcacaagaacaccgucacuugcacccagcagggccugcucgagaaccagccuag
uuuccaccccgccaggcgugaauagggugaucacuagagaggagcucgaggcgcuuaccccgucacgcacuccuagcaggu
cggucucgagaaccagccuggucuccaacccgccaggcguaaauagggugauuacaagagaggaguuugaggcguucguag
cacaacaacaaugacgguuugaugcgggugcauacaucuuuuccuccgacaccggucaagggcauuuacaacaaaaaucag
uaaggcaaacggugcuauccgaaguggugguuggagaggaccgaauuggagauuucguaugccccgcgccucgaccaagaaa
aagaagaauuacuacgcaagaaauuacaguuaaaucccacaccugcuaacagaagcagauaccaguccaggaagguggaga
acaugaaagccauaacagcuagacguauucugcaaggccuagggcauuauuugaaggcagaaggaaaaguggagugcuacc
gaacccugcauccuguuccuuuguauucaucuagugugaaccgugccuuuucaagccccaaggucgcaguggaagccugua
acgccauguugaaagagaacuuuccgacuguggcuucuuacuguauuauuccagaguacgaugccuauuuggacaugguug
acggagcuucaugcugcuuagacacugccaguuuuugcccugcaaagcugcgcagcuuuccaaagaaacacuccuauuugg
aacccacaauacgaucggcagugccuucagcgauccagaacacgcuccagaacguccuggcagcugccacaaaaagaaauu
gcaaugucacgcaaaugagagaauugcccguauuggauucggcggccuuuaauguggaaugcuucaagaaauaugcgugua
auaaugaauauugggaaacguuuaaagaaaaccccaucaggcuuacugaagaaaacgugguaaauuacauuaccaaauuaa
aaggaccaaaagcugcugcucuuuuugcgaagacacauaauuugaauauguugcaggacauaccaauggacagguuuguaa
uggacuuaaagagagacgugaaagugacuccaggaacaaaacauacugaagaacggcccaagguacaggugauccaggcug
ccgauccgcuagcaacagcguaucugugcggaauccaccgagagcugguuaggagauuaaaugcgguccugcuuccgaaca
uucauacacuguuugauaugucggcugaagacuuugacgcuauuauagccgagcacuuccagccuggggauuguguucugg
aaacugacaucgcgucguuugauaaaaagugaggacgacgccauggcucugaccgcguuaaugauucuggaagacuuaggug
uggacgcagagcuguugacgcugauugaggcggcuuucggcgaaauuucaucaauacauuugcccacuaaaacuaaauuua
aauucggagccaugaugaaaucuggaauguuccucacacuguuugugaacacagucauuaacauuguaaucgcaagcagag
uguugagagaacggcuaaccggaucaccaugugcagcauucauuggagaugacaauaucgugaaaggagucaaaucggaca
aauuaauggcagacaggugcgccaccugguugaauauggaagucaagauuauagaugcugugguggcgagaaagcgccuu
auuucuguggaggguuuauuuugugugacuccgugaccggcacagcgugccguguggcagaccccuaaaaaggcuguuua
agcuuggcaaaccucuggcagcagacgaugaacaugaugaugacaggagaagggcauugcaugaagagucaacacgcugga
accgaguggguauucuuucagagcugugcaaggcaguagaaucaagguaugaaaccguaggaacuuccaucauaguuaugg
ccaugacuacucuagcuagcaguguuaaaucauucagcuaccugagaggggccccuauaacucucuacggcuaaccugaau
ggacuacgacauagucuaguccgccaagnuaguaaccgcggugucaaaaaccgcguggacgugguuaacaucccugcuggg
aggaucagccguaauuauuauaauuggcuuggugcuggcuacuauuguggccauguacgugcugaccaaccagaaacauaa
uugaauacagcagcaauuggcaagcugcuuacauagaacucgcggcgauuggcaugccgccuuaaaauuuuuauuuuauuu
uuucuuuucuuuuccgaaucggauuuuguuuuuaauauuucaaaaaaaaaaaaaaaaaaaaaaaaaaaaaaaaaaaaaaaa
aaaaa Vector Backbone RNA Sequence 4

SEQ ID NO: 51 auaggcggcgcaugagagaagcccagaccaauuaccuacccaaaauggagaaaguucacguugacaucgaggaagacagcc
cauuccucagagcuuugcagcggagcuucccgcaguuugagguagaagccaagcaggucacugauaaugaccaugcuaaug
ccagagcguuuucgcaucuggcuucaaaacugaucgaaacggagguggacccauccgacacgauccuugacauuggaagug
cgcccgcccgcagaauguauucuaagcacaaguaucauuguaucuguccgaugagaugugcggaagauccggacagauugu
auaaguaugcaacuaagcugaagaaaaacuguaaggaaauaacugauaaggaauuggacaagaaaaugaaggagcuggccg
ccgucaugagcgacccugaccuggaaacugagacuaugugccuccacgacgacgagucgugucgcuacgaagggcaagucg
cuguuuaccaggauguauacgcgguugacggaccgacaagucucuaucaccaagccaauaagggaguuagagucgccuacu
ggauaggcuuugacaccaccccuuuuauguuuaagaacuuggcuggagcauauccaucauacucuaccaacugggccgacg -continued aaaccguguuaacggcucguaacauaggccuaugcagcucugacguuauggagcggucacguagagggauguccauucuua gaaagaaguauuugaaaccauccaacaauguucuauucucuguuggcucgaccaucuaccacgagaagagggacuuacuga ggagcuggcaccugccgucuguauuucacuuacguggcaagcaaaauuacacaugucggugugagacuauaguuaguugcg acggguacgucguuaaaagaauagcuaucaguccaggccuguaugggaagccuucaggcuaugcugcuacgaugcaccgcg agggauucuugugcugcaaagugacagacacauugaacggggagagggucucuuuucccgugugcacguaugugccagcua cauugugugaccaaaugacuggcauacuggcaacagaugucagugcggacgacgcgcaaaaacugcugguugggcucaacc agcguauagucgucaacggucgcacccagagaaacaccaauaccaugaaaaauuaccuuuugcccguaguggcccaggcau uugcuaggugggcaaaggaauauaaggaagaucaagaagaugaaaggccacuaggacuacgagauagacaguuagucaugg gguguuguugggcuuuuagaaggcacaagauaacaucuauuuauaagcgcccggauacccaaaccaucaucaaagugaaca gcgauuuccacucauucgugcugcccaggauaggcaguaacacauuggagaucgggcugagaacaagaaucaggaaaaugu uagaggagcacaaggagccgucaccucucauuaccgccgaggacguacaagaagcuaagugcgcagccgaugaggcuaagg aggugcgugaagccgaggaguugcgcgcagcucuaccaccuuuggcagcugauguugaggagcccacucuggaggcagacg ucgacuugauguuacaagaggcuggggccggcucaguggagacaccucguggcuugauaaagguuaccagcuacgauggcg aggacaagaucggcucuuacgcugugcuuucuccgcaggcuguacucaagagugaaaaauuaucuugcauccacccucucg cugaacaagucauagugauaacacacucuggccgaaaagggcguuaugccguggaaccauaccaugguaaaguaguggugc cagagggacaugcaauacccguccaggacuuucaagcucugagugaaagugccaccauuguguacaacgaacgugaguucg uaaacagguaccugcaccauauugccacacauggaggagcgcugaacacugaugaagaauauuacaaaacugucaagccca gcgagcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaaguac caaccauagggguguauggcgugccaggaucaggcaagucuggcaucauuaaaagcgcagucaccaaaaaagaucuagugg ugagcgccaagaaagaaaacugugcagaaauuauaagggacgucaagaaaaugaaagggcuggacgucaaugccagaacug uggacucagugcucuugaauggaugcaaacaccccguagagacccuguauauugacgaagcuuuugcuugucaugcaggua cucucagagcgcucauagccauuauaagaccuaaaaaggcagugcucugcggggaucccaaacagugcgguuuuuuuaaca ugaugugccugaaagugcauuuuaaccacgagauuugcacacaagucuuccacaaaagcaucucucgccguugcacuaaau cugugacuucggucgucucaaccuuguuuuacgacaaaaaaaugagaacgacgaauccgaaagagacuaagauugugauug acacuaccggcaguaccaaaccuaagcaggacgaucucauucucacuuguuucagaggguggggugaagcaguugcaaauag auuacaaaggcaacgaaauaaugacggcagcugccucucaagggcugacccguaaaggugugaugccguucgguacaagg ugaaugaaaauccucuguacgcacccaccucagaacaugugaacguccuacugacccgcacggaggaccgcaucgugugga aaacacuagccggcgacccauggauaaaaacacugacugccaaguacccugggaauuucacugccacgauagaggaguggc aagcagagcaugaugccaucaugaggcacaucuuggagagaccggacccuaccgacgucuuccagaauaaggcaaacgugu guugggccaaggcuuuagugccggugcugaagaccgcuggcauagacaugaccacugaacaauggaacacuguggauuauu uugaaacggacaaagcucacucagcagagauaguauugaaccaacuaugcgugagguucuuuggacucgaucuggacuccg gucuauuuucugcacccacuguuccguuauccauuaggaauaaucacugggauaacuccccgucgccuaacauguacgggc ugaauaaagaaguggucgcgucagcucucucgcagguacccacaacugccucgggcaguugccacuggaagagucuaugaca ugaacacugguacacugcgcaauuaugauccgcgcauaaaccuaguaccuguaaacagaagacugccucaugcuuuagucc uccaccauaaugaacacccacagagugacuuuucuucauucgucagcaaauugaagggcagaacuguccugguggucgggg aaaaguuguccgucccaggcaaaaugguugacugguugucagaccggccugaggcuaccuucagagcucggcuggauuuag gcaucccaggugaugugcccaaauaugacauaauauuuguuaaugugaggaccccauauaaauaccaucacuaucagcagu gugaagaccaugccauuaagcuuagcauguugaccaagaaagcuugucugcaucugaaucccggcggaaccugugucagca uagguuaugguuacgcugacagggccagcgaaagcaucauuggugcuauagcgcggcaguucaaguuucccggguaugca aaccgaaauccucacuugaagagacggaaguucuguuuguauucauugguacgaucgcaaggcccguacgcacaauccuu -continued acaagcuuucaucaaccuugaccaacauuuauacagguuccagacuccacgaagccggaugugcacccucauaucaugugg ugcgaggggauauugccacggccaccgaaggagugauuauaaaugcugcuaacagcaaaggacaaccuggcggagggggugu gcggagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcagagg cuuaugaguccaucgcuaagauugucaacgauaacaauuacaagucaguagcgauuccacuguuguccaccggcaucuuuu ccgggaacaaagaucgacuaacccaaucauugaaccauuugcugacagcuuuagacaccacugaugcagauguagccauau acugcagggacaagaaaugggaaaugacucucaaggaagcaguggcuaggagagaagcaguggaggagauaugcauauccg acgacucuucagugacagaaccugaugcagagcuggugagggugcauccgaagaguucuuuggcuggaaggaagggcuaca gcacaagcgauggcaaaacuuucucauauuuggaagggaccaaguuucaccaggcggccaaggauauagcagaaauuaaug ccauguggcccguugcaacggaggccaaugagcagguaugcauguauauccucggagaaagcaugagcaguauuaggucga aaugccccgucgaagagucggaagccuccacaccaccuagcacgcugccuugcuugugcauccaugccaugacuccagaaa gaguacagcgccuaaaagccucacguccagaacaaauuacugugugcucauccuuuccauugccgaaguauagaaucacug gugugcagaagauccaaugcucccagccuauauuguucucaccgaaagugccugcguauauucauccaaggaaguaucucg uggaaacaccaccgguagacgagacuccggagccaucggcagagaaccaauccacagaggggacaccugaacaaccaccac uuauaaccgaggaugagaccaggacuagaacgccugagccgaucaucaucgaagaggaagaagaggauagcauaaguuugc ugucagauggcccgacccaccaggugcugcaagucgaggcagacauucacgggccgcccucuguaucuagcucauccuggu ccauuccucaugcauccgacuuugauguggacaguuuauccauacuugacacccuggagggagcuagcgugaccagcgggg caacgucagccgagacuaacucuuacuucgcaaagaguauggaguuucugcggcgaccggugccugcgccucgaacaguau ucaggaacccuccacaucccgcuccgcgcacaagaacaccgucacuugcacccagcagggccugcucgagaaccagccuag uuuccaccccgccaggcgugaauagggugaucacuagagaggagcucgaggcgcuuaccccgucacgcacuccuagcaggu cggucucgagaaccagccuggucuccaacccgccaggcguaaauagggugauuacaagagaggaguuugaggcguucguag cacaacaacaaugacgguuugaugcgggugcauacaucuuuuccuccgacaccggucaagggcauuuacaacaaaaaucag uaaggcaaacggugcuauccgaagugguguuggagaggaccgaauuggagauuucguaugccccgcgccucgaccaagaaa aagaagaauuacuacgcaagaaauuacaguuaaaucccacaccugcuaacagaagcagauaccaguccaggaagguggaga acaugaaagccauaacagcuagacguauucugcaaggccuagggcauuauuugaaggcagaaggaaaaguggagugcuacc gaacccugcauccuguuccuuuguauucaucuagugugaaccgugccuuuucaagccccaaggucgcaguggaagccugua acgccauguugaaagagaacuuuccgacuguggcuucuuacuguauuauuccagaguacgaugccuauuuggacaugguug acggagcuucaugcugcuuagacacugccaguuuuugcccugcaaagcugcgcagcuuuccaaagaaacacuccuauuugg aacccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgugua auaaugaauauugggaaacguuuaaagaaaaccccaucaggcuuacugaagaaaacgugguaaauuacauuaccaaauuaa aaggaccaaaagcugcugcucuuuuugcgaagacacauaauuugaauauguugcaggacauaccaauggacagguuuguaa uggacuuaaagagagacgugaaagugacuccaggaacaaaacauacugaagaacggcccaagguacaggugauccaggcug ccgauccgcuagcaacagcguaucugugcggaauccaccgagagcugguuaggagauuaaaugcgguccugcuuccgaaca uucauacacuguuugauaugucggcugaagacuuugacgcuauuauagccgagcacuuccagccuggggauuguguucugg aaacugacaucgcgucguuugauaaaagugaggacgacgccauggcucugaccgcguuaaugauucuggaagacuuaggug uggacgcagagcuguugacgcugauugaggcggcuuucggcgaaauuucaucaauacauuugcccacuaaaacuaaauuua aauucggagccaugaugaaaucuggaauguuccucacacuguuugugaacacagucauuaacauuguaaucgcaagcagag uguugagagaacggcuaaccggaucaccaugugcagcauucauuggagaugacaauaucgugaaaggagucaaaucggaca aauuaauggcagacaggugcgccaccugguugaauauggaagucaagauuauagaugcugugguggggcgagaaagcgccuu -continued auuucuguggaggguuuauuuugugugacuccgugaccggcacagcgugccguguggcagaccccuaaaaaggcuguuua agcuuggcaaaccucuggcagcagacgaugaacaugaugaugacaggagaagggcauugcaugaagagucaacacgcugga accgagugguauucuuucagagcugugcaaggcaguagaaucaagguaugaaaccguaggaacuuccaucauaguuaugg ccaugacuacucuagcuagcaguguuaaaucauucagcuaccugagaggggccccuauaacucucuacggcuaaccugaau ggacuacgacauagucuaguccgccaagnugauaaccgcggugucaaaaaccgcguggacgugguuaacaucccugcuggg aggaucagccguaauuauuauaauuggcuuggugcuggcuacuauuguggccauguacgugcugaccaaccagaaacauaa uugaauacagcagcaauuggcaagcugcuuacauagaacucgcggcgauuggcaugccgccuuaaaauuuuuauuuuauuu uuucuuuucuuuuccgaaucggauuuuguuuuuaauauuucaaaaaaaaaaaaaaaaaaaaaaaaaaaaaaaaaaaaaaa aaaaa Vector Backbone RNA Sequence 5

SEQ ID NO: 52 auaggcggcgcaugagagaagcccagaccaauuaccuacccaaaauggagaaaguucacguugacaucgaggaagacagcc cauuccucagagcuuugcagcggagcuucccgcaguuugagguagaagccaagcaggucacugauaaugaccaugcuaaug ccagagcguuuucgcaucuggcuucaaaacugaucgaaacggagguggacccauccgacacgauccuugacauuggaagug cgcccgcccgcagaauguauucuaagcacaaguaucauuguaucuguccgaugagaugugcggaagauccggacagauugu auaaguaugcaacuaagcugaagaaaaacuguaaggaaauaacugauaaggaauuggacaagaaaaugaaggagcuggccg ccgucaugagcgacccugaccuggaaacugagacuaugugccuccacgacgacgagucgugucgcuacgaagggcaagucg cuguuuaccaggauguauacgcgguugacggaccgacaagucucuaucaccaagccaauaagggaguuagagucgccuacu ggauaggcuuugacaccaccccuuuuauguuuaagaacuuggcuggagcauauccaucauacucuaccaacugggccgacg aaaccguguuaacggcucguaacauaggccuaugcagcucugacguuauggagcggucacguagagggauguccauucuua gaaagaaguauuugaaaccauccaacaauguucuauucucuguuggcucgaccaucuaccacgagaagagggacuuacuga ggagcuggcaccugccgucuguauuucacuuacguggcaagcaaaauuacacaugucggugugagacuauaguuaguugcg acggguacgucguuaaaagaauagcuaucaguccaggccuguaugggaagccuucaggcuaugcugcuacgaugcaccgcg agggauucuugugcugcaaagugacagacacauugaacggggagagggucucuuuucccgugugcacguaugugccagcua cauugugugaccaaaugacuggcauacuggcaacagaugucagugcggacgacgcgcaaaaacugcugguugggcucaacc agcguauagucgucaacggucgcacccagagaaacaccaauaccaugaaaaauuaccuuuugcccguaguggcccaggcau uugcuaggugggcaaaggaauauaaggaagaucaagaagaugaaaggccacuaggacuacgagauagacaguuagucaugg gguguuguugggcuuuuagaaggcacaagauaacaucuauuuauaagcgcccggauacccaaaccaucaucaaagugaaca gcgauuuccacucauucgugcugcccaggauaggcaguaacacauuggagaucgggcugagaacaagaaucaggaaaaugu uagaggagcacaaggagccgucaccucucauuaccgccgaggacguacaagaagcuaagugcgcagccgaugaggcuaagg aggugcgugaagccgaggaguugcgcgcagcucuaccaccuuuggcagcugauguugaggagcccacucuggaggcagacg ucgacuugauguuacaagaggcuggggccggcucaguggagacaccucguggcuugauaaagguuaccagcuacgauggcg aggacaagaucggcucuuacgcugugcuuucuccgcaggcuguacucaagagugaaaaauuaucuugcauccacccucucg cugaacaagucauagugauaacacacucuggccgaaaagggcguuaugccguggaaccauaccaugguaaaguaguggugc cagagggacaugcaauacccguccaggacuuucaagcucugagugaaagugccaccauuguguacaacgaacgugaguucg uaaacagguaccugcaccauauugccacacauggaggagcgcugaacacugaugaagaauauuacaaaacugucaagccca gcgagcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaaguac caaccauagggguguauggcgugccaggaucaggcaagucuggcaucauuaaaagcgcagucaccaaaaaagaucuagugg ugagcgccaagaaagaaaacugugcagaaauuauaagggacgucaagaaaaugaaagggcuggacgucaaugccagaacug uggacucagugcucuugaauggaugcaaacaccccguagagacccuguauauugacgaagcuuuugcuugucaugcaggua cucucagagcgcucauagccauuauaagaccuaaaaaggcagugcucugcggggaucccaaacagugcgguuuuuuuaaca -continued ugaugugccugaaagugcauuuuaaccacgagauuugcacacaagucuuccacaaaagcaucucucgccguugcacuaaau cugugacuucggucgucucaaccuuguuuuacgacaaaaaaaugagaacgacgaauccgaaagagacuaagauugugauug acacuacoggcaguaccaaaccuaagcaggacgaucucauucucacuuguuucagagggugggugaagcaguugcaaauag auuacaaaggcaacgaaauaaugacggcagcugccucucaagggcugacccguaaaggugugiuaugccguucgguacaagg ugaaugaaaauccucuguacgcacccaccucagaacaugugaacguccuacugacccgcacggaggaccgcaucgugugga aaacacuagccggcgacccauggauaaaaacacugacugccaaguacccugggaauuucacugccacgauagaggaguggc aagcagagcaugaugccaucaugaggcacaucuuggagagaccggacccuaccgacgucuuccagaauaaggcaaacgugu guugggccaaggcuuuagugccggugcugaagaccgcuggcauagacaugaccacugaacaauggaacacuguggauuauu uugaaacggacaaagcucacucagcagagauaguauugaaccaacuaugcgugagguucuuuggacucgaucuggacuccg gucuauuuucugcacccacuguuccguuauccauuaggaauaaucacugggauaacuccccgucgccuaacauguacgggc ugaauaaagaaguggucgcucagcucucucgcagguacccacaacugccucgggcaguugccacuggaagagucuaugaca ugaacacugguacacugcgcaauuaugauccgcgcauaaaccuaguaccuguaaacagaagacugccucaugcuuuagucc uccaccauaaugaacacccacagagugacuuuucuucauucgucagcaaauugaagggcagaacuguccugguggucgggg aaaaguuguccgucccaggcaaaaugguugacugguugucagaccggccugaggcuaccuucagagcucggcuggauuuag gcaucccaggugaugugcccaaauaugacauaauauuuguuaaugugaggaccccauauaaauaccaucacuaucagcagu gugaagaccaugccauuaagcuuagcauguugaccaagaaagcuugucugcaucugaaucccggcggaaccugugucagca uagguuaugguuacgcugacagggccagcgaaagcaucauuggugcuauagcgcggcaguucaaguuucccggguaugca aaccgaaauccucacuugaagagacggaaguucuguuuguauucauuggguacgaucgcaaggcccguacgcacaauccuu acaagcuuucaucaaccuugaccaacauuuauacagguuccagacuccacgaagccggaugugcacccucauaucaugugg ugcgaggggauauugccacggccaccgaaggagugauuauaaaugcugcuaacagcaaaggacaaccuggcggaggggugu gcggagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcagagg cuuaugaguccaucgcuaagauugucaacgauaacaauuacaagucaguagcgauuccacuguuguccaccggcaucuuuu ccgggaacaaagaucgacuaacccaaucauugaaccauuugcugacagcuuuagacaccacugaugcagauguagccauau acugcagggacaagaaaugggaaaugacucucaaggaagcaguggcuaggagagaagcaguggaggagauaugcauauccg acgacucuucagugacagaaccugaugcagagcuggugagggugcauccgaagaguucuuuggcuggaaggaagggcuaca gcacaagcgauggcaaaacuuucucauauuggaagggaccaaguuucaccaggcggccaaggauauagcagaaauuaaug ccaugugcccguugcaacggaggccaaugagcagguaugcauguauauccucggagaaagcaugagcaguauuaggucga aaugccccgucgaagagucggaagccuccacaccaccuagcacgcugccuugcuugugcauccaugccaugacuccagaaa gaguacagcgccuaaaagccucacguccagaacaaauuacugugugcucauccuuuccauugccgaaguauagaaucacug gugugcagaagauccaaugcucccagccuauauuguucucaccgaaagugccugcguauauucauccaaggaaguaucucg uggaaacaccaccgguagacgagacuccggagccaucggcagagaaccaauccacagaggggacaccugaacaaccaccac uuauaaccgaggaugagaccaggacuagaacgccugagccgaucaucaucgaagaggaagaagaggauagcauaaguuugc ugucagauggcccgacccaccaggugcugcaagucgaggcagacauucacgggccgcccucuguaucuagcucauccuggu ccauuccucaugcauccgacuuugauguggacaguuuauccauacuugacacccuggagggagcuagcgugaccagcgggg caacgucagccgagacuaacucuuacuucgcaaagaguauggaguuucuggcgcgaccggugccugcgccucgaacaguau ucaggaacccuccacaucccgcuccgcgcacaagaacaccgucacuugcacccagcagggccugcucgagaaccagccuag uuuccaccccgccaggcgugaauagggugaucacuagagaggagcucgaggcgcuuaccccgucacgcacuccuagcaggu cggucucgagaaccagccuggucuccaacccgccaggcguaaauagggugauuacaagagaggaguuugaggcguucguag cacaacaacaaugacgguuugaugcgggugcauacaucuuuuccuccgacaccggucaagggcauuuacaacaaaaaucag -continued uaaggcaaacggugcuauccgaaguggugugguggagaggaccgaauuggagauuucguaugccccgcgccucgaccaagaaa aagaagaauuacuacgcaagaaauuacaguuaaaucccacaccugcuaacagaagcagauaccaguccaggaagguggaga acaugaaagccauaacagcuagacguauucugcaaggccuagggcauuauuugaaggcagaaggaaaaguggagugcuacc gaacccugcauccuguuccuuuguauucaucuagugugaaccgugccuuuucaagccccaaggucgcaguggaagccugua acgccauguugaaagagaacuuuccgacuguggcuucuuacuguauuauuccagaguacgaugccuauuuggacaugguug acggagcuucaugcugcuuagacacugccaguuuuugcccugcaaagcugcgcagcuuuccaaagaaacacuccuauuugg aacccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgugua auaaugaauauugggaaacguuuaaagaaaaccccaucaggcuuacugaagaaaacgugguaaauuacauuaccaaauuaa aaggaccaaaagcugcugcucuuuuugcgaagacacauaauuugaauauguugcaggacauaccaauggacagguuuguaa uggacuuaaagagagacgugaaagugacuccaggaacaaaacauacugaagaacggcccaagguacaggugauccaggcug ccgauccgcuagcaacagcguaucugugcggaauccaccgagagcugguuaggagauuaaaugcgguccugcuuccgaaca uucauacacuguuugauaugucggcugaagacuuugacgcuauuauagccgagcacuuccagccuggggauuguguucugg aaacugacaucgcgucguuugauaaaagugaggacgacgccauggcucugaccgcguuaaugauucuggaagacuuaggug uggacgcagagcuguugacgcugauugaggcggcuuucggcgaaauuucaucaauacauuugcccacuaaaacuaaauuua aauucggagccaugaugaaaucuggaauguuccucacacuguuugugaacacagucauuaacauuguaaucgcaagcagag uguugagagaacggcuaaccggaucaccaugugcagcauucauuggagaugacaauaucgugaaaggagucaaaucggaca aauuaauggcagacaggugcgccaccugguugaauauggaagucaagauuauagaugcugugguggggcgagaaagcgccuu auuucuguggaggguuuauuuugugugacuccgugaccggcacagcgugccguguggcagaccccuaaaaaggcuguuua agcuuggcaaaccucuggcagcagacgaugaacaugaugaugacaggagaagggcauugcaugaagagucaacacgcugga accgaguggguauucuuucagagcugugcaaggcaguagaaucaagguaugaaaccguaggaacuuccaucauaguuaugg ccaugacuacucuagcuagcaguguuaaaucauucagcuaccugagagggggccccuauaacucucuacggcuaaccugaau ggacuacgacauagucuaguccgccaagnugauaaccgcggugucaaaaaccgcguggacgugguuaacaucccugcuggg aggaucagccguaauuauuauaauuggcuuggugcuggcuacuauuguggccauguacgugcugaccaaccagaaacauaa uugaauacagcagcaauuggcaagcugcuuacauagaacucgcggcgauuggcaugccgccuuaaaauuuuuauuuuauuu uuucuuuucuuuuccgaaucggauuuuguuuuuaauauuucaaaaaaaaaaaaaaaaaaaaaaaaaaaaaaaaaaaaaaaa aaaaa Vector Backbone RNA Sequence 6

SEQ ID NO: 53 auaggcggcgcaugagagaagcccagaccaauuaccuacccaaaauggagaaaguucacguugacaucgaggaagacagcc cauuccucagagcuuugcagcggagcuucccgcaguuugagguagaagccaagcaggucacugauaaugaccaugcuaaug ccagagcguuuucgcaucuggcuucaaaacugaucgaaacggagguggacccauccgacacgauccuugacauuggaagug cgcccgcccgcagaauguauucuaagcacaaguaucauuguaucuguccgaugagaugugcggaagauccggacagauugu auaaguaugcaacuaagcugaagaaaaacuguaaggaaauaacugauaaggaauuggacaagaaaaugaaggagcuggccg ccgucaugagcgacccugaccuggaaacugagacuaugugccuccacgacgacgagucgugucgcuacgaagggcaagucg cuguuuaccaggauguauacgcgguugacggaccgacaagucucuaucaccaagccaauaagggaguuagagucgccuacu ggauaggcuuugacaccaccccuuuuauguuuaagaacuuggcuggagcauauccaucauacucuaccaacugggccgacg aaaccguguuaacggcucguaacauaggccuaugcagcucugacguuauggagcggucacguagagggauguccauucuua gaaagaaguauuugaaaccauccaacaauguucuauucucuguuggcucgaccaucuaccacgagaagagggacuuacuga ggagcuggcaccugccgucuguauuucacuuacguggcaagcaaaauuacacaugucggugugagacuauaguuaguugcg acggguacgucguuaaaagaauagcuaucaguccaggccuguaugggaagccuucaggcuaugcugcuacgaugcaccgcg agggauucuugugcugcaaagugacagacacauugaacggggagagggucucuuuucccgugugcacguaugugccagcua -continued cauugugugaccaaaugacuggcauacuggcaacagaugucagugcggacgacgcgcaaaaacugcugguugggcucaacc agcguauagucgucaacggucgcacccagagaaacaccaauaccaugaaaaauuaccuuuugcccguaguggcccaggcau uugcuaggugggcaaaggaauauaaggaagaucaagaagaugaaaggccacuaggacuacgagauagacaguuagucaugg gguguuguugggcuuuuagaaggcacaagauaacaucuauuuauaagcgcccggauacccaaaccaucaucaaagugaaca gcgauuuccacucauucgugcugcccaggauaggcaguaacacauuggagaucgggcugagaacaagaaucaggaaaaugu uagaggagcacaaggagccgucaccucucauuaccgccgaggacguacaagaagcuaagugcgcagccgaugaggcuaagg aggugcgugaagccgaggaguugcgcgcagcucuaccaccuuuggcagcugauguugaggagcccacucuggaggcagacg ucgacuugauguuacaagaggcuggggccggcucaguggagacaccucguggcuugauaaagguuaccagcuacgauggcg aggacaagaucggcucuuacgcugugcuuucuccgcaggcuguacucaagagugaaaaauuaucuugcauccacccucucg cugaacaagucauagugauaacacacucuggccgaaaagggcguuaugccguggaaccauaccaugguaaaguaguggugc cagagggacaugcaauacccguccaggacuuucaagcucugagugaaagugccaccauuguguacaacgaacgugaguucg uaaacagguaccugcaccauauugccacacauggaggagcgcugaacacugaugaagaauauuacaaaacugucaagccca gcgagcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaaguac caaccauagggguguauggcgugccaggaucaggcaagucuggcaucauuaaaagcgcagucaccaaaaaagaucuagugg ugagcgccaagaaagaaaacugugcagaaauuauaagggacgucaagaaaaugaaagggcuggacgucaaugccagaacug uggacucagugcucuugaauggaugcaaacaccccguagagacccuguauauugacgaagcuuuugcuugucaugcaggua cucucagagcgcucauagccauuauaagaccuaaaaaggcagugcucugcggggaucccaaacagugcgguuuuuuuaaca ugaugugccugaaagugcauuuuaaccacgagauuugcacacaagucuuccacaaaagcaucucucgccguugcacuaaau cugugacuucggucgucucaaccuuguuuuacgacaaaaaaaugagaacgacgaauccgaaagagacuaagauugugauug acacuacoggcaguaccaaaccuaagcaggacgaucucauucucacuuguuucagaggguggugaagcaguugcaaauag auuacaaaggcaacgaaauaaugacggcagcugccucucaagggcugacccguaaagguguguaugccguucgguacaagg ugaaugaaaauccucuguacgcacccaccucagaacaugugaacguccuacugacccgcacggaggaccgcaucgugugga aaacacuagccggcgacccauggauaaaaacacugacugccaaguacccugggaauuucacugccacgauagaggaguggc aagcagagcaugaugccaucaugaggcacaucuuggagagaccggacccuaccgacgucuuccagaauaaggcaaacgugu guugggccaaggcuuuagugccggugcugaagaccgcuggcauagacaugaccacugaacaauggaacacuguggauuauu uugaaacggacaaagcucacucagcagagauaguauugaaccaacuaugcgugagguucuuuggacucgaucuggacuccg gucuauuuucugcacccacuguuccguuauccauuaggaauaaucacugggauaacuccccgucgccuaacauguacgggc ugaauaaagaaguggucgucagcucucucgcagguacccacaacugccucgggcaguugccacuggaagagucuaugaca ugaacacugguacacugcgcaauuaugauccgcgcauaaaccuaguaccuguaaacagaagacugccucaugcuuuagucc uccaccauaaugaacacccacagagugacuuuucuucauucgucagcaaauugaagggcagaacuguccugguggucgggg aaaaguuguccgucccaggcaaaaugguugacugguugucagaccggccugaggcuaccuucagagcucggcuggauuuag gcaucccaggugaugugcccaaauaugacauaauauuuguuaaugugaggaccccauauaaauaccaucacuaucagcagu gugaagaccaugccauuaagcuuagcauguugaccaagaaagcuugucugcaucugaaucccggcggaaccugugucagca uagguuaugguuacgcugacagggccagcgaaagcaucauuggugcuauagcgcggcaguucaaguuucccggguaugca aaccgaaauccucacuugaagagacggaaguucuguuuguauucauuggguacgaucgcaaggcccguacgcacaauccuu acaagcuuucaucaaccuugaccaacauuuauacagguuccagacuccacgaagccggaugugcacccucauaucaugugg ugcgaggggauauugccacggccaccgaaggagugauuauaaaugcugcuaacagcaaaggacaaccuggcggaggggugu gcggagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcagagg -continued cuuaugaguccaucgcuaagauugucaacgauaacaauuacaagucaguagcgauuccacuguuguccaccggcaucuuuu ccgggaacaaagaucgacuaacccaaucauugaaccauuugcugacagcuuuagacaccacugaugcagauguagccauau acugcagggacaagaaaugggaaaugacucucaaggaagcaguggcuaggagagaagcaguggaggagauaugcauauccg acgacucuucagugacagaaccugaugcagagcuggugagggugcauccgaagaguucuuuggcuggaaggaagggcuaca gcacaagcgauggcaaaacuuucucauauuuggaagggaccaaguuucaccaggcggccaaggauauagcagaaauuaaug ccauguggcccguugcaacggaggccaaugagcagguaugcauguauauccucggagaaagcaugagcaguauuaggucga aaugccccgucgaagagucggaagccuccacaccaccuagcacgcugccuugcuugugcauccaugccaugacuccagaaa gaguacagcgccuaaaagccucacguccagaacaaauuacugugugcucauccuuuccauugccgaaguauagaaucacug gugugcagaagauccaaugcucccagccuauauuguucucaccgaaagugccugcguauauucauccaaggaaguaucucg uggaaacaccaccgguagacgagacuccggagccaucggcagagaaccaauccacagaggggacaccugaacaaccaccac uuauaaccgaggaugagaccaggacuagaacgccugagccgaucaucaucgaagaggaagaagaggauagcauaaguuugc ugucagauggcccgacccaccaggugcugcaagucgaggcagacauucacgggccgcccucuguaucuagcucauccuggu ccauuccucaugcauccgacuuugauguggacaguuuauccauacuugacacccuggagggagcuagcgugaccagcgggg caacgucagccgagacuaacucuuacuucgcaaagaguauggaguuucuggcgcgaccggugccugcgccucgaacaguau ucaggaacccuccacaucccgcuccgcgcacaagaacaccgucacuugcacccagcagggccugcucgagaaccagccuag uuuccaccccgccaggcgugaauagggugaucacuagagaggagcucgaggcgcuuaccccgucacgcacuccuagcaggu cggucucgagaaccagccuggucuccaacccgccaggcguaaauagggugauuacaagagaggaguuugaggcguucguag cacaacaacaaugacgguuugaugcgggugcauacaucuuuuccuccgacaccggucaagggcauuuacaacaaaaaucag uaaggcaaacggugcuauccgaagugguguuggagaggaccgaauuggagauuucguaugccccgcgccucgaccaagaaa aagaagaauuacuacgcaagaaauuacaguuaaaucccacaccugcuaacagaagcagauaccaguccaggaagguggaga acaugaaagccauaacagcuagacguauucugcaaggccuagggcauuauuugaaggcagaaggaaaaguggagugcuacc gaacccugcauccuguuccuuuguauucaucuagugugaaccgugccuuuucaagccccaaggucgcaguggaagccugua acgccauguugaaagagaacuuuccgacuguggcuucuuacuguauuauuccagaguacgaugccuauuuggacaugguug acggagcuucaugcugcuuagacacugccaguuuuugcccugcaaagcugcgcagcuuuccaaagaaacacuccuauuugg aacccacaauacgaucggcagugccuucagcgauccagaacacgcuccagaacguccuggcagcugccacaaaaagaaauu gcaaugucacgcaaaugagagaauugcccguauuggauucggcggccuuuaauguggaaugcuucaagaaauaugcgugua auaaugaauauugggaaacguuuaaagaaaaccccaucaggcuuacugaagaaaacgugguaaauuacauuaccaaauuaa aaggaccaaaagcugcugcucuuuuugcgaagacacauaauuugaauauguugcaggacauaccaauggacagguuuguaa uggacuuaaagagagacgugaaagugacuccaggaacaaaacauacugaagaacggcccaagguacaggugauccaggcug ccgauccgcuagcaacagcguaucugugcggaauccaccgagagcugguuaggagauuaaaugcgguccugcuuccgaaca uucauacacuguuugauaugucggcugaagacuuugacgcuauuauagccgagcacuuccagccuggggauuguguucugg aaacugacaucgcgucguuugauaaaagugaggacgacgccauggcucugaccgcguuaaugauucuggaagacuuaggug uggacgcagagcuguugacgcugauugaggcggcuuucggcgaaauuucaucaauacauuugcccacuaaaacuaaauuua aauucggagccaugaugaaaucuggaauguuccucacacuguuugugaacacagucauuaacauuguaaucgcaagcagag uguugagagaacggcuaaccggaucaccaugugcagcauucauuggagaugacaauaucgugaaaggagucaaaucggaca aauuaauggcagacaggugcgccaccugguugaauauggaagucaagauuauagaugcugugguggcgagaaagcgccuu auuucuguggagguuuauuuugugugacuccgugaccggcacagcgugccguguggcagacccccuaaaaaggcuguuua agcuuggcaaaccucuggcagcagacgaugaacaugaugaugacaggagaagggcauugcaugaagagucaacacgcugga accgaguggguauucuuucagagcugugcaaggcaguagaaucaagguaugaaaccguaggaacuuccaucauaguuaugg ccaugacuacucuagcuagcaguguuaaaucauucagcuaccugagaggggccccuauaacucucuacggcuaaccugaau ggacuacgacauagucuaguccgccaag*AUGUUUCUGCUCACAACCAAACGCACUAUG**UUUGUUUUCCUCGUGCUGCUCCC*

-continued

*UUUGGUAAGUUCU*CAGUGUGUAAACCUGAGAACACGAACCCAGUUGCCUCCAGCUUAUACCAACUCAUUUACUCGCGGAGU

AUAUUAUCCCGAUAAGGUCUUUAGAAGUAGCGUGUUGCACUCUACACAGGAUCUGUUCUUGCCCUUCUUUAGUAACGUUAC

CUGGUUUCAUGCAAUACAUGUGAGCGGAACAAAUGGAACAAAAAGAUUUGACAAUCCAGUGCUUCCAUUUAAUGAUGGGGU

UUACUUUGCCAGUAUCGAAAAGUCAAACAUAAUCCGGGGGUGGAUCUUUGGAACCACUUUGGACUCUAAGACACAGUCUCU

CCUCAUAGUAAACAACGCCACCAAUGUUGUCAUAAAAGUAUGCGAAUUUCAGUUUUGCAACGAUCCCUUUCUCGACGUGUA

UUACCAUAAGAAUAAUAAAUCCUGGAUGGAGUCUGGGGUUUAUAGUAGUGCUAAUAAUUGCACUUUCGAAUACGUGUCCCA

ACCAUUCCUCAUGGACCUUGAGGGCAAACAGGGGAAUUUUAAAAACUUGCGCGAAUUUGUCUUUAAGAAUAUCGACGGAUA

CUUUAAGAUCUAUAGUAAACACACUCCUAUCAACCUCGUUCGGGAUCUUCCCCAAGGCUUUUCUGCUCUCGAACCCCUCGU

AGACUUGCCAAUUGGGAUAAAUAUCACUCGCUUUCAAACUUUGCUUGCCCUCCACAGGAGCUACCUGACACCCGGCGACUC

UUCUUCUGGUUUGACCGCCGGCGCCGCUGCCUAUUAUGUUGGUUACCUUCAGCCACGAACAUUCUUGCUCAAGUAUAACGA

GAAUGGCACCAUUACCGACGCCGUCGAUUGUGCAUUGGAUCCCUUGUCUGAAACAAAAUGUACCUUGAAGUCCUUUACCGU

AGAGAAAGGCAUAUACCAGACUUCCAACUUCCGAGUUCAGCCUACAGAAUCCAUCGUACGAUUUCCCAACAUCACAAACCU

CUGCCCUUUCGGUGAAGUAUUUAAUGCUACACGCUUCGCUUCAGUCUAUGCCUGGAAUAGGAAGCGCAUAUCAAAUUGCGU

GGCCGAUUAUUCAGUCCUCUAUAAUAGCGCAUCCUUCAGUACUUUCAAGUGCUACGGCGUUUCCCCCACCAAACUCAAUGA

UCUUUGCUUCACCAACGUCUAUGCUGACAGUUUUGUCAUACGAGGCGACGAAGUACGCCAGAUUGCCCCGGGCAGACAGG

UAAUAUUGCUGAUUAUAAUUAUAAACUCCCAGAUGACUUUACUGGAUGCGUCAUAGCCUGGAAUUCCAACAAUCUAGAUUC

CAAGGUUGGUGGGAAUUAUAAUUACCGUUAUCGACUGUUCAGAAAGAGUAACUUGAAACCAUUUGAGAGAGACAUAUCCAC

CGAGAUUUACCAGGCAGGCAGUAAGCCUUGUAACGGCGUUGAGGGAUUUAACUGCUAUUUUCCUUUGCAAUCCUAUGGCUU

UCAACCAACAAACGGGGUUGGCUAUCAACCCUAUCGAGUGGUUGUCCUCAGCUUUGAACUUUUGCACGCUCCCGCCACAGU

CUGCGGACCAAAAAAGAGUACAAAUCUUGUCAAGAAUAAGUGCGUAAAUUUCAAUUUCAAUGGCCUUACAGGAACAGGCGU

GCUGACUGAGUCAAACAAGAAUUUCCUGCCAUUUCAGCAGUUUGGGCGGGAUAUAGCAGACACAACUGACGCUGUACGCGA

UCCUCAGACUUUGGAGAUCUUGGACAUCACUCCCUGUUCUUUCGGAGGGGUAUCUGUCAUCACCCCCGGAACUAAUACAUC

AAAUCAGGUCGCUGUGUUGUACCAAGGUGUCAACUGCACAGAAGUCCCCGUUGCUAUACACGCAGACCAGCUCACCCCCAC

AUGGCGGGUGUACUCAACUGGCUCAAACGUAUUCCAGACCAGAGCUGGGUGCUUGAUCGGUGCUGAACACGUGAACAAUAG

CUAUGAAUGCGAUAUUCCCAUCGGUGCCGGGAUCUGCGCUAGCUAUCAGACACAGACCAAUUCCCGCAGGCGGGCUCGCUC

UGUAGCAUCCCAGUCUAUUAUUGCCUACACUAUGUCAUUGGGCGCCGAGAAUAGCGUCGCAUAUUCAAAUAAUUCUAUUGC

AAUACCCACCAACUUCACAAUCUCCGUAACUACAGAAAUACUUCCAGUUUCCAUGACAAAGACAUCAGUGGAUUGUACAAU

GUAUAUAUGCGGAGAUUCCACAGAAUGUUCAAAUUUGCUCUUGCAGUACGGCUCCUUCUGCACCCAGCUCAACAGGGCACU

UACAGGUAUUGCUGUCGAACAGGACAAGAACACACAAGAAGUCUUCGCCCAAGUCAAACAGAUAUACAAAACUCCUCCCAU

AAAGGAUUUUGGCGGCUUCAACUUUAGUCAGAUCCUCCCAGACCCUUCAAAACCAUCUAAACGAUCAUUUAUUGAAGAUCU

GCUGUUCAACAAGGUCACUCUUGCCGAUGCUGGAUUCAUUAAGCAAUACGGUGACUGCCUUGGUGAUAUUGCUGCCCGAGA

UCUGAUCUGUGCCCAGAAAUUCAACGGGCUCACUGUACUCCCUCCACUGCUCACAGACGAAAUGAUUGCACAGUACACAAG

UGCCCUGUUGGCAGGCACAAUCACUAGCGGCUGGACCUUUGGCGCAGGUGCAGCACUCCAAAUACCUUUUGCCAUGCAGAU

GGCCUAUCGGUUUAAUGGGAUAGGCGUGACUCAAAAUGUCCUCUACGAAAACCAAAAGUUGAUAGCUAACCAAUUCAAUUC

AGCAAUCGGGAAGAUACAGGAUUCACUGUCUAGUACUGCUAGUGCCCUUGGUAAGCUGCAGAACGUUGUCAACCAGAAUGC

UCAAGCUCUGAAUACAUUGGUUAAGCAGCUCUCUAGUAAUUUUGGGGCCAUCUCUUCAGUACUUAAUGAUAUUUUGAGCCG

AUUGGACCCACCUGAAGCUGAAGUACAGAUCGACAGGCUGAUAACAGGCCGGCUCCAAUCCCUCCAAACAUACGUGACACA

ACAACUCAUACGCGCAGCCGAAAUCCGAGCCAGCGCUAACCUGGCAGCUACCAAGAUGUCAGAAUGCGUUCUGGGCCAGAG

UAAACGCGUAGAUUUCUGCGGGAAAGGGUACCACCUGAUGUCCUUUCCACAAUCUGCACCUCACGGGGUCGUCUUUUUGCA

UGUAACAUACGUACCCGCACAAGAGAAGAAUUUUACUACCGCUCCUGCCAUCUGUCAUGACGGGAAAGCUCAUUUUCCUCG

-continued

CGAAGGUGUGUUUGUAUCUAAUGGUACACAUUGGUUUGUCACACAGCGGAAUUUCUAUGAACCCCAGAUCAUUACAACUGA

CAACACUUUUGUUUCCGGGAAUUGUGACGUGGUCAUAGGAAUCGUAAAUAACACUGUAUAUGAUCCCCUCCAACCAGAGCU

GGACUCUUUUAAAGAAGAACUGGAUAAAUAUUUCAAGAACCACACAAGUCCCGACGUGGACCUUGGGGACAUAAGUGGUAU

UAACGCAUCUGUGGUUAACAUUCAAAAGGAAAUCGACAGACUCAACGAGGUGGCCAAAAACCUGAACGAAAGCUUGAUAGA

UCUCCAGGAGUUGGGCAAGUAUGAACAGUACAUUAAAUGGCCAUGGUACAUAUGGCUUGGCUUUAUCGCUGGCCUUAUCGC

CAUCGUAAUGGUUACAAUCAUGCUGUGCUGCAUGACCUCCUGCUGUUCUUGUUUGAAAGGGUGUUGUUCUUGUGGUAGUUG

UUGCAAGUUUGACGAAGAUGAUUCCGAACCUGUUCUUAAGGGGGUAAAGCUUCACUAUACAUGAuaaccgcggugucaaaa accgcguggacgugguuaacaucccugcugggaggaucagccguaauuauuauaauuggcuuggugcuggcuacuauugug gccauguacgugcugaccaaccagaaacauaauugaauacagcagcaauuggcaagcugcuuacauagaacucgcggcgau uggcaugccgccuuaaaauuuuuauuuuauuuuuucuuuucuuuuccgaaucggauuuuguuuuuaauauuucaaaaaa aaaaaaaaaaaaaaaaaaaaaaaaaaaaaaaaaaaaaaa Vector Backbone RNA Sequence 7

SEQ ID NO: 54 auaggcggcgcaugagagaagcccagaccaauuaccuacccaaaauggagaaaguucacguugacaucgaggaagacagcc cauuccucagagcuuugcagcggagcuucccgcaguuugagguagaagccaagcaggucacugauaaugaccaugcuaaug ccagagcguuuucgcaucuggcuucaaaacugaucgaaacggagguggacccauccgacacgauccuugacauuggaagug cgcccgcccgcagaauguauucuaagcacaaguaucauuguaucuguccgaugagaugugcggaagauccggacagauugu auaaguaugcaacuaagcugaagaaaaacuguaaggaaauaacugauaaggaauuggacaagaaaaugaaggagcuggccg ccgucaugagcgacccugaccuggaaacugagacuaugugccuccacgacgacgagucgugucgcuacgaagggcaagucg cuguuuaccaggauguauacgcgguugacggaccgacaagucucuaucaccaagccaauaagggaguuagagucgccuacu ggauaggcuuugacaccacccuuuuauguuuaagaacuuggcuggagcauauccaucauacucuaccaacugggccgacg aaaccguguuaacggcucguaacauaggccuaugcagcucugacguuauggagcggucacguagagggauguccauucuua gaaagaaguauuugaaaccauccaacaauguucuauucucuguuggcucgaccaucuaccacgagaagagggacuuacuga ggagcuggcaccugccgucuguauuucacuuacguggcaagcaaaauuacacaugucggugugagacuauaguuaguugcg acggguacgucguuaaaagaauagcuaucaguccaggccuguaugggaagccuucaggcuaugcugcuacgaugcaccgcg agggauucuugugcugcaaagugacagacacauugaacggggagagggucucuuucccgugugcacguaugugccagcua cauugugugaccaaaugacuggcauacuggcaacagaugucagugcggacgacgcgcaaaaacugcugguugggcucaacc agcguauagucgucaacggucgcacccagagaaacaccaauaccaugaaaaauuaccuuuugcccguaguggcccaggcau uugcuaggugggcaaaggaauauaaggaagaucaagaagaugaaaggccacuaggacuacgagauagacaguuagucaugg gguguuguugggcuuuuagaaggcacaagauaacaucuauuuauaagcgcccggauacccaaaccaucaucaaagugaaca gcgauuuccacucauucgugcugcccaggauaggcaguaacacauuggagaucgggcugagaacaagaaucaggaaaaugu uagaggagcacaaggagccgucaccucucauuaccgccgaggacguacaagaagcuaagugcgcagccgaugaggcuaagg aggugcgugaagccgaggaguugcgcgcagcucuaccaccuuuggcagcugauguugaggagcccacucuggaggcagacg ucgacuugauguuacaagaggcuggggccggcucaguggagacaccucguggcuugauaaagguuaccagcuacgauggcg aggacaagaucggcucuuacgcugugcuuucuccgcaggcuguacucaagagugaaaaauuaucuugcauccacccucucg cugaacaagucauagugauaacacacucuggccgaaaagggcguuaugccguggaaccauaccaugguaaaguagguggugc cagagggacaugcaauacccguccaggacuuucaagcucugagugaaagugccaccauuguguacaacgaacgugaguucg uaaacagguaccugcaccauauugccacacauggaggagcgcugaacacugaugaagaauauuacaaaacugucaagccca gcgagcacgacggcgaauaccuguacgacaucgacaggaaacagugcgucaagaaagaacuagucacugggcuagggcuca caggcgagcugguggauccucccuuccaugaauucgccuacgagagucugagaacacgaccagccgcuccuuaccaaguac caaccauagggguguauggcgugccaggaucaggcaagucuggcaucauuaaaagcgcagucaccaaaaaagaucuagugg ugagcgccaagaaagaaaacugugcagaaauuauaagggacgucaagaaaaugaaagggcuggacgucaaugccagaacug -continued uggacucagugcucuugaauggaugcaaacaccccguagagacccuguauauugacgaagcuuuugcuugucaugcaggua cucucagagcgcucauagccauuauaagaccuaaaaaggcagugcucugcggggaucccaaacagugcgguuuuuuuaaca ugaugugccugaaagugcauuuuaaccacgagauuugcacacaagucuuccacaaaagcaucucucgccguugcacuaaau cugugacuucggucgucucaaccuuguuuuacgacaaaaaaaugagaacgacgaauccgaaagagacuaagauugugauug acacuaccggcaguaccaaaccuaagcaggacgaucucauucucacuuguuucagaggugggugaagcaguugcaaauag auuacaaaggcaacgaaauaaugacggcagcugccucucaagggcugacccguaaaggugugugaugccguucgguacaagg ugaaugaaaauccucuguacgcacccaccucagaacaugugaacguccuacugacccgcacggaggaccgcaucgugugga aaacacuagccggcgacccauggauaaaaacacugacugccaaguacccugggaauuucacugccacgauagaggaguggc aagcagagcaugaugccaucaugaggcacaucuuggagagaccggacccuaccgacgucuuccagaauaaggcaaacgugu guugggccaaggcuuuagugccggugcugaagaccgcuggcauagacaugaccacugaacaauggaacacuguggauuauu uugaaacggacaaagcucacucagcagagauaguauugaaccaacuaugcgugagguucuuuggacucgaucuggacuccg gucuauuuucugcacccacuguuccguuauccauuaggaauaaucacugggauaacuccccgucgccuaacauguacgggc ugaauaaagaagugguccgucagcucucucgcagguacccacaacugccucgggcaguugccacuggaagagucuaugaca ugaacacugguacacugcgcaauuaugauccgcgcauaaaccuaguaccuguaaacagaagacugccucaugcuuuagucc uccaccauaaugaacacccacagagugacuuuucuucauucgucagcaaauugaagggcagaacuguccuggugguucgggg aaaaguuguccgucccaggcaaaaugguugacugguugucagaccggccugaggcuaccuucagagcucggcuggauuuag gcaucccaggugaugugcccaaauaugacauaauauuuguuaaugugaggaccccauauaaauaccaucacuaucagcagu gugaagaccaugccauuaagcuuagcauguugaccaagaaagcuugucugcaucugaaucccggcggaaccugugucagca uagguuaugguuacgcugacagggccagcgaaagcaucauuggugcuauagcgcggcaguucaaguuucccggguaugca aaccgaaauccucacuugaagagacggaaguucuguuuguauucauuggguacgaucgcaaggcccguacgcacaauccuu acaagcuuucaucaaccuugaccaacauuuauacagguuccagacuccacgaagccggaugugcacccucauaucaugugg ugcgaggggauauugccacggccaccgaaggagugauuauaaaugcugcuaacagcaaaggacaaccuggcggaggggugu gcggagcgcuguauaagaaauucccggaaagcuucgauuuacagccgaucgaaguaggaaaagcgcgacuggucaaaggug cagcuaaacauaucauucaugccguaggaccaaacuucaacaaaguuucggagguugaaggugacaaacaguuggcagagg cuuaugaguccaucgcuaagauugucaacgauaacaauuacaagucaguagcgauuccacuguuguccaccggcaucuuuu ccgggaacaaagaucgacuaacccaaucauugaaccauuugcugacagcuuuagacaccacugaugcagauguagccauau acugcagggacaagaaaugggaaaugacucucaaggaagcaguggcuaggagagaagcaguggaggagauaugcauauccg acgacucuucagugacagaaccugaugcagagcuggugagggugcauccgaagaguucuuuggcuggaaggaagggcuaca gcacaagcgauggcaaaacuuucucauauuggaagggaccaaguuucaccaggcggccaaggauauagcagaaauuaaug ccauguggcccguugcaacggaggccaaugagcagguaugcauguauauccucggagaaagcaugagcaguauuaggucga aaugccccgucgaagagucggaagccuccacaccaccuagcacgcugccuugcuugugcauccaugccaugacuccagaaa gaguacagcgccuaaaagccucacguccagaacaaauuacugugugcucauccuuuccauugccgaaguauagaaucacug gugugcagaagauccaaugcucccagccuauauuguucucaccgaaagugccugcguauauucauccaaggaaguaucucg uggaaacaccaccgguagacgagacuccggagccaucggcagagaaccaauccacagaggggacaccugaacaaccaccac uuauaaccgaggaugagaccaggacuagaacgccugagccgaucaucaucgaagaggaagaagaggauagcauaaguuugc ugucagauggcccgacccaccaggugcugcaagucgaggcagacauucacgggccgcccucuguaucuagcucauccuggu ccauuccucaugcauccgacuuugauguggacaguuuauccauacuugacacccuggagggagcuagcgugaccagcgggg caacgucagccgagacuaacucuuacuucgcaaagaguauggaguuucuggcgcgaccggugccugcgccucgaacaguau ucaggaacccuccacaucccgcuccgcgcacaagaacaccgucacuugcacccagcagggccugcucgagaaccagccuag uuuccaccccgccaggcgugaauagggugaucacuagagaggagcucgaggcgcuuaccccgucacgcacuccuagcaggu -continued

```
cggucucgagaaccagccuggucuccaacccgccaggcguaaauagggugauuacaagagaggaguuugaggcguucguag

cacaacaacaaugacgguuugaugcgggugcauacaucuuuuccuccgacaccggucaagggcauuuacaacaaaaaucag

uaaggcaaacggugcuauccgaagugguguuggagaggaccgaauuggagauuucguaugccccgcgccucgaccaagaaa

aagaagaauuacuacgcaagaaauuacaguuaaaucccacaccugcuaacagaagcagauaccaguccaggaagguggaga

acaugaaagccauaacagcuagacguauucugcaaggccuagggcauuauuugaaggcagaaggaaaaguggagugcuacc

gaacccugcauccuguuccuuuguauucaucuagugugaaccgugccuuuucaagccccaaggucgcaguggaagccugua

acgccauguugaaagagaacuuuccgacuguggcuucuuacuguauuauuccagaguacgaugccuauuuggacaugguug

acggagcuucaugcugcuuagacacugccaguuuuugcccugcaaagcugcgcagcuuuccaaagaaacacuccuauuugg

aacccacaauacgaucggcagugccuucagcgauccagaacacgcuccagaacguccuggcagcugccacaaaaagaaauu

gcaaugucacgcaaaugagagaauugcccguauuggauucggcggccuuuaauguggaaugcuucaagaaauaugcgugua

auaaugaauauugggaaacguuuaaagaaaaccccaucaggcuuacugaagaaaacgugguaaauuacauuaccaaauuaa

aaggaccaaaagcugcugcucuuuuugcgaagacacauaauuugaauauguugcaggacauaccaauggacagguuuguaa

uggacuuaaagagagacgugaaagugacuccaggaacaaaacauacugaagaacggcccaagguacaggugauccaggcug

ccgauccgcuagcaacagcguaucugugcggaauccaccgagagcugguuaggagauuaaaugcgguccugcuuccgaaca

uucauacacuguuugauaugucggcugaagacuuugacgcuauuauagccgagcacuuccagccuggggauuguguucugg

aaacugacaucgcgucguuugauaaaagugaggacgacgccauggcucugaccgcguuaaugauucuggaagacuuaggug

uggacgcagagcuguugacgcugauugaggcggcuuucggcgaaauuucaucaauacauuugcccacuaaaacuaaauuua

aauucggagccaugaugaaaucuggaauguuccucacacuguuugugaacacagucauuaacauuguaaucgcaagcagag

uguugagagaacggcuaaccggaucaccaugugcagcauucauuggagaugacaauaucgugaaaggagucaaaucggaca

aauuaauggcagacaggugcgccaccugguugaauauggaagucaagauuauagaugcugugguggggcgagaaagcgccuu

auuucuguggaggguuuauuuugugugacuccgugaccggcacagcgugccguguggcagaccccuaaaaaggcuguuua

agcuuggcaaaccucuggcagcagacgaugaacaugaugaugacaggagaagggcauugcaugaagagucaacacgcugga

accgaguggguauucuuucagagcugugcaaggcaguagaaucaagguaugaaaccguaggaacuuccaucauaguuaugg

ccaugacuacucuagcuagcaguguuaaaucauucagcuaccugagaggggccccuauaacucucuacggcuaaccugaau

ggacuacgacauagucuaguccgccgccaccnuaaccgcggugucaaaaaccgcguggacgugguuaacaucccugcuggg

aggaucagccguaauuauuauaauuggcuuggugcuggcuacuauuguggccauguacgugcugaccaaccagaaacauaa

uugaauacagcagcaauuggcaagcugcuuacauagaacucgcggcgauuggcaugccgccuuaaaauuuuuauuuuauuu

uuucuuuucuuuuccgaaucggauuuuguuuuuaauauuucaaaaaaaaaaaaaaaaaaaaaaaaaaaaaaaaaaaaaaaa

aaaaa
```

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A composition comprising:

a lipid carrier, wherein the lipid carrier comprises:

liquid oil;

a cationic lipid;

a hydrophilic surfactant; and a hydrophobic surfactant; and nucleic acids, wherein the nucleic acids comprise a sequence encoding for an antigen from an influenza virus, wherein the sequence is at least 85% identical to SEQ ID NO: 3.

2. The composition of claim 1, wherein the nucleic acids comprise at least one nucleic acid that encodes for an amino acid sequence of any one of SEQ ID NOS: 10-12.

3. The composition of claim 1, wherein the nucleic acids are in complex with the lipid carrier.

4. The composition of claim 1, wherein, the nucleic acids further encode for an RNA polymerase.

5. The composition of claim 4, wherein the RNA polymerase is a Venezuelan equine encephalitis virus (VEEV) RNA polymerase.

6. The composition of claim 4, wherein the nucleic acids encoding for the RNA polymerase comprise SEQ ID NO: 34.

7. The composition of claim 1, wherein the liquid oil is α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, soy lecithin, soybean oil, sunflower oil, a triglyceride, or vitamin E.

8. The composition of claim 7, wherein the triglyceride is capric triglyceride, caprylic triglyceride, a caprylic and capric triglyceride, a triglyceride ester, or myristic acid triglycerin.

9. The composition of claim 1, wherein the lipid carrier comprises a hydrophobic core.

10. The composition of claim 1, wherein the lipid carrier further comprises an inorganic particle.

11. The composition of claim 10, wherein the inorganic particle is within a hydrophobic core of the lipid carrier.

12. The composition of claim 10, wherein the inorganic particle comprises a metal.

13. The composition of claim 12, wherein the metal comprises a metal salt, a metal oxide, a metal hydroxide, or a metal phosphate.

14. The composition of claim 13, wherein the metal oxide comprises aluminum oxide, aluminum oxyhydroxide, iron oxide, titanium dioxide, or silicon dioxide.

15. The composition of claim 1, wherein the hydrophobic surfactant is sorbitan monolaurate, sorbitan monopalmitate, sorbitan monostearate, sorbitan monooleate, or sorbitan trioleate.

16. The composition of claim 1, wherein the hydrophilic surfactant is a polysorbate.

17. The composition of claim 1, wherein the nucleic acids are present in the composition in an amount of up to about 5, about 10, about 25, about 50, or about 100 micrograms (μg).

18. The composition of claim 4, wherein the cationic lipid comprises 1,2-dioleoyloxy-3 (trimethylammonium) propane, 3β-[N—(N',N'-dimethylaminoethane) carbamoyl] cholesterol, dimethyldioctadecylammonium, 1,2-dimyristoyl 3-trimethylammoniumpropane, dipalmitoyl (C16:0) trimethyl ammonium propane, distearoyltrimethylammonium propane, N-[1-(2,3-dioleyloxy)propyl]N,N,Ntrimethylammonium, chloride, N,N-dioleoyl-N,N-dimethylammonium chloride, 1,2-dioleoyl-sn-glycero-3-ethylphosphocholine, 1,2-dioleoyl-3-dimethylammonium-propane, 1,2-dilinoleyloxy-3-dimethylaminopropane, 1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol), tetrakis(8-methylnonyl) 3,3',3",3"-(((methylazanediyl)bis(propane-3,1 diyl))bis (azanetriyl)) tetrapropionate, decyl (2-(dioctylammonio)ethyl) phosphate, ethyl 5,5-di((Z)-heptadec-8-en-1-yl)-1-(3-(pyrrolidin-1-yl) propyl)-2,5-dihydro-1H-imidazole-2-carboxylate, ((4-hydroxybutyl)azanediyl)bis(hexane-6,1-diyl)bis(2-hexyldecanoate), 2-[(polyethylene glycol)-2000]-N,N-ditetradecylacetamide, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol, bis(2-(dodecyldisulfanyl) ethyl) 3,3'-((3-methyl-9-oxo-10-oxa-13,14-dithia-3,6-diazahexacosyl)azanediyl)dipropionate, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl) amino)-N,N-bis(2-hydroxyethyl)-N-methylethan-1-aminium bromide, 3,6-bis(4-(bis(2-hydroxydodecyl)amino) butyl)piperazine-2,5-dione, 3β-[N—(N',N'-dimethylaminoethane)-carbamoyl]cholesterol, (6Z,9Z,28Z,31Z)-heptatriaconta-6,9,28,31-tetraen-19-yl 4-(dimethylamino) butanoate, 1,2-dioleoyl-sn-glycero-3-phosphoethanolamine, 2,3-dioleyloxy-N-[2-(sperminecarboxamido)ethyl]-N,N-dimethyl-1-propanaminium trifluoroacetate, 1,2-distearoyl-sn-glycero-3-phosphocholine, ethylphosphatidylcholine, hexa(octan-3-yl) 9,9',9",9"',9"",9""'-((((benzene-1,3,5-tricarbonyl)yris(azanediyl)) tris (propane-3,1-diyl)) tris(azanetriyl))hexanonanoate, heptadecan-9-yl 8-((2-hydroxyethyl) (6-oxo-6-(undecyloxy)hexyl)amino) octanoate, (((3,6-dioxopiperazine-2,5-diyl)bis(butane-4,1-diyl))bis(azanetriyl))tetrakis(ethane-2,1-diyl) (9Z,9'Z,9"Z,9"Z,12Z,12'Z,12"Z,12"Z)-tetrakis (octadeca-9,12-dienoate), or N1,N3,N5-tris(3-(didodecylamino)propyl)benzene-1,3,5-tricarboxamide.

* * * * *

SEQUENCE LISTING

```
Sequence total quantity: 54
SEQ ID NO: 1            moltype = RNA  length = 900
FEATURE                 Location/Qualifiers
source                  1..900
                        mol_type = other RNA
                        organism = Human orthopneumovirus
SEQUENCE: 1
atgtccaaaa ataaagacca gcgaacggcc aagactctgg agaggacttg ggataccctg  60
aatcatctgt tgtttatttc aagttgcctt tataaattga atctcaaatc cgtcgcgcaa  120
```

-continued

```
atcacgctga gcatactcgc aatgattatc tcaacttcct tgataattgc cgccataatc  180
ttcattgcaa gtgcaaatca taaagtgact cctacaaccg caataataca ggacgcgacc  240
agccaaatta agaacacgac tcccacgtat ctcacccaaa atccccaact cggaattagc  300
ccaagtaatc cgtcagagat tacttcacaa atcaccacca tactggcgag cacaactcca  360
ggcgtaaaat ccaccctcca atctactacc gtcaagacta aaaataccac tactactcag  420
acacaaccta gtaaacctac gactaagcag cgccagaata aaccccccaag caaaccaaac  480
aacgacttcc attttgaagt tttcaacttc gtgccttgtt ctatctgctc taataatcca  540
acatgctggg ccatctgcaa gcgcattccg aataagaaac ccggtaagaa aactacaacg  600
aaacctacca agaagcctac cctgaaaacg acaaagaaag acccgaaacc gcaaacaacc  660
aaaagtaaag aagtgcccac aactaaaccc acagaagaac caacgataaa cacgaccaaa  720
accaacataa taactacgct gcttaccagc aacacgacag gcaaccccgga attgaccagt  780
cagatggaaa cttttcattc aaccagcagc gaaggtaatc caagtcctag tcaggtgtct  840
acgacatctg aatatccatc tcagcctagt tcccctccga acacgccgcg ccagtgataa  900

SEQ ID NO: 2           moltype = RNA  length = 1725
FEATURE                Location/Qualifiers
source                 1..1725
                       mol_type = other RNA
                       organism = Human orthopneumovirus
SEQUENCE: 2
atggagctgc tcatccttaa agcgaatgct ataactacta tacttacagc tgtaaccttt  60
tgcttcgcct ctggccaaaa cattactgag gagttttatc aatccacttg cagcgcagtc  120
tcaaaaggat atctgtcagc attgcgcacc gggtggtaca ccagcgttat cactatcgag  180
ctttccaaca ttaaagagaa taagtgtaac ggcacagacg cgaaagtcaa actcattaag  240
caagaacttg ataaatacaa aaatgcagtt actgaacttc agttgctcat gcaatcaacc  300
ccagcaacga acaataggc caggagagaa ttgccgaggt ttatgaacta cacacttaat  360
aacgctaaaa agactaacgt tacgctctct aagaagcgga agcgcaggtt tctcgggttc  420
cttctggggg ttggcagtgc aatagcatcc ggcgtcgcgg tatcaaaggt gcttcatctt  480
gaaggagaag ttaacaaaat caaaagcgcc ttgctttcaa ctaataaggc agtagtatca  540
ttgtctaacg gtgtcagcgt cttgacttcc aaggttttgg atttgaaaaa ctatatcgac  600
aaacaacttc tcccgatcgt taacaagcag tcatgcagta tctccaacat cgaaaccgtc  660
atcgaattcc aacagaaaaa caatagactg cttgaaatta ctagagagtt ttcagtgaac  720
gctggcgtta ccactccggt atccacttat atgctcacta atagcgaact gctgtctctg  780
ataaatgaca tgccaataac taacgaccag aagaaactta tgagtaacaa cgtccagatc  840
gtgagacagc aatcatatag cattatgagc ataattaagg aggaggtcct tgcatacgta  900
gtccagctcc cactgtacgg ggttatcgac acgccatgtt ggaagcttca tacttccccc  960
ttgtgcacca cgaacacgaa ggaagggtct aacatttgtc tcacgcgcac tgatcggggg  1020
tggtactgtg acaacgccgg gtcagtgtca tttttccctc aggccgagac ctgcaaggtc  1080
caatcaaacc gggtattctg tgatactatg aactccctga ctctgccttc tgaagttaac  1140
ctgtgtaatg tagatatatt caatcctaaa tacgactgca agataatgac cagcaaaacc  1200
gacgtgtcct catctgtcat cacttccctt ggtgctatag taagctgcta tggcaaaacg  1260
aaatgcaccg cgagtaataa aaatcgcggt atcatcaaga catttagtaa cggctgcgat  1320
tatgtttcca acaaaggtgt tgacaccgta tctgtgggga ataccctgta ttacgtaaat  1380
aagcaggaag ggaaatctct ctacgtgaag ggggaaccga taatcaactt ttatgacccg  1440
ctggtttttc cgtccgacga atttgacgcg agtatctccc aagtcaacga gaaaattaac  1500
caaagcctcg cgttcataag aaaatccgat gagctgctgc ataatgtaaa cgcgggcaaa  1560
tcaactacca acatcatgat tacaacaata atcatcgtga taatcgtgat cctgctttca  1620
cttatcgctg tcgggcttct tctctattgt aaggcccgga gtactcccgt gaccttgtct  1680
aaggatcagc tctcaggtat caacaatatt gcattcagca attga                 1725

SEQ ID NO: 3           moltype = RNA  length = 1704
FEATURE                Location/Qualifiers
source                 1..1704
                       mol_type = other RNA
                       organism = Influenza A virus
SEQUENCE: 3
atgaaaacaa ttatcgctct cagttatatt ttctgccttc ctttggggca agacttgccg  60
ggcaatgata atagtacagc gactctctgt ctcggacacc acgcagtacc gaacggcaca  120
cttgtgaaga caatcacaga cgatcaaatc gaagtgacga atgcaacaga gcttgttcaa  180
tcatcatcta ccggcaaaat ctgcaataat ccgcatagaa tccttgatgg aatcgactgc  240
accctgattg acgcactgtt gggagatcct cattgcgatg tgtttcagaa tgagacatgg  300
gacctttttg tcgagaggag caaagcgttt tccaactgct acccgtatga cgtgcctgat  360
tacgcgtcac tccgctcact tgtagcatca agcggtactc tggagttcat caccgaagga  420
ttcacctgga cgggcgtaac tcagaacggc ggttctaacg catgtaagag ggggccaggg  480
tccggcttct tctcacggct caactggttg actaagtctg gttcaacata cccggtcctt  540
aacgttacaa tgccgaataa tgacaacttt gataaactct acatctgggg cattcaccat  600
ccatccacaa atcaagaaca gacaagtttg tacgttcagg cgtcagggcg cgttaccgtg  660
agtacaagaa gatcacagca aacaattata cccaatattg ggtcccgacc ctgggtaaga  720
ggactgtcct ctcgcatctc catatactgg accattgtca aaccgggcga cgtcctggtt  780
atcaatagta atggaaacct tattgctccg cgcggctatt tcaaaatgcg aactggaaag  840
tcaagtataa tgcgctcaga cgcaccgatc gatacttgta tcagtgaatg catcacccct  900
aacgggtcca taccgaacga taagcccttc cagaatgtga ataaaatcac gtatggagca  960
tgccccaaat acgtgaagca aaacaccctc aagttggcta cgggtatgcg caacgtccca  1020
gaaaaacaaa cgcgaggctt gtttggggcg atagcaggtt ttatcgagaa cggctgggaa  1080
ggaatgatcg atgggtggta cggctttcgc catcaaaact cagaaggaac tgggcaggcc  1140
gcagatctta agtctacgca agcggcgata gatcaaatta atggcaagtt gaatagggtg  1200
atagagaaga cgaacgagaa gttccatcaa atagagaaag aattcagtga agtagagggg  1260
cgaattcagg atttggaaaa atatgtcgag gatactaaga tcgacctgtg gagctataac  1320
gcagagcttc tggtagcact tgagaaccag catactattg atctcaccga ttccgagatg  1380
```

```
aacaagcttt ttgagaagac caggagacag ttgcgcgaga atgccgaaga aatgggtaac  1440
ggttgtttta agatttatca caaatgtgac aacgcgtgta ttgagtccat taggaatggt  1500
acatatgatc acgatgtgta tcgcgatgaa gcacttaaca atcggttcca aataaagggc  1560
gtggagctca agagtgggta taaagattgg atcctctgga tctcattcgc gatttcctgc  1620
ttcctcctgt gcgttgtctt gctgggcttt attatgtggg catgtcagag aggtaacatc  1680
cggtgcaaca tatgtatctg ataa                                          1704

SEQ ID NO: 4           moltype = RNA  length = 1993
FEATURE                Location/Qualifiers
source                 1..1993
                       mol_type = other RNA
                       organism = Human alphaherpesvirus 3
SEQUENCE: 4
cgccaccatg ttctatgaag ctttgaaggc cgaacttgta tacacccgag ccgtgcatgg  60
tttccgcccg agagcgaact gcgtcgtact gtcagattac atccccagag tcgcgtgcaa  120
catgggtacg gttaataagc ccgtggtggg ggtgctgatg ggttttggga taatcaccgg  180
aactctgcgc atcacaaatc ctgtaagagc gtcagtgctg aggtatgacg atttccacat  240
agacgaggac aagctggata ccaattccgt ttacgaacca tattatcact ccgatcacgc  300
cgaatccagc tgggtaaatc gaggagagtc ctcacggaag gcatacgacc ataactcccc  360
atatatatgg cctcgcaatg attatgacgg attcctggaa aacgcccatg agcaccacgg  420
cgtttataac cagggtcgcg gtatcgattc tggggaaagg ttgatgcaac caactcagat  480
gtccgctcag gaagatttgg gggatgacac cggaatccat gtgataccta cactcaatgg  540
tgatgatcga cacaaaattg taaacgtgga ccagaggcaa tacggggacg tttttaaggg  600
agacctgaat ccaaaaccac aaggacaacg actcatcgag gtttctgtag aagaaaacca  660
tccgtttacg ctccgcgccc ccatacagcg catatatggc gtgcgctata cggagacctg  720
gtcttttctc cccagtctga catgcactgg tgatgcagct ccagcaattc agcacatatg  780
tctcaagcat accacctgtt tccaagatgt agtagtggat gtggattgcg ccgaaaacac  840
gaaagaagac cagcttgccg agatttcata ccggtttcaa ggaaaaaaag aagccgacca  900
gccgtggata gtagtgaata cgtccacgct cttcgatgaa ctggaattgg accctcctga  960
aattgaaccc ggagtcctga aagttttgcg gactgagaaa cagtatctcg gtgtgtacat  1020
ctggaatatg aggggcagtg atggaacaag cacatacgcg acctttctgg tgacatggaa  1080
aggtgacgaa aagactagaa acccaacccc agcagtgacc ccccaaccta gaggtgctga  1140
gttccacatg tggaattacc actcccatgt attctctgtc ggagacacct tcagcttggc  1200
gatgcacctc caatacaaga tccatgaagc cccgttcgac ctcttgttgg agtggctcta  1260
cgtaccaata gaccctacct gtcaaccaat gaggctttac tctacatgcc tttaccaccc  1320
aaacgcacca caatgtcttt ctcatatgaa tagcggttgt acatttacat ctccccatct  1380
cgcgcaaaga gtcgcgagta cagtttacca aaattgtgag catgcggaca attacacagc  1440
atattgtctt gggatctccc acatggagcc ctcttttggg cttatacttc acgacggggg  1500
tacaacgctt aagttcgtcg atacgccaga atccctctct ggcttgtatg tattcgtggt  1560
ttattttaac ggtcacgttg aggctgtggc ctatactgtt gttagcactg tagaccactt  1620
tgttaacgcc atagaagaga gggggttccc gcccaccgct ggccagccac cggccacaac  1680
gaagcctaaa gagattacgc cggtgaatcc cggcacaagt ccccttatcc ggtacgccgc  1740
atggacagga ggactggcgg ccgtcgtcct cctttgtctg gttatattcc ttatatgcac  1800
ggcaaagcga atgcgggtta aggcttaccg agtggataaa tctccatata atcagagcat  1860
gtattacgca gggctccctg tggacgactt tgaggatagc gagtccacgg atacagaaga  1920
ggaatttgga aacgccatcg gtgggagcca tggagggtca tcttacaccg tttacattga  1980
caaaactaga tga                                                      1993

SEQ ID NO: 5           moltype = RNA  length = 1072
FEATURE                Location/Qualifiers
source                 1..1072
                       mol_type = other RNA
                       organism = Human alphaherpesvirus 3
SEQUENCE: 5
cgccaccatg ttccttattc aatgcctcat atccgcagtc atcttctata ttcaagttac  60
taatgcactt atcttcaagg gcgatcatgt cagcctgcaa gtgaattcaa gtcttacgtc  120
cattttgatt ccaatgcaga atgataacta taccgaaatt aagggacagc tggtttttat  180
tggagaacaa ctgccgaccg gtacaaacta cagcgggacc ctcgagctgc tttacgcaga  240
cactgtggca ttctgcttc ggtcagtaca agttatcaga tacgacggat gcccacgcat  300
taggacatct gccttcattt cttgccgata caagcatagt tggcattacg gaaactctac  360
cgatagaatt tcaactgaac cagatgccgg tgtgatgctc aagataacca aacctgggat  420
caacgacgca ggggtgtatg tcctcttggt gagattggac cattcaagga gtacggacgg  480
gtttatactg ggcgtgaacg tctataccgc aggaagtcat cataacattc acggtgtcat  540
ttataccagc cccagtctcc agaatgggta cagcactcga gccctgttcc agcaagcaag  600
attgtgtgac cttccagcca ctcctaaggg atcaggcaca agtctttttc aacatatgtt  660
ggatctcaga gcagggaaaa gtcttgagga caacccgtgg ctccatgaag acgtggttac  720
tactgaaaca aagtcagtgg tcaaggaggg aatcgagaac catgtgtacc caactgacat  780
gagcacgctg cctgaaaaat cactgaacga cccaccagag aatctgctga taataatacc  840
tattgtagcg agtgttatga ttttgaccgc aatggtcata gttattgtaa taagcgtgaa  900
aaggagacga atcaaaaaac atccgatata caggccgaat acgaagacaa gaagagggat  960
tcagaacgcg actccggaga gtgatgtaat gctcgaagca gccatcgctc aacttgccac  1020
cattcgcgaa gaaagccctc cgcattccgt cgtaaatcct tttgtcaagt ga          1072

SEQ ID NO: 6           moltype = RNA  length = 2079
FEATURE                Location/Qualifiers
source                 1..2079
                       mol_type = other RNA
                       organism = Zika virus
SEQUENCE: 6
```

```
atgcggagag gagcagacac atccgtggga atcgtgggcc tgctgctgac cacagcaatg  60
gcagccgagg tgaccaggag aggcagcgcc tactatatgt acctggacag aaatgatgcc  120
ggcgaggcca tctcctttcc caccacactg ggcatgaaca agtgctacat ccagatcatg  180
gacctgggcc acatgtgcga tgccaccatg agctatgagt gtccaatgct ggacgagggc  240
gtggagcccg acgatgtgga ttgctggtgt aataccacat ctacatgggt ggtgtacggc  300
acctgtcacc acaagaaggg agaggcacgg cgcagcagga gagcagtgac actgccttcc  360
cactctacca ggaagctgca gacaagaagc cagacctggc tggagtccag ggagtataca  420
aagcacctga tcagggtgga gaactggatc tttagaaatc caggattcgc actggctgcc  480
gccgccatcg catggctgct gggcagctcc accagccaga aagtgatcta cctggtcatg  540
atcctgctga tcgcccctgc ctattctatc cggtgcatcg gcgtgagcaa tagggacttc  600
gtggagggaa tgtccggagg cacctgggtg gatgtggtgc tggagcacgg cggctgcgtg  660
acagtgatgg cccaggacaa gccaaccgtg gatatcgagc tggtgaccac aaccgtgtcc  720
aacatggccg aggtgaggtc ttactgctat gaggccagca tctccgacat ggcctctgat  780
agcagatgtc ccacccaggg cgaggcctac ctggacaagc agtccgatac acagtacgtg  840
tgcaagcgga ccctggtgga caggggatgg ggaaatggat gtggcctgtt tggcaagggc  900
tctctggtga catgcgccaa gttcgcctgt agcaagaaga tgaccggcaa gtccatccag  960
ccagagaacc tggagtaccg gatcatgctg tctgtgcacg gctcccagca ctctggcatg  1020
atcgtgaacg acacaggcca cgagacagat gagaatcggg ccaaggtgga gatcacacct  1080
aactccccac gcgccgaggc caccctggga ggatttggct ctctgggcct ggactgcgag  1140
cctaggacag gcctggactt ctccgatctg tactatctga ccatgaacaa taagcactgg  1200
ctggtgcaca aggagtggtt tcacgacatc ccactgccat ggcacgcagg agcagataca  1260
ggcaccccac actggaacaa taaggaggcc ctggtggagt tcaaggacgc ccacgccaag  1320
cggcagacag tggtggtgct gggcagccag gagggagcag tgcacaccgc cctggcaggc  1380
gccctggagg ccgagatgga cggagcaaag ggccgcctgt ctagcggcca cctgaagtgc  1440
aggctgaaga tggataagct gagactgaag ggcgtgtcct actctctgtg cacagccgcc  1500
ttcaccttca ccaagatccc tgccgagaca ctgcacggca cagtgaccgt ggaggtgcag  1560
tatgccggca cagacggccc ctgtaaggtg cctgcccaga tggccgtgga tatgcagaca  1620
ctgacccctg tgggcaggct gatcaccgcc aatccagtga tcacagagtc taccgagaac  1680
agcaagatga tgctggagct ggacccccct ttcggcgata gctatatcgt gatcggcgtg  1740
ggcgagaaga agatcacaca ccactggcac agaagcggct ccacaatcgg caaggccttt  1800
gaggcaaccg tgcggggagc aaagaggatg gccgtgctgg gcgacaccgc atgggatttc  1860
ggatctgtgg gaggcgccct gaacagcctg ggcaagggca tccaccagat cttcggcgcc  1920
gcctttaagt ccctgttcgg cggcatgagc tggttttccc agatcctgat cggcacactg  1980
ctgatgtggc tgggcctgaa caccaagaat ggctctatca gcctgatgtg cctggccctg  2040
ggaggcgtgc tgatcttcct gtccaccgcc gtgtctgcc                        2079

SEQ ID NO: 7           moltype = AA  length = 298
FEATURE                Location/Qualifiers
source                 1..298
                       mol_type = protein
                       organism = Human orthopneumovirus
SEQUENCE: 7
MSKNKDQRTA KTLERTWDTL NHLLFISSCL YKLNLKSVAQ ITLSILAMII STSLIIAAII  60
FIASANHKVT PTTAIIQDAT SQIKNTTPTY LTQNPQLGIS PSNPSEITSQ ITTILASTTP  120
GVKSTLQSTT VKTKNTTTTQ TQPSKPTTKQ RQNKPPSKPN NDFHFEVFNF VPCSICSNNP  180
TCWAICKRIP NKKPGKKTTT KPTKKPTLKT TKKDPKPQTT KSKEVPTTKP TEEPTINTTK  240
TNIITTLLTS NTTGNPELTS QMETFHSTSS EGNPSPSQVS TTSEYPSQPS SPPNTPRQ    298

SEQ ID NO: 8           moltype = AA  length = 166
FEATURE                Location/Qualifiers
source                 1..166
                       mol_type = protein
                       organism = Human orthopneumovirus
SEQUENCE: 8
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNK                166

SEQ ID NO: 9           moltype = AA  length = 574
FEATURE                Location/Qualifiers
source                 1..574
                       mol_type = protein
                       organism = Human orthopneumovirus
SEQUENCE: 9
MELLIHRSSA IFLTLAINAL YLTSSQNITE EFYQSTCSAV SRGYLSALRT GWYTSVITIE  60
LSNIKETKCN GTDTKVKLIK QELDKYKNAV TELQLLMQNT PAVNNRARRE APQYMNYTIN  120
TTKNLNVSIS KKRKRRFLGF LLGVGSAIAS GIAVSKVLHL EGEVNKIKNA LQSTNKAVVS  180
LSNGVSVLTS KVLDLKNYIN NQLLPIVNKQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                             574

SEQ ID NO: 10          moltype = AA  length = 566
FEATURE                Location/Qualifiers
source                 1..566
                       mol_type = protein
```

```
                      organism = Influenza A virus
SEQUENCE: 10
MKTIIALSYI FCLPLGQDLP GNDNSTATLC LGHHAVPNGT LVKTITDDQI EVTNATELVQ  60
SSSTGKICNN PHRILDGIDC TLIDALLGDP HCDVFQNETW DLFVERSKAF SNCYPYDVPD  120
YASLRSLVAS SGTLEFITEG FTWTGVTQNG GSNACKRGPG SGFFSRLNWL TKSGSTYPVL  180
NVTMPNNDNF DKLYIWGIHH PSTNQEQTSL YVQASGRVTV STRRSQQTII PNIGSRPWVR  240
GLSSRISIYW TIVKPGDVLV INSNGNLIAP RGYFKMRTGK SSIMRSDAPI DTCISECITP  300
NGSIPNDKPF QNVNKITYGA CPKYVKQNTL KLATGMRNVP EKQTRGLFGA IAGFIENGWE  360
GMIDGWYGFR HQNSEGTGQA ADLKSTQAAI DQINGKLNRV IEKTNEKFHQ IEKEFSEVEG  420
RIQDLEKYVE DTKIDLWSYN AELLVALENQ HTIDLTDSEM NKLFEKTRRQ LRENAEEMGN  480
GCFKIYHKCD NACIESIRNG TYDHDVYRDE ALNNRFQIKG VELKSGYKDW ILWISFAISC  540
FLLCVVLLGF IMWACQRGNI RCNICI                                      566

SEQ ID NO: 11         moltype = AA  length = 566
FEATURE               Location/Qualifiers
source                1..566
                      mol_type = protein
                      organism = Influenza A virus
SEQUENCE: 11
MKTIIALSYI LCLVFAQKLP GNDNSTATLC LGHHAVPNGT IVKTITNDQI EVTNATELVQ  60
SSSTGGICDS PHQILDGENC TLIDALLGDP QCDGFQNKKW DLFVERSKAY SNCYPYDVPD  120
YASLRSLVAS SGTLEFNNES FNWTGVTQNG TSSACKRRSN NSFFSRLNWL THLKFKYPAL  180
NVTMPNNEKF DKLYIWGVHH PGTDNDQISL YAQASGRITV STKRSQQTVI PSIGSRPRIR  240
DVPSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQNSEGTGQA ADLKSTQAAI NQINGKLNRL IGKTNEKFHQ IEKEFSEVEG  420
RIQDLEKYVE DTKIDLWSYN AELLVALENQ HTIDLTDSEM NKLFERTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                      566

SEQ ID NO: 12         moltype = AA  length = 584
FEATURE               Location/Qualifiers
source                1..584
                      mol_type = protein
                      organism = Influenza B virus
SEQUENCE: 12
MKAIIVLLMV VTSNADRICT GITSSNSPHV VKTATQGEVN VTGVIPLTTT PTKSHFANLK  60
GTQTRGKLCP NCFNCTDLDV ALGRPKCMGN TPSAKVSILH EVKPATSGCF PIMHDRTKIR  120
QLPNLLRGYE NIRLSTSNVI NTETAPGGPY KVGTSGSCPN VANGNGFFNT MAWVIPKDNN  180
KTAINPVTVE VPYICSEGED QITVWGFHSD DKTQMERLYG DSNPQKFTSS ANGVTTHYVS  240
QIGGFPNQTE DEGLKQSGRI VVDYMVQKPG KTGTIVYQRG ILLPQKVWCA SGRSKVIKGS  300
LPLIGEADCL HEKYGGLNKS KPYYTGEHAK AIGNCPIWVK TPLKLANGTK YRPPAKLLKE  360
RGFFGAIAGF LEGGWEGMIA GWHGYTSHGA HGVAVAADLK STQEAINKIT KNLNYLSELE  420
VKNLQRLSGA MNELHDEILE LDEKVDDLRA DTISSQIELA VLLSNEGIIN SEDEHLLALE  480
RKLKKMLGPS AVEIGNGCFE TKHKCNQTCL DRIAAGTFNA GDFSLPTFDS LNITAASLND  540
DGLDNHTILL YYSTAASSLA VTLMIAIFIV YMVSRDNVSC SICL                  584

SEQ ID NO: 13         moltype = AA  length = 661
FEATURE               Location/Qualifiers
source                1..661
                      mol_type = protein
                      organism = Human alphaherpesvirus 3
SEQUENCE: 13
MFYEALKAEL VYTRAVHGFR PRANCVVLSD YIPRVACNMG TVNKPVVGVL MGFGIITGTL  60
RITNPVRASV LRYDDFHIDE DKLDTNSVYE PYYHSDHAES SWVNRGESSR KAYDHNSPYI  120
WPRNDYDGFL ENAHEHHGVY NQGRGIDSGE RLMQPTQMSA QEDLGDDTGI HVIPTLNGDD  180
RHKIVNVDQR QYGDVFKGDL NPKPQGQRLI EVSVEENHPF TLRAPIQRIY GVRYTETWSF  240
LPSLTCTGDA APAIQHICLK HTTCFQDVVV DVDCAENTKE DQLAEISYRF QGKKEADQPW  300
IVVNTSTLFD ELELDPPEIE PGVLKVLRTE KQYLGVYIWN MRGSDGTSTY ATFLVTWKGD  360
EKTRNPTPAV TPQPRGAEFH MWNYHSHVFS VGDTFSLAMH LQYKIHEAPF DLLLEWLYVP  420
IDPTCQPMRL YSTCLYHPNA PQCLSHMNSG CTFTSPHLAQ RVASTVYQNC EHADNYTAYC  480
LGISHMEPSF GLILHDGGTT LKFVDTPESL SGLYVFVVYF NGHVEAVAYT VVSTVDHFVN  540
AIEERGFPPT AGQPPATTKP KEITPVNPGT SPLIRYAAWT GGLAAVVLLC LVIFLICTAK  600
RMRVKAYRVD KSPYNQSMYY AGLPVDDFED SESTDTEEEF GNAIGGSHGG SSYTVYIDKT  660
R                                                                 661

SEQ ID NO: 14         moltype = AA  length = 931
FEATURE               Location/Qualifiers
source                1..931
                      mol_type = protein
                      organism = Human alphaherpesvirus 3
SEQUENCE: 14
MSPCGYYSKW RNRDRPEYRR NLRFRRFFSS IHPNAAAGSG FNGPGVFITS VTGVWLCFLC  60
IFSMFVTAVV SVSPSSFYES LQVEPTQSED ITRSAHLGDG DEIREAIHKS QDAETKPTFY  120
VCPPPTGSTI VRLEPTRTCP DYHLGKNFTE GIAVVYKENI AAYKFKATVY YKDVIVSTAW  180
AGSSYTQITN RYADRVPIPV SEITDTIDKF GKCSSKATYV RNNHKVEAFN EDKNPQDMPL  240
IASKYNSVGS KAWHTTNDTY MVAGTPGTYR TGTSVNCIIE EVEARSIFPY DSFGLSTGDI  300
IYMSPFFGLR DGAYREHSNY AMDRFHQFEG YRQRDLDTRA LLEPAARNFL VTPHLTVGWN  360
WKPKRTEVCS LVKWREVEDV VRDEYAHNFR FTMKTLSTTF ISETNEFNLN QIHLSQCVKE  420
```

-continued

```
EARAIINRIY TTRYNSSHVR TGDIQTYLAR GGFVVVFQPL LSNSLARLYL QELVRENTNH  480
SPQKHPTRNT RSRRSVPVEL RANRTITTTS SVEFAMLQFT YDHIQEHVNE MLARISSSWC  540
QLQNRERALW SGLFPINPSA LASTILDQRV KARILGDVIS VSNCPELGSD TRIILQNSMR  600
VSGSTTRCYS RPLISIVSLN GSGTVEGQLG TDNELIMSRD LLEPCVANHK RYFLFGHHYV  660
YYEDYRYVRE IAVHDVGMIS TYVDLNLTLL KDREFMPLQV YTRDELRDTG LLDYSEIQRR  720
NQMHSLRFYD IDKVVQYDSG TAIMQGMAQF FQGLGTAGQA VGHVVLGATG ALLSTVHGFT  780
TFLSNPFGAL AVGLLVLAGL VAAFFAYRYV LKLKTSPMKA LYPLTTKGLK QLPEGMDPFA  840
EKPNATDTPI EEIGDSQNTE PSVNSGFDPD KFREAQEMIK YMTLVSAAER QESKARKKNK  900
TSALLTSRLT GLALRNRRGY SRVRTENVTG V                                 931

SEQ ID NO: 15          moltype = AA  length = 836
FEATURE                Location/Qualifiers
source                 1..836
                       mol_type = protein
                       organism = Human alphaherpesvirus 3
SEQUENCE: 15
MFALVLAVVI LPLWTTANKS YVTPTPATRS IGHMSALLRE YSDRNMSLKL EAFYPTGFDE  60
ELIKSLHWGN DRKHVFLVIV KVNPTTHEGD VGLVIFPTYL LSPYHFKAEH RAPFPAGRFG  120
FLSHPVTPDV SFFDSSFAPY LTTQHLVAFT TFPPNPLVWH LERAETAATA ERPFGVSLLP  180
ARPTVPKNTI LEHKAHFATW DALARHTFFS AEAIITNSTL RIHVPLFGSV WPIRYWATGS  240
VLLTSDSGRV EVNIGVGFMS SLISLSSGLP IELIVVPHTV KLNAVTSDTT WFQLNPPGPD  300
PGPSYRVYLL GRGLDMNFSK HATVDICAYP EESLDYRYHL SMAHTEALRM TTKADQHDIN  360
EESYYHIAAR IATSIMGRTT EYFLLDEIVD VQYQLKFLNY ILMRIGAGAH PNTISGTSDL  420
IFADPSQLHD ELSLLFGQVK PANVDYFISY DEARDQLKTA YALSRGQDHV NALSLARRVI  480
MSIYKGLLVK QNLNATERQA LFFASMILLN FREGLENSSR VLDGRTTLLL MTSMCTAAHA  540
TQAALNIQEG LAYLNPSKHM FTIPNVYSPC MGSLRTDLTE EIHVMNLLSA IPTRPGLNEV  600
LHTQLDESEI FDAAFKTMMI FTTWTAKDLH ILHTHVPEVF TCQDAAARNG EYVLILPAVQ  660
GHSYVITRNK PQRGLVYSLA DVDVYNPISV VYLSKDTCVS EHGVIETVAL PHPDNLKECL  720
YCGSVFLRYL TTGAIMDIII IDSKDTERQL AAMGNSTIPP FNPDMHGDDS KAVLLFPNGT  780
VVTLLGFERR QAIRMSGQYL GASLGGAFLA VVGFGIIGWM LCGNSRLREY NKIPLT      836

SEQ ID NO: 16          moltype = AA  length = 160
FEATURE                Location/Qualifiers
source                 1..160
                       mol_type = protein
                       organism = Human alphaherpesvirus 3
SEQUENCE: 16
MASHKWLLQM IVFLKTITIA YCLHLQDDTP LFFGAKPLSD VSLIITEPCV SSVYEAWDYA  60
APPVSNLSEA LSGIVVKTKC PVPEVILWFK DKQMAYWTNP YVTLKGLAQS VGEEHKSGDI  120
RDALLDALSG VWVDSTPSST NIPENGCVWG ADRLFQRVCQ                        160

SEQ ID NO: 17          moltype = AA  length = 87
FEATURE                Location/Qualifiers
source                 1..87
                       mol_type = protein
                       organism = Human alphaherpesvirus 3
SEQUENCE: 17
MGSITASFIL ITMQILFFCE DSSGEPNFAE RNFWHASCSA RGVYIDGSMI TTLFFYASLL  60
GVCVALISLA YHACFRLFTR SVLRSTW                                      87

SEQ ID NO: 18          moltype = AA  length = 354
FEATURE                Location/Qualifiers
source                 1..354
                       mol_type = protein
                       organism = Human alphaherpesvirus 3
SEQUENCE: 18
MFLIQCLISA VIFYIQVTNA LIFKGDHVSL QVNSSLTSIL IPMQNDNYTE IKGQLVFIGE  60
QLPTGTNYSG TLELLYADTV AFCFRSVQVI RYDGCPRIRT SAFISCRYKH SWHYGNSTDR  120
ISTEPDAGVM LKITKPGIND AGVYVLLVRL DHSRSTDGFI LGVNVYTAGS HHNIHGVIYT  180
SPSLQNGYST RALFQQARLC DLPATPKGSG TSLFQHMLDL RAGKSLEDNP WLHEDVVTTE  240
TKSVVKEGIE NHVYPTDMST LPEKSLNDPP ENLLIIIPIV ASVMILTAMV IVIVISVKRR  300
RIKKHPIYRP NTKTRRGIQN ATPESDVMLE AAIAQLATIR EESPPHSVVN PFVK        354

SEQ ID NO: 19          moltype = AA  length = 1255
FEATURE                Location/Qualifiers
source                 1..1255
                       mol_type = protein
                       organism = Severe acute respiratory syndrome-related
                        coronavirus
SEQUENCE: 19
MFIFLLFLTL TSGSDLDRCT TFDDVQAPNY TQHTSSMRGV YYPDEIFRSD TLYLTQDLFL  60
PFYSNVTGFH TINHTFGNPV IPFKDGIYFA ATEKSNVVRG WVFGSTMNNK SQSVIIINNS  120
TNVVIRACNF ELCDNPFFAV SKPMGTQTHT MIFDNAFNCT FEYISDAFSL DVSEKSGNFK  180
HLREFVFKNK DGFLYVYKGY QPIDVVRDLP SGFNTLKPIF KLPLGINITN FRAILTAFSP  240
AQDIWGTSAA AYFVGYLKPT TFMLKYDENG TITDAVDCSQ NPLAELKCSV KSFEIDKGIY  300
QTSNFRVVPS GDVVRFPNIT NLCPFGEVFN ATKFPSVYAW ERKKISNCVA DYSVLYNSTF  360
FSTFKCYGVS ATKLNDLCFS NVYADSFVVK GDDVRQIAPG QTGVIADYNY KLPDDFMGCV  420
LAWNTRNIDA TSTGNYNYKY RYLRHGKLRP FERDISNVPF SPDGKPCTPP ALNCYWPLND  480
YGFYTTTGIG YQPYRVVVLS FELLNAPATV CGPKLSTDLI KNQCVNFNFN GLTGTGVLTP  540
```

-continued

```
SSKRFQPFQQ FGRDVSDFTD SVRDPKTSEI LDISPCSFGG VSVITPGTNA SSEVAVLYQD  600
VNCTDVSTAI HADQLTPAWR IYSTGNNVFQ TQAGCLIGAE HVDTSYECDI PIGAGICASY  660
HTVSLLRSTS QKSIVAYTMS LGADSSIAYS NNTIAIPTNF SISITTEVMP VSMAKTSVDC  720
NMYICGDSTE CANLLLQYGS FCTQLNRALS GIAAEQDRNT REVFAQVKQM YKTPTLKYFG  780
GFNFSQILPD PLKPTKRSFI EDLLFNKVTL ADAGFMKQYG ECLGDINARD LICAQKFNGL  840
TVLPPLLTDD MIAAYTAALV SGTATAGWTF GAGAALQIPF AMQMAYRFNG IGVTQNVLYE  900
NQKQIANQFN KAISQIQESL TTTSTALGKL QDVVNQNAQA LNTLVKQLSS NFGAISSVLN  960
DILSRLDKVE AEVQIDRLIT GRLQSLQTYV TQQLIRAAEI RASANLAATK MSECVLGQSK  1020
RVDFCGKGYH LMSFPQAAPH GVVFLHVTYV PSQERNFTTA PAICHEGKAY FPREGVFVFN  1080
GTSWFITQRN FFSPQIITTD NTFVSGNCDV VIGIINNTVY DPLQPELDSF KEELDKYFKN  1140
HTSPDVDLGD ISGINASVVN IQKEIDRLNE VAKNLNESLI DLQELGKYEQ YIKWPWYVWL  1200
GFIAGLIVIV MVTILLCCMT SCCSCLKGAC SCGSCCKFDE DDSEPVLKGV KLHYT       1255

SEQ ID NO: 20          moltype = AA  length = 857
FEATURE                Location/Qualifiers
source                 1..857
                       mol_type = protein
                       organism = Human gammaherpesvirus 4
SEQUENCE: 20
MTRRRVLSVV VLLAALACRL GAQTPEQPAP PATTVQPTAT RQQTSFPFRV CELSSHGDLF  60
RFSSDIQCPS FGTRENHTEG LLMVFKDNII PYSFKVRSYT KIVTNILIYN GWYADSVTNR  120
HEEKFSVDSY ETDQMDTIYQ CYNAVKMTKD GLTRVYVDRD GVNITVNLKP TGGLANGVRR  180
YASQTELYDA PGWLIWTYRT RTTVNCLITD MMAKSNSPFD FFVTTTGQTV EMSPFYDGKN  240
KETFHERADS FHVRTNYKIV DYDNRGTNPQ GERRAFLDKG TYTLSWKLEN RTAYCPLQHW  300
QTFDSTIATE TGKSIHFVTD EGTSSFVTNT TVGIELPDAF KCIEEQVNKT MHEKYEAVQD  360
RYTKGQEAIT YFITSGGLLL AWLPLTPRSL ATVKNLTELT TPTSSPPSSP SPPAPSAARG  420
STPAAVLRRR RRDAGNATTP VPPTAPGKSL GTLNNPATVQ IQFAYDSLRR QINRMLGDLA  480
RAWCLEQKRQ NMVLRELTKI NPTTVMSSIY GKAVAAKRLG DVISVSQCVP VNQATVTLRK  540
SMRVPGSETM CYSRPLVSFS FINDTKTYEG QLGTDNEIFL TKKMTEVCQA TSQYYFQSGN  600
EIHVYNDYHH FKTIELDGIA TLQTFISLNT SLIENIDFAS LELYSRDEQR ASNVFDLEGI  660
FREYNFQAQN IAGLRKDLDN AVSNGRNQFV DGLGELMDSL GSVGQSITNL VSTVGGLFSS  720
LVSGFISFFK NPFGGMLILV LVAGVVILVI SLTRRTRQMS QQPVQMLYPG IDELAQQHAS  780
GEGPGINPIS KTELQAIMLA LHEQNQEQKR AAQRAAGPSV ASRALQAARD RFPGLRRRRY  840
HDPETAAALL GEAETEF                                                857

SEQ ID NO: 21          moltype = AA  length = 158
FEATURE                Location/Qualifiers
source                 1..158
                       mol_type = protein
                       organism = Human papillomavirus
SEQUENCE: 21
MHQKRTAMFQ DPQERPRKLP QLCTELQTTI HDIILECVYC KQQLLRREVY DFAFRDLCIV  60
YRDGNPYAVC DKCLKFYSKI SEYRHYCYSV YGTTLEQQYN KPLCDLLIRC INCQKPLCPE  120
EKQRHLDKKQ RFHNIRGRWT GRCMSCCRSS RTRRETQL                        158

SEQ ID NO: 22          moltype = AA  length = 51
FEATURE                Location/Qualifiers
source                 1..51
                       mol_type = protein
                       organism = Human papillomavirus
SEQUENCE: 22
SQPLKQHYQI VTCCCGCDSN VRLVVQCTET DIREVQQLLL GTLNIVCPIC A         51

SEQ ID NO: 23          moltype = AA  length = 450
FEATURE                Location/Qualifiers
source                 1..450
                       mol_type = protein
                       organism = Rabies lyssavirus
SEQUENCE: 23
MDADKIVFKV NNQVVSLKPE IIVDQYEYKY PAIKDLKKPC ITLGKAPDLN KAYKSVLSCM  60
SAAKLDPDDV CSYLAAAMQF FEGTCPEDWT SYGILIARKG DKITPGSLVE IKRTDVEGNW  120
ALTGGMELTR DPTVPEHASL VGLLLSLYRL SKISGQNTGN YKTNIADRIE QIFETAPFVK  180
IVEHHTLMTT HKMCANWSTI PNFRFLAGTY DMFFSRIEHL YSAIRVGTVV TAYEDCSGLV  240
SFTGFIKQIN LTAREAILYF FHKNFEEEIR RMFEPGQETA VPHSYFIHFR SLGLSGKSPY  300
SSNAVGHVFN LIHFVGCYMG QVRSLNATVI AACAPHEMSV LGGYLGEEFF GKGTFERRFF  360
RDEKELQEYE AAELTKTDVA LADDGTVNSD DEDYFSGETR SPEAVYTRII MNGGRLKRSH  420
IRRYVSVSSN HQARPNSFAE FLNKTYSSDS                                  450

SEQ ID NO: 24          moltype = AA  length = 11
FEATURE                Location/Qualifiers
source                 1..11
                       mol_type = protein
                       organism = Rabies lyssavirus
SEQUENCE: 24
MIDPGEVYDD P                                                      11

SEQ ID NO: 25          moltype = AA  length = 524
FEATURE                Location/Qualifiers
source                 1..524
```

```
                        mol_type = protein
                        organism = Rabies lyssavirus
SEQUENCE: 25
MVPQALLFVP LLVFPLCFGK FPIYTIPDKL GPWSPIDIHH LSCPNNLVVE DEGCTNLSGF  60
SYMELKVGYI SAIKTNGFTC TGVVTEAETY TNFVGYVTTT FKRKHFRPTP DACRAAYNWK  120
MAGDPRYEES LHNPYPDYHW LRTVKTTKES LVIISPSVAD LDPYDRSLHS RVFPGGNCSG  180
VAVSSTYCST NHDYTIWMPE NPRLGMSCDI FTNSRGKRAS KGSETCGFVD ERGLYKSLKG  240
ACKLKLCGVL GLRLMDGTWV AMQTSNETKW CPPGQLVNLH DFRSDEIEHL VVEELVKKRE  300
ECLDALESIM TTKSVSFRRL SHLRKLVPGF GKAYTIFNKT LMEADAHYKS VRTWNEIIPS  360
KGCLRVGGRC HPHVNGVFFN GIILGPDGNV LIPEMQSSLL QQHMELLVSS VIPLMHPMAD  420
PSTVFKNGDE AEDFVEVHLP DVHERISGVD LGLPNWGKYV LLSAGALTAL MLIIFLMTCW  480
RRVNRSEPTQ HNLRGTGREV SVTPQSGKII SSWESYKSGG ETGL                  524

SEQ ID NO: 26           moltype = AA  length = 297
FEATURE                 Location/Qualifiers
source                  1..297
                        mol_type = protein
                        organism = Rabies lyssavirus
SEQUENCE: 26
MSKIFVNPSA IRAGLADLEM AEETVDLINR NIEDNQAHLQ GEPIEVDNLP EDMGRLHLDD  60
GKSPNPGEMA KVGEGKYRED FQMDEGEDPS LLFQSYLDNV GVQIVRQIRS GERFFKIWSQ  120
TVEEIISYVA VNFPNPPGKS SEDKSTQTTG RELKKETTPT PSQRESQSSK ARMAAQTASG  180
PPALEWSATN EEDDLSVEAE IAHQIAESFS KKYKFPSRSS GILLYNFEQL KMNLDDIVKE  240
AKNVPGVTRL ARDGSKLPLR CVLGWVALAN SKKFQLLVES NKLSKIMQDD LNRYTSC     297

SEQ ID NO: 27           moltype = AA  length = 202
FEATURE                 Location/Qualifiers
source                  1..202
                        mol_type = protein
                        organism = Rabies lyssavirus
SEQUENCE: 27
MNFLRKIVKN CRDEDTQKPS PVSAPLDDDD LWLPPPEYVP LKELTSKKNR RNFCINGGVK  60
VCSPNGYSFG ILRHILRSFD EIYSGNHRMI GLVKVVIGLA LSGAPVPEGM NWVYKLRRTL  120
IFQWADSRGP LEGEELEYSQ EITWDDDTEF VGLQIRVSAK QCHIRGRIWC INMNSRAGQL  180
WSDMSLQTQR SEEDKDSSLL LE                                          202

SEQ ID NO: 28           moltype = AA  length = 904
FEATURE                 Location/Qualifiers
source                  1..904
                        mol_type = protein
                        organism = Human alphaherpesvirus 1
SEQUENCE: 28
MRQGAPARGR RWFVVWALLG LTLGVLVASA APSSPGTPGV AAATQAANGG PATPAPPAPG  60
APPTGDPKPK KNKKPKPPKP PRPAGDNATV AAGHATLREH LRDIKAENTD ANFYVCPPPT  120
GATVVQFEQP RRCPTRPEGQ NYTEGIAVVF KENIAPYKFK ATMYYKDVTV SQVWFGHRYS  180
QFMGIFEDRA PVPFEEVIDK INAKGVCRST AKYVRNNLET TAFHRDDHET DMELKPANAA  240
TRTSRGWHTT DLKYNPSRVE AFHRYGTTVN CIVEEVDARS VYPYDEFVLA TGDFVYMSPF  300
YGYREGSHTE HTSYAADRFK QVDGFYARDL TTKARATAPT TRNLLTTPKF TVAWDWVPKR  360
PSVCTMTKWQ EVDEMLRSEY GGSFRFSSDA ISTTFTTNLT EYPLSRVDLG DCIGKDARDA  420
MDRIFARRYN ATHIKVGQPQ YYLANGGFLI AYQPLLSNTL AELYVREHLR EQSRKPPNPT  480
PPPPGASANA SVERIKTTSS IEFARLQFTY NHIQRHVNDM LGRVAIAWCE LQNHELTLWN  540
EARKLNPNAI ASATVGRRVS ARMLGDVMAV STCVPVAADN VIVQNSMRIS SRPGACYSRP  600
LVSFRYEDQG PLVEGQLGEN NELRLTRDAI EPCTVGHRRY FTFGGGYVYF EEYAYSHQLS  660
RADITTVSTF IDLNITMLED HEFVPLEVYT RHEIKDSGLL DYTEVQRRNQ LHDLRFADID  720
TVIHADANAA MFAGLGAFFE GMGDLGRAVG KVVMGIVGGV VSAVSGVSSF MSNPFGALAV  780
GLLVLAGLAA AFFAFRYVMR LQSNPMKALY PLTTKELKNP TNPDASGEGE EGGDFDEAKL  840
AEAREMIRYM ALVSAMERTE HKAKKKGTSA LLSAKVTDMV MRKRRNTNYT QVPNKDGDAD  900
EDDL                                                              904

SEQ ID NO: 29           moltype = AA  length = 698
FEATURE                 Location/Qualifiers
source                  1..698
                        mol_type = protein
                        organism = Human alphaherpesvirus 2
SEQUENCE: 29
MHAIAPRLLL LFVLSGLPGT RGGSGVPGPI NPPNNDVVFP GGSPVAQYCY AYPRLDDPGP  60
LGSADAGRQD LPRRVVRHEP LGRSFLTGGL VLLAPPVRGF GAPNATYAAR VTYYRLTRAC  120
RQPILLRQYG GCRGGEPPSP KTCGSYTYTY QGGGPPTRYA LVNASLLVPI WDRAAETFEY  180
QIELGGELHV GLLWVEVGGE GPGPTAPPQA ARAEGGPCVP PVPAGRPWRS VPPVWYSAPN  240
PGFRGLRFRE RCLPPQTPAA PSDLPRVAFA PQSLLVGITG RTFIRMARPT EDVGVLPPHW  300
APGALDDGPY APFPPRPRFR RALRTDPEGV DPDVRAPLTG RRLMALTEDA SSDSPTSAPE  360
KTPLPVSATA MAPSVDPSAE PTAPATTTPP DEMATQAATV AVTPEETAVA SPPATASVES  420
SPLPAAAATP GAGHTNTSSA PAAKTPPTTP APTTPPPTST HATPRPTTPG PQTTPPGPAT  480
PGPVGASAAP TADSPLTASP PATAPGPSAA NVSVAATTAT PGTRGTARTP PTDPKTHPHG  540
PADAPPGSPA PPPPEHRGGP EEFEGAGDGE PPDDDDSATG LAFRTPNPNK PPPARPGPIR  600
PTLPPGILGP LAPNTPRPPA QAPAKDMPSG PTPQHIPLFW FLTASPALDI LFIISTTIHT  660
AAFVCLVALA AQLWRGRAGR RRYAHPSVRY VCLPPERD                          698

SEQ ID NO: 30           moltype = AA  length = 741
```

```
FEATURE                Location/Qualifiers
source                 1..741
                       mol_type = protein
                       organism = Mycobacterium tuberculosis
SEQUENCE: 30
MTDRVSVGNL RIARVLYDFV NNEALPGTDI DPDSFWAGVD KVVADLTPQN QALLNARDEL  60
QAQIDKWHRR RVIEPIDMDA YRQFLTEIGY LLPEPDDFTI TTSGVDAEIT TTAGPQLVVP  120
VLNARFALNA ANARWGSLYD ALYGTDVIPE TDGAEKGPTY NKVRGDKVIA YARKFLDDSV  180
PLSSGSFGDA TGFTVQDGQL VVALPDKSTG LANPGQFAGY TGAAESPTSV LLINHGLHIE  240
ILIDPESQVG TTDRAGVKDV ILESAITTIM DFEDSVAAVD AADKVLGYRN WLGLNKGDLA  300
AAVDKDGTAF LRVLNRDRNY TAPGGGQFTL PGRSLMFVRN VGHLMTNDAI VDTDGSEVFE  360
GIMDALFTGL IAIHGLKASD VNGPLINSRT GSIYIVKPKM HGPAEVAFTC ELFSRVEDVL  420
GLPQNTMKIG IMDEERRTTV NLKACIKAAA DRVVFINTGF LDRTGDEIHT SMEAGPMVRK  480
GTMKSQPWIL AYEDHNVDAG LAAGFSGRAQ VGKGMWTMTE LMADMVETKI AQPRAGASTA  540
WVPSPTAATL HALHYHQVDV AAVQQGLAGK RRATIEQLLT IPLAKELAWA PDEIREEVDN  600
NCQSILGYVV RWVDQGVGCS KVPDIHDVAL MEDRATLRIS SQLLANWLRH GVITSADVRA  660
SLERMAPLVD RQNAGDVAYR PMAPNFDDSI AFLAAQELIL SGAQQPNGYT EPILHRRRRE  720
FKARAAEKPA PSDRAGDDAA R                                           741

SEQ ID NO: 31          moltype = AA  length = 299
FEATURE                Location/Qualifiers
source                 1..299
                       mol_type = protein
                       organism = Mycobacterium tuberculosis
SEQUENCE: 31
MKGRSALLRA LWIAALSFGL GGVAVAAEPT AKAAPYENLM VPSPSMGRDI PVAFLAGGPH  60
AVYLLDAFNA GPDVSNWVTA GNAMNTLAGK GISVVAPAGG AYSMYTNWEQ DGSKQWDTFL  120
SAELPDWLAA NRGLAPGGHA AVGAAQGGYG AMALAAFHPD RFGFAGSMSG FLYPSNTTTN  180
GAIAAGMQQF GGVDTNGMWG APQLGRWKWH DPWVHASLLA QNNTRVWVWS PTNPGASDPA  240
AMIGQTAEAM GNSRMFYNQY RSVGGHNGHF DFPASGDNGW GSWAPQLGAM SGDIVGAIR   299

SEQ ID NO: 32          moltype = AA  length = 3181
FEATURE                Location/Qualifiers
source                 1..3181
                       mol_type = protein
                       organism = Zika virus
SEQUENCE: 32
MKNPKKKSGG FRIVNMLKRG VARVSPFGGL KRLPAGLLLG HGPIRMVLAI LAFLRFTAIK  60
PSLGLINRWG SVGKKEAMEI IKKFKKDLAA MLRIINARKE KKRRGADTSV GIVGLLLTTA  120
MAAEVTRRGS AYYMYLDRND AGEAISFPTT LGMNKCYIQI MDLGHMCDAT MSYECPMLDE  180
GVEPDDVDCW CNTTSTWVVY GTCHHKKGEA RRSRRAVTLP SHSTRKLQTR SQTWLESREY  240
TKHLIRVENW IFRNPGFALA AAAIAWLLGS STSQKVIYLV MILLIAPAYS IRCIGVSNRD  300
FVEGMSGGTW VDVVLEHGGC VTVMAQDKPT VDIELVTTTV SNMAEVRSYC YEASISDMAS  360
DSRCPTQGEA YLDKQSDTQY VCKRTLVDRG WGNGCGLFGK GSLVTCAKFA CSKKMTGKSI  420
QPENLEYRIM LSVHGSQHSG MIVNDTGHET DENRAKVEIT PNSPRAEATL GGFGSLGLDC  480
EPRTGLDFSD LYYLTMNNKH WLVHKEWFHD IPLPWHAGAD TGTPHWNNKE ALVEFKDAHA  540
KRQTVVVLGS QEGAVHTALA GALEAEMDGA KGRLSSGHLK CRLKMDKLRL KGVSYSLCTA  600
AFTFTKIPAE TLHGTVTVEV QYAGTDGPCK VPAQMAVDMQ TLTPVGRLIT ANPVITESTE  660
NSKMMLELDP PFGDSYIVIG VGEKKITHHW HRSGSTIGKA FEATVRGAKR MAVLGDTAWD  720
FGSVGGALNS LGKGIHQIFG AAFKSLFGGM SWFSQILIGT LLMWLGLNTK NGSISLMCLA  780
LGGVLIFLST AVSADVGCSV DFSKKETRCG TGVFVYNDVE AWRDRYKYHP DSPRRLAAAV  840
KQAWEDGICG ISSVSRMENI MWRSVEGELN AILEENGVQL TVVVGSVKNP MWRAPQRLPV  900
PVNELPHGWK AWGKSYFVRA AKTNNSFVVD GDTLKECPLK HRAWNSFLVE DHGFGVFHTS  960
VWLKVREDYS LECDPAVIGT AVKGKEAVHS DLGYWIESEK NDTWRLKRAH LIEMKTCEWP  1020
KSHTLWTDGI EESDLIIPTS LAGPLSHHNT REGYRTQMKG PWHSEELEIR FEECPGTKVH  1080
VEETCGTRGP SLRSTTASGR VIEEWCCREC TMPPLSFRAK DGCWYGMEIR PRKEPESNLV  1140
RSMVTAGSTD HMDHFSLGVL VILLMVQEGL KKRMTTKIII STSMAVLVAM ILGGFSMSDL  1200
AKLAILMGAT FAEMNTGGDV AHLALIAAFK VRPALLVSFI FRANWTPRES MLLALASCLL  1260
QTAISALEGD LMVLINGFAL AWLAIRAMVV PRTDNITLAI LAALTPLARG TLLVAWRAGL  1320
ATCGGFMLLS LKGKGSVKKN LPFVMALGLT AVRLVDPINV VGLLLLTRSG KRSWPPSEVL  1380
TAVGLICALA GGFAKADIEM AGPMAAVGLL IVSYVVSGKS VDMYIERAGD ITWEKDAEVT  1440
GNSPRLDVAL DESGDFSLVE DDGPPMREII LKVVLMTICG MNPIAIPFAA GAWYVYVKTW  1500
KRSGALWDVP ASKEVKKGET TDGVYRVMTR RLLGSTQVGV GIMQEGVFHT MWHVTKGSAL  1560
RSGEGRLDPY WGDVKQDLVS YCGPWKLDAA WDGHSEVQLL AVPPGERARN IQTLPGIFKT  1620
KDGDIGAVAL DYPAGTSGSP ILDKCGRVIG LYGNGVVIKN GSYVSAITQG RREEETPVEC  1680
FEPSMLKKKQ LTVLDLHPGA GKTRRVLPEI VREAIKTRLR TVILAPTRVV AAEMEEALRG  1740
LPVRYMTTAV NVTHSGTEIV DLMCHATFTS RLLQPIRVPN YNLYIMDEAH FTDPSSIAAR  1800
GYISTRVEMG EAAAIFMTAT PPGTRDAFPD SNSPIMDTEV EVPERAWSSG FDWVTDHSGK  1860
TVWFVPSVRN GNEIAACLTK AGKRVIQLSR KTFETEFQKT KHQEWDFVVT TDISEMGANF  1920
KADRVIDSRR CLKPVILDGE RVILAGPMPV THASAAQRRG RIGRNPNKPG DEYLYGGGCA  1980
ETDEDHAHWL EARMLLDNIY LQDGLIASLY RPEADKVAAI EGEFKLRTEQ RKTFVELMKR  2040
GDLPVWLAYQ VASAGITYTD RRWCFDGTTN NTILEDSVPA EVWTRHGEKR VLKPRWMDAR  2100
VCSDHAALKS FKEFAAGKRG AAFGVMEALG TLPGHMTERF QEAIDNLAVL MRAEIGSRPY  2160
KAAAAQLPET LETIMLLGLL GTVSLGIFFV LMRNKGIGKM GFGMVTLGAS AWLMWLSEIE  2220
PARIACVLIV VFLLLVVLIP EPEKQRSPQD NQMAIIIMVA VGLLGLITAN ELGWLERTKS  2280
DLSHLMGRRE EGATIGFSMD IDLRPASAWA IYAALTTFIT PAVQHAVTTS YNNYSLMAMA  2340
TQAGVLFGMG KGMPFYAWDF GVPLLMIGCY SQLTPLTLIV AIILLVAHYM YLIPGLQAAA  2400
ARAAQKRTAA GIMKNPVVDG IVVTDIDTMT IDPQVEKKMG QVLLIAVAVS SAILSRTAWG  2460
WGEAGALITA ATSTLWEGSP NKYWNSSTAT SLCNIFRGSY LAGASLIYTV TRNAGLVKRR  2520
```

```
GGGTGETLGE KWKARLNQMS ALEFYSYKKS GITEVCREEA RRALKDGVAT GGHAVSRGSA  2580
KLRWLVERGY LQPYGKVIDL GCGRGGWSYY AATIRKVQEV KGYTKGGPGH EEPVLVQSYG  2640
WNIVRLKSGV DVFHMAAEPC DTLLCDIGES SSSPEVEEAR TLRVLSMVGD WLEKRPGAFC  2700
IKVLCPYTST MMETLERLQR RYGGGLVRVP LSRNSTHEMY WVSGAKSNTI KSVSTTSQLL  2760
LGRMDGPRRP VKYEEDVNLG SGTRAVVSCA EAPNMKIIGN RIERIRSEHA ETWFFDENHP  2820
YRTWAYHGSY EAPTQGSASS LINGVVRLLS KPWDVVTGVT GIAMTDTTPY GQQRVFKEKV  2880
DTRVPDPQEG TRQVMSMVSS WLWKELGKHK RPRVCTKEEF INKVRSNAAL GAIFEEEKEW  2940
KTAVEAVNDP RFWALVDKER EHHLRGECQS CVYNMMGKRE KKQGEFGKAK GSRAIWYMWL  3000
GARFLEFEAL GFLNEDHWMG RENSGGGVEG LGLQRLGYVL EEMSCIPGGR MYADDTAGWD  3060
TRISRFDLEN EALITNQMEK GHRALALAII KYTYQNKVVK VLRPAEKGKT VMDIISRQDQ  3120
RGSGQVVTYA LNTFTNLVVQ LIRNMEAEEV LEMQDLWLLR RSEKVTNWLQ SNGWDRLKRM  3180
A                                                                 3181

SEQ ID NO: 33          moltype = AA  length = 397
FEATURE                Location/Qualifiers
source                 1..397
                       mol_type = protein
                       organism = Chlamydia trachomatis
SEQUENCE: 33
MKKLLKSVLV FAALSSASSL QALPVGNPAE PSLMIDGILW EGFGGDPCDP CTTWCDAISM  60
RVGYYGDFVF DRVLKTDVNK EFQMGAAPTT SDVAGLQNDP TINVARPNPA YGKHMQDAEM  120
FTNAAYMALN IWDRFDVFCT LGATTGYLKG NSASFNLVGL FGTKTQSSSF NTAKLIPNTA  180
LNEAVVELYI NTTFAWSVGA RAALWECGCA TLGASFQYAQ SKPKVEELNV LCNASEFTIN  240
KPKGYVGAEF PLNITAGTEA ATGTKDASID YHEWQASLAL SYRLNMFTPY IGVKWSRVSF  300
DADTIRIAQP KLAEAILDVT TLNRTTAGKG SVVSAGTDNE LADTMQIVSL QLNKMKSRKS  360
CGIAVGTTIV DADKYAVTVE ARLIDERAAH VNAQFRF                          397

SEQ ID NO: 34          moltype = RNA  length = 7561
FEATURE                Location/Qualifiers
source                 1..7561
                       mol_type = other RNA
                       organism = Venezuelan equine encephalitis virus
SEQUENCE: 34
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
```

-continued

```
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agtttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
```

-continued

```
gggcccctat aactctctac ggctaacctg aatggactac gacatagtct agtccgccaa  7560
g                                                                   7561

SEQ ID NO: 35          moltype = AA  length = 51
FEATURE                Location/Qualifiers
source                 1..51
                       mol_type = protein
                       organism = Venezuelan equine encephalitis virus
SEQUENCE: 35
RELPVLDSAA FNVECFKKYA CNNEYWETFK ENPIRLTEEN VVNYITKLKG P           51

SEQ ID NO: 36          moltype = AA  length = 41
FEATURE                Location/Qualifiers
source                 1..41
                       mol_type = protein
                       organism = Venezuelan equine encephalitis virus
SEQUENCE: 36
TQMRELPVLD SAAFNVECFK KYACNNEYWE TFKENPIRLT E                      41

SEQ ID NO: 37          moltype = AA  length = 536
FEATURE                Location/Qualifiers
source                 1..536
                       mol_type = protein
                       organism = Venezuelan equine encephalitis virus
SEQUENCE: 37
MKAITARRIL QGLGHYLKAE GKVECYRTLH PVPLYSSSVN RAFSSPKVAV EACNAMLKEN  60
FPTVASYCII PEYDAYLDMI DGASCCLDTA SFCPAKLRSF PKKHSYLEPT IRSAVPSAIQ  120
NTLQNVLAAA TKRNCNVTQM RELPVLDSAA FNVECFKKYA CNNEYWKTFK ENPIRLTEEN  180
VINYITKLKG PKAAALYAKT HNLNMLQDIP MDRFVMDLKR DVKVTPGTKH TEERPKVQVI  240
QAADPLATAY LCGIHRELVR RLNAVLLPNI HTLFDMSAED FDAIIAEHFQ PGDCVLETDI  300
ASFDKSEDDA MALTAMMILE DLGVDAELLT LIEAAFGEIS SIHLPTKTKF KFGAMMKSGM  360
FLTLFVNTVI NIVIASRVLR ERLTGSPCAA FIGDDNIVKG VKSDKLMADR CATWLNMEVK  420
IIDAVVGEKA PYFCGGFILC DSVTGTACRV ADPLKRLFKL GKPLAADDEH DDDRRRALHE  480
ESTRWNRVGI LPELCKAVES RYETVGTSVI VMAMATLASS VKSFSYLRGA PITLYG      536

SEQ ID NO: 38          moltype = RNA  length = 9847
FEATURE                Location/Qualifiers
misc_feature           1..9847
                       note = Description of Artificial Sequence: Synthetic
                        polynucleotide
source                 1..9847
                       mol_type = other RNA
                       organism = synthetic construct
SEQUENCE: 38
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa catagggcta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
```

-continued

```
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agtttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggagggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
```

```
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccatgttc tatgaagctt tgaaggccga acttgtatac acccgagccg tgcatggttt  7620
ccgcccgaga gcgaactgcg tcgtactgtc agattacatc cccagagtcg cgtgcaacat  7680
gggtacggtt aataagcccg tggtgggggt gctgatgggt tttgggataa tcaccggaac  7740
tctgcgcatc acaaatcctg taagagcgtc agtgctgagg tatgacgatt tccacataga  7800
cgaggacaag ctggatacca attccgttta cgaaccatat tatcactccg atcacgccga  7860
atccagctgg gtaaatcgag gagagtcctc acggaaggca tacgaccata actccccata  7920
tatatggcct cgcaatgatt atgacggatt cctggaaaac gcccatgagc accacggcgt  7980
ttataaccag ggtcgcggta tcgattctgg ggaaaggttg atgcaaccaa ctcagatgtc  8040
cgctcaggaa gatttggggg atgacaccgg aatccatgtg atacctacac tcaatggtga  8100
tgatcgacac aaaattgtaa acgtggacca gaggcaatac ggggacgttt ttaagggaga  8160
cctgaatcca aaaccacaag gacaacgact catcgaggtt tctgtagaag aaaaccatcc  8220
gtttacgctc cgcgccccca tacagcgcat atatggcgtg cgctatacgg agacctggtc  8280
ttttctcccc agtctgacat gcactggtga tgcagctcca gcaattcagc acatatgtct  8340
caagcatacc acctgtttcc aagatgtagt agtggatgtg gattgcgccg aaaacacgaa  8400
agaagaccag cttgccgaga tttcataccg gtttcaagga aaaaaagaag ccgaccagcc  8460
gtggatagta gtgaatacgt ccacgctctt cgatgaactg gaattggacc ctcctgaaat  8520
tgaacccgga gtcctgaaag ttttgcggac tgagaaacag tatctcggtg tgtacatctg  8580
gaatatgagg ggcagtgatg gaacaagcac atacgcgacc tttctggtga catggaaagg  8640
tgacgaaaag actagaaacc caaccccagc agtgaccccc caacctagag gtgctgagtt  8700
ccacatgtgg aattaccact cccatgtatt ctctgtcgga gacaccttca gcttggcgat  8760
gcacctccaa tacaagatcc atgaagcccc gttcgacctc ttgttggagt ggctctacgt  8820
accaatagac cctacctgtc aaccaatgag gctttactct acatgccttt accacccaaa  8880
cgcaccacaa tgtctttctc atatgaatag cggttgtaca tttacatctc cccatctcgc  8940
gcaaagagtc gcgagtacag tttaccaaaa ttgtgagcat gcggacaatt acacagcata  9000
ttgtcttggg atctcccaca tggagccctc ttttgggctt atacttcacg acgggggtac  9060
aacgcttaag ttcgtcgata cgccagaatc cctctctggc ttgtatgtat tcgtggttta  9120
ttttaacggt cacgttgagg ctgtggccta tactgttgtt agcactgtag accactttgt  9180
taacgccata gaagagaggg ggttcccgcc caccgctggc cagccaccgg ccacaacgaa  9240
gcctaaagag attacgccgg tgaatcccgg cacaagtccc cttatccggt acgccgcatg  9300
gacaggagga ctggcggccg tcgtcctcct ttgtctggtt atattcctta tatgcacggc  9360
aaagcgaatg cgggttaagg cttaccgagt ggataaatct ccatataatc agagcatgta  9420
ttacgcaggg ctccctgtgg acgactttga ggatagcgag tccacggata cagaagagga  9480
atttggaaac gccatcggtg ggagccatgg agggtcatct tacaccgttt acattgacaa  9540
aactagatga taaccgcggt gtcaaaaacc gcgtggacgt ggttaacatc cctgctggga  9600
ggatcagccg taattattat aattggcttg gtgctggcta ctattgtggc catgtacgtg  9660
ctgaccaacc agaaacataa ttgaatacag cagcaattgg caagctgctt acatagaact  9720
cgcggcgatt ggcatgccgc cttaaaattt ttattttatt ttttcttttc ttttccgaat  9780
cggattttgt ttttaatatt tcaaaaaaaa aaaaaaaaaa aaaaaaaaaa aaaaaaaaaa  9840
aaaaaaa                                                           9847
```

```
SEQ ID NO: 39          moltype = RNA  length = 8926
FEATURE                Location/Qualifiers
misc_feature           1..8926
                       note = Description of Artificial Sequence: Synthetic
                        polynucleotide
source                 1..8926
                       mol_type = other RNA
                       organism = synthetic construct
SEQUENCE: 39
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
```

-continued

```
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccatagggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccacccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
```

-continued

```
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccatgttc cttattcaat gcctcatatc cgcagtcatc ttctatattc aagttactaa  7620
tgcacttatc ttcaagggcg atcatgtcag cctgcaagtg aattcaagtc ttacgtccat  7680
tttgattcca atgcagaatg ataactatac cgaaattaag ggacagctgg tttttattgg  7740
agaacaactg ccgaccggta caaactacag cgggaccctc gagctgcttt acgcagacac  7800
tgtggcattc tgctttcggt cagtacaagt tatcagatac gacggatgcc cacgcattag  7860
gacatctgcc ttcatttctt gccgatacaa gcatagttgg cattacggaa actctaccga  7920
tagaatttca actgaaccag atgccggtgt gatgctcaag ataaccaaac ctgggatcaa  7980
cgacgcaggg gtgtatgtcc tcttggtgag attggaccat tcaaggagta cggacgggtt  8040
tatactgggc gtgaacgtct ataccgcagg aagtcatcat aacattcacg gtgtcattta  8100
taccagcccc agtctccaga atgggtacag cactcgagcc ctgttccagc aagcaagatt  8160
gtgtgacctt ccagccactc ctaagggatc aggcacaagt ctttttcaac atatgttgga  8220
tctcagagca gggaaaagtc ttgaggacaa cccgtggctc catgaagacg tggttactac  8280
tgaaacaaag tcagtggtca aggagggaat cgagaaccat gtgtacccaa ctgacatgag  8340
cacgctgcct gaaaaatcac tgaacgaccc accagagaat ctgctgataa taatacctat  8400
tgtagcgagt gttatgattt tgaccgcaat ggtcatagtt attgtaataa gcgtgaaaag  8460
gagacgaatc aaaaaacatc cgatatacag gccgaatacg aagacaagaa gagggattca  8520
gaacgcgact ccggagagtg atgtaatgct cgaagcagcc atcgctcaac ttgccaccat  8580
tcgcgaagaa agccctccgc attccgtcgt aaatcctttt gtcaagtgat aaccgcggtg  8640
tcaaaaaccg cgtggacgtg gttaacatcc ctgctgggag gatcagccgt aattattata  8700
attggcttgg tgctggctac tattgtggcc atgtacgtgc tgaccaacca gaaacataat  8760
tgaatacagc agcaattggc aagctgctta catagaactc gcggcgattg gcatgccgcc  8820
ttaaaatttt tattttattt tttcttttct tttccgaatc ggattttgtt tttaatattt  8880
caaaaaaaaa aaaaaaaaaa aaaaaaaaaa aaaaaaaaaa aaaaaa                8926
```

```
SEQ ID NO: 40           moltype = RNA  length = 9733
FEATURE                 Location/Qualifiers
misc_feature            1..9733
                        note = Description of Artificial Sequence: Synthetic
                         polynucleotide
source                  1..9733
                        mol_type = other RNA
                        organism = synthetic construct
SEQUENCE: 40
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
```

-continued

```
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gccccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaaatca gtaaggcaaa  5760
```

```
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccatgggt acggttaata agcccgtggt gggggtgctg atgggttttg ggataatcac  7620
cggaactctg cgcatcacaa atcctgtaag agcgtcagtg ctgaggtatg acgatttcca  7680
catagacgag gacaagctgg ataccaattc cgtttacgaa ccatattatc actccgatca  7740
cgccgaatcc agctgggtaa atcgaggaga gtcctcacgg aaggcatacg accataactc  7800
cccatatata tggcctcgca atgattatga cggattcctg gaaaacgccc atgagcacca  7860
cggcgtttat aaccagggtc gcggtatcga ttctggggaa aggttgatgc aaccaactca  7920
gatgtccgct caggaagatt tgggggatga caccggaatc catgtgatac ctacactcaa  7980
tggtgatgat cgacacaaaa ttgtaaacgt ggaccagagg caatacgggg acgtttttaa  8040
gggagacctg aatccaaaac cacaaggaca acgactcatc gaggtttctg tagaagaaaa  8100
ccatccgttt acgctccgcg cccccataca gcgcatatat ggcgtgcgct atacggagac  8160
ctggtctttt ctccccagtc tgacatgcac tggtgatgca gctccagcaa ttcagcacat  8220
atgtctcaag cataccacct gtttccaaga tgtagtagtg gatgtggatt gcgccgaaaa  8280
cacgaaagaa gaccagcttg ccgagatttc ataccggttt caaggaaaaa aagaagccga  8340
ccagccgtgg atagtagtga atacgtccac gctcttcgat gaactggaat tggaccctcc  8400
tgaaattgaa cccggagtcc tgaaagtttt gcggactgag aaacagtatc tcggtgtgta  8460
catctggaat atgaggggca gtgatggaac aagcacatac gcgacctttc tggtgacatg  8520
gaaaggtgac gaaaagacta gaaacccaac cccagcagtg accccccaac ctagaggtgc  8580
tgagttccac atgtggaatt accactccca tgtattctct gtcggagaca ccttcagctt  8640
ggcgatgcac ctccaataca agatccatga agccccgttc gacctcttgt tggagtggct  8700
ctacgtacca atagacccta cctgtcaacc aatgaggctt tactctacat gcctttacca  8760
cccaaacgca ccacaatgtc tttctcatat gaatagcggt tgtacattta catctcccca  8820
tctcgcgcaa agagtcgcga gtacagttta ccaaaattgt gagcatgcgg acaattacac  8880
agcatattgt cttgggatct cccacatgga gccctctttt gggcttatac ttcacgacgg  8940
gggtacaacg cttaagttcg tcgatacgcc agaatccctc tctggcttgt atgtattcgt  9000
ggtttatttt aacggtcacg ttgaggctgt ggcctatact gttgttagca ctgtagacca  9060
ctttgttaac gccatagaag agagggggtt cccgcccacc gctggccagc caccggccac  9120
aacgaagcct aaagagatta cgccggtgaa tcccggcaca agtcccctta tccggtacgc  9180
cgcatggaca ggaggactgg cggccgtcgt cctcctttgt ctggttatat tccttatatg  9240
cacggcaaag cgaatgcggg ttaaggctta ccgagtggat aaatctccat ataatcagag  9300
catgtattac gcagggctcc ctgtggacga ctttgaggat agcgagtcca cggatacaga  9360
agaggaattt ggaaacgcca tcggtgggag ccatggaggg tcatcttaca ccgtttacat  9420
tgacaaaact agatgataac cgcggtgtca aaaaccgcgt ggacgtggtt aacatccctg  9480
ctgggaggat cagccgtaat tattataatt ggcttggtgc tggctactat tgtggccatg  9540
tacgtgctga ccaaccagaa acataattga atacagcagc aattggcaag ctgcttacat  9600
agaactcgcg gcgattggca tgccgcctta aaatttttat tttatttttt cttttctttt  9660
ccgaatcgga ttttgttttt aatatttcaa aaaaaaaaaa aaaaaaaaaa aaaaaaaaaa  9720
aaaaaaaaaa aaa                                                     9733
```

```
SEQ ID NO: 41          moltype = RNA  length = 10984
FEATURE                Location/Qualifiers
misc_feature           1..10984
                       note = Description of Artificial Sequence: Synthetic
                        polynucleotide
source                 1..10984
                       mol_type = other RNA
                       organism = synthetic construct
SEQUENCE: 41
ataggcggcg catgagagaa gcccagacca attacctacc caaaatggag aaagttcacg  60
ttgacatcga ggaagacagc ccattcctca gagctttgca gcggagcttc ccgcagtttg  120
```

-continued

```
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa catagcccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
```

-continued

```
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccacccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccatgttc cttattcaat gcctcatatc cgcagtcatc ttctatattc aagttactaa  7620
tgcacttatc ttcaagggcg atcatgtcag cctgcaagtg aattcaagtc ttacgtccat  7680
tttgattcca atgcagaatg ataactatac cgaaattaag ggacagctgg tttttattgg  7740
agaacaactg ccgaccggta caaactacag cgggaccctc gagctgcttt acgcagacac  7800
tgtggcattc tgctttcggt cagtacaagt tatcagatac gacggatgcc cacgcattag  7860
gacatctgcc ttcatttctt gccgatacaa gcatagttgg cattacggaa actctaccga  7920
tagaatttca actgaaccag atgccggtgt gatgctcaag ataaccaaac ctgggatcaa  7980
cgacgcaggg gtgtatgtcc tcttggtgag attggaccat tcaaggagta cggacgggtt  8040
tatactgggc gtgaacgtct ataccgcagg aagtcatcat aacattcacg gtgtcattta  8100
taccagcccc agtctccaga atgggtacag cactcgagcc ctgttccagc aagcaagatt  8160
gtgtgacctt ccagccactc ctaagggatc aggcacaagt ctttttcaac atatgttgga  8220
tctcagagca gggaaaagtc ttgaggacaa cccgtggctc catgaagacg tggttactac  8280
tgaaacaaag tcagtggtca aggagggaat cgagaaccat gtgtacccaa ctgacatgag  8340
cacgctgcct gaaaaatcac tgaacgaccc accagagaat ctgctgataa taatacctat  8400
tgtagcgagt gttatgattt tgaccgcaat ggtcatagtt attgtaataa gcgtgaaaag  8460
gagacgaatc aaaaaacatc cgatatacag gccgaatacg aagacaagaa gagggattca  8520
gaacgcgact ccggagagtg atgtaatgct cgaagcagcc atcgctcaac ttgccaccat  8580
tcgcgaagaa agccctccgc attccgtcgt aaatcctttt gtcaagcgga ggaaaagggg  8640
atccggggaa ggccggggta gtttgctgac gtgcggagat gttgaagaga acccagggcc  8700
gatgttctat gaagctttga aggccgaact tgtatacacc cgagccgtgc atggtttccg  8760
cccgagagcg aactgcgtcg tactgtcaga ttacatcccc agagtcgcgt gcaacatggg  8820
tacggttaat aagcccgtgg tgggggtgct gatgggtttt gggataatca ccggaactct  8880
gcgcatcaca aatcctgtaa gagcgtcagt gctgaggtat gacgatttcc acatagacga  8940
ggacaagctg gataccaatt ccgtttacga accatattat cactccgatc acgccgaatc  9000
cagctgggta aatcgaggag agtcctcacg gaaggcatac gaccataact ccccatatat  9060
atggcctcgc aatgattatg acggattcct ggaaaacgcc catgagcacc acggcgttta  9120
taaccagggt cgcggtatcg attctgggga aaggttgatg caaccaactc agatgtccgc  9180
tcaggaagat ttgggggatg acaccggaat ccatgtgata cctacactca atggtgatga  9240
tcgacacaaa attgtaaacg tggaccagag gcaatacggg gacgttttta agggagacct  9300
gaatccaaaa ccacaaggac aacgactcat cgaggtttct gtagaagaaa accatccgtt  9360
tacgctccgc gcccccatac agcgcatata tggcgtgcgc tatacggaga cctggtcttt  9420
tctccccagt ctgacatgca ctggtgatgc agctccagca attcagcaca tatgtctcaa  9480
gcataccacc tgtttccaag atgtagtagt ggatgtggat tgcgccgaaa acacgaaaga  9540
agaccagctt gccgagattt cataccggtt tcaaggaaaa aaagaagccg accagccgtg  9600
```

```
gatagtagtg aatacgtcca cgctcttcga tgaactggaa ttggaccctc ctgaaattga  9660
acccggagtc ctgaaagttt tgcggactga gaaacagtat ctcggtgtgt acatctggaa  9720
tatgaggggc agtgatggaa caagcacata cgcgaccttt ctggtgacat ggaaaggtga  9780
cgaaaagact agaaacccaa ccccagcagt gaccccccaa cctagaggtg ctgagttcca  9840
catgtggaat taccactccc atgtattctc tgtcggagac accttcagct tggcgatgca  9900
cctccaatac aagatccatg aagccccgtt cgacctcttg ttggagtggc tctacgtacc  9960
aatagaccct acctgtcaac caatgaggct ttactctaca tgcctttacc acccaaacgc  10020
accacaatgt ctttctcata tgaatagcgg ttgtacattt acatctcccc atctcgcgca  10080
aagagtcgcg agtacagttt accaaaattg tgagcatgcg gacaattaca cagcatattg  10140
tcttgggatc tcccacatgg agccctcttt tgggcttata cttcacgacg ggggtacaac  10200
gcttaagttc gtcgatacgc cagaatccct ctctggcttg tatgtattcg tggtttattt  10260
taacggtcac gttgaggctg tggcctatac tgttgttagc actgtagacc actttgttaa  10320
cgccatagaa gagagggggt tcccgcccac cgctggccag ccaccggcca caacgaagcc  10380
taaagagatt acgccggtga atcccggcac aagtcccctt atccggtacg ccgcatggac  10440
aggaggactg gcggccgtcg tcctcctttg tctggttata ttccttatat gcacggcaaa  10500
gcgaatgcgg gttaaggctt accgagtgga taaatctcca tataatcaga gcatgtatta  10560
cgcagggctc cctgtggacg actttgagga tagcgagtcc acggatacag aagaggaatt  10620
tggaaacgcc atcggtggga gccatggagg gtcatcttac accgtttaca ttgacaaaac  10680
tagatgataa ccgcggtgtc aaaaaccgcg tggacgtggt taacatccct gctgggagga  10740
tcagccgtaa ttattataat tggcttggtg ctggctacta ttgtggccat gtacgtgctg  10800
accaaccaga aacataattg aatacagcag caattggcaa gctgcttaca tagaactcgc  10860
ggcgattggc atgccgcctt aaaattttta ttttattttt tcttttcttt tccgaatcgg  10920
attttgtttt taatatttca aaaaaaaaaa aaaaaaaaaa aaaaaaaaaa aaaaaaaaaa  10980
aaaa                                                               10984

SEQ ID NO: 42          moltype = RNA  length = 11498
FEATURE                Location/Qualifiers
misc_feature           1..11498
                       note = Description of Artificial Sequence: Synthetic
                        polynucleotide
source                 1..11498
                       mol_type = other RNA
                       organism = synthetic construct
SEQUENCE: 42
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
```

-continued

```
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agtttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccacccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
```

```
tcatagttat ggccatgact actctagcta gcagtgttaa atcattcagc tacctgagag  7500
gggcccctat aactctctac ggctaacctg aatggactac gacatagtct agtccgccgc  7560
caccatgttc cttattcaat gcctcatatc cgcagtcatc ttctatattc aagttactaa  7620
tgcacttatc ttcaagggcg atcatgtcag cctgcaagtg aattcaagtc ttacgtccat  7680
tttgattcca atgcagaatg ataactatac cgaaattaag ggacagctgg tttttattgg  7740
agaacaactg ccgaccggta caaactacag cgggaccctc gagctgcttt acgcagacac  7800
tgtggcattc tgctttcggt cagtacaagt tatcagatac gacggatgcc cacgcattag  7860
gacatctgcc ttcatttctt gccgatacaa gcatagttgg cattacggaa actctaccga  7920
tagaatttca actgaaccag atgccggtgt gatgctcaag ataaccaaac ctgggatcaa  7980
cgacgcaggg gtgtatgtcc tcttggtgag attggaccat tcaaggagta cggacgggtt  8040
tatactgggc gtgaacgtct ataccgcagg aagtcatcat aacattcacg gtgtcattta  8100
taccagcccc agtctccaga atgggtacag cactcgagcc ctgttccagc aagcaagatt  8160
gtgtgacctt ccagccactc ctaagggatc aggcacaagt ctttttcaac atatgttgga  8220
tctcagagca gggaaaagtc ttgaggacaa cccgtggctc catgaagacg tggttactac  8280
tgaaacaaag tcagtggtca aggagggaat cgagaaccat gtgtacccaa ctgacatgag  8340
cacgctgcct gaaaaatcac tgaacgaccc accagagaat ctgctgataa taatacctat  8400
tgtagcgagt gttatgattt tgaccgcaat ggtcatagtt attgtaataa gcgtgaaaag  8460
gagacgaatc aaaaaacatc cgatatacag gccgaatacg aagacaagaa gagggattca  8520
gaacgcgact ccggagagtg atgtaatgct cgaagcagcc atcgctcaac ttgccaccat  8580
tcgcgaagaa agccctccgc attccgtcgt aaatcctttt gtcaagtgac ccctctccct  8640
cccccccccc taacgttact ggccgaagcc gcttggaata aggccggtgt gcgtttgtct  8700
atatgttatt ttccaccata ttgccgtctt ttggcaatgt gagggcccgg aaacctggcc  8760
ctgtcttctt gacgagcatt cctaggggtc tttcccctct cgccaaagga atgcaaggtc  8820
tgttgaatgt cgtgaaggaa gcagttcctc tggaagcttc ttgaagacaa acaacgtctg  8880
tagcgaccct ttgcaggcag cggaaccccc cacctggcga caggtgcctc tgcggccaaa  8940
agccacgtgt ataagataca cctgcaaagg cggcacaacc ccagtgccac gttgtgagtt  9000
ggatagttgt ggaaagagtc aaatggctct cctcaagcgt attcaacaag gggctgaagg  9060
atgcccagaa ggtaccccat tgtatgggat ctgatctggg gcctcggtgc acatgcttta  9120
catgtgttta gtcgaggtta aaaaacgtct aggccccccg aaccacgggg acgtggtttt  9180
cctttgaaaa acacgatgat aatatggcca caaccatgtt ctatgaagct ttgaaggccg  9240
aacttgtata cacccgagcc gtgcatggtt tccgcccgag agcgaactgc gtcgtactgt  9300
cagattacat ccccagagtc gcgtgcaaca tgggtacggt taataagccc gtggtggggg  9360
tgctgatggg ttttgggata atcaccggaa ctctgcgcat cacaaatcct gtaagagcgt  9420
cagtgctgag gtatgacgat ttccacatag acgaggacaa gctggatacc aattccgttt  9480
acgaaccata ttatcactcc gatcacgccg aatccagctg ggtaaatcga ggagagtcct  9540
cacggaaggc atacgaccat aactccccat atatatggcc tcgcaatgat tatgacggat  9600
tcctggaaaa cgcccatgag caccacggcg tttataacca gggtcgcggt atcgattctg  9660
gggaaaggtt gatgcaacca actcagatgt ccgctcagga agatttgggg gatgacaccg  9720
gaatccatgt gatacctaca ctcaatggtg atgatcgaca caaaattgta aacgtggacc  9780
agaggcaata cggggacgtt tttaagggag acctgaatcc aaaaccacaa ggacaacgac  9840
tcatcgaggt ttctgtagaa gaaaaccatc cgtttacgct ccgcgccccc atacagcgca  9900
tatatggcgt gcgctatacg gagacctggt cttttctccc cagtctgaca tgcactggtg  9960
atgcagctcc agcaattcag cacatatgtc tcaagcatac cacctgtttc caagatgtag  10020
tagtggatgt ggattgcgcc gaaaacacga aagaagacca gcttgccgag atttcatacc  10080
ggtttcaagg aaaaaaagaa gccgaccagc cgtggatagt agtgaatacg tccacgctct  10140
tcgatgaact ggaattggac cctcctgaaa ttgaacccgg agtcctgaaa gttttgcgga  10200
ctgagaaaca gtatctcggt gtgtacatct ggaatatgag gggcagtgat ggaacaagca  10260
catacgcgac ctttctggtg acatggaaag gtgacgaaaa gactagaaac ccaaccccag  10320
cagtgacccc ccaacctaga ggtgctgagt tccacatgtg gaattaccac tcccatgtat  10380
tctctgtcgg agacaccttc agcttggcga tgcacctcca atacaagatc catgaagccc  10440
cgttcgacct cttgttggag tggctctacg taccaataga ccctacctgt caaccaatga  10500
ggctttactc tacatgcctt taccacccaa acgcaccaca atgtctttct catatgaata  10560
gcggttgtac atttacatct ccccatctcg cgcaaagagt cgcgagtaca gtttaccaaa  10620
attgtgagca tgcggacaat tacacagcat attgtcttgg gatctcccac atggagccct  10680
cttttgggct tatacttcac gacgggggta caacgcttaa gttcgtcgat acgccagaat  10740
ccctctctgg cttgtatgta ttcgtggttt attttaacgg tcacgttgag gctgtggcct  10800
atactgttgt tagcactgta gaccactttg ttaacgccat agaagagagg gggttcccgc  10860
ccaccgctgg ccagccaccg gccacaacga agcctaaaga gattacgccg gtgaatcccg  10920
gcacaagtcc ccttatccgg tacgccgcat ggacaggagg actggcggcc gtcgtcctcc  10980
tttgtctggt tatattcctt atatgcacgg caaagcgaat gcgggttaag gcttaccgag  11040
tggataaatc tccatataat cagagcatgt attacgcagg gctccctgtg gacgactttg  11100
aggatagcga gtccacggat acagaagagg aatttggaaa cgccatcggt gggagccatg  11160
gagggtcatc ttacaccgtt tacattgaca aaactagatg ataaccgcgg tgtcaaaaac  11220
cgcgtggacg tggttaacat ccctgctggg aggatcagcc gtaattatta taattggctt  11280
ggtgctggct actattgtgg ccatgtacgt gctgaccaac cagaaacata attgaataca  11340
gcagcaattg gcaagctgct tacatagaac tcgcggcgat tggcatgccg ccttaaaatt  11400
tttattttat tttttctttt cttttccgaa tcggattttg tttttaatat ttcaaaaaaa  11460
aaaaaaaaaa aaaaaaaaaa aaaaaaaaaa aaaaaaa                          11498
```

```
SEQ ID NO: 43           moltype = RNA  length = 9373
FEATURE                 Location/Qualifiers
misc_feature            1..9373
                        note = Description of Artificial Sequence: Synthetic
                         polynucleotide
source                  1..9373
                        mol_type = other RNA
                        organism = synthetic construct
SEQUENCE: 43
ataggcggcg catgagagaa gcccagacca attacctacc caaaatggag aaagttcacg  60
```

-continued

```
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
```

-continued

```
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gatgggtacc gtaaataagc ccgttgtcgg tgtcttgatg ggctttggaa tcattactgg  7620
aactttgagg attacgaacc ctgtcagagc ctctgttctt cggtacgacg acttccacat  7680
tgacgaagac aagttggata ccaactccgt atacgagccg tattaccact cagatcatgc  7740
cgaatcatca tgggtcaatc gaggcgaatc ttcccgaaag gcgtacgatc ataacagtcc  7800
ctacatatgg cccagaaacg attacgacgg ctttctcgag aacgcgcatg agcatcatgg  7860
ggtgtataat caagggagag gcatagattc tggtgaacgc ttgatgcaac caactcagat  7920
gtccgcacaa gaagatcttg gggacgacac aggaatacac gtcatcccta cactgaacgg  7980
cgatgatcgg cataagatcg taaatgtgga tcaacggcaa tatggcgacg tgtttaaggg  8040
ggaccttaat cccaagcccc agggacaacg gttgattgag gtatctgttg aggaaaacca  8100
ccccctttacg ctgcgggcgc cgattcagcg catctacggt gttcgctata cggagacgtg  8160
gagtttcctg ccatctctca catgtaccgg ggacgctgca ccggcaattc aacatatttg  8220
cctgaaacac acgacatgct ttcaagacgt tgtagtggat gtggactgtg cggagaatac  8280
caaagaggac caacttgcgg aaataagcta ccgattccaa gggaagaagg aggccgacca  8340
gccatggatt gttgttaata catctacact tttgatgaa ctcgaacttg acccacccga  8400
gattgaacct ggcgttttga aagtccttag aacagaaaaa caataccttg gtgtatatat  8460
atggaacatg agggggtccg acggcacgtc tacctatgcc acctttctgg tcacatggaa  8520
aggagatgaa aagactcgca atcctaccc ggcggtcact cctcaaccca gaggcgctga  8580
gttccatatg tggaattatc attcacatgt cttctccgtt ggcgacactt ttagcttggc  8640
gatgcatctg cagtacaaaa tacatgaggc gccgttcgac cttctccttg aatggctcta  8700
tgtgcccatt gatcctactt gtcaaccgat gaggctttac tctacgtgcc tctaccaccc  8760
gaatgcgcct caatgcctgt cccatatgaa ttccgggtgt acctttacat cccctcatct  8820
tgctcagcga gttgctagca cggtttacca gaactgcgag catgcggaca attatacagc  8880
ctactgtctt ggcataagtc acatggaacc tagcttcggc ctgattctcc atgatggagg  8940
aacaacgctt aaattcgtag acacccccga atcattgagc ggtttgtatg tttttgtagt  9000
ttatttcaat gggcatgtgg aggcggtagc ttacaccgtc gtgtcaacag ttgaccattt  9060
tgtcaacgcc atcgaagaaa gaggatttcc gccgaccgcg ggtcagccgc ccgctactac  9120
caaacctaag gaaattactc ccgtgaaccc cggcaccagt ccgctgataa gatatgcggc  9180
ttggacggga ggcttggcgt gaggcgcgcc atacagcagc aattggcaag ctgcttacat  9240
agaactcgcg gcgattggca tgccgcctta aaatttttat tttatttttt cttttctttt  9300
ccgaatcgga ttttgttttt aatatttcaa aaaaaaaaaa aaaaaaaaaa aaaaaaaaaa  9360
aaaaaaaaaa aaa                                                     9373

SEQ ID NO: 44          moltype = RNA  length = 9937
```

-continued

```
FEATURE                Location/Qualifiers
misc_feature           1..9937
                       note = Description of Artificial Sequence: Synthetic
                        polynucleotide
source                 1..9937
                       mol_type = other RNA
                       organism = synthetic construct
SEQUENCE: 44
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa catagggcta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttccttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
```

```
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gatgcggaga ggagcagaca catccgtggg aatcgtgggc ctgctgctga ccacagcaat  7620
ggcagccgag gtgaccagga gaggcagcgc ctactatatg tacctggaca gaaatgatgc  7680
cggcgaggcc atctcctttc ccaccacact gggcatgaac aagtgctaca tccagatcat  7740
ggacctgggc cacatgtgcg atgccaccat gagctatgag tgtccaatgc tggacgaggg  7800
cgtggagccc gacgatgtgg attgctggtg taataccaca tctacatggg tggtgtacgg  7860
cacctgtcac cacaagaagg gagaggcacg gcgcagcagg agagcagtga cactgccttc  7920
ccactctacc aggaagctgc agacaagaag ccagacctgg ctggagtcca gggagtatac  7980
aaagcacctg atcagggtgg agaactggat ctttagaaat ccaggattcg cactggctgc  8040
cgccgccatc gcatggctgc tgggcagctc caccagccag aaagtgatct acctggtcat  8100
gatcctgctg atcgcccctg cctattctat ccggtgcatc ggcgtgagca atagggactt  8160
cgtggaggga atgtccggag gcacctgggt ggatgtggtg ctggagcacg gcggctgcgt  8220
gacagtgatg gcccaggaca agccaaccgt ggatatcgag ctggtgacca caaccgtgtc  8280
caacatggcc gaggtgaggt cttactgcta tgaggccagc atctccgaca tggcctctga  8340
tagcagatgt cccacccagg gcgaggccta cctggacaag cagtccgata cacagtacgt  8400
gtgcaagcgg accctggtgg acaggggatg gggaaatgga tgtggcctgt ttggcaaggg  8460
ctctctggtg acatgcgcca agttcgcctg tagcaagaag atgaccggca agtccatcca  8520
gccagagaac ctggagtacc ggatcatgct gtctgtgcac ggctcccagc actctggcat  8580
gatcgtgaac gacacaggcc acgagacaga tgagaatcgg gccaaggtgg agatcacacc  8640
taactcccca cgcgccgagg ccaccctggg aggatttggc tctctgggcc tggactgcga  8700
gcctaggaca ggcctggact tctccgatct gtactatctg accatgaaca ataagcactg  8760
gctggtgcac aaggagtggt ttcacgacat cccactgcca tggcacgcag gagcagatac  8820
aggcacccca cactggaaca ataaggaggc cctggtggag ttcaaggacg cccacgccaa  8880
gcggcagaca gtggtggtgc tgggcagcca ggagggagca gtgcacaccg ccctggcagg  8940
cgccctggag gccgagatgg acggagcaaa gggccgcctg tctagcggcc acctgaagtg  9000
```

-continued

```
caggctgaag atggataagc tgagactgaa gggcgtgtcc tactctctgt gcacagccgc  9060
cttcaccttc accaagatcc ctgccgagac actgcacggc acagtgaccg tggaggtgca  9120
gtatgccggc acagacggcc cctgtaaggt gcctgcccag atggccgtgg atatgcagac  9180
actgacccct gtgggcaggc tgatcaccgc caatccagtg atcacagagt ctaccgagaa  9240
cagcaagatg atgctggagc tggacccccc tttcggcgat agctatatcg tgatcggcgt  9300
gggcgagaag aagatcacac accactggca cagaagcggc tccacaatcg gcaaggcctt  9360
tgaggcaacc gtgcggggag caaagaggat ggccgtgctg ggcgacaccg catgggattt  9420
cggatctgtg ggaggcgccc tgaacagcct gggcaagggc atccaccaga tcttcggcgc  9480
cgcctttaag tccctgttcg gcggcatgag ctggttttcc cagatcctga tcggcacact  9540
gctgatgtgg ctgggcctga acaccaagaa tggctctatc agcctgatgt gcctggccct  9600
gggaggcgtg ctgatcttcc tgtccaccgc cgtgtctgcc tgaccgcggt gtcaaaaacc  9660
gcgtggacgt ggttaacatc cctgctggga ggatcagccg taattattat aattggcttg  9720
gtgctggcta ctattgtggc catgtacgtg ctgaccaacc agaaacataa ttgaatacag  9780
cagcaattgg caagctgctt acatagaact cgcggcgatt ggcatgccgc cttaaaattt  9840
ttattttatt ttttctttc ttttccgaat cggattttgt ttttaatatt tcaaaaaaaa  9900
aaaaaaaaaa aaaaaaaaaa aaaaaaaaaa aaaaaaa                        9937

SEQ ID NO: 45          moltype = RNA  length = 9457
FEATURE                Location/Qualifiers
misc_feature           1..9457
                       note = Description of Artificial Sequence: Synthetic
                        polynucleotide
source                 1..9457
                       mol_type = other RNA
                       organism = synthetic construct
SEQUENCE: 45
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa catagccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
```

-continued

```
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gatggagctg ctcatcctta aagcgaatgc tataactact atacttacag ctgtaacctt  7620
ttgcttcgcc tctggccaaa acattactga ggagttttat caatccactt gcagcgcagt  7680
ctcaaaagga tatctgtcag cattgcgcac cgggtggtac accagcgtta tcactatcga  7740
gctttccaac attaaagaga ataagtgtaa cggcacagac gcgaaagtca aactcattaa  7800
gcaagaactt gataaataca aaaatgcagt tactgaactt cagttgctca tgcaatcaac  7860
cccagcaacg aacaataggg ccaggagaga attgccgagg tttatgaact acacacttaa  7920
```

-continued

```
taacgctaaa aagactaacg ttacgctctc taagaagcgg aagcgcaggt ttctcgggtt  7980
ccttctgggg gttggcagtg caatagcatc cggcgtcgcg gtatcaaagg tgcttcatct  8040
tgaaggagaa gttaacaaaa tcaaaagcgc cttgctttca actaataagg cagtagtatc  8100
attgtctaac ggtgtcagcg tcttgacttc caaggttttg gatttgaaaa actatatcga  8160
caaacaactt ctcccgatcg ttaacaagca gtcatgcagt atctccaaca tcgaaaccgt  8220
catcgaattc caacagaaaa acaatagact gcttgaaatt actagagagt tttcagtgaa  8280
cgctggcgtt accactccgg tatccactta tatgctcact aatagcgaac tgctgtctct  8340
gataaatgac atgccaataa ctaacgacca gaagaaactt atgagtaaca acgtccagat  8400
cgtgagacag caatcatata gcattatgag cataattaag gaggaggtcc ttgcatacgt  8460
agtccagctc ccactgtacg gggttatcga cacgccatgt tggaagcttc atacttcccc  8520
cttgtgcacc acgaacacga aggaagggtc taacatttgt ctcacgcgca ctgatcgggg  8580
gtggtactgt gacaacgccg ggtcagtgtc atttttccct caggccgaga cctgcaaggt  8640
ccaatcaaac cgggtattct gtgatactat gaactccctg actctgcctt ctgaagttaa  8700
cctgtgtaat gtagatatat tcaatcctaa atacgactgc aagataatga ccagcaaaac  8760
cgacgtgtcc tcatctgtca tcacttccct tggtgctata gtaagctgct atggcaaaac  8820
gaaatgcacc gcgagtaata aaaatcgcgg tatcatcaag acatttagta acggctgcga  8880
ttatgtttcc aacaaaggtg ttgacaccgt atctgtgggg aatacccctgt attacgtaaa  8940
taagcaggaa gggaaatctc tctacgtgaa gggggaaccg ataatcaact tttatgaccc  9000
gctggttttt ccgtccgacg aatttgacgc gagtatctcc caagtcaacg agaaaattaa  9060
ccaaagcctc gcgttcataa gaaaatccga tgagctgctg cataatgtaa acgcgggcaa  9120
atcaactacc aacatcatga ttacaacaat aatcatcgtg ataatcgtga tcctgctttc  9180
acttatcgct gtcgggcttc ttctctattg taaggcccgg agtactcccg tgaccttgtc  9240
taaggatcag ctctcaggta tcaacaatat tgcattcagc aattgaggcg cgccatacag  9300
cagcaattgg caagctgctt acatagaact cgcggcgatt ggcatgccgc cttaaaattt  9360
ttattttatt ttttcttttc ttttccgaat cggattttgt ttttaatatt tcaaaaaaaa  9420
aaaaaaaaaa aaaaaaaaaa aaaaaaaaaa aaaaaaa                          9457

SEQ ID NO: 46          moltype = RNA  length = 8755
FEATURE                Location/Qualifiers
misc_feature           1..8755
                       note = Description of Artificial Sequence: Synthetic
                        polynucleotide
source                 1..8755
                       mol_type = other RNA
                       organism = synthetic construct
SEQUENCE: 46
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
```

-continued

```
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
```

-continued

```
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gatgtccaaa aataaagacc agcgaacggc caagactctg gagaggactt gggataccct  7620
gaatcatctg ttgtttattt caagttgcct ttataaattg aatctcaaat ccgtcgcgca  7680
aatcacgctg agcatactcg caatgattat ctcaacttcc ttgataattg ccgccataat  7740
cttcattgca agtgcaaatc ataaagtgac tcctacaacc gcaataatac aggacgcgac  7800
cagccaaatt aagaacacga ctcccacgta tctcacccaa aatccccaac tcggaattag  7860
cccaagtaat ccgtcagaga ttacttcaca aatcaccacc atactggcga gcacaactcc  7920
aggcgtaaaa tccaccctcc aatctactac cgtcaagact aaaaatacca ctactactca  7980
gacacaacct agtaaaccta cgactaagca gcgccagaat aaacccccaa gcaaaccaaa  8040
caacgacttc cattttgaag ttttcaactt cgtgccttgt tctatctgct ctaataatcc  8100
aacatgctgg gccatctgca agcgcattcc gaataagaaa cccggtaaga aaactacaac  8160
gaaacctacc aagaagccta ccctgaaaac gacaaagaaa gacccgaaac cgcaaacaac  8220
caaaagtaaa gaagtgccca caactaaacc cacagaagaa ccaacgataa acacgaccaa  8280
aaccaacata ataactacgc tgcttaccag caacacgaca ggcaacccgg aattgaccag  8340
tcagatggaa acttttcatt caaccagcag cgaaggtaat ccaagtccta gtcaggtgtc  8400
tacgacatct gaatatccat ctcagcctag ttcccctccg aacacgccgc gccagtgata  8460
accgcggtgt caaaaaccgc gtggacgtgg ttaacatccc tgctgggagg atcagccgta  8520
attattataa ttggcttggt gctggctact attgtggcca tgtacgtgct gaccaaccag  8580
aaacataatt gaatacagca gcaattggca agctgcttac atagaactcg cggcgattgg  8640
catgccgcct taaaattttt attttatttt ttcttttctt ttccgaatcg gattttgttt  8700
ttaatatttc aaaaaaaaaa aaaaaaaaaa aaaaaaaaaa aaaaaaaaaa aaaaa       8755

SEQ ID NO: 47          moltype = RNA  length = 9559
FEATURE                Location/Qualifiers
misc_feature           1..9559
                       note = Description of Artificial Sequence: Synthetic
                        polynucleotide
source                 1..9559
                       mol_type = other RNA
                       organism = synthetic construct
SEQUENCE: 47
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
```

-continued

```
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agtttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggagggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
```

-continued

```
tcatagttat ggccatgact actctagcta gcagtgttaa atcattcagc tacctgagag  7500
gggcccctat aactctctac ggctaacctg aatggactac gacatagtct agtccgccaa  7560
gatgaaaaca attatcgctc tcagttatat tttctgcctt cctttggggc aagacttgcc  7620
gggcaatgat aatagtacag cgactctctg tctcggacac cacgcagtac cgaacggcac  7680
acttgtgaag acaatcacag acgatcaaat cgaagtgacg aatgcaacag agcttgttca  7740
atcatcatct accggcaaaa tctgcaataa tccgcataga atccttgatg gaatcgactg  7800
caccctgatt gacgcactgt tgggagatcc tcattgcgat gtgtttcaga atgagacatg  7860
ggaccttttt gtcgagagga gcaaagcgtt ttccaactgc tacccgtatg acgtgcctga  7920
ttacgcgtca ctccgctcac ttgtagcatc aagcggtact ctggagttca tcaccgaagg  7980
attcacctgg acgggcgtaa ctcagaacgg cggttctaac gcatgtaaga gggggccagg  8040
gtccggcttc ttctcacggc tcaactggtt gactaagtct ggttcaacat acccggtcct  8100
taacgttaca atgccgaata atgacaactt tgataaactc tacatctggg gcattcacca  8160
tccatccaca aatcaagaac agacaagttt gtacgttcag gcgtcagggc gcgttaccgt  8220
gagtacaaga agatcacagc aaacaattat acccaatatt gggtcccgac cctgggtaag  8280
aggactgtcc tctcgcatct ccatatactg gaccattgtc aaaccgggcg acgtcctggt  8340
tatcaatagt aatggaaacc ttattgctcc gcgcggctat ttcaaaatgc gaactggaaa  8400
gtcaagtata atgcgctcag acgcaccgat cgatacttgt atcagtgaat gcatcacccc  8460
taacgggtcc ataccgaacg ataagccctt ccagaatgtg aataaaatca cgtatggagc  8520
atgccccaaa tacgtgaagc aaaacaccct caagttggct acgggtatgc gcaacgtccc  8580
agaaaaacaa acgcgaggct tgtttggggc gatagcaggt tttatcgaga acggctggga  8640
aggaatgatc gatgggtggt acggctttcg ccatcaaaac tcagaaggaa ctgggcaggc  8700
cgcagatctt aagtctacgc aagcggcgat agatcaaatt aatggcaagt tgaatagggt  8760
gatagagaag acgaacgaga agttccatca aatagagaaa gaattcagtg aagtagaggg  8820
gcgaattcag gatttggaaa aatatgtcga ggatactaag atcgacctgt ggagctataa  8880
cgcagagctt ctggtagcac ttgagaacca gcatactatt gatctcaccg attccgagat  8940
gaacaagctt tttgagaaga ccaggagaca gttgcgcgag aatgccgaag aaatgggtaa  9000
cggttgtttt aagatttatc acaaatgtga caacgcgtgt attgagtcca ttaggaatgg  9060
tacatatgat cacgatgtgt atcgcgatga agcacttaac aatcggttcc aaataaaggg  9120
cgtggagctc aagagtgggt ataaagattg gatcctctgg atctcattcg cgatttcctg  9180
cttcctcctg tgcgttgtct tgctgggctt tattatgtgg gcatgtcaga gaggtaacat  9240
ccggtgcaac atatgtatct gataaccgcg gtgtcaaaaa ccgcgtggac gtggttaaca  9300
tccctgctgg gaggatcagc cgtaattatt ataattggct tggtgctggc tactattgtg  9360
gccatgtacg tgctgaccaa ccagaaacat aattgaatac agcagcaatt ggcaagctgc  9420
ttacatagaa ctcgcggcga ttggcatgcc gccttaaaat ttttatttta tttttttctt  9480
tcttttccga atcggatttt gtttttaata tttcaaaaaa aaaaaaaaaa aaaaaaaaaa  9540
aaaaaaaaaa aaaaaaaaa                                               9559
```

```
SEQ ID NO: 48          moltype = RNA  length = 7862
FEATURE                Location/Qualifiers
misc_feature           1..7862
                       note = Description of Artificial Sequence: Synthetic
                        polynucleotide
misc_difference        7562
source                 1..7862
                       mol_type = other RNA
                       organism = synthetic construct
SEQUENCE: 48
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
```

-continued

```
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
```

```
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntgataacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttattttttc ttttcttttc cgaatcggat  7800
tttgttttta atatttcaaa aaaaaaaaaa aaaaaaaaaa aaaaaaaaaa aaaaaaaaaa  7860
aa                                                                 7862
```

```
SEQ ID NO: 49          moltype = RNA  length = 7862
FEATURE                Location/Qualifiers
source                 1..7862
                       mol_type = other RNA
                       organism = synthetic construct
SEQUENCE: 49
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
```

-continued

```
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggagggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntgataacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttatttttc ttttcttttc cgaatcggat  7800
```

```
tttgttttta atatttcaaa aaaaaaaaaa aaaaaaaaaa aaaaaaaaaa aaaaaaaaaa  7860
aa                                                                 7862

SEQ ID NO: 50          moltype = RNA  length = 7862
FEATURE                Location/Qualifiers
source                 1..7862
                       mol_type = other RNA
                       organism = synthetic construct
SEQUENCE: 50
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
```

-continued

```
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntagtaacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttattttttc ttttcttttc cgaatcggat  7800
tttgttttta atatttcaaa aaaaaaaaaa aaaaaaaaaa aaaaaaaaaa aaaaaaaaaa  7860
aa                                                                 7862
```

```
SEQ ID NO: 51          moltype = RNA  length = 7862
FEATURE                Location/Qualifiers
source                 1..7862
                       mol_type = other RNA
                       organism = synthetic construct
SEQUENCE: 51
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
```

-continued

```
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
```

```
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gntgataacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttattttttc ttttcttttc cgaatcggat  7800
tttgttttta atatttcaaa aaaaaaaaaa aaaaaaaaaa aaaaaaaaaa aaaaaaaaaa  7860
aa                                                                 7862

SEQ ID NO: 52          moltype = RNA  length = 7862
FEATURE                Location/Qualifiers
source                 1..7862
                       mol_type = other RNA
                       organism = synthetic construct
SEQUENCE: 52
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
```

-continued

```
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
```

-continued aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gntgataacc gcggtgtcaa aaaccgcgtg gacgtggtta acatccctgc tgggaggatc 7620
agccgtaatt attataattg gcttggtgct ggctactatt gtggccatgt acgtgctgac 7680
caaccagaaa cataattgaa tacagcagca attggcaagc tgcttacata gaactcgcgg 7740
cgattggcat gccgccttaa aatttttatt ttatttttc ttttcttttc cgaatcggat 7800
tttgttttta atatttcaaa aaaaaaaaaa aaaaaaaaaa aaaaaaaaaa aaaaaaaaaa 7860
aa 7862

SEQ ID NO: 53 moltype = RNA length = 11701
FEATURE Location/Qualifiers
misc_feature 1..11701
note = Description of Artificial Sequence: Synthetic polynucleotide
source 1..11701
mol_type = other RNA
organism = synthetic construct
SEQUENCE: 53
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg tttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700

-continued

```
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
```

-continued

```
tcatagttat ggccatgact actctagcta gcagtgttaa atcattcagc tacctgagag  7500
gggcccctat aactctctac ggctaacctg aatggactac gacatagtct agtccgccaa  7560
gatgtttctg ctcacaacca aacgcactat gtttgttttc ctcgtgctgc tccctttggt  7620
aagttctcag tgtgtaaacc tgagaacacg aacccagttg cctccagctt ataccaactc  7680
atttactcgc ggagtatatt atcccgataa ggtctttaga agtagcgtgt tgcactctac  7740
acaggatctg ttcttgccct tctttagtaa cgttacctgg tttcatgcaa tacatgtgag  7800
cggaacaaat ggaacaaaaa gatttgacaa tccagtgctt ccatttaatg atggggttta  7860
ctttgccagt atcgaaaagt caaacataat ccgggggtgg atctttggaa ccactttgga  7920
ctctaagaca cagtctctcc tcatagtaaa caacgccacc aatgttgtca taaaagtatg  7980
cgaatttcag ttttgcaacg atccctttct cgacgtgtat taccataaga ataataaatc  8040
ctggatggag tctggggttt atagtagtgc taataattgc actttcgaat acgtgtccca  8100
accattcctc atggaccttg agggcaaaca ggggaatttt aaaaacttgc gcgaatttgt  8160
ctttaagaat atcgacggat actttaagat ctatagtaaa cacactccta tcaacctcgt  8220
tcgggatctt ccccaaggct ttctgctct cgaacccctc gtagacttgc caattgggat  8280
aaatatcact cgctttcaaa ctttgcttgc cctccacagg agctacctga cacccggcga  8340
ctcttcttct ggtttgaccg ccggcgccgc tgcctattat gttggttacc ttcagccacg  8400
aacattcttg ctcaagtata acgagaatgg caccattacc gacgccgtcg attgtgcatt  8460
ggatcccttg tctgaaacaa aatgtacctt gaagtccttt accgtagaga aaggcatata  8520
ccagacttcc aacttccgag ttcagcctac agaatccatc gtacgatttc ccaacatcac  8580
aaacctctgc cctttcggtg aagtatttaa tgctacacgc ttcgcttcag tctatgcctg  8640
gaataggaag cgcatatcaa attgcgtggc cgattattca gtcctctata atagcgcatc  8700
cttcagtact ttcaagtgct acggcgtttc ccccaccaaa ctcaatgatc tttgcttcac  8760
caacgtctat gctgacagtt ttgtcatacg aggcgacgaa gtacgccaga ttgccccccgg  8820
gcagacaggt aatattgctg attataatta taaactccca gatgacttta ctggatgcgt  8880
catagcctgg aattccaaca atctagattc caaggttggt gggaattata attaccgtta  8940
tcgactgttc agaaagagta acttgaaacc atttgagaga gacatatcca ccgagattta  9000
ccaggcaggc agtaagcctt gtaacggcgt tgagggattt aactgctatt ttcctttgca  9060
atcctatggc tttcaaccaa caaacggggt tggctatcaa ccctatcgag tggttgtcct  9120
cagctttgaa cttttgcacg ctcccgccac agtctgcgga ccaaaaaaga gtacaaatct  9180
tgtcaagaat aagtgcgtaa atttcaattt caatggcctt acaggaacag gcgtgctgac  9240
tgagtcaaac aagaatttcc tgccatttca gcagtttggg cgggatatag cagacacaac  9300
tgacgctgta cgcgatcctc agactttgga gatcttggac atcactccct gttctttcgg  9360
aggggtatct gtcatcaccc ccggaactaa tacatcaaat caggtcgctg tgttgtacca  9420
aggtgtcaac tgcacagaag tccccgttgc tatacacgca gaccagctca cccccacatg  9480
gcgggtgtac tcaactggct caaacgtatt ccagaccaga gctgggtgct tgatcggtgc  9540
tgaacacgtg aacaatagct atgaatgcga tattcccatc ggtgccggga tctgcgctag  9600
ctatcagaca cagaccaatt cccgcaggcg ggctcgctct gtagcatccc agtctattat  9660
tgcctacact atgtcattgg gcgccgagaa tagcgtcgca tattcaaata attctattgc  9720
aatacccacc aacttcacaa tctccgtaac tacagaaata cttccagttt ccatgacaaa  9780
gacatcagtg gattgtacaa tgtatatatg cggagattcc acagaatgtt caaatttgct  9840
cttgcagtac ggctccttct gcacccagct caacagggca cttacaggta ttgctgtcga  9900
acaggacaag aacacacaag aagtcttcgc ccaagtcaaa cagatataca aaactcctcc  9960
cataaaggat tttggcggct tcaactttag tcagatcctc ccagaccctt caaaaccatc  10020
taaacgatca tttattgaag atctgctgtt caacaaggtc actcttgccg atgctggatt  10080
cattaagcaa tacggtgact gccttggtga tattgctgcc cgagatctga tctgtgccca  10140
gaaattcaac gggctcactg tactccctcc actgctcaca gacgaaatga ttgcacagta  10200
cacaagtgcc ctgttggcag gcacaatcac tagcggctgg acctttggcg caggtgcagc  10260
actccaaata ccttttgcca tgcagatggc ctatcggttt aatgggatag gcgtgactca  10320
aaatgtcctc tacgaaaacc aaaagttgat agctaaccaa ttcaattcag caatcgggaa  10380
gatacaggat tcactgtcta gtactgctag tgcccttggt aagctgcaga acgttgtcaa  10440
ccagaatgct caagctctga atacattggt taagcagctc tctagtaatt ttggggccat  10500
ctcttcagta cttaatgata ttttgagccg attggaccca cctgaagctg aagtacagat  10560
cgacaggctg ataacaggcc ggctccaatc cctccaaaca tacgtgacac aacaactcat  10620
acgcgcagcc gaaatccgag ccagcgctaa cctggcagct accaagatgt cagaatgcgt  10680
tctgggccag agtaaacgcg tagatttctg cgggaaaggg taccacctga tgtcctttcc  10740
acaatctgca cctcacgggg tcgtcttttt gcatgtaaca tacgtacccg cacaagagaa  10800
gaattttact accgctcctg ccatctgtca tgacgggaaa gctcatttc ctcgcgaagg  10860
tgtgtttgta tctaatggta cacattggtt tgtcacacag cggaatttct atgaacccca  10920
gatcattaca actgacaaca cttttgtttc cgggaattgt gacgtggtca taggaatcgt  10980
aaataacact gtatatgatc ccctccaacc agagctggac tcttttaaag aagaactgga  11040
taaatatttc aagaaccaca caagtcccga cgtggacctt ggggacataa gtggtattaa  11100
cgcatctgtg gttaacattc aaaaggaaat cgacagactc aacgaggtgg ccaaaaacct  11160
gaacgaaagc ttgatagatc tccaggagtt gggcaagtat gaacagtaca ttaaatggcc  11220
atggtacata tggcttggct ttatcgctgg ccttatcgcc atcgtaatgg ttacaatcat  11280
gctgtgctgc atgacctcct gctgttcttg tttgaaaggg tgttgttctt gtggtagttg  11340
ttgcaagttt gacgaagatg attccgaacc tgttcttaag gggtaaagc ttcactatac  11400
atgataaccg cggtgtcaaa aaccgcgtgg acgtggttaa catccctgct gggaggatca  11460
gccgtaatta ttataattgg cttggtgctg gctactattg tggccatgta cgtgctgacc  11520
aaccagaaac ataattgaat acagcagcaa ttggcaagct gcttacatag aactcgcggc  11580
gattggcatg ccgccttaaa atttttattt tatttttct tttcttttcc gaatcggatt  11640
ttgtttttaa tatttcaaaa aaaaaaaaaa aaaaaaaaaa aaaaaaaaaa aaaaaaaaaa  11700
a                                                                  11701
```

```
SEQ ID NO: 54          moltype = RNA  length = 7862
FEATURE                Location/Qualifiers
source                 1..7862
                       mol_type = other RNA
                       organism = synthetic construct
SEQUENCE: 54
```

-continued

```
ataggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
```

-continued

```
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccgc  7560
caccntaacc gcggtgtcaa aaaccgcgtg gacgtggtta acatccctgc tgggaggatc  7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttatttttc ttttctttc cgaatcggat  7800
tttgttttta atatttcaaa aaaaaaaaaa aaaaaaaaaa aaaaaaaaaa aaaaaaaaaa  7860
aa                                                                 7862
```